US012788770B2

(12) United States Patent
Grey et al.

(10) Patent No.: US 12,788,770 B2
(45) Date of Patent: Nov. 10, 2026

(54) COMPOUNDS AND METHODS FOR TREATING FUNGAL INFECTIONS

(71) Applicant: Basilea Pharmaceutica International Ag, Allschwil, Allschwil (CH)

(72) Inventors: Michael Grey, San Diego, CA (US); Jason Brittain, San Diego, CA (US); Michael Hodges, San Diego, CA (US)

(73) Assignee: Basilea Pharmaceutica International AG, Allschwil, Allschwil (CH)

( * ) Notice: Subject to any disclaimer, the term of this patent is extended or adjusted under 35 U.S.C. 154(b) by 0 days.

(21) Appl. No.: 17/271,020

(22) PCT Filed: Aug. 30, 2019

(86) PCT No.: PCT/US2019/049223

§ 371 (c)(1),
(2) Date: Feb. 24, 2021

(87) PCT Pub. No.: WO2020/047510

PCT Pub. Date: Mar. 5, 2020

(65) Prior Publication Data

US 2021/0290644 A1 Sep. 23, 2021

Related U.S. Application Data

(60) Provisional application No. 62/725,971, filed on Aug. 31, 2018.

(51) Int. Cl.

| | |
|---|---|
| ***A61K 31/675*** | (2006.01) |
| ***A61K 9/00*** | (2006.01) |
| ***A61K 9/08*** | (2006.01) |
| ***A61K 9/10*** | (2006.01) |
| ***A61K 9/107*** | (2006.01) |
| ***A61K 9/16*** | (2006.01) |
| ***A61K 9/20*** | (2006.01) |
| ***A61K 9/28*** | (2006.01) |
| ***A61K 9/50*** | (2006.01) |
| ***A61K 9/51*** | (2006.01) |
| ***A61K 31/4402*** | (2006.01) |
| ***A61K 31/4427*** | (2006.01) |
| ***A61K 31/444*** | (2006.01) |
| ***A61K 45/06*** | (2006.01) |
| ***A61K 47/02*** | (2006.01) |
| ***A61P 31/10*** | (2006.01) |

(52) U.S. Cl.

CPC .......... *A61K 31/675* (2013.01); *A61K 9/0019* (2013.01); *A61K 9/0053* (2013.01); *A61K 9/0073* (2013.01); *A61K 9/0095* (2013.01); *A61K 9/08* (2013.01); *A61K 9/10* (2013.01); *A61K 9/107* (2013.01); *A61K 9/16* (2013.01); *A61K 9/2009* (2013.01); *A61K 9/2013* (2013.01); *A61K 9/2027* (2013.01); *A61K 9/2054* (2013.01); *A61K 9/2059* (2013.01); *A61K 9/282* (2013.01); *A61K 9/5057* (2013.01); *A61K 9/51* (2013.01); *A61K 31/4402* (2013.01); *A61K 31/4427* (2013.01); *A61K 31/444* (2013.01); *A61K 45/06* (2013.01); *A61K 47/02* (2013.01); *A61P 31/10* (2018.01)

(58) Field of Classification Search

None

See application file for complete search history.

(56) References Cited

U.S. PATENT DOCUMENTS

| | | | | |
|---|---|---|---|---|
| 4,861,760 | A | 8/1989 | Mazuel et al. | |
| 4,911,920 | A | 3/1990 | Jani et al. | |
| 5,212,162 | A | 5/1993 | Missel et al. | |
| 5,403,841 | A | 4/1995 | Lang et al. | |
| 7,691,882 | B2 | 4/2010 | Tanaka et al. | |
| 8,058,444 | B2 | 11/2011 | Niijima et al. | |
| 8,153,662 | B2 | 4/2012 | Tanaka et al. | |
| 8,158,657 | B2 | 4/2012 | Tanaka et al. | |
| 8,188,119 | B2 | 5/2012 | Tanaka | |
| 8,507,530 | B2 | 8/2013 | Tanaka et al. | |
| 8,513,287 | B2 | 8/2013 | Matsukura | |
| 8,841,327 | B2 | 9/2014 | Tanaka et al. | |
| 2004/0170632 | A1 * | 9/2004 | Mahler ............ | A61K 39/39591 424/155.1 |
| 2006/0247237 | A1 | 11/2006 | Freyne et al. | |
| 2009/0233883 | A1 | 9/2009 | Matsukura | |
| 2010/0004235 | A1 | 1/2010 | Schirok et al. | |
| 2010/0168173 | A1 | 7/2010 | Tanaka et al. | |
| 2010/0216751 | A1 * | 8/2010 | Jacob ..................... | A61K 47/34 514/169 |
| 2011/0195999 | A1 | 8/2011 | Nakamoto et al. | |
| 2013/0288956 | A1 | 10/2013 | Watanabe et al. | |
| 2021/0163461 | A1 | 6/2021 | Trzoss et al. | |

FOREIGN PATENT DOCUMENTS

| | | |
|---|---|---|
| WO | 2015110820 | 7/2015 |
| WO | WO-2019113542 A1 | 6/2019 |
| WO | 2013138628 | 9/2019 |
| WO | WO-2020047510 A1 | 3/2020 |

OTHER PUBLICATIONS

Zhao et al ("In Vivo Pharmacokinetics and Pharmacodynamics of APX001 against *Candida* spp. In a Neutropenic Disseminated Candidiasis Mouse Model", Antimicrobial Agents and Chemotherapy, vol. 62(4), Mar. 27, 2018, p. 1-9) (Year: 2018).*

"Fosmanogepix", a product information sheet obtained from the website: https://www.medchemexpress.com/fosmanogepix.html.*

"E1210", a product information sheet obtained from the website: https://www.medchemexpress.com/e1210.html?utm_source=google&utm_medium=CPC&utm_campaign=US&utm_term=APX001A&utm_content=APX001A&gclid=EAIaIQobChMIwN2b36_d-QIVxMDICh3tEQ0ZEAAYASAAEgJnHvD_BWE.*

"Human body weight", a Wikipedia article obtained from the website: https://en.wikipedia.org/wiki/Human_body_weight.*

(Continued)

*Primary Examiner* — Sin J Lee

(57) ABSTRACT

Provided herein are compositions and methods of use thereof for the treatment of fungal infections and diseases.

28 Claims, 11 Drawing Sheets

(56) References Cited

OTHER PUBLICATIONS

EPR ("Breaking old habits: Moving away from commonly used buffers in pharmaceuticals", European Pharmaceutical Review, an internet article obtained at the website: https://www.europeanpharmaceuticalreview.com/article/13699/breaking-old-habits-moving-away-from-commonly-used-buffers-in-pharmaceuticals/) (Jul. 2012).*
University of Oklahoma ("Buffers", an internet article dated Apr. 7, 2004 and obtained at the website: https://www.ou.edu/research/electron/bmz5364/buffers.html) (Apr. 2004).*
DeAngelis ("Phosphate Buffer", University of Nebraska-Lincoln, an internet article dated Jan. 15, 2007 and obtained at the website: https://www.unl.edu/cahoonlab/phosphate%20buffer.pdf) (Jan. 2007).*
Pikal-Cleland et al ("Protein Denaturation during Freezing and Thawing in Phosphate Buffer Systems: Monomeric and Tetrameric B-Galactosidase" Archives of Biochemistry and Biophysics, vol. 384(2), Dec. 15, 2000, p. 398-406) (Year: 2000).*
Al-Muhammed et al. In-vivo studies on dexamethasone sodium phosphate liposomes. J Microencapsul. 13(3):293-306 (1996).
Arendrup et al. APX001A In Vitro Activity against Contemporary Blood Isolates and Candida auris Determined by the EUCAST Reference Method. Antimicrob Agents Chemother 62(10):e01225-18 (2018).
Berge et al. Pharmaceutical Salts. Journal of Pharmaceutical Sciences 66(1):1-19 (Jan. 1977).
Berkow et al. Activity of novel antifungal compound APX001A against a large collection of Candida auris. J Antimicrob Chemother 73(11):3060-3062 (2018).
Bundgard, H. Design of Prodrugs. 1985; pp. 7-9, 21-24 (Elsevier, Amsterdam).
Chiang et al. An Fc domain protein-small molecule conjugate as an enhanced immunomodulator. J. Am. Chem. Soc. 136(9):3370-73 (2014).
Chonn et al. Recent advances in liposomal drug-delivery systems. Curr Opin Biotechnol. 6(6):698-708(1995).
Covel et al. Chapter 12: The Discovery Of Manogepix/Fosmanogepix And Other GWT1 Inhibitors For The Treatment Of Invasive Fungal Infections. 2019 Medicinal Chemistry Reviews vol. 54 (18 pgs).
Eyles et al. Oral delivery and fate of poly(lactic acid) microsphere-encapsulated interferon in rats. J Pharm Pharmacol. 49(7):669-74 (1997).
Gao et al. Controlled release of a contraceptive steroid from biodegradable and injectable gel formulations: in vitro evaluation. Pharm Res. 12(6):857-63 (1995).
Gebremariam et al. APX001 Is Effective in the Treatment of Murine Invasive Pulmonary Aspergillosis. Antimicrob Agents Chemother 63(2):e01713-18 (2019).
Gebremariam et al. Galactomannan Is a Biomarker of Fosmanogepix (APX001) Efficacy in Treating Experimental Invasive Pulmonary Aspergillosis. Antimicrob Agents Chemother 64(1):e01966-19 (2019).
Hager et al. In Vitro and In Vivo Evaluation of the Antifungal Activity of APX001A/APX001 against Candida auris. Antimicrob Agents Chemother 62(3):e02319-17 (2018).
Hata et al. Efficacy of Oral E1210, a New Broad-Spectrum Antifungal with a Novel Mechanism of Action, in Murine Models of Candidiasis, Aspergillosis, and Fusariosis. Antimicrob Agents Chemother 55(1):4543-4551 (2011).
Kapoor et al. Evaluation of Resistance Development to the Gwt1 Inhibitor Manogepix (APX001A) in Candida Species. Antimicrob Agents Chemother 64(1):e01387-19 (2019).
Li et al. Current drug research on PEGylation with small molecular agents. Progress in Polymer Science 38:421-44 (2013).
McGuigan et al. Application of phosphoramidate pronucleotide technology to abacavir leads to a significant enhancement of antiviral potency. J. Med. Chem. 48:3504-3515 (2005).
Miyazaki et al. In Vitro Activity of E1210, a Novel Antifungal, against Clinically Important Yeasts and Molds. Antimicrob Agents Chemother 55(10):4652-4658 (2011).
Ostro et al. Use of Liposomes as Injectable-Drug Delivery Systems. Am J Hosp Pharm 46(8):1576-1587 (Aug. 1989).
PCT/US2019/049223 International Search Report and Written Opinion dated Nov. 20, 2019.
Pfaller et al. In Vitro Activity of a Novel Broad-Spectrum Antifungal, E1210, Tested against *Aspergillus* spp. Determined by CLSI and EUCAST Broth Microdilution Methods. Antimicrob Agents Chemother 55(11):5155-8 (2011).
Pfaller et al. In Vitro Activity of APX001A (Manogepix) and Comparator Agents against 1,706 Fungal Isolates Collected during an International Surveillance Program in 2017. Antimicrob Agents Chemother 63(8):e00840-19 (2019).
PubChem CID 68452548 Entry for [3-[3-[[4-(Pyridin-2-yloxymethyl)phenyl]methyl]-1,2-oxazol-5-yl]pyridin-2-yl]carbamic acid; https://pubchem.ncbi.nlm.nih.gov/compound/68452548 Entry created Nov. 30, 2012.
Rao. Recent developments of collagen-based materials for medical applications and drug delivery systems. J Biomater Sci Polym Ed. 7(7):623-45 (1995).
Rivero-Menendez et al. In vitro activity of APX001A against rare moulds using EUCAST and CLSI methodologies. J Antimicrob Chemother 74(5):1295-1299 (2019).
Shaw et al. Fosmanogepix: A Review of the First-in-Class Broad Spectrum Agent for the Treatment of Invasive Fungal Infections. J Fungi (Basel) 6(4):239 (2020).
Shaw et al. In Vitro and In Vivo Evaluation of APX001A/APX001 and Other Gwt1 Inhibitors against Cryptococcus. Antimicrob Agents Chemother 62(8):e00523-18 (2018).
Silverman. Chapter 8: Prodrugs and Drug Delivery Systems. The Organic Chemistry of Drug Design and Drug Action, Academic Press, Inc., San Diego (pp. 352-401) (1992).
Thomas et al. Synthesis and biological evaluation of glucuronide prodrugs of the histone deacetylase inhibitor CI-994 for application in selective cancer chemotherapy. Bioorg. Med. Chem. 16:8109-16 (2008).
Trzoss et al. Synthesis of analogs of the Gwt1 inhibitor manogepix (APX001A) and in vitro evaluation against *Cryptococcus* spp. Bioorg Med Chem Lett 29(23):126713 (2019).
Viriyakosol et al. APX001 and Other Gwt1 Inhibitor Prodrugs Are Effective in Experimental Coccidioides immitis Pneumonia. Antimicrob Agents Chemother 63(2):e01715-18 (2019).
Watanabe et al. E1210, a new broad-spectrum antifungal, suppresses Candida albicans hyphal growth through inhibition of glycosylphosphatidylinositol biosynthesis. Antimicrob Agents Chemother 56(2):960-971 (2012).
Wiederhold et al. Efficacy of Delayed Therapy with Fosmanogepix (APX001) in a Murine Model of Candida auris Invasive Candidiasis. Antimicrob Agents Chemother 63(11):e01120-19 (2019).
Wiederhold et al. The Investigational Agent E1210 Is Effective in Treatment of Experimental Invasive Candidiasis Caused by Resistant Candida albicans. Antimicrob Agents Chemother 59(1):690-692 (2015).
Zhao et al. APX001 Pharmacokinetic/Pharmacodynamic Target Determination against Aspergillus fumigatus in an In Vivo Model of Invasive Pulmonary Aspergillosis. Antimicrob Agents Chemother 63(4):e02372-18 (2019).
Zhao et al. In Vivo Pharmacokinetics and Pharmacodynamics of APX001 against *Candida* spp. in a Neutropenic Disseminated Candidiasis Mouse Model. Antimicrob Agents Chemother 62(4):e02542-17 (2018).
Zhao et al. Significantly Improved Pharmacokinetics Enhances In Vivo Efficacy of APX001 against Echinocandin- and Multidrug-Resistant Candida Isolates in a Mouse Model of Invasive Candidiasis. Antimicrob Agents Chemother 62(10):e00425-18 (2018).
The indian Office Action, dated Mar. 30, 2026, in the related Indian Appl. No. 202117010323.
Jornada et al., "The Prodrug Approach: A Successful Tool for Improving Drug Solubility," Molecules. Dec. 29, 2015;21(1):42.

(56) References Cited

OTHER PUBLICATIONS

The English translation of the Eurasian Search Report, mailed on Jul. 14, 2026, in the corresponding Eurasian Patent Appl. No. 202690697.
Michael R Hodges, et al. Phase 1 Study to Assess Safety. Tolerability and Pharmacokinetics of Single and Multiple Oral Doses of APX001 and to Investigate the Effect of Food on APX001 Bioavailability. Open Forum Infectious Diseases. vol. 4. Issue suppl_1, Fall 2017. p. S534. https://doi.org/10.1093/ofid/ofx163.1390. Methods, Results.
Michael R Hodges, et al. First-in-Human Study to Assess Safety, Tolerability and Pharmacokinetics of APX001 Administered by Intravenous Infusion to Healthy Subjects. Open Forum Infectious Diseases. vol. 4. Issue suppl_1, Fall 2017. p. S526. https://doi.org/10.1093/ofid/ofx163.1370. Methods, Results & Conclusion.

* cited by examiner

COMPOUNDS AND METHODS FOR TREATING FUNGAL INFECTIONS

CROSS REFERENCE TO RELATED APPLICATIONS

This application is the National Stage Entry of International Application No. PCT/US2019/049223, filed Aug. 30, 2019, which claims the benefit of U.S. Provisional Application No. 62/725,971, filed Aug. 31, 2018, the contents of each are incorporated herein by reference in their entirety for all purposes.

BACKGROUND

Fungi infect humans and are a major cause of human health problems. They also infect plants and cause enormous losses in agricultural productivity. The present disclosure generally relates to the treatment and/or prevention of fungal infections and diseases.

BRIEF SUMMARY OF THE DISCLOSURE

In an aspect, provided herein is a pharmaceutical composition, comprising:

(i) a compound of Formula (I):

(I)

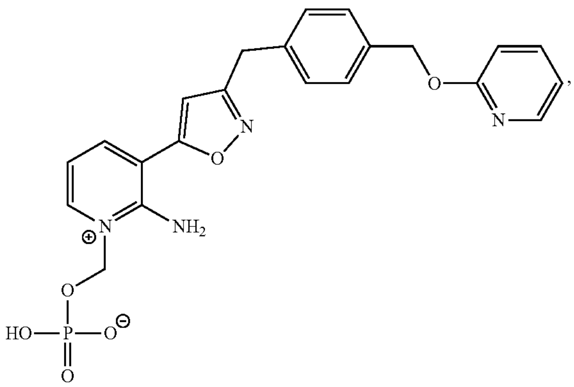

or an isotopic variant, tautomer, pharmaceutically acceptable salt, solvate, or hydrate thereof; and (ii) at least one pharmaceutically acceptable excipient, wherein the pharmaceutical composition is in a dosage form for oral dosing or administration.

In another aspect, there is provided a pharmaceutical composition, comprising:

(i) fine particles of the compound of Formula (I); or an isotopic variant, tautomer, pharmaceutically acceptable salt, solvate, or hydrate thereof; and (ii) at least one pharmaceutically acceptable excipient, wherein the pharmaceutical composition is in a dosage form for oral dosing or administration or in a dosage form for inhalation delivery.

In some embodiments, the particles are micronized. In some embodiments, the particles have a particle size of from about 1 μm to about 750 μm. In some embodiments, at least about 10% of the particles have a particle size of from about 1 μm to about 750 μm. In some embodiments, at least about 20% of the particles have a particle size of from about 1 μm to about 750 μm. In some embodiments, at least about 30% of the particles have a particle size of from about 1 μm to about 750 μm. In some embodiments, at least about 40% of the particles have a particle size of from about 1 μm to about 750 μm. In some embodiments, at least about 50% of the particles have a particle size of from about 1 μm to about 750 μm. In some embodiments, at least about 60% of the particles have a particle size of from about 1 μm to about 750 μm. In some embodiments, at least about 70% of the particles have a particle size of from about 1 μm to about 750 μm. In some embodiments, at least about 80% of the particles have a particle size of from about 1 μm to about 750 μm. In some embodiments, at least about 90% of the particles have a particle size of from about 1 μm to about 750 μm. In some embodiments, at least about 95% of the particles have a particle size of from about 1 μm to about 750 μm.

In some embodiments, the particles are nanomilled. In some embodiments, at least about 10% of the particles have a particle size of from about 1 μm to about 750 nm. In some embodiments, at least about 20% of the particles have a particle size of from about 1 nm to about 750 nm. In some embodiments, at least about 30% of the particles have a particle size of from about 1 nm to about 750 nm. In some embodiments, at least about 40% of the particles have a particle size of from about 1 nm to about 750 nm. In some embodiments, at least about 50% of the particles have a particle size of from about 1 nm to about 750 nm. In some embodiments, at least about 60% of the particles have a particle size of from about 1 nm to about 750 nm. In some embodiments, at least about 70% of the particles have a particle size of from about 1 nm to about 750 nm. In some embodiments, at least about 80% of the particles have a particle size of from about 1 nm to about 750 nm. In some embodiments, at least about 90% of the particles have a particle size of from about 1 nm to about 750 nm. In some embodiments, at least about 95% of the particles have a particle size of from about 1 nm to about 750 nm.

In some embodiments, the dosage form is a self-microemulsifying drug delivery system (SMEDDS). In some embodiments, the dosage form is a self-emulsifying drug delivery system (SEDDS). In some embodiments, the dosage form is a suspension or a solution. In some embodiments, the dosage form is a nanosuspension. In some embodiments, the dosage form is a solid dosage form. In some embodiments, the dosage form is a spray-dried dispersion dosage form. In some embodiments, the dosage form is a hot melt granulation dosage form. In some embodiments, the dosage form is a hot melt extrusion dosage form. In some embodiments, the dosage form is a microprecipitated bulk powder (MBP) dosage form. In some embodiments, the dosage form is a liquid. In some embodiments, the dosage form is a suspension, solution, syrup, or elixir. In some embodiments, the pharmaceutical composition is in a dosage form for oral dosing or administration.

In some embodiments, the dosage form is a tablet or a capsule. In some embodiments, the tablet or capsule has an enteric coating. In some embodiments, the dosage form is a tablet. In some embodiments, the tablet is an osmotic floating tablet. In some embodiments, the capsule is a liquid-filled hard capsule. In some embodiments, the capsule is a soft gelatin capsule.

In some embodiments, the dosage form is a modified-release dosage form. In some embodiments, the modified-release dosage form is a delayed-release dosage form, an extended-release (ER) dosage form, or a targeted-release dosage form. In some embodiments, the ER dosage form is a sustained-release (SR) dosage form or controlled-release (CR) dosage form. In some embodiments, the dosage form is an immediate release dosage form.

In some embodiments, the pharmaceutical composition comprises from about 10 mg to about 1,000 mg of a compound of Formula (I), or an isotopic variant, tautomer, pharmaceutically acceptable salt, solvate, or hydrate thereof. In some embodiments, the pharmaceutical composition comprises from about 50 mg to about 600 mg of a compound of Formula (I), or an isotopic variant, tautomer, pharmaceutically acceptable salt, solvate, or hydrate thereof. In some embodiments, about 50 mg to about 150 mg, about 150 mg to about 250 mg, about 250 mg to about 350 mg, about 350 mg to about 450 mg, about 450 mg to about 550 mg, about 550 mg to about 650 mg, about 650 mg to about 750 mg, about 850 mg to about 950 mg, or about 950 mg to about 1050 mg of a compound of Formula (I), or an isotopic variant, tautomer, pharmaceutically acceptable salt, solvate, or hydrate thereof.

In some embodiments, the pharmaceutical composition comprises about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg of a compound of Formula (I), or an isotopic variant, tautomer, pharmaceutically acceptable salt, solvate, or hydrate thereof.

In some embodiments, the pharmaceutical composition comprises about 50 mg, about 100 mg, about 150 mg, about 200 mg, about 250 mg, about 300 mg, about 350 mg, about 400 mg, or about 500 mg of a compound of Formula (I), or an isotopic variant, tautomer, pharmaceutically acceptable salt, solvate, or hydrate thereof.

In some embodiments, the pharmaceutical composition comprises about 50 mg, about 100 mg, about 200 mg, about 300 mg, about 400 mg, or about 500 mg of a compound of Formula (I), or an isotopic variant, tautomer, pharmaceutically acceptable salt, solvate, or hydrate thereof.

In some embodiments, the at least one pharmaceutically acceptable excipient is a filler, a disintegrant, a binder, a glidant, a lubricant, or any combination thereof. In some embodiments, the at least one pharmaceutically acceptable excipient is, microcrystalline cellulose, pregelatinized starch, povidone, magnesium stearate, colloidal silicon dioxide, or any combination thereof.

In some embodiments, the pharmaceutical composition is stable for up to 36 months at a temperature of from about 2° C. to about 25° C. In some embodiments, the pharmaceutical composition is stable for a period of from about 24 to about 36 months at a temperature of about 2° C. to about 8° C. In some embodiments, the pharmaceutical composition is stable for up to 36 months at a temperature of from about 2° C. to about 25° C. when stored as a solid. In some embodiments, the pharmaceutical composition is stable for a period of from about 24 to about 36 months at a temperature of about 2° C. to about 8° C. when stored as a solid. In some embodiments, the pharmaceutical composition comprises about 50 mg, about 100 mg, about 200 mg, about 300 mg, or about 400 mg of a compound of Formula (I), or an isotopic variant, tautomer, pharmaceutically acceptable salt, solvate, or hydrate thereof.

In an aspect, provided herein is a pharmaceutical composition, comprising:

(i) the compound of Formula (I), or an isotopic variant, tautomer, pharmaceutically acceptable salt, solvate, or hydrate thereof; and (ii) at least one pharmaceutically acceptable excipient, wherein the pharmaceutical composition is in a dosage form for dosing or administration by injection.

In some embodiments, the pharmaceutical composition is in a dosage form for intravenous (I.V.) injection or infusion, or intramuscular, subcutaneous, or intradermal injection.

In some embodiments, the pharmaceutical composition is in a dosage form for I.V. injection or infusion. In some embodiments, the dosage form is an I.V. dosage form. In some embodiments, the pharmaceutical composition is a solution. In some embodiments, the dosage form comprises a co-solvent.

In some embodiments, the co-solvent comprises PEG200, PEG300, PEG400, PEG600, propylene glycol, ethanol, polysorbate 20, polysorbate 80, cremephor, glycerin, benzyl alcohol, dimethylacetamide (DMA), N-methyl-2-pyrrolidone (NMP), tert-butanol, or any combination thereof. In some embodiments, the dosage form further comprises an oil. In some embodiments, the oil comprises sesame oil, soybean oil, vegetable oil, poppyseed oil, safflower oil, or combinations thereof.

In some embodiments, the dosage form further comprises a buffer. In some embodiments, the IV dosage form further comprises a buffer. In some embodiments, the buffer is a phosphate buffer. In some embodiments, the phosphate buffer is potassium phosphate. In some embodiments, the potassium phosphate is monobasic or dibasic.

In some embodiments, the pharmaceutical composition has a pH of from about 2.5 to about 11.0. In some embodiments, the pharmaceutical composition has a pH of from about 2.5 to about 5.0 or from about 6.5 to about 10.5. In some embodiments, the pharmaceutical composition has a pH of from about 2.5 to about 4.5 or from about 7.0 to about 9.0.

In some embodiments, the pH of the pharmaceutical composition is formulated for administration by IV is adjusted with hydrochloric acid and/or sodium hydroxide.

In some embodiments, the pharmaceutical composition comprises from about 5 mg/mL to about 250 mg/mL of a compound of Formula (I), or an isotopic variant, tautomer, pharmaceutically acceptable salt, solvate, or hydrate thereof. In some embodiments, the pharmaceutical composition comprises from about 10 mg/mL to about 50 mg/mL of a compound of Formula (I), or an isotopic variant, tautomer, pharmaceutically acceptable salt, solvate, or hydrate thereof.

In some embodiments, the pharmaceutical composition comprises from about 20 mg/mL to about 40 mg/mL of a compound of Formula (I), or an isotopic variant, tautomer, pharmaceutically acceptable salt, solvate, or hydrate thereof. In some embodiments, the pharmaceutical composition comprises about 10 mg/mL, about 15 mg/mL, about 20 mg/mL, about 25 mg/mL, or about 30 mg/mL of a compound of Formula (I), or an isotopic variant, tautomer, pharmaceutically acceptable salt, solvate, or hydrate thereof.

In some embodiments, the pharmaceutical composition is stable for up to about 24 months at a temperature of from about −20° C. to 8° C. In some embodiments, the pharmaceutical composition is stable for a period of from about 12 to about 24 months at a temperature of about −20° C. In some embodiments, the pharmaceutical composition comprises about 20 mg/mL of a compound of Formula (I), or an isotopic variant, tautomer, pharmaceutically acceptable salt, solvate, or hydrate thereof.

In some embodiments, the compound of Formula (I) or an isotopic variant, tautomer, pharmaceutically acceptable salt, solvate, or hydrate thereof; is crystalline, microcrystalline, amorphous, or lyophilized. In some embodiments, the compound of Formula (I) or an isotopic variant, tautomer, pharmaceutically acceptable salt, solvate, or hydrate thereof; is crystalline. In some embodiments, the compound of Formula (I) or an isotopic variant, tautomer, pharmaceutically acceptable salt, solvate, or hydrate thereof; is amorphous. In some embodiments, the compound of Formula (I) or an isotopic variant, tautomer, pharmaceutically acceptable salt, solvate, or hydrate thereof; is lyophilized.

In some embodiments, the pharmaceutical composition is substantially free of impurities. In some embodiments, the pharmaceutical composition is at least about 90% pure. In some embodiments, the pharmaceutical composition is at least about 95% pure. In some embodiments, the pharmaceutical composition is at least about 96% pure. In some embodiments, the pharmaceutical composition is at least about 97% pure. In some embodiments, the pharmaceutical composition is at least about 98% pure. In some embodiments, the pharmaceutical composition is at least about 99% pure. In some embodiments, the pharmaceutical composition is at least about 99.1%, about 99.2%, about 99.3%, about 99.4%, about 99.5%, about 99.6%, about 99.7%, about 99.8%, about 99.9%, or about 100% pure. In some embodiments, the pharmaceutical composition comprises up to about 10% (w/w) of at least one impurity. In some embodiments, the pharmaceutical composition comprises less than about 10% (w/w), about 9% (w/w), about 8% (w/w), about 7% (w/w), about 6% (w/w), about 5% (w/w), about 4% (w/w), about 3% (w/w), about 2% (w/w), or about 1% (w/w) of at least one impurity. In some embodiments, the pharmaceutical composition comprises less than about 5% (w/w), about 4% (w/w), about 3% (w/w), about 2% (w/w), or about 1% (w/w) of at least one impurity. In some embodiments, the pharmaceutical composition comprises less than about 0.9% (w/w), about 0.8% (w/w), about 0.7% (w/w), about 0.6% (w/w), about 0.5% (w/w), about 0.4% (w/w), about 0.3% (w/w), about 0.2% (w/w), or about 0.1% (w/w) of at least one impurity.

In some embodiments, the at least one impurity is a degradant. In some embodiments, the at least one impurity is:

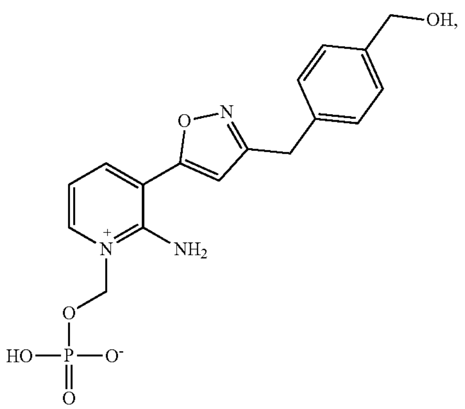

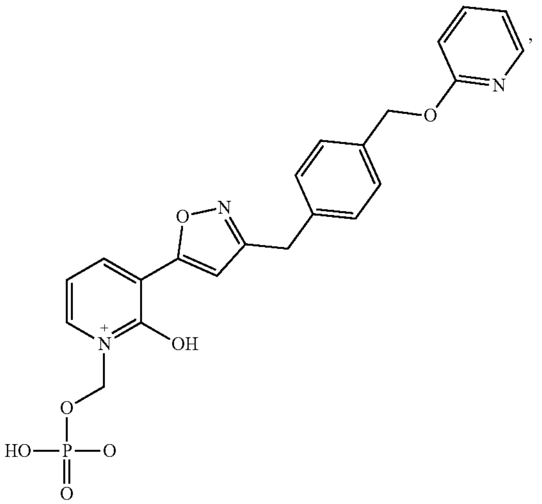

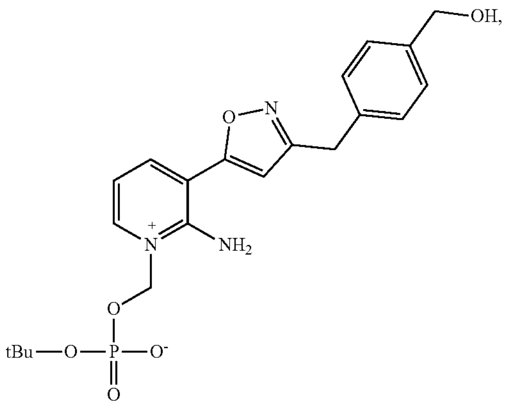

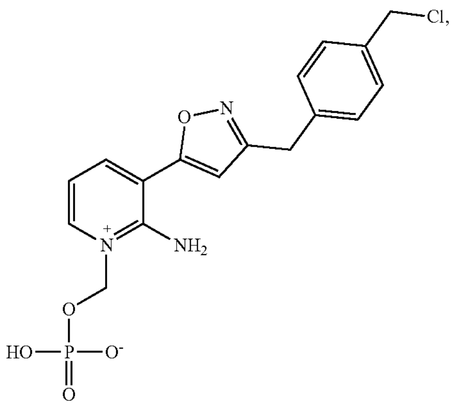

-continued
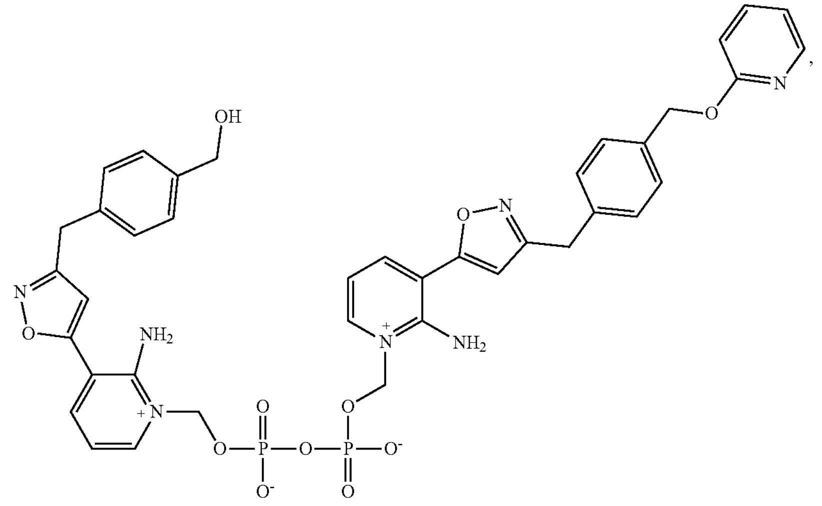
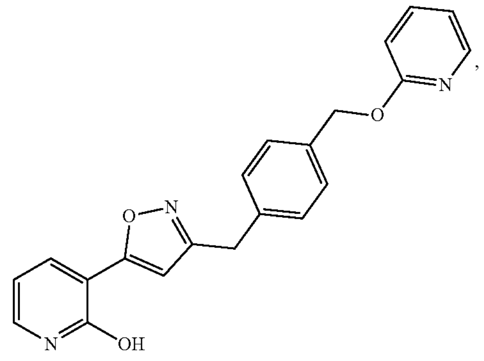
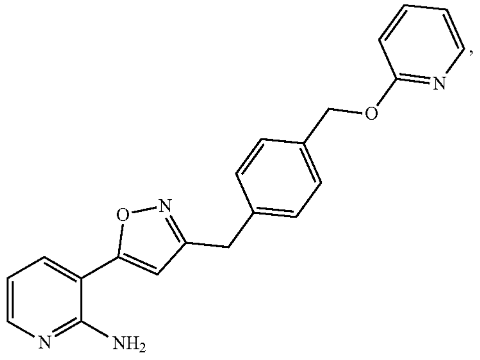 [SMILES: Nc1ncccc1-c1cc(Cc2ccc(COc3ccccn3)cc2)no1]
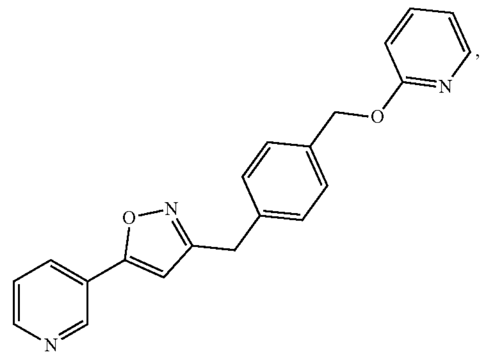
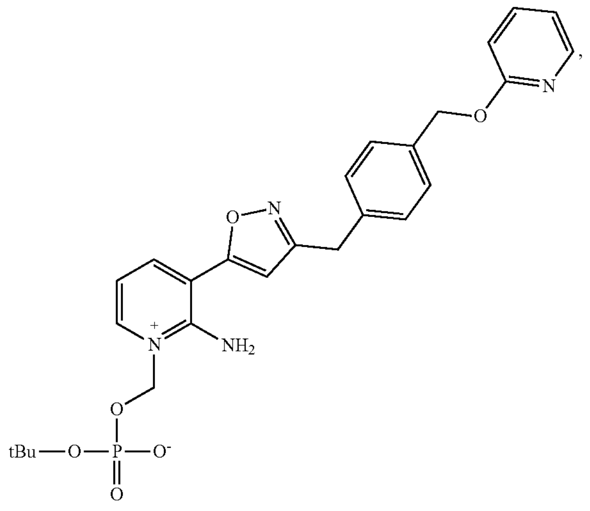

-continued

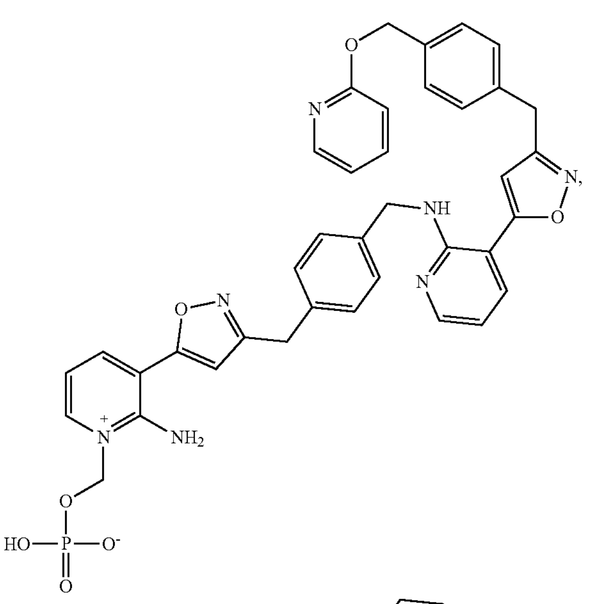

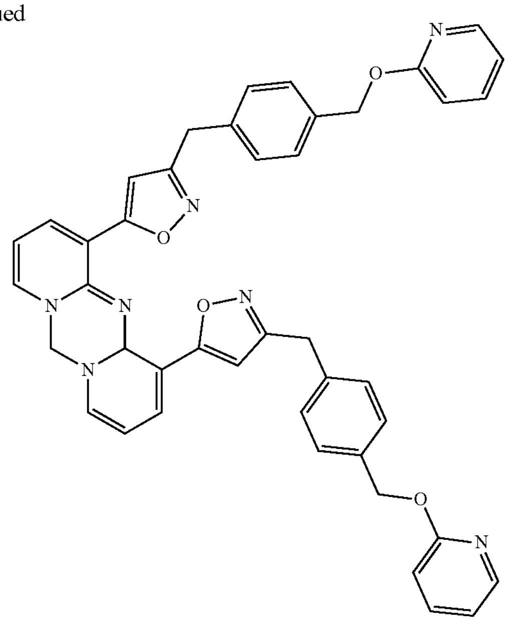

,

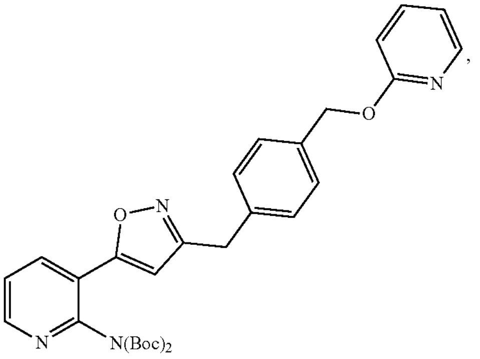 [SMILES: Nc1ncccc1-c1cc(Cc2ccc(COc3ccccn3)cc2)no1]

or any combination thereof.

In some embodiments, the at least one impurity is:

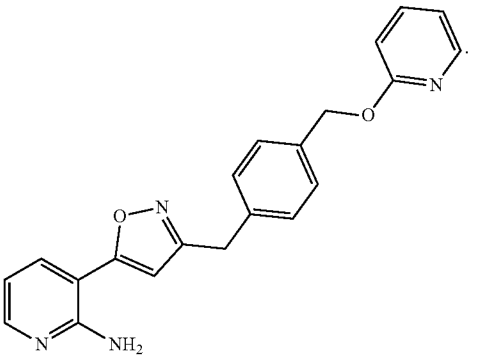 [SMILES: Nc1ncccc1-c1cc(Cc2ccc(COc3ccccn3)cc2)no1]

In some embodiments, the pharmaceutical composition comprises up to about 4.0% (w/w) total impurities. In some embodiments, the pharmaceutical composition comprises up to about 0.5% (w/w) of any individual impurity. In some embodiments, the pharmaceutical composition comprises up to about 1.5% (w/w) of the compound:

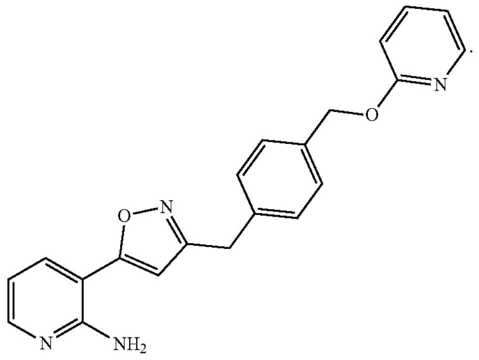 [SMILES: Nc1ncccc1-c1cc(Cc2ccc(COc3ccccn3)cc2)no1]

In another aspect, there is provided a combination composition, comprising: (i) the compound of Formula (I); or an isotopic variant, tautomer, pharmaceutically acceptable salt, solvate, or hydrate thereof; and (ii) at least one an antifungal agent.

In some embodiments, the at least one antifungal agent is an azole, an echinocandin, amphotericin B deoxycholate, amphotericin B cochleate, 5-fluorocytosine, terbinafine, griseofulvin, VL-2397, ibrexafungerp, orotomide F901318, or combinations thereof. In some embodiments, the azole is ketoconazole, fluconazole, posaconazole, itraconazole, voriconazole, isavuconazole, or miconazole. In some embodiments, the echinocandin is caspofungin, anidulafungin, micafungin, or rezafungin.

In an aspect, provided herein is a combination composition, comprising:

(i) a compound of Formula (I):

(I)

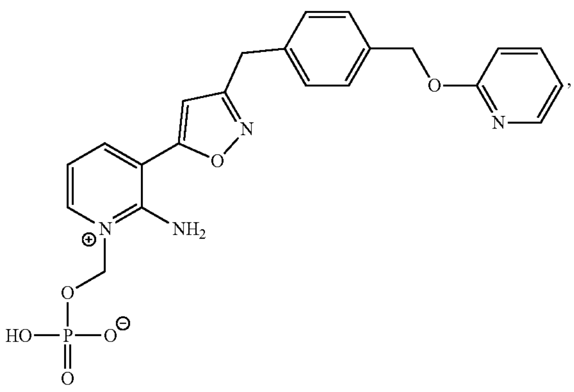

or an isotopic variant, tautomer, pharmaceutically acceptable salt, solvate, or hydrate thereof; and (ii) a compound of Formula (II)

(II)

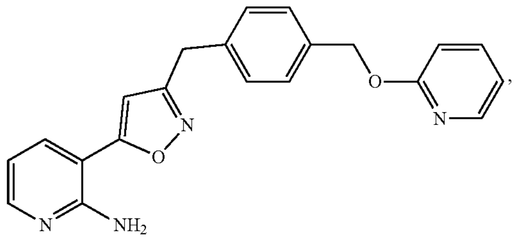

or an isotopic variant, tautomer, pharmaceutically acceptable salt, solvate, or hydrate thereof.

In some embodiments, the combination composition further comprises at least one pharmaceutically acceptable excipient.

In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are both crystalline.

In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 10:1. In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 9:1 to about 9.99:0.01. In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 9.5:0.5 to about 9.9:0.1. In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of about 9:1, about 9.1:0.9, about 9.2:0.8, about 9.3:0.7, about 9.4:0.6, about 9.5:0.5, about 9.6:0.4, about 9.7:0.3, about 9.8:0.2, or about 9.9:0.1.

In an aspect, provided herein is a method of treating or preventing a fungal infection or disease, comprising administering to a subject in need thereof a therapeutically effective amount of any of the pharmaceutical compositions or combination compositions described herein.

In some embodiments of the methods provided herein, about 10 mg to about 8,000 mg of the compound of Formula (I), or an isotopic variant, tautomer, pharmaceutically acceptable salt, solvate, or hydrate thereof is administered to the subject. In some embodiments of the methods provided herein, from about 10 mg to about 2,400 mg of the compound of Formula (I), or an isotopic variant, tautomer, pharmaceutically acceptable salt, solvate, or hydrate thereof is administered to the subject. In some embodiments of the methods provided herein, about 10 mg, about 30 mg, about 50 mg, about 100 mg, about 150 mg, about 200 mg, about 275 mg, about 300 mg, about 350 mg, about 400 mg, about 500 mg, about 600 mg, about 700 mg, about 800 mg, about 900 mg, about 1,000 mg, about 1,200 mg, about 1,500 mg, about 1,800 mg, about 2,000 mg, about 2,100 mg, about 2,400 mg, about 2,500 mg, about 3,000 mg, about 4,000 mg, about 5,000 mg, about 6,000 mg, about 7,000 mg, or about 8,000 mg of the compound of Formula (I), or an isotopic variant, tautomer, pharmaceutically acceptable salt, solvate, or hydrate thereof is administered to the subject.

In some embodiments of the methods provided herein, about 40 mg, about 50 mg, about 100 mg, about 200 mg, about 250 mg, about 350 mg, about 400 mg, about 500 mg, about 600 mg, about 700 mg, about 800 mg, or about 900 mg of the compound of Formula (I), or an isotopic variant, tautomer, pharmaceutically acceptable salt, solvate, or hydrate thereof is administered to the subject. In some embodiments of the methods provided herein, about 600 mg, about 700 mg, about 800 mg, about 900 mg, 1,000 mg, about 2,000 mg, or about 3,000 mg of the compound of Formula (I), or an isotopic variant, tautomer, pharmaceutically acceptable salt, solvate, or hydrate thereof is administered to the subject.

In some embodiments of the methods provided herein, the pharmaceutical composition is administered to the subject daily. In some embodiments of the methods provided herein, the pharmaceutical composition is administered to the subject once per day, twice per day, three times per day, or four times per day. In some embodiments of the methods provided herein, the pharmaceutical composition is administered to the subject once per day. In some embodiments of the methods provided herein, the pharmaceutical composition is administered to the subject twice per day.

In some embodiments of the methods provided herein, the pharmaceutical composition is administered to the subject for a period of up to about 12 weeks. In some embodiments of the methods provided herein, the pharmaceutical composition is administered to the subject for a period of at least one week. In some embodiments of the methods provided herein, the pharmaceutical composition is administered to the subject for a period of at least two weeks. In some embodiments of the methods provided herein, the pharmaceutical composition is administered to the subject for a period of up to about 2 weeks. In some embodiments of the methods provided herein, the pharmaceutical composition is administered to the subject for a period of one week, two weeks, 6 weeks, 12 weeks, 24 weeks, 48 weeks, or 52 weeks.

In some embodiments of the methods provided herein, from about to about 10 mg to about 8,000 mg of the compound of Formula (I), or an isotopic variant, tautomer, pharmaceutically acceptable salt, solvate, or hydrate thereof is administered to the subject. In some embodiments of the methods provided herein, about 10 mg, about 20 mg, about 30 mg, about 40 mg, about 50 mg, about 100 mg, about 125 mg, about 150 mg, about 175 mg, about 200 mg, about 225 mg, about 250 mg, about 275 mg, about 300 mg, about 350 mg, about 400 mg, about 450 mg, about 500 mg, about 600 mg, about 700 mg, about 800 mg, about 900 mg, about 1,000 mg, or about 2,000 mg of a compound of Formula (I), or an isotopic variant, tautomer, pharmaceutically acceptable salt, solvate, or hydrate thereof is administered to the subject.

In some embodiments of the methods provided herein, the pharmaceutical composition is administered to the subject over a period of about 20 minutes, about 30 minutes, about 60 minutes, about 90 minutes, about 2 hours, about 3 hours, about 4 hours, about 5 hours, about 6 hours, about 7 hours, about 8 hours, about 9 hours, about 10 hours, about 12 hours, about 18 hours, or about 24 hours by I.V. infusion.

In some embodiments of the methods provided herein, the pharmaceutical composition is administered to the subject over a period of up to about 3 hours by I.V infusion.

In some embodiments of the methods provided herein, a loading dose is administered to the subject followed by a maintenance dose. In some embodiments of the methods provided herein, the loading dose comprises from about 1,000 mg to about 8,000 mg of a compound of Formula (I), or an isotopic variant, tautomer, pharmaceutically acceptable salt, solvate, or hydrate thereof. In some embodiments of the methods provided herein, the maintenance dose comprises from about 600 mg to about 2,400 mg of a compound of Formula (I), or an isotopic variant, tautomer, pharmaceutically acceptable salt, solvate, or hydrate thereof. In some embodiments of the methods provided herein, the loading dose comprises from about 1,000 mg to about 2,000 mg. In some embodiments of the methods provided herein, the loading dose is administered over a period of about 2 to about 3 hours by I.V. infusion. In some embodiments of the methods provided herein, the loading dose is administered twice on the first day of treatment. In some embodiments of the methods provided herein, the second loading dose is administered about 9 hours after the first loading dose.

In some embodiments of the methods provided herein, the maintenance dose comprises about 600 mg, about 700 mg, about 800 mg, about 900 mg, or about 1,000 mg of a compound of Formula (I), or an isotopic variant, tautomer, pharmaceutically acceptable salt, solvate, or hydrate thereof. In some embodiments of the methods provided herein, the maintenance dose comprises about 800 mg or about 1,000 mg of a compound of Formula (I), or an isotopic variant, tautomer, pharmaceutically acceptable salt, solvate, or hydrate thereof is administered to the subject. In some embodiments of the methods provided herein, the maintenance dose comprises about 600 mg or about 900 mg of a compound of Formula (I), or an isotopic variant, tautomer, pharmaceutically acceptable salt, solvate, or hydrate thereof. In some embodiments of the methods provided herein, the maintenance dose comprises about 600 mg or about 900 mg of a compound of Formula (I), or an isotopic variant, tautomer, pharmaceutically acceptable salt, solvate, or hydrate thereof and is administered orally.

In some embodiments of the methods provided herein, the maintenance dose comprises about 600 mg or about 900 mg of a compound of Formula (I), or an isotopic variant, tautomer, pharmaceutically acceptable salt, solvate, or hydrate thereof is administered over a period of about 1 hour to about 3 hours by I.V. infusion.

In some embodiments of the methods provided herein, The method of any one of Embodiments 157-164, wherein about 600 mg of a compound of Formula (I), or an isotopic variant, tautomer, pharmaceutically acceptable salt, solvate, or hydrate thereof is administered over a period of about 3 hours by I.V. infusion.

In some embodiments of the methods provided herein, the maintenance dose is administered once daily.

In some embodiments of the methods provided herein, the maintenance dose is administered once daily starting on the second day of treatment.

In some embodiments of the methods provided herein, about 600 mg or about 800 mg of a compound of Formula (I), or an isotopic variant, tautomer, pharmaceutically acceptable salt, solvate, or hydrate thereof is administered over a period of about 3 hours by I.V. infusion starting on the second, third, or fourth day of treatment.

In some embodiments of the methods provided herein, about 800 mg or about 1,000 mg of a compound of Formula (I), or an isotopic variant, tautomer, pharmaceutically acceptable salt, solvate, or hydrate thereof is administered orally starting on the second, third, or fourth day of treatment.

In some embodiments of the methods provided herein, the maintenance dose comprises about 600 mg or about 800 mg of a compound of Formula (I), or an isotopic variant, tautomer, pharmaceutically acceptable salt, solvate, or hydrate thereof. In some embodiments of the methods provided herein, about 600 mg of a compound of Formula (I), or an isotopic variant, tautomer, pharmaceutically acceptable salt, solvate, or hydrate thereof is administered to the subject. In some embodiments of the methods provided herein, about 800 mg of a compound of Formula (I), or an isotopic variant, tautomer, pharmaceutically acceptable salt, solvate, or hydrate thereof is administered to the subject. In some embodiments of the methods provided herein, about 600 mg of a compound of Formula (I), or an isotopic variant, tautomer, pharmaceutically acceptable salt, solvate, or hydrate thereof is administered over a period of about 1 hour to about 3 hours by I.V. infusion and/or about 800 mg of a compound of Formula (I), or an isotopic variant, tautomer, pharmaceutically acceptable salt, solvate, or hydrate thereof and is administered orally. In some embodiments of the methods provided herein, the maintenance dose is administered once daily. In some embodiments of the methods provided herein, the maintenance dose is administered once daily starting on the second day of treatment. In some embodiments of the methods provided herein, about 600 mg of a compound of Formula (I), or an isotopic variant, tautomer, pharmaceutically acceptable salt, solvate, or hydrate thereof is administered over a period of about 3 hours by I.V. infusion.

In some embodiments of the methods provided herein, about 600 mg of a compound of Formula (I), or an isotopic variant, tautomer, pharmaceutically acceptable salt, solvate, or hydrate thereof is administered over a period of about 3 hours by I.V. infusion starting on the second day of treatment.

In some embodiments of the methods provided herein, about 800 mg of a compound of Formula (I), or an isotopic variant, tautomer, pharmaceutically acceptable salt, solvate, or hydrate thereof is administered orally starting on the fourth day of treatment.

In some embodiments of the methods provided herein, the fungal infection is caused by an invasive fungus. In some embodiments of the methods provided herein, the method further comprises administering to the subject at least one antifungal agent in combination with the pharmaceutical composition comprising the compound of Formula (I), or an isotopic variant, tautomer, pharmaceutically acceptable salt, solvate, or hydrate thereof. In some embodiments of the methods provided herein, the at least one antifungal agent is an azole, an echinocandin, amphotericin B deoxycholate, amphotericin B cochleate, 5-fluorocytosine, terbinafine, griseofulvin, VL-2397, ibrexafungerp, orotomide F901318, or combinations thereof. In some embodiments of the methods provided herein, the azole is ketoconazole, fluconazole, posaconazole, itraconazole, voriconazole, isavuconazole, or miconazole. In some embodiments of the methods provided herein, the echinocandin is caspofungin, anidulafungin, micafungin, or rezafungin, or combinations thereof.

In some embodiments of the methods provided herein, the pharmaceutical composition comprising the compound of Formula (I), or an isotopic variant, tautomer, pharmaceutically acceptable salt, solvate, or hydrate thereof; and the antifungal agent are administered simultaneously, approximately simultaneously, or sequentially, in any order. In some embodiments of the methods provided herein, the pharmaceutical composition comprising the compound of Formula (I), or an isotopic variant, tautomer, pharmaceutically acceptable salt, solvate, or hydrate thereof; and the antifungal agent are administered simultaneously or approximately simultaneously. In some embodiments of the methods provided herein, the pharmaceutical composition comprising the compound of Formula (I), or an isotopic variant, tautomer, pharmaceutically acceptable salt, solvate, or hydrate thereof; and the antifungal agent are administered sequentially. In some embodiments of the methods provided herein, the pharmaceutical composition comprising the pharmaceutical composition comprising the compound of Formula (I), or an isotopic variant, tautomer, pharmaceutically acceptable salt, solvate, or hydrate thereof; or a pharmaceutically acceptable salt thereof, is administered before the at least one antifungal agent. In some embodiments of the methods provided herein, the pharmaceutical composition comprising the compound of Formula (I), or an isotopic variant, tautomer, pharmaceutically acceptable salt, solvate, or hydrate thereof; or a pharmaceutically acceptable salt thereof, is administered after the at least one antifungal agent.

In some embodiments of the methods provided herein, the fungal infection or disease is caused by a *Aspergillus fumigatus, Blastomyces, Ajellomyces, Candida, Coccidioides, Cryptococcus, Histoplasm, Rhizopus muco, Cunninghamell, Apophysomyces, Absidi, Saksenaea, Entomophthora, Conidiobolus, Basidiobolus, Sporothrix, Pneumocystis, Talaromyces, Asclepias, Fusarium, Scedosporium* fungus or from a fungus from the Mucorales order, or any combination thereof. In some embodiments of the methods provided herein, the fungal infection or disease is caused by a *Cryptococcus, Aspergillus, Candida, Fusarium, Scedosporium* fungus or from a fungus from the Mucorales order, or any combination thereof. In some embodiments of the methods provided herein, the fungal infection or disease is caused by *Aspergillus fumigatus, Aspergillus flavus, Blastomyces dermatitidis, Ajellomyces dermatitidi, Candida albican, Candida glabrata, Candida rugosa, Candida auris, Coccidioides immitis, Coccidioides posadasii, Cryptococcus neoformans, Cryptococcus gattii, Histoplasma capsulatum, Rhizopus stolonifer, Rhizopus arrhizus, Mucor indicus, Cunninghamella bertholletiae, Apophysomyces elegans, Absidia* species, *Saksenaea* species, *Rhizomucor pusillus, Entomophthora* species, *Conidiobolus* species, *Basidiobolus* species, *Sporothrix schenckii, Pneumocystis jirovecii, Talaromyces marneffei, Asclepias albicans, Fusarium solani, Scedosporium apiospermum, Rhizomucor pusillus*, or any combination thereof. In some embodiments of the methods provided herein, the fungal infection or disease is caused by a *Cryptococcus* fungus or a *Candida* fungus. In some embodiments of the methods provided herein, the fungal infection or disease is caused by *Cryptococcus neoformans, Cryptococcus gattii*, or *Candida auris.*

In some embodiments of the methods provided herein, the fungal infection or disease is azole-resistant and/or echinocandin-resistant.

In some embodiments of the methods provided herein, the subject is immunocompromised. In some embodiments of the methods provided herein, the subject is infected with HIV/AIDS or has cancer. In some embodiments of the methods provided herein, the subject has cancer. In some embodiments of the methods provided herein, the cancer is acute myeloid leukemia (AML). In some embodiments of the methods provided herein, the subject has neutropenia. In some embodiments of the methods provided herein, the subject is undergoing or has undergone cancer chemotherapy treatment. In some embodiments of the methods provided herein, the subject is undergoing or has undergone corticosteroid treatment. In some embodiments of the methods provided herein, the subject is undergoing or has undergone TNF inhibitor treatment. In some embodiments of the methods provided herein, the subject is a transplant recipient. In some embodiments of the methods provided herein, the fungal infection or disease is in the bloodstream of the subject. In some embodiments of the methods provided herein, the subject has reduced colony counts of fungi in the lungs after administration of the pharmaceutical composition.

In some embodiments of the methods provided herein, the plasma concentration versus time curve of the compound of Formula (I) in the subject has a $t_{max}$ of less than from about 30 minutes to about 180 minutes. In some embodiments of the methods provided herein, the subject has a maximum plasma concentration ($C_{max}$) of from about 12,000 ng/mL to about 25,000 ng/ml of the compound of Formula (I).

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

Figures 1A, 1B:
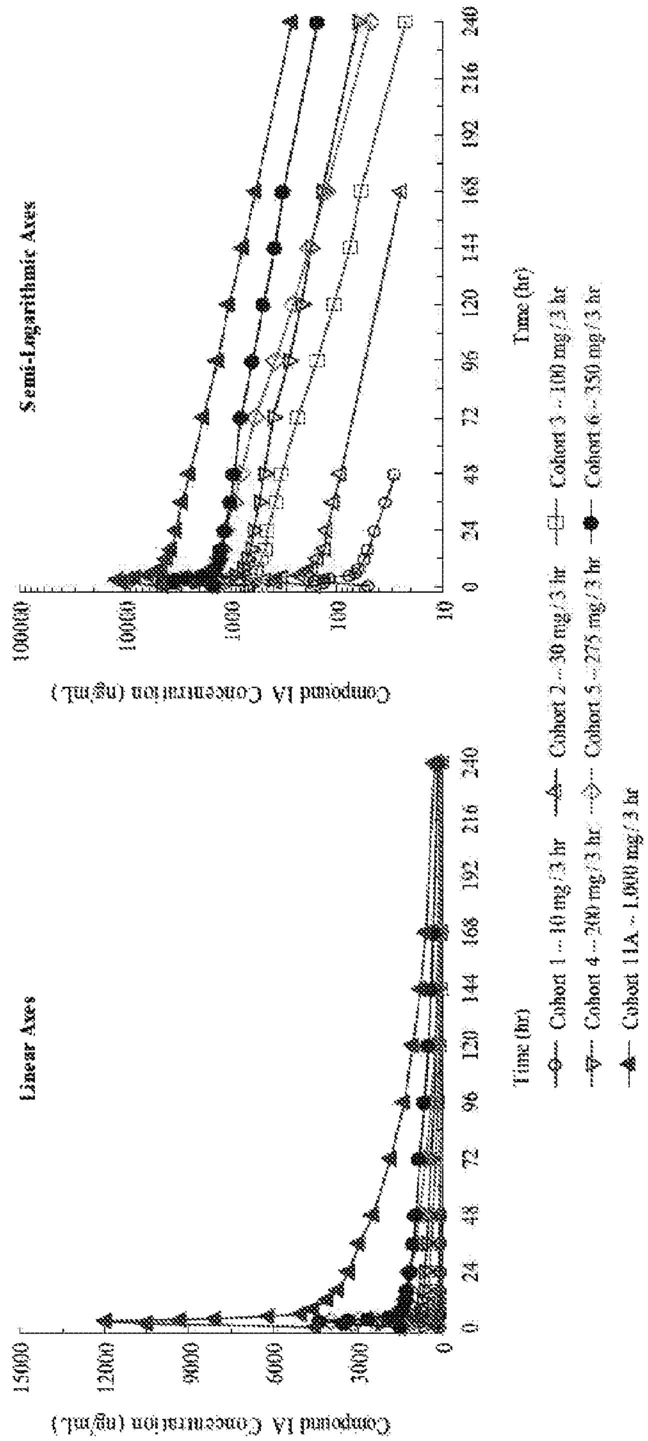
FIG. 1A-1B. Geometric mean plasma concentrations of Compound 1A after IV infusion of 10 to 1000 mg of Compound 1 over 3 hrs to healthy subjects-linear (FIG. 1A) and semi logarithmic (FIG. 1B) axes.

Provided herein are, for example, compositions for treating and/or preventing a fungal infection or disease. Also provided herein are, for example, methods of treating and/or preventing a fungal infection or disease.

I. DEFINITIONS

The abbreviations used herein have their conventional meaning within the chemical and biological arts. The chemical structures and formulae set forth herein are constructed according to the standard rules of chemical valency known in the chemical arts.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$.). All isotopic variations of the compounds of the present invention, whether radioactive or not, are encompassed within the scope of the present invention.

The term "isotopic variant" refers to a compound that contains an unnatural proportion of an isotope at one or more of the atoms that constitute such a compound. In some embodiments, an "isotopic variant" of a compound contains unnatural proportions of one or more isotopes, including, but not limited to, hydrogen ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{19}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In some embodiments, an "isotopic variant" of a compound is in a stable form, that is, non-radioactive. In some embodiments, an "isotopic variant" of a compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{19}Br$), bromine-81 ($^{81}Br$), and iodine-127 ($^{127}I$). In some embodiments, an "isotopic variant" of a compound is in an unstable form, that is, radioactive. In some embodiments, an "isotopic variant" of a compound contains unnatural proportions of one or more isotopes, including, but not limited to, tritium ($^{3}H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^{2}H$, for example, or any carbon can be $^{13}C$, for example, or any nitrogen can be 1'N, for example, or any oxygen can be 180, for example, where feasible according to the judgment of one of skill. In some embodiments, an "isotopic variant" of a compound contains unnatural proportions of deuterium (D).

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a [n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

The term "acceptable" with respect to a formulation, composition or ingredient, as used herein, means having no persistent detrimental effect on the general health of the subject being treated.

The term "pharmaceutically acceptable salt" as used herein includes both acid and base addition salts, i.e., including salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts," *Journal of Pharmaceutical Science,* 1977, 66, 1-19). Certain specific compounds of the present invention contain both basic and acidic functionalities that allow the compounds to be converted into either base or acid addition salts, or to exist as Zwitterions.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In some embodiments, compounds of the present invention contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of a compound to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "disease" or "condition" refer to a state of being or health status of a patient or subject capable of being treated with the compounds or methods provided herein. The disease may be a a fungal infection. In some further instances, "fungal infection or disease" refers to human fungal infections or diseases, including a *Cryptococcus*, *Aspergillus*, or *Candida* disease or infection.

As used herein, the terms "fungal infection" or "fungal disease" refer to a disease caused by pathogenic fungi. The fungal infection may be opportunistic or a primary infection and may be caused by fungi that are yeasts and/or molds.

The terms "treating" or "treatment" refer to any indicia of success in therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof may include prevention of an injury, pathology, condition, or disease. In some embodiments, treating is preventing. In other embodiments, treating does not include preventing.

"Treating," "treatment," "palliating," or "ameliorating" are used interchangeably herein. These terms as used herein (and as well-understood in the art) also broadly include any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., itching, swelling, burning, cough, fever, chest pain, difficulty breathing), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and duration sufficient to treat the patient.

The terms "prevent," "preventing," and "prevention" refer to a decrease in the occurrence of disease symptoms in a patient. The preventing or prevention may be complete (no detectable symptoms) or partial, such that fewer symptoms are observed than would likely occur absent treatment. In some embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals including, but not limited to, fish and birds. In some embodiments, a patient is human.

Treatment, as referred to herein, also refers to the systemic delivery of the compounds disclosed herein to any type of plant, including trees, shrubs, flowering plants, foliage plants, house plants, groundcover and grass, and agronomic plants (including crops of agronomic plants).

As used herein, "hydrates" are compounds that contain either stoichiometric or non-stoichiometric amounts of water, and, in some embodiments, are formed during the process of crystallization with water.

As used herein, the term "agronomic plant" refers to a plant of which a part or all is, or has been, harvested or cultivated on a commercial scale, or serves as an important source of feed, food, fiber, or other chemical compounds.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding ([1999]); Pickar, Dosage Calculations ([1999]); and Remington: The Science and Practice of Pharmacy, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a compound of Formula (I) or an isotopic variant, tautomer, pharmaceutically acceptable salt, solvate, or hydrate thereof (or, e.g., a metabolite thereof) at a particular time post-administration may be indicative of whether a therapeutically effective amount has been administered.

For any compound described herein, therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means parenteral or enteral administration. Accordingly, as used herein, "administering" refers to administration including, but not limited to, oral administration, administration as a suppository, topical contact, intravenous, intraperitoneal, intramuscular, inhalation, nebulization, intralesional, intrathecal, intracranial, intranasal, subcutaneous administration, or the implantation of a slow-release device, e.g., a mini-osmotic pump, to a subject. Administration is by any route, including transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, by ocular route, by otic route, etc. By "co-administer" it is meant that a composition described herein is administered at the same time, just prior to, or just after the administration of one or more additional therapies (e.g., antifungal agent, antibacterial agent, antiviral agent, and/or chemotherapeutic agent). The compound of the invention can be administered alone or can be co-administered to the patient. Co-administration is meant to include simultaneous, approximately simultaneous, or sequential administration of the compound individually or in combination (more than one compound or agent). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

By "co-administer" it is meant that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). The compositions of the present invention can be delivered transdermally, by a topical route, or formulated as applicator sticks, solutions, suspensions, emulsions, gels, creams, ointments, pastes, jellies, paints, powders, and aerosols.

For any compound described herein, therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating infections (e.g., fungal infections).

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for infections (e.g., fungal infections, bacterial infections, viral infections, etc.).

The compounds described herein can be administered to treat a fungal infection or disease. In this regard, the compounds disclosed herein may be administered either alone to treat such infections or diseases or may be co-administered with another therapeutic agent to treat such infections or diseases.

The compounds disclosed herein may be co-administered with an antifungal agent, such as polyenes, azoles, nucleoside analogs, echinocandins, and allylamines.

"Antifungal agent" is used in accordance with its plain ordinary meaning and refers to a composition (e.g., compound, drug, antagonist, inhibitor, modulator) having antifungal properties or the ability to inhibit the growth or proliferation of fungi. In some embodiments, an antifungal agent is an agent identified herein having utility in methods of treating fungal infections or diseases. In some embodiments, an antifungal agent is an agent approved by the FDA or similar regulatory agency of a country other than the USA, for treating fungal infections or disease. Examples of antifungal agents include, but are not limited to A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

"Substantially pure" indicates that a component makes up greater than about 75% of the total content of the composition excluding excipients, and typically greater than about 85% of the total content. More typically, "substantially pure" refers to compositions in which at least 90%, at least 95%, at least 96%, at least 97% or more of the total composition excluding excipients is the component of interest. In some cases, the component of interest will make up greater than about 90%, greater than about 95%, or greater than about 96% of the total content of the composition excluding excipients (percentage in a weight per weight basis). "Substantially pure" indicates that the composition contains less than, up to, or no more than about 25%, 15%, 10%, 5%, or 4% of known or unknown impurities. Impurities do not include excipients (e.g., binders, fillers, diluents, glidants, lubricants, disintegrants, etc.)

I. Compositions

In an aspect, provided herein is a pharmaceutical composition, comprising:

(i) a compound of Formula (I):

(I)

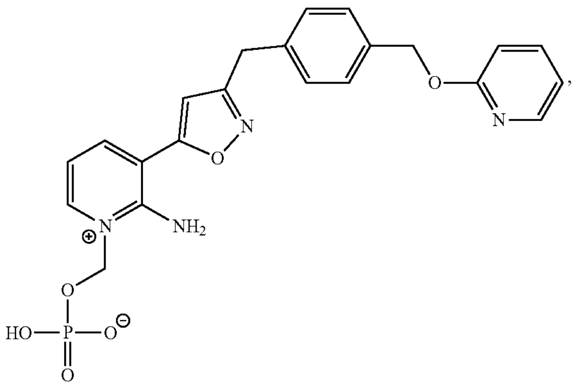

or an isotopic variant, tautomer, pharmaceutically acceptable salt, solvate, or hydrate thereof; and (ii) at least one pharmaceutically acceptable excipient, at least one pharmaceutically acceptable excipient, wherein the pharmaceutical composition is in a dosage form for oral dosing or administration.

In another aspect, there is provided a pharmaceutical composition, comprising:

(i) fine particles of the compound of Formula (I); or an isotopic variant, tautomer, pharmaceutically acceptable salt, solvate, or hydrate thereof; and (ii) at least one pharmaceutically acceptable excipient, wherein the pharmaceutical composition is in a dosage form for oral dosing or administration or in a dosage form for inhalation delivery.

In some embodiments, the particles are micronized. In some embodiments, the particles have a particle size of from about 1 μm to about 750 μm. In some embodiments, at least about 10% of the particles have a particle size of from about 1 μm to about 750 μm. In some embodiments, at least about 20% of the particles have a particle size of from about 1 μm to about 750 μm. In some embodiments, at least about 30% of the particles have a particle size of from about 1 μm to about 750 μm. In some embodiments, at least about 40% of the particles have a particle size of from about 1 μm to about 750 μm. In some embodiments, at least about 50% of the particles have a particle size of from about 1 μm to about 750 μm. In some embodiments, at least about 60% of the particles have a particle size of from about 1 μm to about 750 μm. In some embodiments, at least about 70% of the particles have a particle size of from about 1 μm to about 750 μm. In some embodiments, at least about 80% of the particles have a particle size of from about 1 μm to about 750 μm. In some embodiments, at least about 90% of the particles have a particle size of from about 1 μm to about 750 μm. In some embodiments, at least about 95% of the particles have a particle size of from about 1 μm to about 750 μm.

In some embodiments, the particles are nanomilled. In some embodiments, at least about 10% of the particles have a particle size of from about 1 μm to about 750 nm. In some embodiments, at least about 20% of the particles have a particle size of from about 1 nm to about 750 nm. In some embodiments, at least about 30% of the particles have a particle size of from about 1 nm to about 750 nm. In some embodiments, at least about 40% of the particles have a particle size of from about 1 nm to about 750 nm. In some embodiments, at least about 50% of the particles have a particle size of from about 1 nm to about 750 nm. In some embodiments, at least about 60% of the particles have a particle size of from about 1 nm to about 750 nm. In some embodiments, at least about 70% of the particles have a particle size of from about 1 nm to about 750 nm. In some embodiments, at least about 80% of the particles have a particle size of from about 1 nm to about 750 nm. In some embodiments, at least about 90% of the particles have a particle size of from about 1 nm to about 750 nm. In some embodiments, at least about 95% of the particles have a particle size of from about 1 nm to about 750 nm.

In some embodiments, the dosage form is a self-microemulsifying drug delivery system (SMEDDS). In some embodiments, the dosage form is a self-emulsifying drug delivery system (SEDDS). In some embodiments, the dosage form is a suspension or a solution. In some embodiments, the suspension is a colloidal suspension. In some embodiments, the dosage form is a nanosuspension. In some embodiments, the dosage form is a solid dosage form. In some embodiments, the dosage form is a spray-dried dispersion dosage form. In some embodiments, the dosage form is a hot melt granulation dosage form. In some embodiments, the dosage form is a hot melt extrusion dosage form. In some embodiments, the dosage form is a microprecipitated bulk powder (MBP) dosage form. In some embodiments, the dosage form is a liquid. In some embodiments, the dosage form is a suspension, solution, syrup, or elixir. In some embodiments, the pharmaceutical composition is in a dosage form for oral dosing or administration.

In some embodiments, the dosage form is a tablet or a capsule. In some embodiments, the tablet or capsule has an enteric coating. In some embodiments, the dosage form is a tablet. In some embodiments, the tablet is an osmotic floating tablet. In some embodiments, the capsule is a liquid-filled hard capsule. In some embodiments, the capsule is a soft gelatin capsule.

In some embodiments, the dosage form is a modified-release dosage form. In some embodiments, the modified-release dosage form is a delayed-release dosage form, an extended-release (ER) dosage form, or a targeted-release dosage form. In some embodiments, the ER dosage form is a sustained-release (SR) dosage form or controlled-release (CR) dosage form. In some embodiments, the dosage form is an immediate release dosage form.

In some embodiments, the pharmaceutical composition comprises from about 10 mg to about 1,000 mg of a compound of Formula (I), or an isotopic variant, tautomer, pharmaceutically acceptable salt, solvate, or hydrate thereof. In some embodiments, the pharmaceutical composition comprises from about 50 mg to about 600 mg of a compound of Formula (I), or an isotopic variant, tautomer, pharmaceutically acceptable salt, solvate, or hydrate thereof. In some embodiments, about 50 mg to about 150 mg, about 150 mg to about 250 mg, about 250 mg to about 350 mg, about 350 mg to about 450 mg, about 450 mg to about 550 mg, about 550 mg to about 650 mg, about 650 mg to about 750 mg, about 850 mg to about 950 mg, or about 950 mg to about 1050 mg of a compound of Formula (I), or an isotopic variant, tautomer, pharmaceutically acceptable salt, solvate, or hydrate thereof.

In some embodiments, the pharmaceutical composition comprises about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg of a compound of Formula (I), or an isotopic variant, tautomer, pharmaceutically acceptable salt, solvate, or hydrate thereof.

In some embodiments, the pharmaceutical composition comprises about 50 mg, about 100 mg, about 150 mg, about 200 mg, about 250 mg, about 300 mg, about 350 mg, about 400 mg, or about 500 mg of a compound of Formula (I), or an isotopic variant, tautomer, pharmaceutically acceptable salt, solvate, or hydrate thereof.

In some embodiments, the pharmaceutical composition comprises about 50 mg, about 100 mg, about 200 mg, about 300 mg, about 400 mg, or about 500 mg of a compound of Formula (I), or an isotopic variant, tautomer, pharmaceutically acceptable salt, solvate, or hydrate thereof.

In some embodiments, the at least one pharmaceutically acceptable excipient is a filler, a disintegrant, a binder, a glidant, a lubricant, or any combination thereof. In some embodiments, the at least one pharmaceutically acceptable excipient is, microcrystalline cellulose, pregelatinized starch, povidone, magnesium stearate, colloidal silicon dioxide, or any combination thereof.

In some embodiments, the pharmaceutical composition is stable for up to 36 months at a temperature of from about 2° C. to about 25° C. In some embodiments, the pharmaceutical composition is stable for a period of from about 24 to about 36 months at a temperature of about 2° C. to about 8° C.

In some embodiments, the pharmaceutical composition comprises about 50 mg, about 100 mg, about 200 mg, about 300 mg, or about 400 mg of a compound of Formula (I), or an isotopic variant, tautomer, pharmaceutically acceptable salt, solvate, or hydrate thereof.

In an aspect, provided herein is a pharmaceutical composition, comprising:

(i) the compound of Formula (I), or an isotopic variant, tautomer, pharmaceutically acceptable salt, solvate, or hydrate thereof; and (ii) at least one pharmaceutically acceptable excipient, wherein the pharmaceutical composition is in a dosage form for dosing or administration by intravenous (I.V.), intramuscular, subcutaneous, or intradermal injection.

In some embodiments, the compound of Formula (I) or an isotopic variant, tautomer, pharmaceutically acceptable salt, solvate, or hydrate thereof; is crystalline, microcrystalline, amorphous, or lyophilized. In some embodiments, the compound of Formula (I) or an isotopic variant, tautomer, pharmaceutically acceptable salt, solvate, or hydrate thereof; is crystalline. In some embodiments, the compound of Formula (I) or an isotopic variant, tautomer, pharmaceutically acceptable salt, solvate, or hydrate thereof; is amorphous. In some embodiments, the compound of Formula (I) or an isotopic variant, tautomer, pharmaceutically acceptable salt, solvate, or hydrate thereof; is lyophilized.

In some embodiments, the dosage form is an I.V. dosage form. In some embodiments, the pharmaceutical composition is a solution. In some embodiments, the dosage form comprises a co-solvent.

In some embodiments, the co-solvent comprises PEG200, PEG300, PEG400, PEG600, propylene glycol, ethanol, polysorbate 20, polysorbate 80, cremephor, glycerin, benzyl alcohol, dimethylacetamide (DMA), N-methyl-2-pyrrolidone (NMP), tert-butanol, or any combination thereof. In some embodiments, the dosage form further comprises an oil. In some embodiments, the oil comprises sesame oil, soybean oil, vegetable oil, poppyseed oil, safflower oil, or combinations thereof.

In some embodiments, the dosage form further comprises a buffer. In some embodiments, the IV dosage form further comprises a buffer. In some embodiments, the buffer is a phosphate buffer. In some embodiments, the phosphate buffer is potassium phosphate. In some embodiments, the potassium phosphate is monobasic or dibasic.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 2.5 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 2.5 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 2.5 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 2.5 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 2.5 to about 9.0. In some embodiments of the pharmaceutical composition, wherein the dosage form is an I.V. dosage form, the pH is from about 2.5 to about 8.5. In some embodiments of the pharmaceutical composition, wherein the dosage form is an I.V. dosage form, the pH is from about 2.5 to about 8.0. In some embodiments of the pharmaceutical composition, wherein the dosage form is an I.V. dosage form, the pH is from about 2.5 to about 7.5. In some embodiments of the pharmaceutical composition, wherein the dosage form is an I.V. dosage form, the pH is from about 2.5 to about 7.0. In some embodiments of the pharmaceutical composition, wherein the dosage form is an I.V. dosage form, the pH is from about 2.5 to about 6.5. In some embodiments of the pharmaceutical composition, wherein the dosage form is an I.V. dosage form, the pH is from about 2.5 to about 6.0. In some embodiments of the pharmaceutical composition, wherein the dosage form is an I.V. dosage form, the pH is from about 2.5 to about 5.5. In some embodiments of the pharmaceutical composition, wherein the dosage form is an I.V. dosage form, the pH is from about 2.5 to about 5.0. In some embodiments of the pharmaceutical composition, wherein the dosage form is an I.V. dosage form, the pH is from about 2.5 to about 4.5. In some embodiments of the pharmaceutical composition, wherein the dosage form is an I.V. dosage form, the pH is from about 2.5 to about 4.0. In some embodiments of the pharmaceutical composition, wherein the dosage form is an I.V. dosage form, the pH is from about 2.5 to about 3.5. In some embodiments of the pharmaceutical composition, wherein the dosage form is an I.V. dosage form, the pH is from about 2.5 to about 3.0.

In some embodiments of the pharmaceutical compositions disclosed herein, the dosage form is an I.V. (i.e., infusion) dosage form. In some embodiments of the pharmaceutical composition, wherein the dosage form is an I.V.

dosage form, the pH is from about 3.0 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.0 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.0 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.0 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.0 to about 9.0. In some embodiments of the pharmaceutical composition, wherein the dosage form is an I.V. dosage form, the pH is from about 3.0 to about 8.5. In some embodiments of the pharmaceutical composition, wherein the dosage form is an I.V. dosage form, the pH is from about 3.0 to about 8.0. In some embodiments of the pharmaceutical composition, wherein the dosage form is an I.V. dosage form, the pH is from about 3.0 to about 7.5. In some embodiments of the pharmaceutical composition, wherein the dosage form is an I.V. dosage form, the pH is from about 3.0 to about 7.0. In some embodiments of the pharmaceutical composition, wherein the dosage form is an I.V. dosage form, the pH is from about 3.0 to about 6.5. In some embodiments of the pharmaceutical composition, wherein the dosage form is an I.V. dosage form, the pH is from about 3.0 to about 6.0. In some embodiments of the pharmaceutical composition, wherein the dosage form is an I.V. dosage form, the pH is from about 3.0 to about 5.5. In some embodiments of the pharmaceutical composition, wherein the dosage form is an I.V. dosage form, the pH is from about 3.0 to about 5.0. In some embodiments of the pharmaceutical composition, wherein the dosage form is an I.V. dosage form, the pH is from about 3.0 to about 4.5. In some embodiments of the pharmaceutical composition, wherein the dosage form is an I.V. dosage form, the pH is from about 3.0 to about 4.0. In some embodiments of the pharmaceutical composition, wherein the dosage form is an I.V. dosage form, the pH is from about 3.0 to about 3.5.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.5 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.5 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.5 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.5 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 3.5 to about 9.0. In some embodiments of the pharmaceutical composition, wherein the dosage form is an I.V. dosage form, the pH is from about 3.5 to about 8.5. In some embodiments of the pharmaceutical composition, wherein the dosage form is an I.V. dosage form, the pH is from about 3.5 to about 8.0. In some embodiments of the pharmaceutical composition, wherein the dosage form is an I.V. dosage form, the pH is from about 3.5 to about 7.5. In some embodiments of the pharmaceutical composition, wherein the dosage form is an I.V. dosage form, the pH is from about 3.5 to about 7.0. In some embodiments of the pharmaceutical composition, wherein the dosage form is an I.V. dosage form, the pH is from about 3.5 to about 6.5. In some embodiments of the pharmaceutical composition, wherein the dosage form is an I.V. dosage form, the pH is from about 3.5 to about 6.0. In some embodiments of the pharmaceutical composition, wherein the dosage form is an I.V. dosage form, the pH is from about 3.5 to about 5.5. In some embodiments of the pharmaceutical composition, wherein the dosage form is an I.V. dosage form, the pH is from about 3.5 to about 5.0. In some embodiments of the pharmaceutical composition, wherein the dosage form is an I.V. dosage form, the pH is from about 3.5 to about 4.5. In some embodiments of the pharmaceutical composition, wherein the dosage form is an I.V. dosage form, the pH is from about 3.5 to about 4.0.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.0 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.0 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.0 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.0 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.0 to about 9.0. In some embodiments of the pharmaceutical composition, wherein the dosage form is an I.V. dosage form, the pH is from about 4.0 to about 8.5. In some embodiments of the pharmaceutical composition, wherein the dosage form is an I.V. dosage form, the pH is from about 4.0 to about 8.0. In some embodiments of the pharmaceutical composition, wherein the dosage form is an I.V. dosage form, the pH is from about 4.0 to about 7.5. In some embodiments of the pharmaceutical composition, wherein the dosage form is an I.V. dosage form, the pH is from about 4.0 to about 7.0. In some embodiments of the pharmaceutical composition, wherein the dosage form is an I.V. dosage form, the pH is from about 4.0 to about 6.5. In some embodiments of the pharmaceutical composition, wherein the dosage form is an I.V. dosage form, the pH is from about 4.0 to about 6.0. In some embodiments of the pharmaceutical composition, wherein the dosage form is an I.V. dosage form, the pH is from about 4.0 to about 5.5. In some embodiments of the pharmaceutical composition, wherein the dosage form is an I.V. dosage form, the pH is from about 4.0 to about 5.0. In some embodiments of the pharmaceutical composition, wherein the dosage form is an I.V. dosage form, the pH is from about 4.0 to about 4.5.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.5 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.5 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.5 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.5 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 4.5 to about 9.0. In some embodiments of the pharmaceutical composition, wherein the dosage form is an I.V. dosage form, the pH is from about 4.5 to about 8.5. In some embodiments of the pharmaceutical composition, wherein the dosage form is an I.V. dosage form, the pH is from about 4.5 to about 8.0. In some embodiments of the pharmaceutical composition, wherein the dosage form is an I.V. dosage form, the pH is from about 4.5 to about 7.5. In some embodiments of the pharmaceutical composition, wherein the dosage form is an I.V. dosage form, the pH is from about 4.5 to about 7.0. In some embodiments of the pharmaceutical composition, wherein the dosage form is an I.V. dosage form, the pH is from about 4.5 to about 6.5. In some embodiments of the pharmaceutical composition, wherein the dosage form is an I.V. dosage form, the pH is from about 4.5 to about 6.0. In some embodiments of the pharmaceutical composition, wherein the dosage form is an I.V. dosage form, the pH is from about 4.5 to about 5.5. In some embodiments of the pharmaceutical composition, wherein the dosage form is an I.V. dosage form, the pH is from about 4.5 to about 5.0.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.0 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.0 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.0 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.0 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.0 to about 9.0. In some embodiments of the pharmaceutical composition, wherein the dosage form is an I.V. dosage form, the pH is from about 5.0 to about 8.5. In some embodiments of the pharmaceutical composition, wherein the dosage form is an I.V. dosage form, the pH is from about 5.0 to about 8.0. In some embodiments of the pharmaceutical composition, wherein the dosage form is an I.V. dosage form, the pH is from about 5.0 to about 7.5. In some embodiments of the pharmaceutical composition, wherein the dosage form is an I.V. dosage form, the pH is from about 5.0 to about 7.0. In some embodiments of the pharmaceutical composition, wherein the dosage form is an I.V. dosage form, the pH is from about 5.0 to about 6.5. In some embodiments of the pharmaceutical composition, wherein the dosage form is an I.V. dosage form, the pH is from about 5.0 to about 6.0. In some embodiments of the pharmaceutical composition, wherein the dosage form is an I.V. dosage form, the pH is from about 5.0 to about 5.5.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.5 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.5 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.5 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.5 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 5.5 to about 9.0. In some embodiments of the pharmaceutical composition, wherein the dosage form is an I.V. dosage form, the pH is from about 5.5 to about 8.5. In some embodiments of the pharmaceutical composition, wherein the dosage form is an I.V. dosage form, the pH is from about 5.5 to about 8.0. In some embodiments of the pharmaceutical composition, wherein the dosage form is an I.V. dosage form, the pH is from about 5.5 to about 7.5. In some embodiments of the pharmaceutical composition, wherein the dosage form is an I.V. dosage form, the pH is from about 5.5 to about 7.0. In some embodiments of the pharmaceutical composition, wherein the dosage form is an I.V. dosage form, the pH is from about 5.5 to about 6.5. In some embodiments of the pharmaceutical composition, wherein the dosage form is an I.V. dosage form, the pH is from about 5.5 to about 6.0.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.0 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.0 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.0 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.0 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.0 to about 9.0. In some embodiments of the pharmaceutical composition, wherein the dosage form is an I.V. dosage form, the pH is from about 6.0 to about 8.5. In some embodiments of the pharmaceutical composition, wherein the dosage form is an I.V. dosage form, the pH is from about 6.0 to about 8.0. In some embodiments of the pharmaceutical composition, wherein the dosage form is an I.V. dosage form, the pH is from about 6.0 to about 7.5. In some embodiments of the pharmaceutical composition, wherein the dosage form is an I.V. dosage form, the pH is from about 6.0 to about 7.0. In some embodiments of the pharmaceutical composition, wherein the dosage form is an I.V. dosage form, the pH is from about 6.0 to about 6.5

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.5 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.5 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.5 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.5 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 6.5 to about 9.0. In some embodiments of the pharmaceutical composition, wherein the dosage form is an I.V. dosage form, the pH is from about 6.5 to about 8.5. In some embodiments of the pharmaceutical composition, wherein the dosage form is an I.V. dosage form, the pH is from about 6.5 to about 8.0. In some embodiments of the pharmaceutical composition, wherein the dosage form is an I.V. dosage form, the pH is from about 6.5 to about 7.5. In some embodiments of the pharmaceutical composition, wherein the dosage form is an I.V. dosage form, the pH is from about 6.5 to about 7.0.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.0 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.0 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.0 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.0 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.0 to about 9.0. In some embodiments of the pharmaceutical composition, wherein the dosage form is an I.V. dosage form, the pH is from about 7.0 to about 8.5. In some embodiments of the pharmaceutical composition, wherein the dosage form is an I.V. dosage form, the pH is from about 7.0 to about 8.0. In some embodiments of the pharmaceutical composition, wherein the dosage form is an I.V. dosage form, the pH is from about 7.0 to about 7.5.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.5 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.5 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.5 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.5 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 7.5 to about 9.0. In some embodiments of the pharmaceutical composition, wherein the dosage form is an I.V. dosage form, the pH is from about 7.5 to about 8.5. In some embodiments of the pharmaceutical composition, wherein the dosage form is an I.V. dosage form, the pH is from about 7.5 to about 8.0.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.0 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.0 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.0 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.0 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.0 to about 9.0. In some embodiments of the pharmaceutical composition, wherein the dosage form is an I.V. dosage form, the pH is from about 8.0 to about 8.5.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.5 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.5 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.5 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.5 to about 9.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 8.5 to about 9.0.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 9.0 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 9.0 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 9.0 to about 10.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 9.0 to about 9.5.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 9.5 to about 11.0. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 9.5 to about 10.5. In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 9.5 to about 10.0.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 10.0 to about 11.0. In some embodiments of the pharmaceutical compositions disclosed herein, the dosage form is an I.V. (i.e., infusion) dosage form.

In some embodiments of the pharmaceutical compositions disclosed herein, the dosage form is an I.V. (i.e., infusion) dosage form. In some embodiments of the pharmaceutical composition, wherein the dosage form is an I.V. dosage form, the pH is from about 10.5 to about 11.0.

In some embodiments of the pharmaceutical composition, wherein the dosage form is an I.V. dosage form, the pH is about 2.5. In some embodiments of the pharmaceutical composition, wherein the dosage form is an I.V. dosage form, the pH is about 3.0. In some embodiments of the pharmaceutical composition, wherein the dosage form is an I.V. dosage form, the pH is about 3.5. In some embodiments of the pharmaceutical composition, wherein the dosage form is an I.V. dosage form, the pH is about 4.0. In some embodiments of the pharmaceutical composition, wherein the dosage form is an I.V. dosage form, the pH is about 4.5. In some embodiments of the pharmaceutical composition, wherein the dosage form is an I.V. dosage form, the pH is about 5.0. In some embodiments of the pharmaceutical composition, wherein the dosage form is an I.V. dosage form, the pH is about 5.5. In some embodiments of the pharmaceutical composition, wherein the dosage form is an I.V. dosage form, the pH is about 6.0. In some embodiments of the pharmaceutical composition, wherein the dosage form is an I.V. dosage form, the pH is about 6.1. In some embodiments of the pharmaceutical composition, wherein the dosage form is an I.V. dosage form, the pH is about 6.2. In some embodiments of the pharmaceutical composition, wherein the dosage form is an I.V. dosage form, the pH is about 6.3. In some embodiments of the pharmaceutical composition, wherein the dosage form is an I.V. dosage form, the pH is about 6.4. In some embodiments of the pharmaceutical composition, wherein the dosage form is an I.V. dosage form, the pH is about 6.5. In some embodiments of the pharmaceutical composition, wherein the dosage form is an I.V. dosage form, the pH is about 6.6. In some embodiments of the pharmaceutical composition, wherein the dosage form is an I.V. dosage form, the pH is about 6.6. In some embodiments of the pharmaceutical composition, wherein the dosage form is an I.V. dosage form, the pH is about 6.8. In some embodiments of the pharmaceutical composition, wherein the dosage form is an I.V. dosage form, the pH is about 6.9. In some embodiments of the pharmaceutical composition, wherein the dosage form is an I.V. dosage form, the pH is about 7.0. In some embodiments of the pharmaceutical composition, wherein the dosage form is an I.V. dosage form, the pH is about 7.1. In some embodiments of the pharmaceutical composition, wherein the dosage form is an I.V. dosage form, the pH is about 7.2. In some embodiments of the pharmaceutical composition, wherein the dosage form is an I.V. dosage form, the pH is about 7.3. In some embodiments of the pharmaceutical composition, wherein the dosage form is an I.V. dosage form, the pH is about 7.4. In some embodiments of the pharmaceutical composition, wherein the dosage form is an I.V. dosage form, the pH is about 7.5. In some embodiments of the pharmaceutical composition, wherein the dosage form is an I.V. dosage form, the pH is about 7.6. In some embodiments of the pharmaceutical composition, wherein the dosage form is an I.V. dosage form, the pH is about 7.7. In some embodiments of the pharmaceutical composition, wherein the dosage form is an I.V. dosage form, the pH is about 7.8. In some embodiments of the pharmaceutical composition, wherein the dosage form is an I.V. dosage form, the pH is about 7.9. In some embodiments of the pharmaceutical composition, wherein the dosage form is an I.V. dosage form, the pH is about 8.0. In some embodiments of the pharmaceutical composition, wherein the dosage form is an I.V. dosage form, the pH is about 8.1. In some embodiments of the pharmaceutical composition, wherein the dosage form is an I.V. dosage form, the pH is about 8.2. In some embodiments of the pharmaceutical composition, wherein the dosage form is an I.V. dosage form, the pH is about 8.3. In some embodiments of the pharmaceutical composition, wherein the dosage form is an I.V. dosage form, the pH is about 8.4. In some embodiments of the pharmaceutical composition, wherein the dosage form is an I.V. dosage form, the pH is about 8.5. In some embodiments of the pharmaceutical composition, wherein the dosage form is an I.V. dosage form, the pH is about 8.6. In some embodiments of the pharmaceutical composition, wherein the dosage form is an I.V. dosage form, the pH is about 8.7. In some embodiments of the pharmaceutical composition, wherein the dosage form is an I.V. dosage form, the pH is about 8.8. In some embodiments of the pharmaceutical composition, wherein the dosage form is an I.V. dosage form, the pH is about 8.9. In some embodiments of the pharmaceutical composition, wherein the dosage form is an I.V. dosage form, the pH is about 9.0. In some embodiments of the pharmaceutical composition, wherein the dosage form is an I.V. dosage form, the pH is about 9.1. In some embodiments of the pharmaceutical composition, wherein the dosage form is an I.V. dosage form, the pH is about 9.2. In some embodiments of the pharmaceutical composition, wherein the dosage form is an I.V. dosage form, the pH is about 9.3. In some embodiments of the pharmaceutical composition, wherein the dosage form is an I.V. dosage form, the pH is about 9.4. In some embodiments of the pharmaceutical composition, wherein the dosage form is an I.V. dosage form, the pH is about 9.5. In some embodiments of the pharmaceutical composition, wherein the dosage form is an I.V. dosage form, the pH is about 9.6. In some embodiments of the pharmaceutical composition, wherein the dosage form is an I.V. dosage form, the pH is about 9.9. In some embodiments of the pharmaceutical composition, wherein the dosage form is an I.V. dosage form, the pH is about 9.8. In some embodiments of the pharmaceutical composition, wherein the dosage form is an I.V. dosage form, the pH is about 9.9. In some embodiments of the pharmaceutical composition, wherein the dosage form is an I.V. dosage form, the pH is about 10.0. In some embodiments of the pharmaceutical composition, wherein the dosage form is an I.V. dosage form, the pH is about 10.1. In some embodiments of the pharmaceutical composition, wherein the dosage form is an I.V. dosage form, the pH is about 10.2. In some embodiments of the pharmaceutical composition, wherein the dosage form is an I.V. dosage form, the pH is about 10.3. In some embodiments of the pharmaceutical composition, wherein the dosage form is an I.V. dosage form, the pH is about 10.4. In some embodiments of the pharmaceutical composition, wherein the dosage form is an I.V. dosage form, the pH is about 10.5. In some embodiments of the pharmaceutical composition, wherein the dosage form is an I.V. dosage form, the pH is about 10.6. In some embodiments of the pharmaceutical composition, wherein the dosage form is an I.V. dosage form, the pH is about 10.7. In some embodiments of the pharmaceutical composition, wherein the dosage form is an I.V. dosage form, the pH is about 10.8. In some embodiments of the pharmaceutical composition, wherein the dosage form is an I.V. dosage form, the pH is about 10.9. In some embodiments of the pharmaceutical composition, wherein the dosage form is an I.V. dosage form, the pH is about 11.0.

In some embodiments, the pharmaceutical composition is formulated for administration by IV has a pH of from about 2.5 to about 11.0. In some embodiments, the pharmaceutical composition is formulated for administration by IV has a pH of from about 2.5 to about 5.0 or from about 2.5 to about 5.0. In some embodiments, the pharmaceutical composition is formulated for administration by IV has a pH of from about 2.5 to about 4.5 or from about 7.0 to about 5.0. In some embodiments, the pH of the pharmaceutical composition is formulated for administration by IV is adjusted with hydrochloric acid and/or sodium hydroxide.

In some embodiments, the pharmaceutical composition comprises from about 5 mg/mL to about 250 mg/mL of a compound of Formula (I), or an isotopic variant, tautomer, pharmaceutically acceptable salt, solvate, or hydrate thereof. In some embodiments, the pharmaceutical composition comprises from about 10 mg/mL to about 50 mg/mL of a compound of Formula (I), or an isotopic variant, tautomer, pharmaceutically acceptable salt, solvate, or hydrate thereof.

In some embodiments, the pharmaceutical composition comprises from about 20 mg/mL to about 40 mg/mL of a compound of Formula (I), or an isotopic variant, tautomer, pharmaceutically acceptable salt, solvate, or hydrate thereof. In some embodiments, the pharmaceutical composition comprises about 10 mg/mL, about 15 mg/mL, about 20 mg/mL, about 25 mg/mL, or about 30 mg/mL of a compound of Formula (I), or an isotopic variant, tautomer, pharmaceutically acceptable salt, solvate, or hydrate thereof.

In some embodiments, the pharmaceutical composition is stable for up to about 24 months at a temperature of from about −20° C. to 8° C. In some embodiments, the pharmaceutical composition is stable for a period of from about 12 to about 24 months at a temperature of about −20° C. In some embodiments, the pharmaceutical composition comprises about 20 mg/mL of a compound of Formula (I), or an isotopic variant, tautomer, pharmaceutically acceptable salt, solvate, or hydrate thereof.

In some embodiments, the pharmaceutical composition is stable for up to about 24 months at a temperature of from about −20° C. to 8° C. when stored as a liquid. In some embodiments, the pharmaceutical composition is stable for a period of from about 12 to about 24 months at a temperature of about −20° C. when stored as a liquid. In some embodiments, the pharmaceutical composition is stored in a pH-insensitive container. In some embodiments, the pH-insensitive container is comprised of glass or plastic. In some embodiments, the pharmaceutical composition is stable for up to about 24 months at a temperature of from about −20° C. to 8° C. when stored as a liquid in a pH-insensitive container. In some embodiments, the pharmaceutical composition is stable for a period of from about 12 to about 24 months at a temperature of about −20° C. when stored as a liquid in a pH-insensitive container. In some embodiments, the pharmaceutical composition is stable for up to about 24 months at a temperature of from about −20° C. to 8° C. when stored as a liquid having a pH of from about 2.5 to about 11.0. In some embodiments, the pharmaceutical composition is stable for a period of from about 12 to about 24 months at a temperature of about −20° C. when stored as a liquid having a pH of from about 2.5 to about 11.0. In some embodiments, the pharmaceutical composition is stable for up to about 24 months at a temperature of from about −20° C. to 8° C. when stored as a liquid having a pH of from about 2.5 to about 11.0 in a pH-insensitive container. In some embodiments, the pharmaceutical composition is stable for a period of from about 12 to about 24 months at a temperature of about −20° C. when stored as a liquid having a pH of from about 2.5 to about 11.0 in a pH-insensitive container.

In certain embodiments, in the treatment, prevention, or amelioration of one or more symptoms of the disorders, diseases, or conditions described herein, an appropriate dosage level of a compound of Formula (I), or an isotopic variant; or a pharmaceutically acceptable salt, solvate, hydrate, or prodrug thereof generally is ranging from about 1 to 8,000 mg, from about 10 to about 2,000 mg, from about 100 to about 800 mg, from about 200 to about 600 mg, from about 1000 to about 2000 mg or from about 600 to about 800 mg which can be administered in single or multiple doses. In certain embodiments, the compound of Formula (I), or an isotopic variant; or a pharmaceutically acceptable salt, solvate, hydrate, or prodrug thereof is administered in an amount of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1,000, 1,100, 1,200, 1,300, 1,400, 1,500, 1,600, 1,700, 1,800, 1,900, 2,000 2,500, 3,000, 3,500, 4,000, 4,500, 5,000, 5,500, 6,000, 6,500, 7,000, 7,500, or 8,000 mg. In certain embodiments, the compound of Formula (I), or an isotopic variant; or a pharmaceutically acceptable salt, solvate, hydrate, or prodrug thereof is administered in an amount of about 10 mg, about 2,000 mg, about 600 mg, or about 2,000 mg. In certain embodiments, the compound of Formula (I), or an isotopic variant; or a pharmaceutically acceptable salt, solvate, hydrate, or prodrug thereof is administered in an amount of about 600 mg. In certain embodiments, the compound of Formula (I), or an isotopic variant; or a pharmaceutically acceptable salt, solvate, hydrate, or prodrug thereof is administered in an amount of about 700 mg. In certain embodiments, the compound of Formula (I), or an isotopic variant; or a pharmaceutically acceptable salt, solvate, hydrate, or prodrug thereof is administered in an amount of about 800 mg. In certain embodiments, the compound of Formula (I), or an isotopic variant; or a pharmaceutically acceptable salt, solvate, hydrate, or prodrug thereof is administered in an amount of about 900 mg. In certain embodiments, the compound of Formula (I), or an isotopic variant; or a pharmaceutically acceptable salt, solvate, hydrate, or prodrug thereof is administered in an amount of about 1,000 mg. In certain embodiments, the compound of Formula (I), or an isotopic variant; or a pharmaceutically acceptable salt, solvate, hydrate, or prodrug thereof is administered in an amount of about 2,000 mg. In certain embodiments, the compound of Formula (I), or an isotopic variant; or a pharmaceutically acceptable salt, solvate, hydrate, or prodrug thereof is administered in an amount of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1,000, 1,100, 1,200, 1,300, 1,400, 1,500, 1,600, 1,700, 1,800, 1,900, 2,000 2,500, 3,000, 3,500, 4,000, 4,500, 5,000, 5,500, 6,000, 6,500, 7,000, 7,500, or 8,000 mg/day. In certain embodiments, the compound of Formula (I), or an isotopic variant; or a pharmaceutically acceptable salt, solvate, hydrate, or prodrug thereof is administered in an amount of about 10 mg/day. In certain embodiments, the compound of Formula (I), or an isotopic variant; or a pharmaceutically acceptable salt, solvate, hydrate, or prodrug thereof is administered in an amount of about 15 mg/day. In certain embodiments, the compound of Formula (I), or an isotopic variant; or a pharmaceutically acceptable salt, solvate, hydrate, or prodrug thereof is administered in an amount of about 20 mg/day. In certain embodiments, the compound of Formula (I), or an isotopic variant; or a pharmaceutically acceptable salt, solvate, hydrate, or prodrug thereof is administered in an amount of about 25 mg/day. In certain embodiments, the compound of Formula (I), or an isotopic variant; or a pharmaceutically acceptable salt, solvate, hydrate, or prodrug thereof is administered in an amount of about 30 mg/day. In certain embodiments, the compound of Formula (I), or an isotopic variant; or a pharmaceutically acceptable salt, solvate, hydrate, or prodrug thereof is administered in an amount of about 35 mg/day. In certain embodiments, the compound of Formula (I), or an isotopic variant; or a pharmaceutically acceptable salt, solvate, hydrate, or prodrug thereof is administered in an amount of about 40 mg/day. In certain embodiments, the compound of Formula (I), or an isotopic variant; or a pharmaceutically acceptable salt, solvate, hydrate, or prodrug thereof is administered in an amount of about 45 mg/day. In certain embodiments, the compound of Formula (I), or an isotopic variant; or a pharmaceutically acceptable salt, solvate, hydrate, or prodrug thereof is administered in an amount of about 50 mg/day. In certain embodiments, the compound of Formula (I), or an isotopic variant; or a pharmaceutically acceptable salt, solvate, hydrate, or prodrug thereof is administered in an amount of about 100 mg/day. In certain embodiments, the compound of Formula (I), or an isotopic variant; or a pharmaceutically acceptable salt, solvate, hydrate, or prodrug thereof is administered in an amount of about 150 mg/day. In certain embodiments, the compound of Formula (I), or an isotopic variant; or a pharmaceutically acceptable salt, solvate, hydrate, or prodrug thereof is administered in an amount of about 200 mg/day. In certain embodiments, the compound of Formula (I), or an isotopic variant; or a pharmaceutically acceptable salt, solvate, hydrate, or prodrug thereof is administered in an amount of about 300 mg/day. In certain embodiments, the compound of Formula (I), or an isotopic variant; or a pharmaceutically acceptable salt, solvate, hydrate, or prodrug thereof is administered in an amount of about 400 mg/day. In certain embodiments, the compound of Formula (I), or an isotopic variant; or a pharmaceutically acceptable salt, solvate, hydrate, or prodrug thereof is administered in an amount of about 500 mg/day. In certain embodiments, the compound of Formula (I), or an isotopic variant; or a pharmaceutically acceptable salt, solvate, hydrate, or prodrug thereof is administered in an amount of about 600 mg/day. In certain embodiments, the compound of Formula (I), or an isotopic variant; or a pharmaceutically acceptable salt, solvate, hydrate, or prodrug thereof is administered in an amount of about 700 mg/day. In certain embodiments, the compound of Formula (I), or an isotopic variant; or a pharmaceutically acceptable salt, solvate, hydrate, or prodrug thereof is administered in an amount of about 800 mg/day. In certain embodiments, the compound of Formula (I), or an isotopic variant; or a pharmaceutically acceptable salt, solvate, hydrate, or prodrug thereof is administered in an amount of about 900 mg/day. In certain embodiments, the compound of Formula (I), or an isotopic variant; or a pharmaceutically acceptable salt, solvate, hydrate, or prodrug thereof is administered in an amount of about 1,000 mg/day. In certain embodiments, the compound of Formula (I), or an isotopic variant; or a pharmaceutically acceptable salt, solvate, hydrate, or prodrug thereof is administered in an amount of about 2,000 mg/day.

For oral administration, the pharmaceutical compositions provided herein can be formulated in a solid dosage form containing from about 1.0 to about 1,500 mg or about 1.0 to about 1,000 mg of a compound of Formula (I), or an isotopic variant; or a pharmaceutically acceptable salt, solvate, hydrate, or prodrug thereof, in one embodiment, about 1, about 5, about 10, about 15, about 20, about 25, about 50, about 75, about 100, about 150, about 200, about 250, about 300, about 350, about 400, about 450, about 500, about 600, about 700, about 800, about 900, and about 1,000 mg of the a compound of Formula (I), or an isotopic variant; or a pharmaceutically acceptable salt, solvate, hydrate, or prodrug thereof for the symptomatic adjustment of the dosage to the patient to be treated.

For oral administration, the pharmaceutical compositions provided herein can be formulated in a solid dosage form containing about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1,000, 1,100, 1,200, 1,300, 1,400, or 1,500 of a compound of Formula (I), or an isotopic variant; or a pharmaceutically acceptable salt, solvate, hydrate, or prodrug thereof. In some embodiments, the solid dosage form is a tablet. In some embodiments, the solid dosage form is a capsule. In some embodiments, the solid dosage form is a powder. In some embodiments, the solid dosage form is a granulate.

In some embodiments, the pharmaceutical compositions provided herein can be formulated in a solid dosage form containing about 50 mg of a compound of Formula (I), or an isotopic variant; or a pharmaceutically acceptable salt, solvate, hydrate, or prodrug thereof. In some embodiments, the pharmaceutical compositions provided herein can be formulated in a solid dosage form containing about 100 mg of a compound of Formula (I), or an isotopic variant; or a pharmaceutically acceptable salt, solvate, hydrate, or prodrug thereof. In some embodiments, the pharmaceutical compositions provided herein can be formulated in a solid dosage form containing about 150 mg of a compound of Formula (I), or an isotopic variant; or a pharmaceutically acceptable salt, solvate, hydrate, or prodrug thereof. In some embodiments, the pharmaceutical compositions provided herein can be formulated in a solid dosage form containing about 200 mg of a compound of Formula (I), or an isotopic variant; or a pharmaceutically acceptable salt, solvate, hydrate, or prodrug thereof. In some embodiments, the pharmaceutical compositions provided herein can be formulated in a solid dosage form containing about 250 mg of a compound of Formula (I), or an isotopic variant; or a pharmaceutically acceptable salt, solvate, hydrate, or prodrug thereof. In some embodiments, the pharmaceutical compositions provided herein can be formulated in a solid dosage form containing about 300 mg of a compound of Formula (I), or an isotopic variant; or a pharmaceutically acceptable salt, solvate, hydrate, or prodrug thereof. In some embodiments, the pharmaceutical compositions provided herein can be formulated in a solid dosage form containing about 400 mg of a compound of Formula (I), or an isotopic variant; or a pharmaceutically acceptable salt, solvate, hydrate, or prodrug thereof.

For oral administration, the pharmaceutical compositions provided herein can be formulated in the form of tablets containing from about 1.0 to about 1,500 mg orabout 1.0 to about 1,000 mg of a compound of Formula (I), or an isotopic variant; or a pharmaceutically acceptable salt, solvate, hydrate, or prodrug thereof, in one embodiment, about 1, about 5, about 10, about 15, about 20, about 25, about 50, about 75, about 100, about 150, about 200, about 250, about 300, about 350, about 400, about 450, about 500, about 600, about 700, about 800, about 900, and about 1,000 mg of the a compound of Formula (I), or an isotopic variant; or a pharmaceutically acceptable salt, solvate, hydrate, or prodrug thereof for the symptomatic adjustment of the dosage to the patient to be treated.

For oral administration, the pharmaceutical compositions provided herein can be formulated in the form of tablets containing about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1,000, 1,100, 1,200, 1,300, 1,400, or 1,500 of a compound of Formula (I), or an isotopic variant; or a pharmaceutically acceptable salt, solvate, hydrate, or prodrug thereof.

In some embodiments, the pharmaceutical compositions provided herein can be formulated in the form of tablets containing about 50 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 100 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 150 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 200 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 250 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 300 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 400 mg of a compound of Formula (I), or an isotopic variant; or a pharmaceutically acceptable salt, solvate, hydrate, or prodrug thereof.

For oral administration, the pharmaceutical compositions provided herein can be formulated in the form of a liquid (e.g., a solution, suspension, or syrup) containing from about 1.0 to about 1,500 mg or about 1.0 to about 1,000 mg of a compound of Formula (I), or an isotopic variant; or a pharmaceutically acceptable salt, solvate, hydrate, or prodrug thereof, in one embodiment, about 1, about 5, about 10, about 15, about 20, about 25, about 50, about 75, about 100, about 150, about 200, about 250, about 300, about 350, about 400, about 450, about 500, about 600, about 700, about 800, about 900, and about 1,000 mg of the a compound of Formula (I), or an isotopic variant; or a pharmaceutically acceptable salt, solvate, hydrate, or prodrug thereof for the symptomatic adjustment of the dosage to the patient to be treated.

For oral administration, the pharmaceutical compositions provided herein can be formulated in the form of a liquid (e.g., a solution, suspension, or syrup) containing about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1,000, 1,100, 1,200, 1,300, 1,400, or 1,500 of a compound of Formula (I), or an isotopic variant; or a pharmaceutically acceptable salt, solvate, hydrate, or prodrug thereof.

In some embodiments, the pharmaceutical compositions provided herein can be formulated in the form of a liquid (e.g., a solution, suspension, or syrup) containing about 50 mg of a compound of Formula (I), or an isotopic variant; or a pharmaceutically acceptable salt, solvate, hydrate, or prodrug thereof. In some embodiments, the pharmaceutical compositions provided herein can be formulated in the form of a liquid (e.g., a solution, suspension, or syrup) containing about 100 mg of a compound of Formula (I), or an isotopic variant; or a pharmaceutically acceptable salt, solvate, hydrate, or prodrug thereof. In some embodiments, the pharmaceutical compositions provided herein can be formulated in the form of a liquid (e.g., a solution, suspension, or syrup) containing about 150 mg of a compound of Formula (I), or an isotopic variant; or a pharmaceutically acceptable salt, solvate, hydrate, or prodrug thereof. In some embodiments, the pharmaceutical compositions provided herein can be formulated in the form of a liquid (e.g., a solution, suspension, or syrup) containing about 200 mg of a compound of Formula (I), or an isotopic variant; or a pharmaceutically acceptable salt, solvate, hydrate, or prodrug thereof. In some embodiments, the pharmaceutical compositions provided herein can be formulated in the form of a liquid (e.g., a solution, suspension, or syrup) containing about 250 mg of a compound of Formula (I), or an isotopic variant; or a pharmaceutically acceptable salt, solvate, hydrate, or prodrug thereof. In some embodiments, the pharmaceutical compositions provided herein can be formulated in the form of a liquid (e.g., a solution, suspension, or syrup) containing about 300 mg of a compound of Formula (I), or an isotopic variant; or a pharmaceutically acceptable salt, solvate, hydrate, or prodrug thereof. In some embodiments, the pharmaceutical compositions provided herein can be formulated in the form of a liquid (e.g., a solution, suspension, or syrup) containing about 400 mg of a compound of Formula (I), or an isotopic variant; or a pharmaceutically acceptable salt, solvate, hydrate, or prodrug thereof.

In some embodiments, the pharmaceutical compositions provided herein can be formulated in a liquid (e.g., IV) dosage form containing from about 1.0 to about 1,500 mg or about 1.0 to about 1,000 mg of a compound of Formula (I), or an isotopic variant; or a pharmaceutically acceptable salt, solvate, hydrate, or prodrug thereof, in one embodiment, about 1, about 5, about 10, about 15, about 20, about 25, about 50, about 75, about 100, about 150, about 200, about 250, about 300, about 350, about 400, about 450, about 500, about 600, about 700, about 800, about 900, and about 1,000 mg of the a compound of Formula (I), or an isotopic variant; or a pharmaceutically acceptable salt, solvate, hydrate, or prodrug thereof for the symptomatic adjustment of the dosage to the patient to be treated.

For oral administration, the pharmaceutical compositions provided herein can be formulated in a liquid (e.g., IV) dosage form containing about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1,000, 1,100, 1,200, 1,300, 1,400, or 1,500 of a compound of Formula (I), or an isotopic variant; or a pharmaceutically acceptable salt, solvate, hydrate, or prodrug thereof.

In some embodiments, the pharmaceutical compositions provided herein can be formulated in a liquid (e.g., IV) dosage form containing about 50 mg of a compound of Formula (I), or an isotopic variant; or a pharmaceutically acceptable salt, solvate, hydrate, or prodrug thereof. In some embodiments, the pharmaceutical compositions provided herein can be formulated in a liquid (e.g., IV) dosage form containing about 100 mg of a compound of Formula (I), or an isotopic variant; or a pharmaceutically acceptable salt, solvate, hydrate, or prodrug thereof. In some embodiments, the pharmaceutical compositions provided herein can be formulated in a liquid (e.g., IV) dosage form containing about 150 mg of a compound of Formula (I), or an isotopic variant; or a pharmaceutically acceptable salt, solvate, hydrate, or prodrug thereof. In some embodiments, the pharmaceutical compositions provided herein can be formulated in a liquid (e.g., IV) dosage form containing about 200 mg of a compound of Formula (I), or an isotopic variant; or a pharmaceutically acceptable salt, solvate, hydrate, or prodrug thereof. In some embodiments, the pharmaceutical compositions provided herein can be formulated in a liquid (e.g., IV) dosage form containing about 250 mg of a compound of Formula (I), or an isotopic variant; or a pharmaceutically acceptable salt, solvate, hydrate, or prodrug thereof. In some embodiments, the pharmaceutical compositions provided herein can be formulated in a liquid (e.g., IV) dosage form containing about 300 mg of a compound of Formula (I), or an isotopic variant; or a pharmaceutically acceptable salt, solvate, hydrate, or prodrug thereof. In some embodiments, the pharmaceutical compositions provided herein can be formulated in a liquid (e.g., IV) dosage form containing about 400 mg of a compound of Formula (I), or an isotopic variant; or a pharmaceutically acceptable salt, solvate, hydrate, or prodrug thereof.

The pharmaceutical compositions can be administered on a regimen of 1 to 4 times per day, including once, twice, three times, and four times per day. In certain embodiments, a compound of Formula (I), or an isotopic variant; or a pharmaceutically acceptable salt, solvate, hydrate, or prodrug thereof is administered to a patient in need thereof in an amount of about 1,000 mg twice daily for one day followed by 600 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for one day followed by 800 mg once daily for the duration of treatment.

In other embodiments, a compound of Formula (I), or an isotopic variant; or a pharmaceutically acceptable salt, solvate, hydrate, or prodrug thereof is administered to a patient in need thereof in an amount of about 1,000 mg twice daily for one day followed by 900 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for one day followed by 1000 mg once daily for the duration of treatment.

In certain embodiments, a compound of Formula (I), or an isotopic variant; or a pharmaceutically acceptable salt, solvate, hydrate, or prodrug thereof is administered to a patient in need thereof in an amount of about 1,000 mg twice daily for two days followed by 600 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for two days followed by 800 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for two days followed by 900 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for two days followed by 1000 mg once daily for the duration of treatment.

In certain embodiments, a compound of Formula (I), or an isotopic variant; or a pharmaceutically acceptable salt, solvate, hydrate, or prodrug thereof is administered to a patient in need thereof in an amount of about 1,000 mg twice daily for three days followed by 600 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for three days followed by 800 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for three days followed by 900 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for three days followed by 1000 mg once daily for the duration of treatment.

In certain embodiments, a compound of Formula (I), or an isotopic variant; or a pharmaceutically acceptable salt, solvate, hydrate, or prodrug thereof is administered to a patient in need thereof in an amount of about 1,000 mg twice daily for four days followed by 600 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for four days followed by 800 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for four days followed by 900 mg once daily for the duration of treatment. In other embodiments, a compound of Formula (I), or an isotopic variant; or a pharmaceutically acceptable salt, solvate, hydrate, or prodrug thereof is administered to a patient in need thereof in an amount of about 1,000 mg twice daily for four days followed by 1000 mg once daily for the duration of treatment.

In certain embodiments, a compound of Formula (I), or an isotopic variant; or a pharmaceutically acceptable salt, solvate, hydrate, or prodrug thereof is administered to a patient in need thereof in an amount of about 1,000 mg once daily. In certain embodiments, a compound of Formula (I), or an isotopic variant; or a pharmaceutically acceptable salt, solvate, hydrate, or prodrug thereof is administered to a patient in need thereof in an amount of from about 40 mg to about 145 mg, about 40 to about 1,000, about 600 to about 1,000, or about 600 mg to about 2,000 mg daily until disease remission, recovery, or intolerable toxicity.

In another aspect, there is provided a combination composition, comprising:

(i) the compound of Formula (I); or an isotopic variant, tautomer, pharmaceutically acceptable salt, solvate, or hydrate thereof; and (ii) at least one an antifungal agent.

In some embodiments, the at least one antifungal agent is an azole, an echinocandin, amphotericin B deoxycholate, amphotericin B cochleate, 5-fluorocytosine, terbinafine, griseofulvin, VL-2397, ibrexafungerp, orotomide F901318, or combinations thereof. In some embodiments, the azole is ketoconazole, fluconazole, posaconazole, itraconazole, voriconazole, isavuconazole, or miconazole. In some embodiments, the echinocandin is caspofungin, anidulafungin, micafungin, or rezafungin. In an aspect, provided herein is a combination composition, comprising:

(i) a compound of Formula (I):

(I)

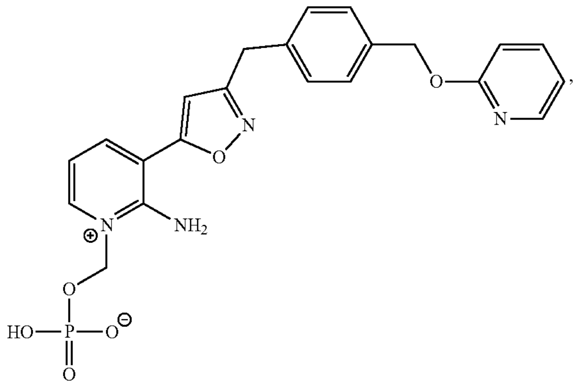, or an isotopic variant, tautomer, pharmaceutically acceptable salt, solvate, or hydrate thereof; and (ii) a compound of Formula (II)

(II)

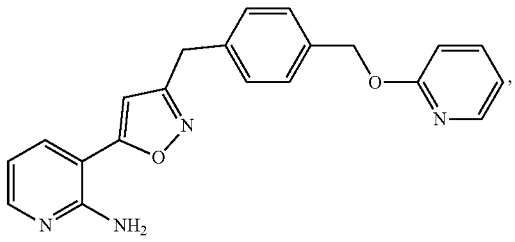, or an isotopic variant, tautomer, pharmaceutically acceptable salt, solvate, or hydrate thereof.

In some embodiments, the combination composition further comprises at least one pharmaceutically acceptable excipient.

In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are both crystalline.

In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 10:1. In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 9:1 to about 9.99:0.01. In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 9.5:0.5 to about 9.9:0.1. In some embodiments, the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of about 9:1, about 9.1:0.9, about 9.2:0.8, about 9.3:0.7, about 9.4:0.6, about 9.5:0.5, about 9.6:0.4, about 9.7:0.3, about 9.8:0.2, or about 9.9:0.1.

In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is from about 100:0.01 to about 0.01:100. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 100:0.01. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 100:0.1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 100:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 100:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 80:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 70:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 60:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 50:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 40:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 30:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 10:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 9:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 8:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 7:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 6:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 5:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 4:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 3:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 2:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1.5:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:1. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:1.5. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:2. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:3. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:4. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:5. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:6. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:7. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:8. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:9. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:10. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:20. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:30. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:40. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:50. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:60. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:70. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:80. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:90. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 1:100. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 0.1:100. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is about 0.01:100.

In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is at least about 100:0.01, 100:0.1, 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1.5:1, 1:1, 1:1.5, 1:2, 1:3, 1:4, 1:5, 1:6, 1:7, 1:8, 1:9, 1:10, 1:20, 1:30, 1:40, 1:50, 1:60, 1:70, 1:80, 1:90 1:100, 0.1:100, or about 0.01:100. In certain embodiments, the ratio of the compound of Formula (I), or an isotopic variant, tautomer, pharmaceutically acceptable salt, solvate, or hydrate thereof, to the ratio of the compound of Formula (II), or an isotopic variant, tautomer, pharmaceutically acceptable salt, solvate, or hydrate thereof, in the pharmaceutical composition is up to about 100:0.01, 100:0.1, 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1.5:1, 1:1, 1:1.5, 1:2, 1:3, 1:4, 1:5, 1:6, 1:7, 1:8, 1:9, 1:10, 1:20, 1:30, 1:40, 1:50, 1:60, 1:70, 1:80, 1:90 1:100, 0.1:100, or about 0.01:100.

In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is from about 10:0.1 to about 0.1:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.2. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.3. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.4. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.5. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.6. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.7. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.8. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:0.9. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 10:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 9:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 8:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 7:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 6:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 5:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 4:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 3:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 2:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1.5:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:1. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:1.5. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:2. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:2. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:3. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:4. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:5. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:6. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:7. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:8. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:9. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 1:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.9:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.8:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.7:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.6:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.5:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.4:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.3:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.2:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.1:10. In certain embodiments, the ratio of the compound of Formula (I) or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is about 0.01:10.

In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is at least about 10:0.1, 10:0.2, 10:0.3, 10:0.4, 10:0.5, 10:0.6, 10:0.7, 10:0.8, 10:0.9, 10:1, 9:1, 8:1, 7:1, 6:1, 5:1, 4:1, 3:1, 2:1, 1.5:1, 1:1, 1:1.5, 1:2, 1:3, 1:4, 1:5, 1:6, 1:7, 1:8, 1:9, 1:10, 0.9:10, 0.8:10, 0.8:10, 0.7:10, 0.6:10, 0.5:10, 0.4:10, 0.3:10, 0.2:10, or about 0.1:10. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is up to about 10:0.1, 10:0.2, 10:0.3, 10:0.4, 10:0.5, 10:0.6, 10:0.7, 10:0.8, 10:0.9, 10:1, 9:1, 8:1, 7:1, 6:1, 5:1, 4:1, 3:1, 2:1, 1.5:1, 1:1, 1:1.5, 1:2, 1:3, 1:4, 1:5, 1:6, 1:7, 1:8, 1:9, 1:10, 0.9:10, 0.8:10, 0.8:10, 0.7:10, 0.6:10, 0.5:10, 0.4:10, 0.3:10, 0.2:10, or about 0.1:10.

In certain embodiments, the ratio of the compound of Formula (I), or an isotopic variant, tautomer, pharmaceutically acceptable salt, solvate, or hydrate thereof to the ratio of the compound of Formula (II) or an isotopic variant, tautomer, pharmaceutically acceptable salt, solvate, or hydrate thereof in the pharmaceutical composition is from about 5:1 to about 1:5. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 5:1. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 4:1. In certain embodiments, the ratio of the compound of Formula (I) or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 3:1. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 2:1. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 1.5:1. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 1:1. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 1:1.5. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 1:2. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 1:3. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 1:4. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is about 1:5.

In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is at least about 5:1, 4:1, 3:1, 2:1, 1.5:1, 1:1, 1:1.5, 1:2, 1:3, 1:4, or about 1:5. In certain embodiments, the ratio of the compound of Formula (I), or an isotopic variant, tautomer, pharmaceutically acceptable salt, solvate, or hydrate thereof to the ratio of the compound of Formula (II), or an isotopic variant, tautomer, pharmaceutically acceptable salt, solvate, or hydrate thereof in the pharmaceutical composition is up to about 5:1, 4:1, 3:1, 2:1, 1.5:1, 1:1, 1:1.5, 1:2, 1:3, 1:4, or about 1:5.

In some embodiments of the pharmaceutical compositions disclosed herein, the compound of Formula (I), or an isotopic variant, tautomer, pharmaceutically acceptable salt, solvate, or hydrate thereof, is substantially pure. In some embodiments of the pharmaceutical compositions disclosed herein, the compound of Formula (I), or an isotopic variant, tautomer, pharmaceutically acceptable salt, solvate, or hydrate thereof, is substantially free of impurities. In some embodiments of the pharmaceutical compositions disclosed herein, substantially free of impurities is defined as less than about 10.0% (w/w) content of impurities. In some embodiments of the pharmaceutical compositions disclosed herein, substantially free of impurities is defined as less than about 9.0% (w/w) content of impurities. In some embodiments of the pharmaceutical compositions disclosed herein, substantially free of impurities is defined as less than about 8.0% (w/w) content of impurities. In some embodiments of the pharmaceutical compositions disclosed herein, substantially free of impurities is defined as less than about 7.0% (w/w) content of impurities. In some embodiments of the pharmaceutical compositions disclosed herein, substantially free of impurities is defined as less than about 6.0% (w/w) content of impurities. In some embodiments of the pharmaceutical compositions disclosed herein, substantially free of impurities is defined as less than about 5.0% content of impurities. In some embodiments of the pharmaceutical compositions disclosed herein, substantially free of impurities is defined as less than about 4.0% (w/w) content of impurities. In some embodiments of the pharmaceutical compositions disclosed herein, substantially free of impurities is defined as less than about 3.9% (w/w) content of impurities. In some embodiments of the pharmaceutical compositions disclosed herein, substantially free of impurities is defined as less than about 3.8% (w/w) content of impurities. In some embodiments of the pharmaceutical compositions disclosed herein, substantially free of impurities is defined as less than about 3.7% (w/w) content of impurities. In some embodiments of the pharmaceutical compositions disclosed herein, substantially free of impurities is defined as less than about 3.6% (w/w) content of impurities. In some embodiments of the pharmaceutical compositions disclosed herein, substantially free of impurities is defined as less than about 3.5% (w/w) content of impurities. In some embodiments of the pharmaceutical compositions disclosed herein, substantially free of impurities is defined as less than about 3.4% (w/w) content of impurities. In some embodiments of the pharmaceutical compositions disclosed herein, substantially free of impurities is defined as less than about 3.3% (w/w) content of impurities. In some embodiments of the pharmaceutical compositions disclosed herein, substantially free of impurities is defined as less than about 3.2% (w/w) content of impurities. In some embodiments of the pharmaceutical compositions disclosed herein, substantially free of impurities is defined as less than about 3.1% (w/w) content of impurities. In some embodiments of the pharmaceutical compositions disclosed herein, substantially free of impurities is defined as less than about 3.0% (w/w) content of impurities. In some embodiments of the pharmaceutical compositions disclosed herein, substantially free of impurities is defined as less than about 2.9% (w/w) content of impurities. In some embodiments of the pharmaceutical compositions disclosed herein, substantially free of impurities is defined as less than about 2.8% (w/w) content of impurities. In some embodiments of the pharmaceutical compositions disclosed herein, substantially free of impurities is defined as less than about 2.7% (w/w) content of impurities. In some embodiments of the pharmaceutical compositions disclosed herein, substantially free of impurities is defined as less than about 2.6% (w/w) content of impurities. In some embodiments of the pharmaceutical compositions disclosed herein, substantially free of impurities is defined as less than about 2.5% (w/w) content of impurities. In some embodiments of the pharmaceutical compositions disclosed herein, substantially free of impurities is defined as less than about 2.4% (w/w) content of impurities. In some embodiments of the pharmaceutical compositions disclosed herein, substantially free of impurities is defined as less than about 2.3% (w/w) content of impurities. In some embodiments of the pharmaceutical compositions disclosed herein, substantially free of impurities is defined as less than about 2.2% (w/w) content of impurities. In some embodiments of the pharmaceutical compositions disclosed herein, substantially free of impurities is defined as less than about 2.1% (w/w) content of impurities. In some embodiments of the pharmaceutical compositions disclosed herein, substantially free of impurities is defined as less than about 2.0% (w/w) content of impurities. In some embodiments of the pharmaceutical compositions disclosed herein, substantially free of impurities is defined as less than about 1.9% (w/w) content of impurities. In some embodiments of the pharmaceutical compositions disclosed herein, substantially free of impurities is defined as less than about 1.8% (w/w) content of impurities. In some embodiments of the pharmaceutical compositions disclosed herein, substantially free of impurities is defined as less than about 1.7% (w/w) content of impurities. In some embodiments of the pharmaceutical compositions disclosed herein, substantially free of impurities is defined as less than about 1.6% (w/w) content of impurities. In some embodiments of the pharmaceutical compositions disclosed herein, substantially free of impurities is defined as less than about 1.5% (w/w) content of impurities. In some embodiments of the pharmaceutical compositions disclosed herein, substantially free of impurities is defined as less than about 1.4% (w/w) content of impurities. In some embodiments of the pharmaceutical compositions disclosed herein, substantially free of impurities is defined as less than about 1.3% (w/w) content of impurities. In some embodiments of the pharmaceutical compositions disclosed herein, substantially free of impurities is defined as less than about 1.2% (w/w) content of impurities. In some embodiments of the pharmaceutical compositions disclosed herein, substantially free of impurities is defined as less than about 1.1% (w/w) content of impurities. In some embodiments of the pharmaceutical compositions disclosed herein, substantially free of impurities is defined as less than about 1.0% (w/w) content of impurities. In some embodiments of the pharmaceutical compositions disclosed herein, substantially free of impurities is defined as less than about 0.9% (w/w) content of impurities. In some embodiments of the pharmaceutical compositions disclosed herein, substantially free of impurities is defined as less than about 0.8% (w/w) content of impurities. In some embodiments of the pharmaceutical compositions disclosed herein, substantially free of impurities is defined as less than about 0.7% (w/w) content of impurities. In some embodiments of the pharmaceutical compositions disclosed herein, substantially free of impurities is defined as less than about 0.6% (w/w) content of impurities. In some embodiments of the pharmaceutical compositions disclosed herein, substantially free of impurities is defined as less than about 0.5% (w/w) content of impurities. In some embodiments of the pharmaceutical compositions disclosed herein, substantially free of impurities is defined as less than about 0.4% (w/w) content of impurities. In some embodiments of the pharmaceutical compositions disclosed herein, substantially free of impurities is defined as less than about 0.3% (w/w) content of impurities. In some embodiments of the pharmaceutical compositions disclosed herein, substantially free of impurities is defined as less than about 0.2% (w/w) content of impurities. In some embodiments of the pharmaceutical compositions disclosed herein, substantially free of impurities is defined as less than about 0.1% content of impurities. In some embodiments of the pharmaceutical compositions disclosed herein, substantially free of impurities is defined as less than about 0.05% (w/w) content of impurities.

In some embodiments of the pharmaceutical compositions disclosed herein, the compound of Formula (I), or an isotopic variant, tautomer, pharmaceutically acceptable salt, solvate, or hydrate thereof, is substantially free of impurities. In some embodiments of the pharmaceutical compositions disclosed herein, substantially free of impurities is defined as up to about 10.0% (w/w) content of impurities. In some embodiments of the pharmaceutical compositions disclosed herein, substantially free of impurities is defined as up to about 9.0% (w/w) content of impurities. In some embodiments of the pharmaceutical compositions disclosed herein, substantially free of impurities is defined as up to about 8.0% (w/w) content of impurities. In some embodiments of the pharmaceutical compositions disclosed herein, substantially free of impurities is defined as up to about 7.0% (w/w) content of impurities. In some embodiments of the pharmaceutical compositions disclosed herein, substantially free of impurities is defined as up to about 6.0% (w/w) content of impurities. In some embodiments of the pharmaceutical compositions disclosed herein, substantially free of impurities is defined as up to about 5.0% content of impurities. In some embodiments of the pharmaceutical compositions disclosed herein, substantially free of impurities is defined as up to about 4.0% (w/w) content of impurities. In some embodiments of the pharmaceutical compositions disclosed herein, substantially free of impurities is defined as up to about 3.9% (w/w) content of impurities. In some embodiments of the pharmaceutical compositions disclosed herein, substantially free of impurities is defined as up to about 3.8% (w/w) content of impurities. In some embodiments of the pharmaceutical compositions disclosed herein, substantially free of impurities is defined as up to about 3.7% (w/w) content of impurities. In some embodiments of the pharmaceutical compositions disclosed herein, substantially free of impurities is defined as up to about 3.6% (w/w) content of impurities. In some embodiments of the pharmaceutical compositions disclosed herein, substantially free of impurities is defined as up to about 3.5% (w/w) content of impurities. In some embodiments of the pharmaceutical compositions disclosed herein, substantially free of impurities is defined as up to about 3.4% (w/w) content of impurities. In some embodiments of the pharmaceutical compositions disclosed herein, substantially free of impurities is defined as up to about 3.3% (w/w) content of impurities. In some embodiments of the pharmaceutical compositions disclosed herein, substantially free of impurities is defined as up to about 3.2% (w/w) content of impurities. In some embodiments of the pharmaceutical compositions disclosed herein, substantially free of impurities is defined as up to about 3.1% (w/w) content of impurities. In some embodiments of the pharmaceutical compositions disclosed herein, substantially free of impurities is defined as up to about 3.0% (w/w) content of impurities. In some embodiments of the pharmaceutical compositions disclosed herein, substantially free of impurities is defined as up to about 2.9% (w/w) content of impurities. In some embodiments of the pharmaceutical compositions disclosed herein, substantially free of impurities is defined as up to about 2.8% (w/w) content of impurities. In some embodiments of the pharmaceutical compositions disclosed herein, substantially free of impurities is defined as up to about 2.7% (w/w) content of impurities. In some embodiments of the pharmaceutical compositions disclosed herein, substantially free of impurities is defined as up to about 2.6% (w/w) content of impurities. In some embodiments of the pharmaceutical compositions disclosed herein, substantially free of impurities is defined as up to about 2.5% (w/w) content of impurities. In some embodiments of the pharmaceutical compositions disclosed herein, substantially free of impurities is defined as up to about 2.4% (w/w) content of impurities. In some embodiments of the pharmaceutical compositions disclosed herein, substantially free of impurities is defined as up to about 2.3% (w/w) content of impurities. In some embodiments of the pharmaceutical compositions disclosed herein, substantially free of impurities is defined as up to about 2.2% (w/w) content of impurities. In some embodiments of the pharmaceutical compositions disclosed herein, substantially free of impurities is defined as up to about 2.1% (w/w) content of impurities. In some embodiments of the pharmaceutical compositions disclosed herein, substantially free of impurities is defined as up to about 2.0% (w/w) content of impurities. In some embodiments of the pharmaceutical compositions disclosed herein, substantially free of impurities is defined as up to about 1.9% (w/w) content of impurities. In some embodiments of the pharmaceutical compositions disclosed herein, substantially free of impurities is defined as up to about 1.8% (w/w) content of impurities. In some embodiments of the pharmaceutical compositions disclosed herein, substantially free of impurities is defined as up to about 1.7% (w/w) content of impurities. In some embodiments of the pharmaceutical compositions disclosed herein, substantially free of impurities is defined as up to about 1.6% (w/w) content of impurities. In some embodiments of the pharmaceutical compositions disclosed herein, substantially free of impurities is defined as up to about 1.5% (w/w) content of impurities. In some embodiments of the pharmaceutical compositions disclosed herein, substantially free of impurities is defined as up to about 1.4% (w/w) content of impurities. In some embodiments of the pharmaceutical compositions disclosed herein, substantially free of impurities is defined as up to about 1.3% (w/w) content of impurities. In some embodiments of the pharmaceutical compositions disclosed herein, substantially free of impurities is defined as up to about 1.2% (w/w) content of impurities. In some embodiments of the pharmaceutical compositions disclosed herein, substantially free of impurities is defined as up to about 1.1% (w/w) content of impurities. In some embodiments of the pharmaceutical compositions disclosed herein, substantially free of impurities is defined as up to about 1.0% (w/w) content of impurities. In some embodiments of the pharmaceutical compositions disclosed herein, substantially free of impurities is defined as up to about 0.9% (w/w) content of impurities. In some embodiments of the pharmaceutical compositions disclosed herein, substantially free of impurities is defined as up to about 0.8% (w/w) content of impurities. In some embodiments of the pharmaceutical compositions disclosed herein, substantially free of impurities is defined as up to about 0.7% (w/w) content of impurities. In some embodiments of the pharmaceutical compositions disclosed herein, substantially free of impurities is defined as up to about 0.6% (w/w) content of impurities. In some embodiments of the pharmaceutical compositions disclosed herein, substantially free of impurities is defined as up to about 0.5% (w/w) content of impurities. In some embodiments of the pharmaceutical compositions disclosed herein, substantially free of impurities is defined as up to about 0.4% (w/w) content of impurities. In some embodiments of the pharmaceutical compositions disclosed herein, substantially free of impurities is defined as up to about 0.3% (w/w) content of impurities. In some embodiments of the pharmaceutical compositions disclosed herein, substantially free of impurities is defined as up to about 0.2% (w/w) content of impurities. In some embodiments of the pharmaceutical compositions disclosed herein, substantially free of impurities is defined as up to about 0.1% content of impurities. In some embodiments of the pharmaceutical compositions disclosed herein, substantially free of impurities is defined as up to about 0.05% (w/w) content of impurities.

In some embodiments of the pharmaceutical compositions disclosed herein, the pharmaceutical composition is at least about 90% pure. In some embodiments of the pharmaceutical compositions disclosed herein, the pharmaceutical composition is at least about 91% pure. In some embodiments of the pharmaceutical compositions disclosed herein, the pharmaceutical composition is at least about 92% pure. In some embodiments of the pharmaceutical compositions disclosed herein, the pharmaceutical composition is at least about 93% pure. In some embodiments of the pharmaceutical compositions disclosed herein, the pharmaceutical composition is at least about 94% pure. In some embodiments of the pharmaceutical compositions disclosed herein, the pharmaceutical composition is at least about 95% pure. In some embodiments of the pharmaceutical compositions disclosed herein, the pharmaceutical composition is at least about 96% pure. In some embodiments of the pharmaceutical compositions disclosed herein, the pharmaceutical composition is at least about 97% pure. In some embodiments of the pharmaceutical compositions disclosed herein, the pharmaceutical composition is at least about 98% pure. In some embodiments of the pharmaceutical compositions disclosed herein, the pharmaceutical composition is at least about 99% pure. In some embodiments of the pharmaceutical compositions disclosed herein, the pharmaceutical composition is at least about 99.1%, about 99.2%, about 99.3%, about 99.4%, about 99.5%, about 99.6%, about 99.7%, about 99.8%, about 99.9%, or about 100% pure.

In some embodiments of the pharmaceutical compositions disclosed herein, the pharmaceutical composition is up to about 90% pure. In some embodiments of the pharmaceutical compositions disclosed herein, the pharmaceutical composition is up to about 91% pure. In some embodiments of the pharmaceutical compositions disclosed herein, the pharmaceutical composition is up to about 92% pure. In some embodiments of the pharmaceutical compositions disclosed herein, the pharmaceutical composition is up to about 93% pure. In some embodiments of the pharmaceutical compositions disclosed herein, the pharmaceutical composition is up to about 94% pure. In some embodiments of the pharmaceutical compositions disclosed herein, the pharmaceutical composition is up to about 95% pure. In some embodiments of the pharmaceutical compositions disclosed herein, the pharmaceutical composition is up to about 96% pure. In some embodiments of the pharmaceutical compositions disclosed herein, the pharmaceutical composition is up to about 97% pure. In some embodiments of the pharmaceutical compositions disclosed herein, the pharmaceutical composition is up to about 98% pure. In some embodiments of the pharmaceutical compositions disclosed herein, the pharmaceutical composition is up to about 99% pure. In some embodiments of the pharmaceutical compositions disclosed herein, the pharmaceutical composition is up to about 99.1%, about 99.2%, about 99.3%, about 99.4%, about 99.5%, about 99.6%, about 99.7%, about 99.8%, about 99.9%, or about 100% pure.

In some embodiments of the pharmaceutical compositions disclosed herein, the compound of Formula (I), or an isotopic variant, tautomer, pharmaceutically acceptable salt, solvate, or hydrateor an isotopic variant, tautomer, pharmaceutically acceptable salt, solvate, or hydrate thereof; comprises less than about 10% of at least one impurity. In some embodiments of the pharmaceutical compositions disclosed herein, the pharmaceutical composition comprises less than about 9% of at least one impurity. In some embodiments of the pharmaceutical compositions disclosed herein, the pharmaceutical composition comprises less than about 8% of at least one impurity. In some embodiments of the pharmaceutical compositions disclosed herein, the pharmaceutical composition comprises less than about 7% of at least one impurity. In some embodiments of the pharmaceutical compositions disclosed herein, the pharmaceutical composition comprises less than about 6% of at least one impurity. In some embodiments of the pharmaceutical compositions disclosed herein, the pharmaceutical composition comprises less than about 5% of at least one impurity. In some embodiments of the pharmaceutical compositions disclosed herein, the pharmaceutical composition comprises less than about 4% of at least one impurity. In some embodiments of the pharmaceutical compositions disclosed herein, the pharmaceutical composition comprises less than about 3% of at least one impurity. In some embodiments of the pharmaceutical compositions disclosed herein, the pharmaceutical composition comprises less than about 2% of at least one impurity. In some embodiments of the pharmaceutical compositions disclosed herein, the pharmaceutical composition comprises less than about 1% of at least one impurity. In some embodiments of the pharmaceutical compositions disclosed herein, the pharmaceutical composition comprises less than about 0.9% of at least one impurity. In some embodiments of the pharmaceutical compositions disclosed herein, the pharmaceutical composition comprises less than about 0.8% of at least one impurity. In some embodiments of the pharmaceutical compositions disclosed herein, the pharmaceutical composition comprises less than about 0.7% of at least one impurity. In some embodiments of the pharmaceutical compositions disclosed herein, the pharmaceutical composition comprises less than about 0.6% of at least one impurity. In some embodiments of the pharmaceutical compositions disclosed herein, the pharmaceutical composition comprises less than about 0.5% of at least one impurity. In some embodiments of the pharmaceutical compositions disclosed herein, the pharmaceutical composition comprises less than about 0.4% of at least one impurity. In some embodiments of the pharmaceutical compositions disclosed herein, the pharmaceutical composition comprises less than about 0.3% of at least one impurity. In some embodiments of the pharmaceutical compositions disclosed herein, the pharmaceutical composition comprises less than about 0.2% of at least one impurity. In some embodiments of the pharmaceutical compositions disclosed herein, the pharmaceutical composition comprises less than about 0.1% of at least one impurity.

In some embodiments of the pharmaceutical compositions disclosed herein, the pharmaceutical composition comprises up to about 10% of at least one impurity. In some embodiments of the pharmaceutical compositions disclosed herein, the pharmaceutical composition comprises up to about 9% of at least one impurity. In some embodiments of the pharmaceutical compositions disclosed herein, the pharmaceutical composition comprises up to about 8% of at least one impurity. In some embodiments of the pharmaceutical compositions disclosed herein, the pharmaceutical composition comprises up to about 7% of at least one impurity. In some embodiments of the pharmaceutical compositions disclosed herein, the pharmaceutical composition comprises up to about 6% of at least one impurity. In some embodiments of the pharmaceutical compositions disclosed herein, the pharmaceutical composition comprises up to about 5% of at least one impurity. In some embodiments of the pharmaceutical compositions disclosed herein, the pharmaceutical composition comprises up to about 4% of at least one impurity. In some embodiments of the pharmaceutical compositions disclosed herein, the pharmaceutical composition comprises up to about 3% of at least one impurity. In some embodiments of the pharmaceutical compositions disclosed herein, the pharmaceutical composition comprises up to about 2% of at least one impurity. In some embodiments of the pharmaceutical compositions disclosed herein, the pharmaceutical composition comprises up to about 1% of at least one impurity. In some embodiments of the pharmaceutical compositions disclosed herein, the pharmaceutical composition comprises up to about 0.9% of at least one impurity. In some embodiments of the pharmaceutical compositions disclosed herein, the pharmaceutical composition comprises up to about 0.8% of at least one impurity. In some embodiments of the pharmaceutical compositions disclosed herein, the pharmaceutical composition comprises up to about 0.7% of at least one impurity. In some embodiments of the pharmaceutical compositions disclosed herein, the pharmaceutical composition comprises up to about 0.6% of at least one impurity. In some embodiments of the pharmaceutical compositions disclosed herein, the pharmaceutical composition comprises up to about 0.5% of at least one impurity. In some embodiments of the pharmaceutical compositions disclosed herein, the pharmaceutical composition comprises up to about 0.4% of at least one impurity. In some embodiments of the pharmaceutical compositions disclosed herein, the pharmaceutical composition comprises up to about 0.3% of at least one impurity. In some embodiments of the pharmaceutical compositions disclosed herein, the pharmaceutical composition comprises up to about 0.2% of at least one impurity. In some embodiments of the pharmaceutical compositions disclosed herein, the pharmaceutical composition comprises up to about 0.1% of at least one impurity.

In some embodiments, the pharmaceutical composition is substantially free of impurities. In some embodiments, the pharmaceutical composition is at least about 90% pure. In some embodiments, the pharmaceutical composition is at least about 95% pure. In some embodiments, the pharmaceutical composition is at least about 96% pure. In some embodiments, the pharmaceutical composition is at least about 97% pure. In some embodiments, the pharmaceutical composition is at least about 98% pure. In some embodiments, the pharmaceutical composition is at least about 99% pure. In some embodiments, the pharmaceutical composition is at least about 99.1%, about 99.2%, about 99.3%, about 99.4%, about 99.5%, about 99.6%, about 99.7%, about 99.8%, about 99.9%, or about 100% pure. In some embodiments, the pharmaceutical composition comprises up to about 10% (w/w) of at least one impurity. In some embodiments, the pharmaceutical composition comprises less than about 10% (w/w), about 9% (w/w), about 8% (w/w), about 7% (w/w), about 6% (w/w), about 5% (w/w), about 4% (w/w), about 3% (w/w), about 2% (w/w), or about 1% (w/w) of at least one impurity. In some embodiments, the pharmaceutical composition comprises less than about 5% (w/w), about 4% (w/w), about 3% (w/w), about 2% (w/w), or about 1% (w/w) of at least one impurity. In some embodiments, the pharmaceutical composition comprises less than about 0.9% (w/w), about 0.8% (w/w), about 0.7% (w/w), about 0.6% (w/w), about 0.5% (w/w), about 0.4% (w/w), about 0.3% (w/w), about 0.2% (w/w), or about 0.1% (w/w) of at least one impurity.

In some embodiments, the at least one impurity is a degradant. In some embodiments, the at least one impurity is:

-continued
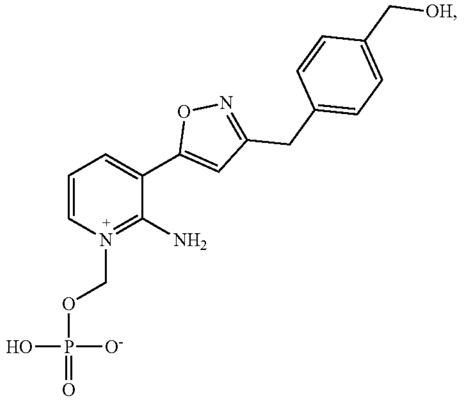
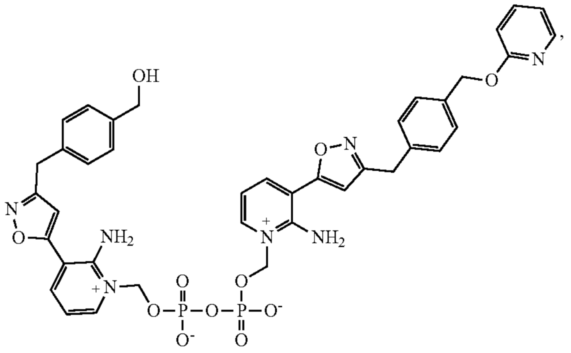
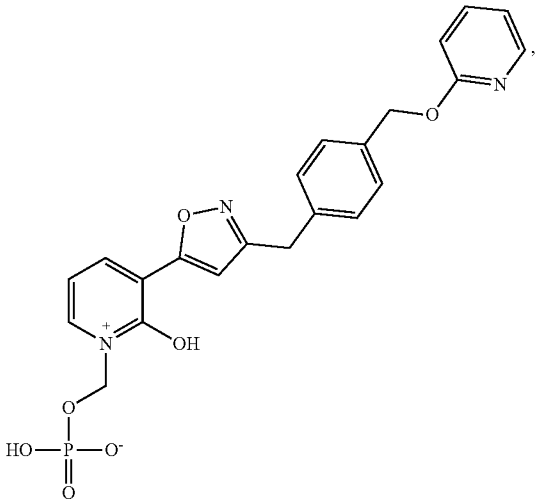
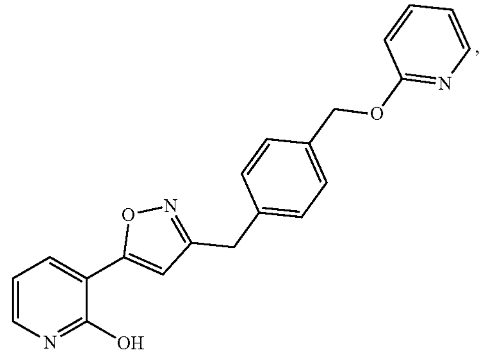
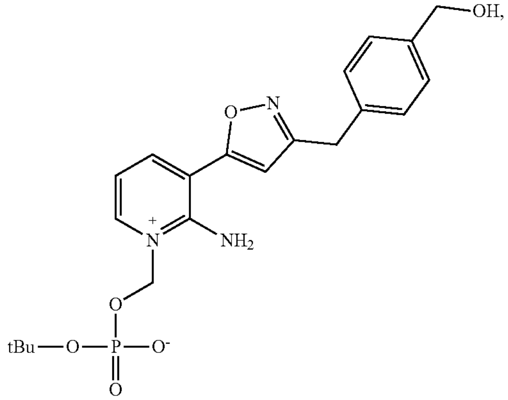
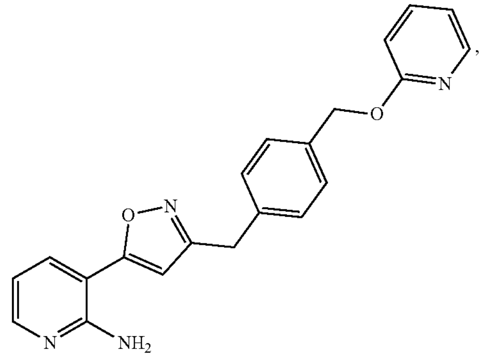
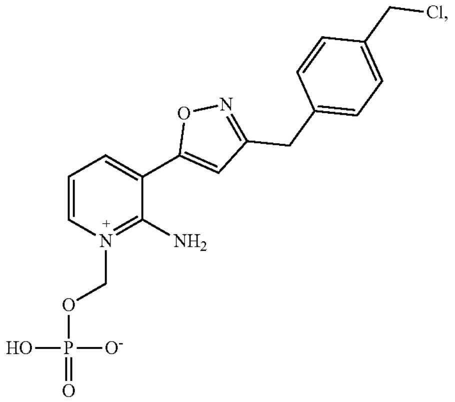
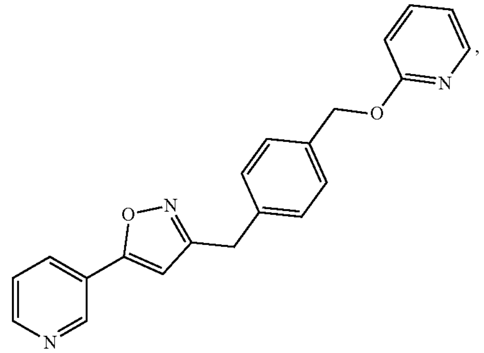

-continued

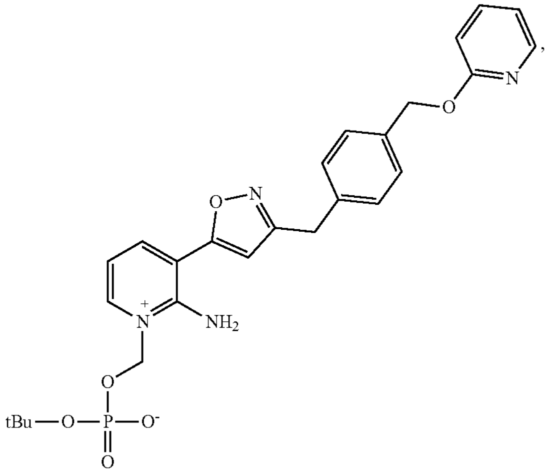

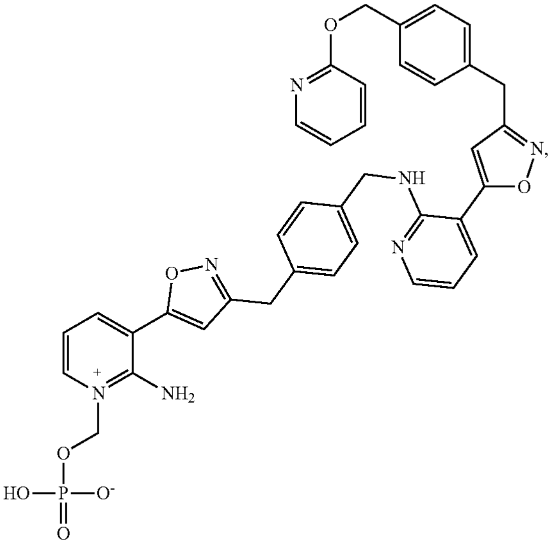

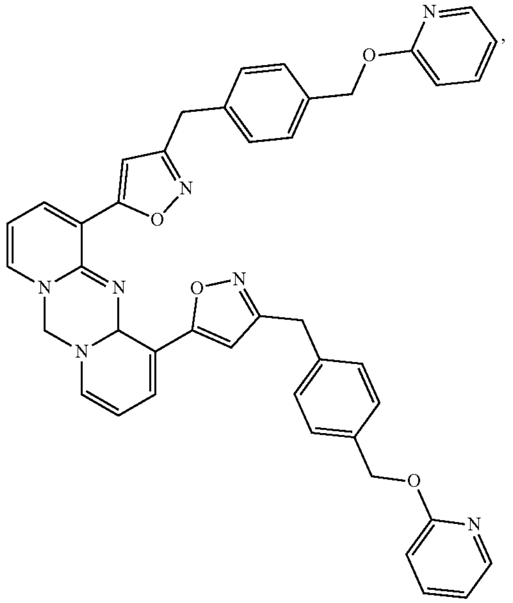

-continued

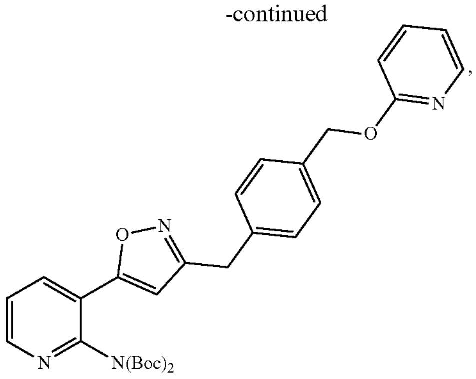

or any combination thereof.

In some embodiments, the at least one impurity is:

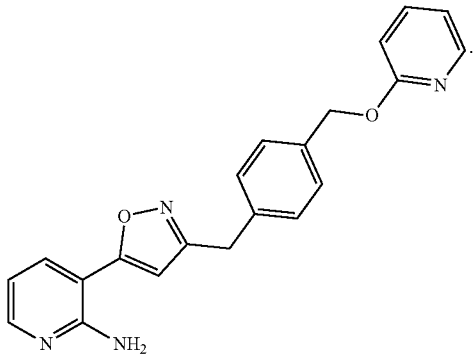 [SMILES: Nc1ncccc1-c1cc(Cc2ccc(COc3ccccn3)cc2)no1]

In some embodiments, the pharmaceutical composition comprises up to about 4.0% (w/w) total impurities. In some embodiments, the pharmaceutical composition comprises up to about 0.5% (w/w) of any individual impurity. In some embodiments, the pharmaceutical composition comprises up to about 1.5% (w/w) of the compound:

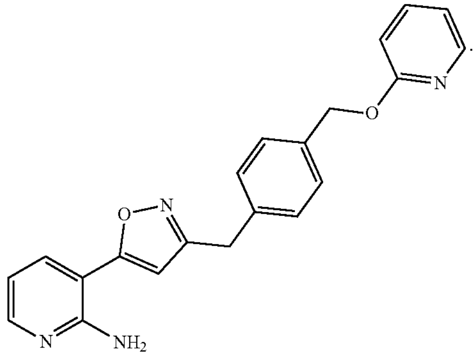

In some embodiments, the impurity in the pharmaceutical compositions disclosed herein is:

Compound 1A

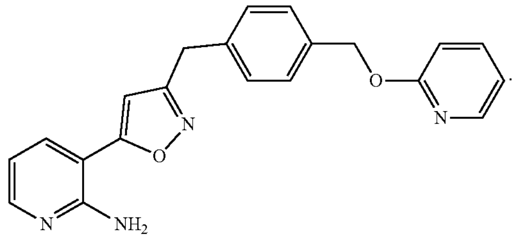

The compound of Formula (I), or an isotopic variant, tautomer, pharmaceutically acceptable salt, solvate, or hydrate thereof of the present disclosure may be in the form of compositions suitable for administration to a subject. In general, such compositions are "pharmaceutical compositions" comprising a compound of Formula (I), or an isotopic variant, tautomer, pharmaceutically acceptable salt, solvate, or hydrate thereof and one or more pharmaceutically acceptable or physiologically acceptable diluents, carriers or excipients. In certain embodiments, the compound of Formula (I), or an isotopic variant, tautomer, pharmaceutically acceptable salt, solvate, or hydrate thereof are present in a therapeutically acceptable amount. The pharmaceutical compositions may be used in the methods of the present invention; thus, for example, the pharmaceutical compositions can be administered ex vivo or in vivo to a subject in order to practice therapeutic and prophylactic methods and uses described herein.

The pharmaceutical compositions of the present invention can be formulated to be compatible with the intended method or route of administration; exemplary routes of administration are set forth herein.

The pharmaceutical compositions containing the a compound of Formula (I), or an isotopic variant, tautomer, pharmaceutically acceptable salt, solvate, or hydrate thereof may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound of Formula (I), or an isotopic variant, tautomer, pharmaceutically acceptable salt, solvate, or hydrate thereof; and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof (e.g., potassium phosphate monobasic, potassium phosphate dibasic, etc.). Acceptable buffering agents include, for example, a Tris buffer; N-(2-Hydroxyethyl) piperazine-N'-(2-ethanesulfonic acid) (HEPES); 2-(N-Morpholino) ethanesulfonic acid (MES); 2-(N-Morpholino) ethanesulfonic acid sodium salt (MES); 3-(N-Morpholino) propanesulfonic acid (MOPS); and N-tris [Hydroxymethyl]methyl-3-aminopropanesulfonic acid (TAPS), potassium phosphate monobasic, and potassium phosphate dibasic.

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a a compound of Formula (I), or an isotopic variant, tautomer, pharmaceutically acceptable salt, solvate, or hydrate thereof; including implants (e.g., implantable pumps) and catheter systems, slow injection pumps and devices, all of which are well known to the skilled artisan.

Depot injections, which are generally administered subcutaneously or intramuscularly, may also be utilized to release the compound (e.g., a compound of Formula (I), or an isotopic variant, tautomer, pharmaceutically acceptable salt, solvate, or hydrate thereof) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, NJ) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present invention contemplates the administration of the compound of Formula (I) or an isotopic variant, tautomer, pharmaceutically acceptable salt, solvate, or hydrate thereof in the form of suppositories for rectal administration. The suppositories can be prepared by mixing the drug with a suitable non-irritating excipient, which is solid at ordinary temperatures but liquid at the rectal temperature and will therefore melt in the rectum to release the drug. Such materials include, but are not limited to, cocoa butter and polyethylene glycols.

The compound of Formula (I) or an isotopic variant, tautomer, pharmaceutically acceptable salt, solvate, or hydrate thereof may be in the form of any other suitable pharmaceutical composition (e.g., sprays for nasal or inhalation use) currently known or developed in the future

II. METHODS OF USE

In an aspect, provided herein is a method of treating and/or preventing a fungal infection or disease, comprising administering to a subject in need thereof a therapeutically effective amount of any of the pharmaceutical compositions or combination compositions described herein.

In an aspect, provided herein is a method of treating and/or preventing a fungal infection or disease, comprising administering to a subject in need thereof a therapeutically effective amount of a pharmaceutical composition, comprising: (i) the compound of Formula (I), or an isotopic variant, tautomer, pharmaceutically acceptable salt, solvate, or hydrate thereof; and (ii) at least one pharmaceutically acceptable excipient, the pharmaceutical composition is in a dosage form for oral dosing or administration.

In another aspect, provided herein is a method of treating and/or preventing a fungal infection or disease, comprising administering to a subject in need thereof a therapeutically effective amount of a pharmaceutical composition, comprising: (i) fine particles of the compound of Formula (I), or an isotopic variant, tautomer, pharmaceutically acceptable salt, solvate, or hydrate thereof; and (ii) at least one pharmaceutically acceptable excipient, wherein the pharmaceutical composition is in a dosage form for oral dosing or administration or in a dosage form for inhalation delivery.

In some embodiments of the methods provided herein, the dosage form is a self-microemulsifying drug delivery system (SMEDDS). In some embodiments of the methods provided herein, the dosage form is a self-emulsifying drug delivery system (SEDDS). In some embodiments of the methods provided herein, the dosage form is a suspension or a solution. In some embodiments of the methods provided herein, the dosage form is a nanosuspension. In some embodiments of the methods provided herein, the dosage form is a solid dosage form. In some embodiments of the methods provided herein, the dosage form is a spray-dried dispersion dosage form. In some embodiments of the methods provided herein, the dosage form is a hot melt granulation dosage form. In some embodiments of the methods provided herein, the dosage form is a hot melt extrusion dosage form. In some embodiments of the methods provided herein, the dosage form is a microprecipitated bulk powder (MBP) dosage form. In some embodiments of the methods provided herein, the dosage form is a liquid. In some embodiments of the methods provided herein, the dosage form is a suspension, solution, syrup, or elixir. In some embodiments of the methods provided herein, the pharmaceutical composition is in a dosage form for oral dosing or administration.

In some embodiments of the methods described herein, the dosage form is a tablet or a capsule. In some embodiments of the methods described herein, the tablet or capsule has an enteric coating. In some embodiments of the methods described herein, the dosage form is a tablet. In some embodiments of the methods described herein, the tablet is an osmotic floating tablet. In some embodiments of the methods described herein, the capsule is a liquid-filled hard capsule. In some embodiments of the methods described herein, the capsule is a soft gelatin capsule.

In some embodiments of the methods described herein, the dosage form is a modified-release dosage form. In some embodiments of the methods described herein, the modified-release dosage form is a delayed-release dosage form, an extended-release (ER) dosage form, or a targeted-release dosage form. In some embodiments of the methods described herein, the ER dosage form is a sustained-release (SR) dosage form or controlled-release (CR) dosage form. In some embodiments of the methods described herein, the dosage form is an immediate release dosage form.

In an aspect, provided herein is a method of treating and/or preventing a fungal infection or disease, comprising administering to a subject in need thereof a therapeutically effective amount of a pharmaceutical composition, comprising: (i) the compound of Formula (I) or an isotopic variant, tautomer, pharmaceutically acceptable salt, solvate, or hydrate thereof; and (ii) at least one pharmaceutically acceptable excipient, wherein the pharmaceutical composition is in a dosage form for dosing or administration by intravenous (I.V.), intramuscular, subcutaneous, or intradermal injection. In some embodiments of the methods described herein, the form is an I.V. dosage form.

In some embodiments of the methods provided herein, the pharmaceutical composition is administered to the subject over a period of about 20 minutes, about 30 minutes, about 60 minutes, about 90 minutes, about 2 hours, about 3 hours, about 4 hours, about 5 hours, about 6 hours, about 7 hours, about 8 hours, about 9 hours, about 10 hours, about 12 hours, about 18 hours, or about 24 hours by I.V. infusion.

In some embodiments of the methods provided herein, the pharmaceutical composition is administered to the subject over a period of up to about 1 hour by I.V infusion. In some embodiments of the methods provided herein, the pharmaceutical composition is administered to the subject over a period of up to about 2 hours by I. V infusion. In some embodiments of the methods provided herein, the pharmaceutical composition is administered to the subject over a period of up to about 3 hours by I.V infusion.

In another aspect, there is provided a method of treating a fungal infection or disease, comprising administering to a subject in need thereof a therapeutically effective amount of a combination composition, comprising: (i) the compound of Formula (I), or an isotopic variant, tautomer, pharmaceutically acceptable salt, solvate, or hydrate thereof; and (ii) at least one an antifungal agent.

In an aspect, provided herein is a method of treating and/or preventing a fungal infection or disease, comprising administering to a subject in need thereof a therapeutically effective amount of a combination composition, comprising:

(i) a compound of Formula (I):

(I)

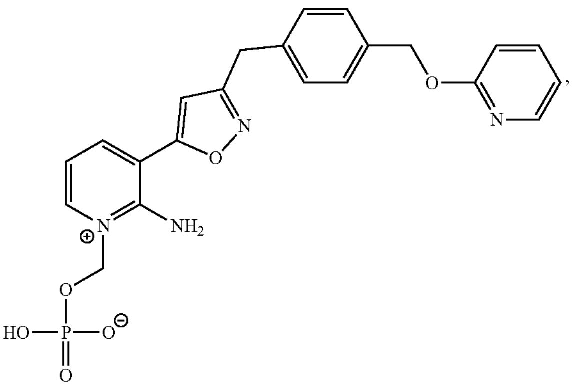

or an isotopic variant, tautomer, pharmaceutically acceptable salt, solvate, or hydrate thereof; and (ii) a compound of Formula (II):

(II)

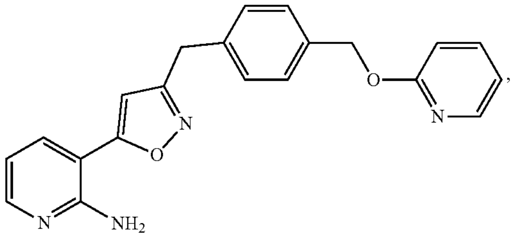

or an isotopic variant, tautomer, pharmaceutically acceptable salt, solvate, or hydrate thereof.

In some embodiments of the methods described herein, the compound of Formula (I) or an isotopic variant, tautomer, pharmaceutically acceptable salt, solvate, or hydrate thereof; is crystalline, microcrystalline, amorphous, or lyophilized. In some embodiments of the methods described herein, the compound of Formula (I) or an isotopic variant, tautomer, pharmaceutically acceptable salt, solvate, or hydrate thereof; is crystalline. In some embodiments of the methods described herein, the compound of Formula (I) or an isotopic variant, tautomer, pharmaceutically acceptable salt, solvate, or hydrate thereof; is amorphous. In some embodiments of the methods described herein, the compound of Formula (I) or an isotopic variant, tautomer, pharmaceutically acceptable salt, solvate, or hydrate thereof; is lyophilized.

In some embodiments of the methods provided herein, about 10 mg to about 8,000 mg of the compound of Formula (I), or an isotopic variant, tautomer, pharmaceutically acceptable salt, solvate, or hydrate thereof is administered to the subject. In some embodiments of the methods provided herein, from about 10 mg to about 2,400 mg of the compound of Formula (I), or an isotopic variant, tautomer, pharmaceutically acceptable salt, solvate, or hydrate thereof is administered to the subject. In some embodiments of the methods provided herein, about 10 mg, about 30 mg, about 50 mg, about 100 mg, about 150 mg, about 200 mg, about 275 mg, about 300 mg, about 350 mg, about 400 mg, about 500 mg, about 600 mg, about 700 mg, about 800 mg, about 900 mg, about 1,000 mg, about 1,200 mg, about 1,500 mg, about 1,800 mg, about 2,000 mg, about 2,100 mg, about 2,400 mg, about 2,500 mg, about 3,000 mg, about 4,000 mg, about 5,000 mg, about 6,000 mg, about 7,000 mg, or about 8,000 mg of the compound of Formula (I), or an isotopic variant, tautomer, pharmaceutically acceptable salt, solvate, or hydrate thereof is administered to the subject.

In some embodiments of the methods provided herein, about 40 mg, about 50 mg, about 100 mg, about 200 mg, about 250 mg, about 350 mg, about 400 mg, about 500 mg, about 600 mg, about 700 mg, about 800 mg, or about 900 mg of the compound of Formula (I), or an isotopic variant, tautomer, pharmaceutically acceptable salt, solvate, or hydrate thereof is administered to the subject. In some embodiments of the methods provided herein, about 600 mg, about 700 mg, about 800 mg, about 900 mg, 1,000 mg, about 2,000 mg, or about 3,000 mg of the compound of Formula (I), or an isotopic variant, tautomer, pharmaceutically acceptable salt, solvate, or hydrate thereof is administered to the subject.

In some embodiments of the methods provided herein, the pharmaceutical composition is administered to the subject daily. In some embodiments of the methods provided herein, the pharmaceutical composition is administered to the subject once per day, twice per day, three times per day, or four times per day. In some embodiments of the methods provided herein, the pharmaceutical composition is administered to the subject once per day. In some embodiments of the methods provided herein, the pharmaceutical composition is administered to the subject twice per day.

In some embodiments of the methods provided herein, the pharmaceutical composition is administered to the subject for a period of up to about 12 weeks. In some embodiments of the methods provided herein, the pharmaceutical composition is administered to the subject for a period of at least one week. In some embodiments of the methods provided herein, the pharmaceutical composition is administered to the subject for a period of at least two weeks. In some embodiments of the methods provided herein, the pharmaceutical composition is administered to the subject for a period of up to about 2 weeks. In some embodiments of the methods provided herein, the pharmaceutical composition is administered to the subject for a period of one week, two weeks, 6 weeks, 12 weeks, 24 weeks, 48 weeks, or 52 weeks.

In some embodiments of the methods provided herein, from about to about 10 mg to about 8,000 mg of the compound of Formula (I), or an isotopic variant, tautomer, pharmaceutically acceptable salt, solvate, or hydrate thereof is administered to the subject. In some embodiments of the methods provided herein, about 10 mg, about 20 mg, about 30 mg, about 40 mg, about 50 mg, about 100 mg, about 125 mg, about 150 mg, about 175 mg, about 200 mg, about 225 mg, about 250 mg, about 275 mg, about 300 mg, about 350 mg, about 400 mg, about 450 mg, about 500 mg, about 600 mg, about 700 mg, about 800 mg, about 900 mg, about 1,000 mg, or about 2,000 mg of a compound of Formula (I), or an isotopic variant, tautomer, pharmaceutically acceptable salt, solvate, or hydrate thereof is administered to the subject.

In some embodiments of the methods provided herein, the pharmaceutical composition is administered to the subject over a period of about 20 minutes, about 30 minutes, about 60 minutes, about 90 minutes, about 2 hours, about 3 hours, about 4 hours, about 5 hours, about 6 hours, about 7 hours, about 8 hours, about 9 hours, about 10 hours, about 12 hours, about 18 hours, or about 24 hours by I.V. infusion.

In some embodiments of the methods provided herein, the pharmaceutical composition is administered to the subject over a period of up to about 3 hours by I. V infusion.

In some embodiments of the methods provided herein, a loading dose is administered to the subject followed by a maintenance dose. In some embodiments of the methods provided herein, the loading dose comprises from about 1,000 mg to about 8,000 mg of a compound of Formula (I), or an isotopic variant, tautomer, pharmaceutically acceptable salt, solvate, or hydrate thereof. In some embodiments of the methods provided herein, the maintenance dose comprises from about 600 mg to about 2,400 mg of a compound of Formula (I), or an isotopic variant, tautomer, pharmaceutically acceptable salt, solvate, or hydrate thereof. In some embodiments of the methods provided herein, the loading dose comprises from about 1,000 mg to about 2,000 mg. In some embodiments of the methods provided herein, the loading dose is administered over a period of about 2 to about 3 hours by I.V. infusion. In some embodiments of the methods provided herein, the loading dose is administered twice on the first day of treatment. In some embodiments of the methods provided herein, the second loading dose is administered about 9 hours after the first loading dose.

In some embodiments of the methods provided herein, the maintenance dose comprises about 600 mg, about 700 mg, about 800 mg, about 900 mg, or about 1,000 mg of a compound of Formula (I), or an isotopic variant, tautomer, pharmaceutically acceptable salt, solvate, or hydrate thereof. In some embodiments of the methods provided herein, the maintenance dose comprises about 800 mg or about 1,000 mg of a compound of Formula (I), or an isotopic variant, tautomer, pharmaceutically acceptable salt, solvate, or hydrate thereof is administered to the subject. In some embodiments of the methods provided herein, the maintenance dose comprises about 600 mg or about 900 mg of a compound of Formula (I), or an isotopic variant, tautomer, pharmaceutically acceptable salt, solvate, or hydrate thereof. In some embodiments of the methods provided herein, the maintenance dose comprises about 600 mg or about 900 mg of a compound of Formula (I), or an isotopic variant, tautomer, pharmaceutically acceptable salt, solvate, or hydrate thereof and is administered orally.

In some embodiments of the methods provided herein, the maintenance dose comprises about 600 mg or about 900 mg of a compound of Formula (I), or an isotopic variant, tautomer, pharmaceutically acceptable salt, solvate, or hydrate thereof is administered over a period of about 1 hour to about 3 hours by I.V. infusion.

In some embodiments of the methods provided herein, The method of any one of Embodiments 157-164, wherein about 600 mg of a compound of Formula (I), or an isotopic variant, tautomer, pharmaceutically acceptable salt, solvate, or hydrate thereof is administered over a period of about 3 hours by I.V. infusion.

In some embodiments of the methods provided herein, the maintenance dose is administered once daily.

In some embodiments of the methods provided herein, the maintenance dose is administered once daily starting on the second day of treatment.

In some embodiments of the methods provided herein, about 600 mg or about 800 mg of a compound of Formula (I), or an isotopic variant, tautomer, pharmaceutically acceptable salt, solvate, or hydrate thereof is administered over a period of about 3 hours by I.V. infusion starting on the second, third, or fourth day of treatment.

In some embodiments of the methods provided herein, about 800 mg or about 1,000 mg of a compound of Formula (I), or an isotopic variant, tautomer, pharmaceutically acceptable salt, solvate, or hydrate thereof is administered orally starting on the second, third, or fourth day of treatment.

In some embodiments of the methods provided herein, the maintenance dose comprises about 600 mg or about 800 mg of a compound of Formula (I), or an isotopic variant, tautomer, pharmaceutically acceptable salt, solvate, or hydrate thereof. In some embodiments of the methods provided herein, about 600 mg of a compound of Formula (I), or an isotopic variant, tautomer, pharmaceutically acceptable salt, solvate, or hydrate thereof is administered to the subject. In some embodiments of the methods provided herein, about 800 mg of a compound of Formula (I), or an isotopic variant, tautomer, pharmaceutically acceptable salt, solvate, or hydrate thereof is administered to the subject. In some embodiments of the methods provided herein, about 600 mg of a compound of Formula (I), or an isotopic variant, tautomer, pharmaceutically acceptable salt, solvate, or hydrate thereof is administered over a period of about 1 hour to about 3 hours by I.V. infusion and/or about 800 mg of a compound of Formula (I), or an isotopic variant, tautomer, pharmaceutically acceptable salt, solvate, or hydrate thereof and is administered orally. In some embodiments of the methods provided herein, the maintenance dose is administered once daily. In some embodiments of the methods provided herein, the maintenance dose is administered once daily starting on the second day of treatment. In some embodiments of the methods provided herein, about 600 mg of a compound of Formula (I), or an isotopic variant, tautomer, pharmaceutically acceptable salt, solvate, or hydrate thereof is administered over a period of about 3 hours by I.V. infusion.

In some embodiments of the methods provided herein, about 600 mg of a compound of Formula (I), or an isotopic variant, tautomer, pharmaceutically acceptable salt, solvate, or hydrate thereof is administered over a period of about 3 hours by I.V. infusion starting on the second day of treatment.

In some embodiments of the methods provided herein, about 800 mg of a compound of Formula (I), or an isotopic variant, tautomer, pharmaceutically acceptable salt, solvate, or hydrate thereof is administered orally starting on the fourth day of treatment.

In some embodiments of the methods provided herein, the fungal infection is caused by an invasive fungus. In some embodiments of the methods provided herein, the method further comprises administering to the subject at least one antifungal agent in combination with the pharmaceutical composition comprising the compound of Formula (I), or an isotopic variant, tautomer, pharmaceutically acceptable salt, solvate, or hydrate thereof. In some embodiments of the methods provided herein, the at least one antifungal agent is an azole, an echinocandin, amphotericin B deoxycholate, amphotericin B cochleate, 5-fluorocytosine, terbinafine, griseofulvin, VL-2397, ibrexafungerp, orotomide F901318, or combinations thereof. In some embodiments of the methods provided herein, the azole is ketoconazole, fluconazole, posaconazole, itraconazole, voriconazole, isavuconazole, or miconazole. In some embodiments of the methods provided herein, the echinocandin is caspofungin, anidulafungin, micafungin, or rezafungin, or combinations thereof.

In some embodiments of the methods provided herein, the pharmaceutical composition comprising the compound of Formula (I), or an isotopic variant, tautomer, pharmaceutically acceptable salt, solvate, or hydrate thereof; and the antifungal agent are administered simultaneously, approximately simultaneously, or sequentially, in any order. In some embodiments of the methods provided herein, the pharmaceutical composition comprising the compound of Formula (I), or an isotopic variant, tautomer, pharmaceutically acceptable salt, solvate, or hydrate thereof; and the antifungal agent are administered simultaneously or approximately simultaneously. In some embodiments of the methods provided herein, the pharmaceutical composition comprising the compound of Formula (I), or an isotopic variant, tautomer, pharmaceutically acceptable salt, solvate, or hydrate thereof; and the antifungal agent are administered sequentially. In some embodiments of the methods provided herein, the pharmaceutical composition comprising the compound of Formula (I), or an isotopic variant, tautomer, pharmaceutically acceptable salt, solvate, or hydrate thereof; or a pharmaceutically acceptable salt thereof, is administered before the at least one antifungal agent. In some embodiments of the methods provided herein, the pharmaceutical composition comprising the compound of Formula (I), or an isotopic variant, tautomer, pharmaceutically acceptable salt, solvate, or hydrate thereof; or a pharmaceutically acceptable salt thereof, is administered after the at least one antifungal agent.

In some embodiments of the methods provided herein, the fungal infection or disease is caused by *Aspergillus fumigatus, Blastomyces, Ajellomyces, Candida, Coccidioides, Cryptococcus, Histoplasm, Rhizopus muco, Cunninghamell, Apophysomyces, Absidi, Saksenaea, Entomophthora, Conidiobolus, Basidiobolus, Sporothrix, Pneumocystis, Talaromyces, Asclepias, Fusarium, Scedosporium* fungus or from a fungus from the Mucorales order, or any combination thereof. In some embodiments of the methods provided herein, the fungal infection or disease is caused by a *Cryptococcus, Aspergillus, Candida, Fusarium, Scedosporium* fungus or from a fungus from the Mucorales order, or any combination thereof. In some embodiments of the methods provided herein, the fungal infection or disease is caused by *Aspergillus fumigatus, Aspergillus flavus, Blastomyces dermatitidis, Ajellomyces dermatitidi, Candida albican, Candida glabrata, Candida rugosa, Candida auris, Coccidioides immitis, Coccidioides posadasii, Cryptococcus neoformans, Cryptococcus gattii, Histoplasma capsulatum, Rhizopus stolonifer, Rhizopus arrhizus, Mucor indicus, Cunninghamella bertholletiae, Apophysomyces elegans, Absidia* species, *Saksenaea* species, *Rhizomucor pusillus, Entomophthora* species, *Conidiobolus* species, *Basidiobolus* species, *Sporothrix schenckii, Pneumocystis jirovecii, Talaromyces marneffei, Asclepias albicans, Fusarium solani, Scedosporium apiospermum, Rhizomucor pusillus*, or any combination thereof. In some embodiments of the methods provided herein, the fungal infection or disease is caused by a *Cryptococcus* fungus or a *Candida* fungus. In some embodiments of the methods provided herein, the fungal infection or disease is caused by *Cryptococcus neoformans, Cryptococcus gattii*, or *Candida auris*.

In some embodiments of the methods provided herein, the fungal infection or disease is azole-resistant and/or echinocandin-resistant.

In some embodiments of the methods provided herein, the subject is immunocompromised. In some embodiments of the methods provided herein, the subject is infected with HIV/AIDS or has cancer. In some embodiments of the methods provided herein, the subject has cancer. In some embodiments of the methods provided herein, the cancer is acute myeloid leukemia (AML). In some embodiments of the methods provided herein, the subject has neutropenia. In some embodiments of the methods provided herein, the subject is undergoing or has undergone cancer chemotherapy treatment. In some embodiments of the methods provided herein, the subject is undergoing or has undergone corticosteroid treatment. In some embodiments of the methods provided herein, the subject is undergoing or has undergone TNF inhibitor treatment. In some embodiments of the methods provided herein, the subject is a transplant recipient. In some embodiments of the methods described herein, the compound of Formula (I), or an isotopic variant, tautomer, pharmaceutically acceptable salt, solvate, or hydrate thereof is administered to the subject in combination with posaconazole.

In some embodiments of the methods described herein, the compound of Formula (I), or an isotopic variant, tautomer, pharmaceutically acceptable salt, solvate, or hydrate thereof is administered to the subject for the prevention of a fungal infection or disease. In some embodiments of the methods described herein, the compound of Formula (I), or an isotopic variant, tautomer, pharmaceutically acceptable salt, solvate, or hydrate thereof is administered to the subject for the treatment of an existing fungal infection or disease.

In some embodiments of the methods provided herein, the fungal infection or disease is in the bloodstream of the subject. In some embodiments of the methods provided herein, the subject has reduced colony counts of fungi in the lungs after administration of the pharmaceutical composition. In some embodiments of the methods provided herein, the plasma concentration versus time curve of the compound of Formula (I) in the subject has a $t_{max}$ of less than from about 30 minutes to about 180 minutes. In some embodiments of the methods provided herein, the subject has a maximum plasma concentration ($C_{max}$) of from about 12,000 ng/ml to about 25,000 ng/ml of the compound of Formula (I) Dosing In some embodiments, the compound of Formula (I) or an isotopic variant, tautomer, pharmaceutically acceptable salt, solvate, or hydrate thereof pharmaceutical compositions described herein are provided at the maximum tolerated dose (MTD) for the compound of Formula (I). In other embodiments, the amount of the compound of Formula (I) or an isotopic variant, tautomer, pharmaceutically acceptable salt, solvate, or hydrate thereof pharmaceutical composition administered is from about 10% to about 90% of the maximum tolerated dose (MTD), from about 25% to about 75% of the MTD, or about 50% of the MTD. In some other embodiments, the amount of the compound of Formula (I) or an isotopic variant, tautomer, pharmaceutically acceptable salt, solvate, or hydrate thereof pharmaceutical compositions administered is from about 5%, 10%, 15%, 20%, 25%, 30%, 35%, 40%, 45%, 50%, 55%, 60%, 65%, 70%, 75%, 80%, 85%, 90%, 95%, 99%, or higher, or any range derivable therein, of the MTD for the compound of Formula (I).

In certain embodiments, in the treatment, prevention, or amelioration of one or more symptoms of the disorders, diseases, or conditions described herein (e.g., a fungal infection or disease), an appropriate dosage level of the compound of Formula (I) or an isotopic variant, tautomer, pharmaceutically acceptable salt, solvate, or hydrate thereof generally is ranging from about 1 to 8,000 mg, about 10 to 8,000 mg, about 10 to 2,000 mg, about 1 to about 1,000 mg, from about 25 to about 1,000 mg, from about 25 to about 800 mg, from about 25 to about 600 mg, from about 50 to about 600 mg, from about 50 to about 300 mg, from about 50 to about 150 mg, from about 150 to about 250 mg, from about 250 mg to about 350 mg, from about 350 to about 450 mg, from about 450 to about 550 mg, from about 550 to about 650 mg, from about 650 to about 750 mg, from about 750 to about 850 mg, which can be administered in single or multiple doses. In certain embodiments, the compound of Formula (I) or an isotopic variant, tautomer, pharmaceutically acceptable salt, solvate, or hydrate thereof, is administered in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 240, about 250, about 260, about 270, about 275, about 280, about 290, about 300, about 310, about 320, about 330, about 340, about 350, about 360 mg, about 370 mg, about 380 mg, about 390 mg, about 400 mg, 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, 910 mg, about 920 mg, about 930 mg, about 940 mg, about 950 mg, about 960 mg, about 970 mg, about 980 mg, about 990 mg, about 1,000, about 1,100, about 1,200, about 1,300, about 1,400, about 1,500, about 1,600, about 1,700, about 1,800, about 1,900, about 2,000, about 2,100, about 2,200, about 2,300, about 2,400, about 2,500, about 2,600, about 2,700, about 2,800, about 3,000, about 4,000, about 5,000, about 6,000, about 7,000, about 8,000 mg, or any range derivable therein.

In certain embodiments, the compound of Formula (I) or an isotopic variant, tautomer, pharmaceutically acceptable salt, solvate, or hydrate thereof is administered to the subject in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 240, about 250, about 260, about 270, about 275, about 280, about 290, about 300, about 310, about 320, about 330, about 340, about 350, about 360 mg, about 370 mg, about 380 mg, about 390 mg, about 400 mg, 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, 910 mg, about 920 mg, about 930 mg, about 940 mg, about 950 mg, about 960 mg, about 970 mg, about 980 mg, about 990 mg, about 1,000, about 1,100, about 1,200, about 1,300, about 1,400, about 1,500, about 1,600, about 1,700, about 1,800, about 1,900, about 2,000, about 2,100, about 2,200, about 2,300, about 2,400, about 2,500, about 2,600, about 2,700, about 2,800, about 3,000, about 4,000, about 5,000, about 6,000, about 7,000, about 8,000 mg.

In certain embodiments, the compound of Formula (I) or an isotopic variant, tautomer, pharmaceutically acceptable salt, solvate, or hydrate thereof is administered in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 240, about 250, about 260, about 270, about 275, about 280, about 290, about 300, about 310, about 320, about 330, about 340, about 350, about 360 mg, about 370 mg, about 380 mg, about 390 mg, about 400 mg, 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, 910 mg, about 920 mg, about 930 mg, about 940 mg, about 950 mg, about 960 mg, about 970 mg, about 980 mg, about 990 mg, about 1,000, about 1,100, about 1,200, about 1,300, about 1,400, about 1,500, about 1,600, about 1,700, about 1,800, about 1,900, about 2,000, about 2,100, about 2,200, about 2,300, about 2,400, about 2,500, about 2,600, about 2,700, about 2,800, about 3,000, about 4,000, about 5,000, about 6,000, about 7,000, about 8,000 mg/day.

For oral administration, the pharmaceutical compositions provided herein can be formulated in the form of tablets or capsules containing from about 1 to 2,000 mg, about 10 to 2,000 mg, from about 1 to about 1,000 mg, about 25 to about 1,000 mg, about 25 to about 800 mg, about 25 to about 600 mg, about 50 to about 600 mg, about 50 to about 300 mg, about 50 to about 150 mg, about 150 to about 250 mg, about 250 mg to about 350 mg, about 350 to about 450 mg, about 450 to about 550 mg, about 550 to about 650 mg, about 650 to about 750 mg, about 750 to about 850 mg; in one embodiment, 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, 910 mg, about 920 mg, about 930 mg, about 940 mg, about 950 mg, about 960 mg, about 970 mg, about 980 mg, about 990 mg, about 1,000, or about 2,000 mg of the compound of Formula (I) or an isotopic variant, tautomer, pharmaceutically acceptable salt, solvate, or hydrate thereof for the symptomatic adjustment of the dosage to the patient to be treated.

In some embodiments, the pharmaceutical compositions provided herein can be formulated in the form of tablets or capsules containing about 50 mg, about 100 mg, about 150 mg, about 200 mg, about 250 mg, about 300 mg, about 350 mg, about 400 mg, about 450 mg, 500 mg, about 550 mg, about 600 mg, about 650 mg, about 700 mg, about 750 mg, or about 800 mg of a compound of Formula (I) or an isotopic variant, tautomer, pharmaceutically acceptable salt, solvate, or hydrate thereof.

In some embodiments, the pharmaceutical compositions provided herein can be formulated for oral administration containing about 200 mg of a compound of Formula (I), or an isotopic variant; or a pharmaceutically acceptable salt, solvate, hydrate, or prodrug thereof. In some embodiments, the pharmaceutical compositions provided herein can be formulated for oral administration containing about 300 mg of a compound of Formula (I), or an isotopic variant; or a pharmaceutically acceptable salt, solvate, hydrate, or prodrug thereof. In some embodiments, the pharmaceutical compositions provided herein can be formulated for oral administration containing about 400 mg of a compound of Formula (I), or an isotopic variant; or a pharmaceutically acceptable salt, solvate, hydrate, or prodrug thereof. In some embodiments, the pharmaceutical compositions provided herein can be formulated for oral administration containing about 500 mg of a compound of Formula (I), or an isotopic variant; or a pharmaceutically acceptable salt, solvate, hydrate, or prodrug thereof.

In some embodiments, the pharmaceutical compositions provided herein can be formulated in the form of tablets containing about 200 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 300 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 400 mg of a compound of Formula (I), or an isotopic variant; or a pharmaceutically acceptable salt, solvate, hydrate, or prodrug thereof. In some embodiments, the pharmaceutical compositions provided herein can be formulated in the form of tablets containing about 500 mg of a compound of Formula (I), or an isotopic variant; or a pharmaceutically acceptable salt, solvate, hydrate, or prodrug thereof.

The pharmaceutical compositions provided herein can be formulated for administration by IV injection or infusion and contain from about 1 to 2,000 mg, about 10 to 2,000 mg, from about 1 to about 1,000 mg, about 25 to about 1,000 mg, about 25 to about 800 mg, about 25 to about 600 mg, about 50 to about 600 mg, about 50 to about 300 mg, about 50 to about 150 mg, about 150 to about 250 mg, about 250 mg to about 350 mg, about 350 to about 450 mg, about 450 to about 550 mg, about 550 to about 650 mg, about 650 to about 750 mg, about 750 to about 850 mg, about 850 to about 950 mg, about 950 to about 1050 mg; in one embodiment, 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, 910 mg, about 920 mg, about 930 mg, about 940 mg, about 950 mg, about 960 mg, about 970 mg, about 980 mg, about 990 mg, about 1,000, or about 2,000 mg of the compound of Formula (I) or an isotopic variant, tautomer, pharmaceutically acceptable salt, solvate, or hydrate thereof for the symptomatic adjustment of the dosage to the patient to be treated.

In some embodiments, the pharmaceutical compositions provided herein can be formulated for administration by IV injection or infusion and contain about 50 mg, about 100 mg, about 150 mg, about 200 mg, about 250 mg, about 300 mg, about 350 mg, about 400 mg, about 450 mg, 500 mg, about 550 mg, about 600 mg, about 650 mg, about 700 mg, about 750 mg, about 800 mg, about 950 mg, or about 1,000 mg of a compound of Formula (I) or an isotopic variant, tautomer, pharmaceutically acceptable salt, solvate, or hydrate thereof.

In some embodiments, the pharmaceutical compositions provided herein can be formulated for administration by IV injection or infusion containing about 200 mg of a compound of Formula (I), or an isotopic variant; or a pharmaceutically acceptable salt, solvate, hydrate, or prodrug thereof. In some embodiments, the pharmaceutical compositions provided herein can be formulated for administration by IV injection or infusion containing about 300 mg of a compound of Formula (I), or an isotopic variant; or a pharmaceutically acceptable salt, solvate, hydrate, or prodrug thereof. In some embodiments, the pharmaceutical compositions provided herein can be formulated for administration by IV injection or infusion containing about 400 mg of a compound of Formula (I), or an isotopic variant; or a pharmaceutically acceptable salt, solvate, hydrate, or prodrug thereof. In some embodiments, the pharmaceutical compositions provided herein can be formulated for administration by IV injection or infusion containing about 500 mg of a compound of Formula (I), or an isotopic variant; or a pharmaceutically acceptable salt, solvate, hydrate, or prodrug thereof. In some embodiments, the pharmaceutical compositions provided herein can be formulated for administration by IV injection or infusion containing about 600 mg of a compound of Formula (I), or an isotopic variant; or a pharmaceutically acceptable salt, solvate, hydrate, or prodrug thereof. In some embodiments, the pharmaceutical compositions provided herein can be formulated for administration by IV injection or infusion containing about 700 mg of a compound of Formula (I), or an isotopic variant; or a pharmaceutically acceptable salt, solvate, hydrate, or prodrug thereof. In some embodiments, the pharmaceutical compositions provided herein can be formulated for administration by IV injection or infusion containing about 800 mg of a compound of Formula (I), or an isotopic variant; or a pharmaceutically acceptable salt, solvate, hydrate, or prodrug thereof. In some embodiments, the pharmaceutical compositions provided herein can be formulated for administration by IV injection or infusion containing about 900 mg of a compound of Formula (I), or an isotopic variant; or a pharmaceutically acceptable salt, solvate, hydrate, or prodrug thereof. In some embodiments, the pharmaceutical compositions provided herein can be formulated for administration by IV injection or infusion containing about 1,000 mg of a compound of Formula (I), or an isotopic variant; or a pharmaceutically acceptable salt, solvate, hydrate, or prodrug thereof.

In some embodiments, the pharmaceutical compositions provided herein can be formulated in the form of an injection or I.V. infusion containing from about 5 mg/mL to about 250 mg/mL, from about 10 mg/mL to about 150 mg/mL, from about 10 mg/mL to about 100 mg/mL, from about 10 mg/mL to about 50 mg/mL, from about 10 mg/mL to about 40 mg/mL, or from about 10 mg/mL to about 30 mg/mL; in one embodiment, 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL,of a compound of Formula (I), or an isotopic variant, tautomer, pharmaceutically acceptable salt, solvate, or hydrate thereof.

In some embodiments, the pharmaceutical composition comprises from about 20 mg/mL to about 40 mg/mL of a compound of Formula (I), or an isotopic variant, tautomer, pharmaceutically acceptable salt, solvate, or hydrate thereof. In some embodiments, the pharmaceutical composition comprises about 10 mg/mL, about 15 mg/mL, about 20 mg/mL, about 25 mg/mL, or about 30 mg/mL of a compound of Formula (I) or an isotopic variant, tautomer, pharmaceutically acceptable salt, solvate, or hydrate thereof.

In some embodiments, the pharmaceutical composition comprises about 20 mg/mL of a compound of Formula (I) or an isotopic variant, tautomer, pharmaceutically acceptable salt, solvate, or hydrate thereof. The dose per day described herein may be given once per day or multiple times per day in the form of sub-doses given b.i.d., t.i.d., q.i.d., or the like where the number of sub-doses equal the dose per day. The pharmaceutical compositions can be administered on a regimen of 1 to 4 times per day, including once, twice, three times, and four times per day. In some embodiments, the pharmaceutical compositions are administered once per day. In some embodiments, the pharmaceutical compositions are administered twice per day. In some embodiments, the pharmaceutical compositions are administered three times per day. In some embodiments, the pharmaceutical compositions are administered four or more times per day. In some embodiments, a loading dose, followed by maintance doses, of a compound of Formula (I), or an isotopic variant, tautomer, pharmaceutically acceptable salt, solvate, or hydrate thereof is administered.

In some embodiments, the pharmaceutical compositions provided herein are administered as a tablet. In some embodiments, the pharmaceutical compositions provided herein are administered as a capsule. In some embodiments, the pharmaceutical compositions provided herein are administered as an injection. In some embodiments, the pharmaceutical compositions provided herein are administered as an I.V. injection or infusion.

In some embodiments, the pharmaceutical compositions provided herein are administered as an I.V. infusion over a period of about 10 minutes. In some embodiments, the pharmaceutical compositions provided herein are administered as an I.V. infusion over a period of about 15 minutes. In some embodiments, the pharmaceutical compositions provided herein are administered as an I.V. infusion over a period of about 20 minutes. In some embodiments, the pharmaceutical compositions provided herein are administered as an I.V. infusion over a period of about 30 minutes. In some embodiments, the pharmaceutical compositions provided herein are administered as an I.V. infusion over a period of about 45 minutes. In some embodiments, the pharmaceutical compositions provided herein are administered as an I.V. infusion over a period of about one hour. In some embodiments, the pharmaceutical compositions provided herein are administered as an I.V. infusion over a period of about 90 minutes. In some embodiments, the pharmaceutical compositions provided herein are administered as an I.V. infusion over a period of about two hours. In some embodiments, the pharmaceutical compositions provided herein are administered as an I.V. infusion over a period of about three hours. In some embodiments, the pharmaceutical compositions provided herein are administered as an I.V. infusion over a period of up to about three hours. In some embodiments, the pharmaceutical compositions provided herein are administered as an I.V. infusion over a period of at least three hours. In some embodiments, the pharmaceutical compositions provided herein are administered as an I.V. infusion over a period of at least 30 minutes. In some embodiments, the pharmaceutical compositions provided herein are administered as an I.V. infusion over a period of at least 2 hours. In some embodiments, the pharmaceutical compositions provided herein are administered as an I.V. infusion over a period of up to 2 hours.

In some embodiments, the pharmaceutical compositions provided herein are administered as an I.V. infusion over a period of up to 30 minutes.

In some embodiments, a loading dose followed by a maintenance dose of the pharmaceutical compositions provided herein is administered. In some embodiments, the loading dose and the maintenance dose are both administered by I.V. infusion. In some embodiments, the loading dose and the maintenance dose are both administered orally (PO). In some embodiments, the loading dose is administered by I.V. infusion and the maintenance dose is administered orally (PO). In some embodiments, a loading dose comprising about 2,000 mg of a compound of Formula (I), or an isotopic variant, tautomer, pharmaceutically acceptable salt, solvate, or hydrate thereof is administered by I.V. infusion. In some embodiments, a loading dose comprising about 1,000 mg of of a compound of Formula (I), or an isotopic variant, tautomer, pharmaceutically acceptable salt, solvate, or hydrate thereof is administered twice daily (BID) by I.V. infusion. In some embodiments, a loading dose comprising about 1,000 mg of a compound of Formula (I), or an isotopic variant, tautomer, pharmaceutically acceptable salt, solvate, or hydrate thereof is administered BID by I.V. infusion on the first day of treatment. In some embodiments, a loading dose comprising about 1,000 mg of a compound of Formula (I), or an isotopic variant, tautomer, pharmaceutically acceptable salt, solvate, or hydrate thereof is administered BID by I.V. infusion on the first day of treatment only. In some embodiments, a loading dose comprising about 1,000 mg of of a compound of Formula (I), or an isotopic variant, tautomer, pharmaceutically acceptable salt, solvate, or hydrate thereof is administered BID I.V. by 2-hour or 3-hour infusion. In some embodiments, a maintenance dose comprising about 600 mg of a compound of Formula (I), or an isotopic variant, tautomer, pharmaceutically acceptable salt, solvate, or hydrate thereof is administered QD by I.V. infusion. In some embodiments, a maintenance dose comprising about 600 mg of a compound of Formula (I), or an isotopic variant, tautomer, pharmaceutically acceptable salt, solvate, or hydrate thereof is administered QD by I.V. infusion starting on the second day of treatment. In some embodiments, a maintenance dose comprising about 600 mg of the pharmaceutical compositions provided herein is administered QD by 1-hour or 2-hour I.V. infusion. In some embodiments, a maintenance dose comprising about 800 mg of a compound of Formula (I), or an isotopic variant, tautomer, pharmaceutically acceptable salt, solvate, or hydrate thereof is administered QD PO. In some embodiments, a 1,000 mg I.V. infusion BID (loading dose) followed by a 600 mg I.V. infusion QD (maintenance dose) of a compound of Formula (I), or an isotopic variant, tautomer, pharmaceutically acceptable salt, solvate, or hydrate thereof are administered. In some embodiments, a 1,000 mg BID I.V. 2-hour or 3-hour infusion (loading dose) followed by a 600 mg I.V. QD 1-hour, 2-hour, or 3-hour infusion (maintenance dose) of a compound of Formula (I), or an isotopic variant, tautomer, pharmaceutically acceptable salt, solvate, or hydrate thereof are administered. In some embodiments, a 1,000 mg BID I.V. 3-hour infusion (loading dose) followed by a 600 mg I.V. QD 3-hour infusion (maintenance dose) of a compound of Formula (I), or an isotopic variant, tautomer, pharmaceutically acceptable salt, solvate, or hydrate thereof are administered. In some embodiments, a 1,000 mg BID I.V. 3-hour infusion (loading dose) followed by a 800 mg PO QD (maintenance dose) of a compound of Formula (I), or an isotopic variant, tautomer, pharmaceutically acceptable salt, solvate, or hydrate thereof are administered. In some embodiments, a 1,000 mg BID I.V. loading dose by 2-hour or 3-hour I.V. infusion is administered where the second dose is administered from about 9 to about 12 hours after the first dose.

In some embodiments, the pharmaceutical compositions provided herein are administered administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

In some embodiments, the pharmaceutical compositions provided herein are administered administered daily, every other day, every other day 3 times a week, every 2 weeks, every 3 weeks, every 4 weeks, every 5 weeks, every 3 days, every 4 days, every 5 days, every 6 days, weekly, bi-weekly, 3 times a week, 4 times a week, 5 times a week, 6 times a week, once a month, twice a month, 3 times a month, once every 2 months, once every 3 months, once every 4 months, once every 5 months, or once every 6 months.

In some instances, the method for the administration of multiple compounds (e.g., a compound of Formula (I) or an isotopic variant, tautomer, pharmaceutically acceptable salt, solvate, or hydrate thereof and an antifungal agent) comprises administering compounds within 48 hours or less of each other. In some embodiments administration occurs within 24 hours, 16 hours, 12 hours, 11 hours, 10 hours, 9 hours, 8 hours, 7 hours, 6 hours, 5 hours, 4 hours, 3 hours, 2 hours, 1 hour, 30 minutes, 20 minutes, 15 minutes, or 10 minutes. In some instances, the compounds are administered simultaneously. One example of simultaneous administration is the injection of one compound immediately before, after, or during the oral administration of the second compound, immediately referring to a time less than about 5 minutes.

In some embodiments of the pharmaceutical compositions described herein, a second dose is administered about 10 minutes after the first dose, a second dose is administered about 15 minutes after the first dose, a second dose is administered about 20 minutes after the first dose, a second dose is administered about 30 minutes after the first dose, a second dose is administered about 40 minutes after the first dose, a second dose is administered about 45 minutes after the first dose, a second dose is administered about 1 hour after the first dose, a second dose is administered about 2 hours after the first dose, a second dose is administered about 3 hours after the first dose, a second dose is administered about 4 hours after the first dose, a second dose is administered about 5 hours after the first dose, a second dose is administered about 6 hours after the first dose, a second dose is administered about 7 hours after the first dose, a second dose is administered about 8 hours after the first dose, a second dose is administered about 9 hours after the first dose, a second dose is administered about 10 hours after the first dose, a second dose is administered about 11 hours after the first dose, a second dose is administered about 12 hours after the first dose, a second dose is administered about 13 hours after the first dose, a second dose is administered about 14 hours after the first dose, a second dose is administered about 15 hours after the first dose, a second dose is administered about 16 hours after the first dose, a second dose is administered about 17 hours after the first dose, a second dose is administered about 18 hours after the first dose, a second dose is administered about 19 hours after the first dose, a second dose is administered about 20 hours after the first dose, a second dose is administered about 21 hours after the first dose, a second dose is administered about 22 hours after the first dose, a second dose is administered about 23 hours after the first dose, or a second dose is administered about 24 hours after the first dose. In some embodiments of the pharmaceutical compositions described herein, the second dose is administered about 10 minutes, about 15 minutes, about 20 minutes, about 30 minutes, about 40 minutes, about 45 minutes, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 22, or about 48 hours after completion of administration of the first dose by I.V. infusion. In some embodiments of the pharmaceutical compositions, the second dose is administered about 10 minutes, about 15 minutes, about 20 minutes, about 30 minutes, about 40 minutes, about 45 minutes, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 22, or about 48 after initiation of administration of the first dose by I.V. infusion.

In some embodiments, the pharmaceutical compositions described herein are administered in combination with an antifungal agent. In some embodiments, the pharmaceutical compositions described herein are administered before the antifungal. In some embodiments, the pharmaceutical compositions described herein are administered after the antifungal. In some embodiments, the pharmaceutical compositions described herein are administered simultaneously with the antifungal agent. In some embodiments, the pharmaceutical compositions described herein and the antifungal agent are bout administered as an I.V. infusion. In some embodiments, the pharmaceutical compositions described herein and the antifungal agent are both administered orally. In some embodiments, the pharmaceutical compositions described herein are administered orally and the antifungal agent is administered as an I.V. infusion. In some embodiments, the pharmaceutical compositions described herein are administered as an I.V. infusion and the antifungal agent is administered orally. In some embodiments, the pharmaceutical compositions described herein and the antifungal agent are administered orally. In some embodiments, the pharmaceutical compositions described herein and the antifungal agent are administered by I.V. infusion.

In some embodiments, the pharmaceutical formulations provided herein are formulated to achieve, following administration after a minimum time period, a maximum plasma concentration ($C_{max}$) of from about 12,000 ng/mL to about 25,000 ng/mL (i.e., about 12 μg/mL to about 25 μg/mL). In some embodiments, the pharmaceutical formulations provided herein are formulated to achieve, following administration after a minimum time period, a $C_{max}$ of from about 12 μg/mL to about 13 μg/mL, 12 μg/mL to about 14 μg/mL, 12 μg/mL to about 15 μg/mL, 12 μg/mL to about 16 μg/mL, 12 μg/mL to about 17 μg/mL, 12 μg/mL to about 18 μg/mL, 12 μg/mL to about 19 μg/mL, 12 μg/mL to about 20 μg/mL, 12 μg/mL to about 21 μg/mL, 12 μg/mL to about 22 μg/mL, 12 μg/mL to about 23 μg/mL, 12 μg/mL to about 24 μg/mL, 13 μg/mL to about 14 μg/mL, 13 μg/mL to about 15 μg/mL, 13 μg/mL to about 16 μg/mL, 13 μg/mL to about 17 μg/mL, 13 μg/mL to about 18 μg/mL, 13 μg/mL to about 19 μg/mL, 13 μg/mL to about 20 μg/mL, 13 μg/mL to about 21 μg/mL, 13 μg/mL to about 22 μg/mL, 13 μg/mL to about 23 μg/mL, 13 μg/mL to about 24 μg/mL, 13 μg/mL to about 25 μg/mL, 14 μg/mL to about 15 μg/mL, 14 μg/mL to about 16 μg/mL, 14 μg/mL to about 17 μg/mL, 14 μg/mL to about 18 μg/mL, 14 μg/mL to about 19 μg/mL, 14 μg/mL to about 20 μg/mL, 14 μg/mL to about 21 μg/mL, 14 μg/mL to about 22 μg/mL, 14 μg/mL to about 23 μg/mL, 14 μg/mL to about 24 μg/mL, 14 μg/mL to about 25 μg/mL, 15 μg/mL to about 16 μg/mL, 15 μg/mL to about 17 μg/mL, 15 μg/mL to about 18 μg/mL, 15 μg/mL to about 19 μg/mL, 15 μg/mL to about 20 μg/mL, 15 μg/mL to about 21 μg/mL, 15 μg/mL to about 22 μg/mL, 15 μg/mL to about 23 μg/mL, 15 μg/mL to about 24 μg/mL, 15 μg/mL to about 25 μg/mL, 16 μg/mL to about 17 μg/mL, 16 μg/mL to about 18 μg/mL, 16 μg/mL to about 19 μg/mL, 16 μg/mL to about 20 μg/mL, 16 μg/mL to about 21 μg/mL, 16 μg/mL to about 22 μg/mL, 16 μg/mL to about 23 μg/mL, 16 μg/mL to about 24 μg/mL, 16 μg/mL to about 25 μg/mL, 18 μg/mL to about 19 μg/mL, 18 μg/mL to about 20 μg/mL, 18 μg/mL to about 21 μg/mL, 18 μg/mL to about 22 μg/mL, 18 μg/mL to about 23 μg/mL, 18 μg/mL to about 24 μg/mL, 18 μg/mL to about 25 μg/mL, 19 μg/mL to about 20 μg/mL, 19 μg/mL to about 21 μg/mL, 19 μg/mL to about 22 μg/mL, 19 μg/mL to about 23 μg/mL, 19 μg/mL to about 24 μg/mL, 19 μg/mL to about 25 μg/mL, 20 μg/mL to about 21 μg/mL, 20 μg/mL to about 22 μg/mL, 20 μg/mL to about 23 μg/mL, 20 μg/mL to about 24 μg/mL, 20 μg/mL to about 25 μg/mL, 21 μg/mL to about 22 μg/mL, 21 μg/mL to about 23 μg/mL, 21 μg/mL to about 24 μg/mL, 21 μg/mL to about 25 μg/mL, 22 μg/mL to about 23 μg/mL, 22 μg/mL to about 24 μg/mL, 22 μg/mL to about 25 μg/mL, 23 μg/mL to about 24 μg/mL, 23 μg/mL to about 25 μg/mL, or 24 μg/mL to about 25 μg/mL.

In some embodiments, the pharmaceutical formulations provided herein are formulated to achieve, following administration after a minimum time period, a $C_{max}$ of about 1 μg/mL, about 2 μg/mL, about 3 μg/mL, about 4 μg/mL, about 5 μg/mL, about 6 μg/mL, about 7 μg/mL, about 8 μg/mL, about 9 μg/mL, about 10 μg/mL, about 11 μg/mL, about 12 μg/mL, about 13 μg/mL, about 14 μg/mL, about 15 μg/mL, about 16 μg/mL, about 17 μg/mL, about 18 μg/mL, about 19 μg/mL, about 20 μg/mL, about 21 μg/mL, about 22 μg/mL, about 23 μg/mL, about 24 μg/mL, about 25 μg/mL, about 26 μg/mL, about 27 μg/mL, about 28 μg/mL, about 29 μg/mL, or about 30 g/mL.

In some embodiments, the pharmaceutical spray formulation is formulated to achieve, following administration after a minimum time period, a $C_{max}$ of at least about 10 μg/mL, about 11 μg/mL, about 12 μg/mL, about 13 μg/mL, about 14 μg/mL, about 15 μg/mL, about 16 μg/mL, about 17 μg/mL, about 18 μg/mL, about 19 μg/mL, about 20 μg/mL, about 21 μg/mL, about 22 μg/mL, about 23 μg/mL, about 24 μg/mL, about 25 μg/mL.

Fungal Diseases

In some embodiments, the fungal disease is selected from the group consisting of aspergillosis, blastomycosis, candidiasis, coccidioidomycosis (Valley Fever), cryptococcosis, histoplasmosis, mucormycosis, *Pneumocystis* pneumonia (PCP), ringworm, sporotrichosis, and talaromycosis.

In some embodiments, the fungal disease is aspergillosis. In some embodiments, aspergillosis is allergic bronchopulmonary aspergillosis (abpa), allergic *aspergillus* sinusitis, chronic pulmonary aspergillosis, invasive aspergillosis or cutaneous (skin) aspergillosis. In some embodiments, the subject has an aspergilloma.

In some embodiments, the fungal disease is blastomycosis. In some embodiments, the fungal disease is candidiasis. In some embodiments, candidiasis is oropharyngeal candidiasis (thrush), vulvovaginal candidiasis (vaginal candidiasis), fungemia, or invasive candidiasis. In some embodiments, the fungal disease is coccidioidomycosis (Valley Fever). In some embodiments, coccidioidomycosis is acute coccidioidomycosis (primary pulmonary coccidioidomycosis), chronic coccidioidomycosis, or disseminated coccidioidomycosis, including primary cutaneous coccidioidomycosis. In some embodiments, the fungal disease is cryptococcosis. In some embodiments, cryptococcosis is wound or cutaneous cryptococcosis, pulmonary cryptococcosis, or cryptococcal meningitis. In some embodiments, the fungal disease is a fungal eye infection. In some embodiments, the fungal eye infection is fungal keratitis, fungal exogenous endophthalmitis, or fungal endogenous endophthalmitis. In some embodiments, the fungal disease is histoplasmosis. In some embodiments, histoplasmosis is acute histoplasmosis. In some embodiments, histoplasmosis is chronic histoplasmosis. In some embodiments, the fungal disease is mucormycosis. In some embodiments, mucormycosis is rhinocerebral (sinus and brain) mucormycosis, pulmonary (lung) mucormycosis, gastrointestinal mucormycosis, cutaneous (skin) mucormycosis, or disseminated mucormycosis. In some embodiments, the fungal disease is *Pneumocystis* pneumonia (PCP). In some embodiments, the fungal disease is ringworm. In some embodiments, the ringworm is tinea pedis, tinea cruris, tinea capitis, tinea barbae, tinea manuum, tinea unguium, or tinum corporis. In some embodiments, the ringworm is caused by a type of fungi including *Trichophyton, Microsporum*, or *Epidermophyton*. In some embodiments, the fungal disease is sporotrichosis. In some embodiments, sporotrichosis is cutaneous (skin) sporotrichosis, pulmonary (lung) sporotrichosis, or disseminated sporotrichosis. In some embodiments, the fungal disease is talaromycosis.

In some embodiments, the fungal disease or infection is caused by a *Cryptococcus, Aspergillus, Candida, Coccidioides, Blastomyces, Ajellomyces, Histoplasma, Rhizopus, Apophysomyces, Absidia, Saksenaea, Rhizomucor pusillus, Entomophthora, Conidiobolus, Basidiobolus, Sporothrix, Pneumocystis jirovecii, Talaromyces marneffei, Asclepias, Fusarium*, or *Scedosporium* fungus/species. In some embodiments, the fungal disease is caused by a fungal species including, but not limited to, *Aspergillus fumigatus, Aspergillus flavus, Aspergillus niger, Aspergillus terreus, Blastomyces dermatitidis, Ajellomyces dermatitidis, Candida albicans, Candida auris, Candida glabrata, Candida parapsilosis, Candida rugosa, Candida tropicalis, Coccidioides immitis, Coccidioides posadasii, Cryptococcus neoformans, Cryptococcus gattii, Histoplasma capsulatum, Rhizopus stolonifer, Rhizopus arrhizus, Mucor indicus, Cunninghamella bertholletiae, Apophysomyces elegans, Absidia* species, *Saksenaea* species, *Rhizomucor pusillus, Entomophthora* species, *Conidiobolus* species, *Basidiobolus* species, *Sporothrix schenckii, Pneumocystis jirovecii, Talaromyces marneffei, Asclepias albicans, Fusarium solani, Scedosporium apiospermum*, and *Rhizomucor pusillus*. In some embodiments, the fungal disease is caused by the fungal species *Aspergillus fumigatus*. In some embodiments, the fungal disease is caused by the fungal species *Candida albicans*. In some embodiments, the fungal disease is caused by the fungal species *Fusarium solani*. In some embodiments, the fungal disease is caused by the fungal species *Mucor indicus*. In some embodiments, the fungal disease is caused by the fungal species *Scedosporium apiospermum*. In some embodiments, the fungal disease is caused by the fungal species *Cryptococcus neoformans*. In some embodiments, the fungal disease is caused by the fungal species *Cryptococcus gattii*. In some embodiments, the fungal disease is caused by the fungal species *Candida auris*.

In some embodiments, the fungal disease or infection is caused by a *Aspergillus fumigatus, Blastomyces, Ajellomyces, Candida, Coccidioides, Cryptococcus, Histoplasm, Rhizopus muco, Cunninghamell, Apophysomyces, Absidi, Saksenaea, Entomophthora, Conidiobolus, Basidiobolus, Sporothrix, Pneumocystis, Talaromyces, Asclepias, Fusarium, Scedosporium* fungus or from a fungus from the Mucorales order, or any combination thereof.

In some embodiments, the fungal disease or infection is caused by a *Cryptococcus, Aspergillus, Candida, Fusarium, Scedosporium* fungus or from a fungus from the Mucorales order, or any combination thereof. In some embodiments, the fungal disease or infection is caused by *Aspergillus fumigatus, Aspergillus flavus, Blastomyces dermatitidis, Ajellomyces dermatitidi, Candida albican, Candida glabrata, Candida rugosa, Candida auris, Coccidioides immitis, Coccidioides posadasii, Cryptococcus neoformans, Cryptococcus gattii, Histoplasma capsulatum, Rhizopus stolonifer, Rhizopus arrhizus, Mucor indicus, Cunninghamella bertholletiae, Apophysomyces elegans, Absidia* species, *Saksenaea* species, *Rhizomucor pusillus, Entomophthora* species, *Conidiobolus* species, *Basidiobolus* species, *Sporothrix schenckii, Pneumocystis jirovecii, Talaromyces marneffei, Asclepias albicans, Fusarium solani, Scedosporium apiospermum, Rhizomucor pusillus*, or any combination thereof.

In some embodiments, a compound described herein is active against the fungal Gwt1 protein. This conserved enzyme catalyzes the glycosylphosphatidyl inositol (GPI) post-translational modification that anchors eukaryotic cell surface proteins to the cell membrane. In yeasts, GPI mediates cross-linking of cell wall mannoproteins to β-1,6-glucan. Inhibition of this enzyme in both *Candida albicans* and *Saccharomyces cerevisiae* has been shown to result in inhibition of maturation and localization of GPI-anchored mannoproteins thus demonstrating pleiotropic effects that include inhibition of fungal adherence to surfaces, inhibition of biofilm formation, inhibition of germ tube formation, severe growth defects, or lethality.

Subjects

In some embodiments, the subject is immunocompromised. In some embodiments, the subject is an immunocompromised human subject. In some embodiments, the human subject is under the age of 1 year. In some embodiments, the human subject is an infant under 1 month old. In some embodiments, the human subject is over the age of 70 years. In some embodiments, the subject is infected with HIV/AIDS. In some embodiments, the subject is undergoing or has undergone cancer chemotherapy treatment. In some embodiments, the subject is undergoing or has undergone corticosteroid treatment. In some embodiments, the subject is undergoing or has undergone TNF inhibitor treatment. In some embodiments, the subject is a transplant recipient. In some embodiments, the subject is a recipient of a hematopoietic stem-cell transplant, bone marrow transplant, lung transplant, liver transplant, heart transplant, kidney transplant, pancreas transplant or a combination thereof. In some embodiments, the subject is a recipient of a hematopoietic stem-cell transplant. In some embodiments, the subject is a recipient of a bone marrow transplant. In some embodiments, the subject is a recipient of a lung transplant. In some embodiments, the subject is a recipient of a liver transplant. In some embodiments, the subject is a recipient of a heart transplant. In some embodiments, the subject is a recipient of a kidney transplant. In some embodiments, the subject is a recipient of a pancreas transplant.

In some embodiments, the subject is a vertebrate. In some embodiments, the vertebrate is a fish, an amphibian, a reptile, a bird, a marsupial, or a mammal. In some embodiments, the subject is a fish. In some embodiments, the subject is a mammal. In some embodiments, the mammal is a human. In some embodiments, the mammal is a dog. In some embodiments, the mammal is a cat. In some embodiments, the mammal is livestock. In some embodiments, the livestock is selected from the group consisting of cattle, sheep, goats, swine, poultry, bovine, and equine animals. In some embodiments, the subject is an invertebrate. In some embodiments, the invertebrate is an insect. In some embodiments, the subject is a plant.

It is frequently beneficial to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity. Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136 ($^9$): 3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

The compounds of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of the compounds of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In some embodiments, the dosage of the desired compound is contained in a "unit dosage form." The phrase "unit dosage form" refers to physically discrete units, each unit including a predetermined amount of the compound (e.g., a compound of Formula (I) or an isotopic variant, tautomer, pharmaceutically acceptable salt, solvate, or hydrate thereof), sufficient to produce the desired effect. It will be appreciated that the parameters of a unit dosage form will depend on the particular agent and the effect to be achieved.

Combination Therapy

In certaininstances, the compound of Formula (I), or an isotopic variant, tautomer, pharmaceutically acceptable salt, solvate, or hydrate thereof; or a pharmaceutically acceptable salt thereof is administered in combination with a second therapeutic agent.

In some embodiments, the benefit experienced by a subject is increased by administering one of the compounds described herein with a second therapeutic agent (which also includes a therapeutic regimen) that also has therapeutic benefit.

In one embodiment, a compound of Formula (I), or an isotopic variant, tautomer, pharmaceutically acceptable salt, solvate, or hydrate thereof; or a pharmaceutically acceptable salt thereof is co-administered with a second therapeutic agent, wherein the compound of Formula (I), or an isotopic variant, tautomer, pharmaceutically acceptable salt, solvate, or hydrate thereof; or a pharmaceutically acceptable salt thereof and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the subject is simply additive of the two therapeutic agents, or the subject experiences a synergistic benefit.

In some embodiments, different therapeutically-effective dosages of the compounds disclosed herein will be utilized in formulating a pharmaceutical composition and/or in treatment regimens when the compounds disclosed herein are administered in combination with a second therapeutic agent.

Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), or an isotopic variant, tautomer, pharmaceutically acceptable salt, solvate, or hydrate thereof; or a pharmaceutically acceptable salt thereof is initiated prior to, during, or after treatment with a second agent described herein, and continues until any time during treatment with the second agent or after termination of treatment with the second agent. It also includes treatments in which a compound of Formula (I), or an isotopic variant, tautomer, pharmaceutically acceptable salt, solvate, or hydrate thereof; or a pharmaceutically acceptable salt thereof and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g., the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously or approximately simultaneously with the second therapeutic agent, or sequentially.

In combination therapies, the multiple therapeutic agents (one of which is one of the compounds described herein) are administered in any order or even simultaneously or approximately simultaneously. If administration is simultaneous or approximately simultaneous, the multiple therapeutic agents are, by way of example only, provided in a single, unified form, or in multiple forms (e.g., as a single pill or as two separate pills).

The compounds of Formula (I), or an isotopic variant, tautomer, pharmaceutically acceptable salt, solvate, or hydrate thereof; or a pharmaceutically acceptable salt thereof as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the second therapeutic agent is antifungal agent. In some embodiments, the second therapeutic agent is an antifungal agent selected from the group consisting of: a polyene antifungal agent, an azole antifungal agent, an allylamine antifungal agent, and an echinocandin antifungal agent.

In some embodiments, the polyene antifungal agent is amphotericin B, candicidin, filipin, hamycin, natamycin, nystatin, or rimocidin.

In some embodiments, the azole antifungal agent is an imidazole, a triazole, or a thiazole. In some embodiments, the imidazole is bifonazole, butoconazole, clotrimazole, econazole, fenticonazole, isavuconazole, ketoconazole, luliconazole, miconazole, omoconazole, oxiconazole, sertaconazole, sulconazole, or tioconazole. In some embodiments, the triazole is albaconazole, efinaconazole, epoxiconazole, fluconazole, isavuconazole, itraconazole, posaconazole, propiconazole, ravuconazole, terconazole, or voriconazole. In some embodiments, the thiazole is abafungin.

In some embodiments, the allylamine antifungal agent is amorolfin, butenafine, naftifine, or terbinafine.

In some embodiments, the echinocandin antifungal agent is selected from the group consisting of: anidulafungin, caspofungin, micafungin and rezafungin.

In some embodiments, are methods for treating a subject with a fungal disease comprising administering to the subject a combination treatment of a compound of Formula (I), or an isotopic variant, tautomer, pharmaceutically acceptable salt, solvate, or hydrate thereof; or a pharmaceutically acceptable salt thereof and fluconazole, wherein the subject is selected from the group consisting of cattle, sheep, goats, swine, poultry, bovine, and equine animals.

In some embodiments, are methods for treating a subject with a fungal disease comprising administering to the subject a combination treatment of a compound of Formula (I), or an isotopic variant, tautomer, pharmaceutically acceptable salt, solvate, or hydrate thereof; or a pharmaceutically acceptable salt thereof and ketoconazole, wherein the subject is selected from the group consisting of cattle, sheep, goats, swine, poultry, bovine, and equine animals.

In some embodiments, are methods for treating a subject with a fungal disease comprising administering to the subject a combination treatment of a compound of Formula (I), or an isotopic variant, tautomer, pharmaceutically acceptable salt, solvate, or hydrate thereof; or a pharmaceutically acceptable salt thereof and itraconazole, wherein the subject is selected from the group consisting of cattle, sheep, goats, swine, poultry, bovine, and equine animals.

Additional Embodiments

Embodiments include Embodiments 1-212 following.

Embodiment 1. A pharmaceutical composition, comprising:

(i) a compound of Formula (I):

(I)

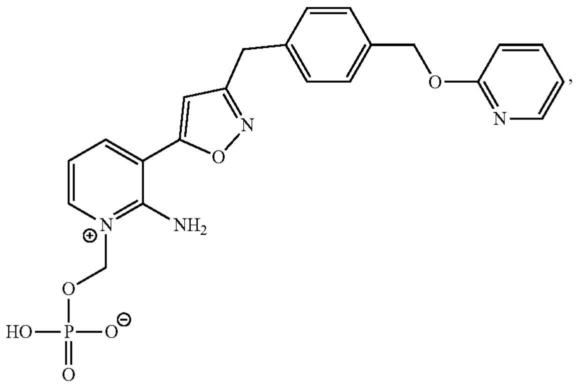

or an isotopic variant, tautomer, pharmaceutically acceptable salt, solvate, or hydrate thereof; and (ii) at least one pharmaceutically acceptable excipient, wherein the pharmaceutical composition is in a dosage form for oral dosing or administration.

Embodiment 2. A pharmaceutical composition, comprising:

(i) fine particles of a compound of Formula (I):

(I)

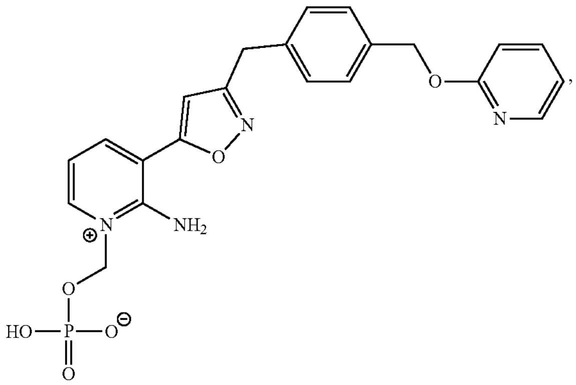

or an isotopic variant, tautomer, pharmaceutically acceptable salt, solvate, or hydrate thereof; and (ii) at least one pharmaceutically acceptable excipient, wherein the pharmaceutical composition is in a dosage form for oral dosing or administration or in a dosage form for inhalation delivery.

Embodiment 3. The pharmaceutical composition of Embodiment 1 or 2, wherein the compound of Formula (I) or an isotopic variant, tautomer, pharmaceutically acceptable salt, solvate, or hydrate thereof; is crystalline, microcrystalline, amorphous, or lyophilized.

Embodiment 4. The pharmaceutical composition of Embodiment 3, wherein the compound of Formula (I) or an isotopic variant, tautomer, pharmaceutically acceptable salt, solvate, or hydrate thereof; is crystalline.

Embodiment 5. The pharmaceutical composition Embodiment 3, wherein the compound of Formula (I) or an isotopic variant, tautomer, pharmaceutically acceptable salt, solvate, or hydrate thereof; is amorphous.

Embodiment 6. The pharmaceutical composition of Embodiment 3, wherein the compound of Formula (I) or an isotopic variant, tautomer, pharmaceutically acceptable salt, solvate, or hydrate thereof; is lyophilized.

Embodiment 7. The pharmaceutical composition of any one of Embodiments 2-6, wherein the particles are micronized.

Embodiment 8. The pharmaceutical composition of Embodiment 7, wherein the particles have a particle size of from about 1 μm to about 750 μm.

Embodiment 9. The pharmaceutical composition of Embodiment 7 or 8, wherein at least about 10% of the particles have a particle size of from about 1 μm to about 750 μm.

Embodiment 10. The pharmaceutical composition of any one of Embodiments 7-9, wherein at least about 20% of the particles have a particle size of from about 1 μm to about 750 μm.

Embodiment 11. The pharmaceutical composition of any one of Embodiments 7-10, wherein at least about 30% of the particles have a particle size of from about 1 μm to about 750 μm.

Embodiment 12. The pharmaceutical composition of any one of Embodiments 7-11, wherein at least about 40% of the particles have a particle size of from about 1 μm to about 750 μm.

Embodiment 13. The pharmaceutical composition of any one of Embodiments 7-12, wherein at least about 50% of the particles have a particle size of from about 1 μm to about 750 μm.

Embodiment 14. The pharmaceutical composition of any one of Embodiments 7-13, wherein at least about 60% of the particles have a particle size of from about 1 μm to about 750 μm.

Embodiment 15. The pharmaceutical composition of any one of Embodiments 7-14, wherein at least about 70% of the particles have a particle size of from about 1 μm to about 750 μm.

Embodiment 16. The pharmaceutical composition of any one of Embodiments 7-15, wherein at least about 80% of the particles have a particle size of from about 1 μm to about 750 μm.

Embodiment 17. The pharmaceutical composition of any one of Embodiments 7-16, wherein at least about 90% of the particles have a particle size of from about 1 μm to about 750 μm.

Embodiment 18. The pharmaceutical composition of any one of Embodiments 7-17, wherein at least about 95% of the particles have a particle size of from about 1 μm to about 750 μm.

Embodiment 19. The pharmaceutical composition of any one of Embodiments 2-6, wherein the particles are nanomilled.

Embodiment 20. The pharmaceutical composition of Embodiment 19 wherein the particles have a particle size of from about 1 nm to about 750 nm.

Embodiment 21. The pharmaceutical composition of Embodiment 19 or 20, wherein at least about 10% of the particles have a particle size of from 1 nm to about 750 nm.

Embodiment 22. The pharmaceutical composition of any one of Embodiments 19-21, wherein at least about 20% of the particles have a particle size of from 1 nm to about 750 nm.

Embodiment 23. The pharmaceutical composition of any one of Embodiments 19-22, wherein at least about 30% of the particles have a particle size of from 1 nm to about 750 nm.

Embodiment 24. The pharmaceutical composition of any one of Embodiments 19-23, wherein at least about 40% of the particles have a particle size of from 1 nm to about 750 nm.

Embodiment 25. The pharmaceutical composition of any one of Embodiments 19-24, wherein at least about 50% of the particles have a particle size of from 1 nm to about 750 nm.

Embodiment 26. The pharmaceutical composition of any one of Embodiments 19-25, wherein at least about 60% of the particles have a particle size of from 1 nm to about 750 nm.

Embodiment 27. The pharmaceutical composition of any one of Embodiments 19-26, wherein at least about 70% of the particles have a particle size of from 1 nm to about 750 nm.

Embodiment 28. The pharmaceutical composition of any one of Embodiments 19-27, wherein at least about 80% of the particles have a particle size of from 1 nm to about 750 nm.

Embodiment 29. The pharmaceutical composition of any one of Embodiments 19-28, wherein at least about 90% of the particles have a particle size of from 1 nm to about 750 nm.

Embodiment 30. The pharmaceutical composition of any one of Embodiments 19-29, wherein at least about 95% of the particles have a particle size of from 1 nm to about 750 nm.

Embodiment 31. The pharmaceutical composition of any one of Embodiments 1-30, wherein the dosage form is a self-microemulsifying drug delivery system (SMEDDS).

Embodiment 32. The pharmaceutical composition of any one of Embodiments 1-30, wherein the dosage form is a self-emulsifying drug delivery system (SEDDS).

Embodiment 33. The pharmaceutical composition of any one of Embodiments 1-30, wherein the dosage form is a spray-dried dispersion dosage form.

Embodiment 34. The pharmaceutical composition of any one of Embodiments 1-30, wherein the dosage form is a hot melt granulation dosage form.

Embodiment 35. The pharmaceutical composition of any one of Embodiments 1-30, wherein the dosage form is a hot melt extrusion dosage form.

Embodiment 36. The pharmaceutical composition of any one of Embodiments 1-30, wherein the dosage form is a microprecipitated bulk powder (MBP) dosage form.

Embodiment 37. The pharmaceutical composition of any one of Embodiments 1-30, wherein the dosage form is a liquid.

Embodiment 38. The pharmaceutical composition of Embodiment 37, wherein the dosage form is a suspension, solution, syrup, or elixir.

Embodiment 39. The pharmaceutical composition of Embodiment 37 or 38, wherein the dosage form is a nanosuspension.

Embodiment 40. The pharmaceutical composition of any one of Embodiments 37-39, wherein the dosage form is a suspension.

Embodiment 41. The pharmaceutical composition of any one of Embodiment 40, wherein the dosage form is a colloidal suspension.

Embodiment 42. The pharmaceutical composition of any one of Embodiments 1-36, wherein the dosage form is a solid dosage form.

Embodiment 43. The pharmaceutical composition of any one of Embodiments 1-36 or 42, wherein the dosage form is a granulate or powder.

Embodiment 44. The pharmaceutical composition of Embodiment 1-36 or 42-43, wherein the dosage form is a tablet or a capsule.

Embodiment 45. The pharmaceutical composition of Embodiment 44, wherein the tablet or capsule has an enteric coating.

Embodiment 46. The pharmaceutical composition of Embodiment 44, wherein the dosage form is a tablet.

Embodiment 47. The pharmaceutical composition of Embodiment 44, wherein the tablet is an osmotic floating tablet.

Embodiment 48. The pharmaceutical composition of Embodiment 47, wherein the capsule is a liquid-filled hard capsule or a soft gelatin capsule.

Embodiment 49. The pharmaceutical composition of any one of Embodiments 1-48, wherein the dosage form is a modified-release dosage form.

Embodiment 50. The pharmaceutical composition of Embodiment 49, wherein the modified-release dosage form is a delayed-release dosage form, an extended-release (ER) dosage form, or a targeted-release dosage form.

Embodiment 51. The pharmaceutical composition of Embodiment 50, wherein the ER dosage form is a sustained-release (SR) dosage form or controlled-release (CR) dosage form.

Embodiment 52. The pharmaceutical composition of any one of Embodiments 1-48, wherein the dosage form is an immediate release dosage form Embodiment 53. The pharmaceutical composition of any one of Embodiments 1-52, wherein the pharmaceutical composition comprises from about 10 mg to about 1,000 mg of a compound of Formula (I), or an isotopic variant, tautomer, pharmaceutically acceptable salt, solvate, or hydrate thereof.

Embodiment 54. The pharmaceutical composition of any one of Embodiments 1-52, wherein the pharmaceutical composition comprises from about 50 mg to about 600 mg of a compound of Formula (I), or an isotopic variant, tautomer, pharmaceutically acceptable salt, solvate, or hydrate thereof.

Embodiment 55. The pharmaceutical composition of any one of Embodiments 1-52, wherein the pharmaceutical composition comprises from about 50 mg to about 150 mg, about 150 mg to about 250 mg, about 250 mg to about 350 mg, about 350 mg to about 450 mg, about 450 mg to about 550 mg, about 550 mg to about 650 mg, about 650 mg to about 750 mg, about 850 mg to about 950 mg, or about 950 mg to about 1050 mg of a compound of Formula (I), or an isotopic variant, tautomer, pharmaceutically acceptable salt, solvate, or hydrate thereof.

Embodiment 56. The pharmaceutical composition of any one of Embodiments 1-52, wherein the pharmaceutical composition comprises about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg of a compound of Formula (I), or an isotopic variant, tautomer, pharmaceutically acceptable salt, solvate, or hydrate thereof.

Embodiment 57. The pharmaceutical composition of any one of Embodiments 1-52, wherein the pharmaceutical composition comprises about 50 mg, about 100 mg, about 150 mg, about 200 mg, about 250 mg, about 300 mg, about 350 mg, about 400 mg, or about 500 mg of a compound of Formula (I), or an isotopic variant, tautomer, pharmaceutically acceptable salt, solvate, or hydrate thereof.

Embodiment 58. The pharmaceutical composition of any one of Embodiments 1-57, wherein the at least one pharmaceutically acceptable excipient is a filler, a disintegrant, a binder, a glidant, a lubricant, or any combination thereof.

Embodiment 59. The pharmaceutical composition of any one of Embodiments 1-58, wherein the at least one pharmaceutically acceptable excipient is, microcrystalline cellulose, pregelatinized starch, povidone, magnesium stearate, colloidal silicon dioxide, or any combination thereof.

Embodiment 60. The pharmaceutical composition of any one of Embodiments 1-59, wherein the pharmaceutical composition is stable for up to 36 months at a temperature of from about 2° C. to about 25° C.

Embodiment 61. The pharmaceutical composition of Embodiment 60, wherein the pharmaceutical composition is stable for a period of from about 24 to about 36 months at a temperature of about 2° C. to about 8° C.

Embodiment 62. The pharmaceutical composition of any one of Embodiments 1-61, wherein the pharmaceutical composition is substantially free of impurities.

Embodiment 63. The pharmaceutical composition of any one of Embodiments 1-62, wherein the pharmaceutical composition is at least about 90% pure.

Embodiment 64. The pharmaceutical composition of any one of Embodiments 1-63, wherein the pharmaceutical composition is at least about 95% pure.

Embodiment 65. The pharmaceutical composition of any one of Embodiments 1-64, wherein the pharmaceutical composition is at least about 96% pure.

Embodiment 66. The pharmaceutical composition of any one of Embodiments 1-65, wherein the pharmaceutical composition is at least about 97% pure.

Embodiment 67. The pharmaceutical composition of any one of Embodiments 1-66, wherein the pharmaceutical composition is at least about 98% pure.

Embodiment 68. The pharmaceutical composition of any one of Embodiments 1-67, wherein the pharmaceutical composition is at least about 99% pure.

Embodiment 69. The pharmaceutical composition of any one of Embodiments 1-68, wherein the pharmaceutical composition is at least about 99.1%, about 99.2%, about 99.3%, about 99.4%, about 99.5%, about 99.6%, about 99.7%, about 99.8%, about 99.9%, or about 100% pure.

Embodiment 70. The pharmaceutical composition of any one of Embodiments 1-62, wherein the pharmaceutical composition comprises up to about 10% (w/w) of at least one impurity.

Embodiment 71. The pharmaceutical composition of any one of Embodiments 1-62 or 70, wherein the pharmaceutical composition comprises less than about 10% (w/w), about 9% (w/w), about 8% (w/w), about 7% (w/w), about 6% (w/w), about 5% (w/w), about 4% (w/w), about 3% (w/w), about 2% (w/w), or about 1% (w/w) of at least one impurity.

Embodiment 72. The pharmaceutical composition of any one of Embodiments 1-62 or 70-71, wherein the pharmaceutical composition comprises less than about 5% (w/w), about 4% (w/w), about 3% (w/w), about 2% (w/w), or about 1% (w/w) of at least one impurity.

Embodiment 73. The pharmaceutical composition of any one of Embodiments 70-72, wherein the pharmaceutical composition comprises less than about 0.9% (w/w), about 0.8% (w/w), about 0.7% (w/w), about 0.6% (w/w), about 0.5% (w/w), about 0.4% (w/w), about 0.3% (w/w), about 0.2% (w/w), or about 0.1% (w/w) of at least one impurity.

Embodiment 74. The pharmaceutical composition of any one of Embodiments 70-72, wherein the at least one impurity is a degradant.

Embodiment 75. The pharmaceutical composition of any one of Embodiments 70-72, wherein the at least one impurity is:

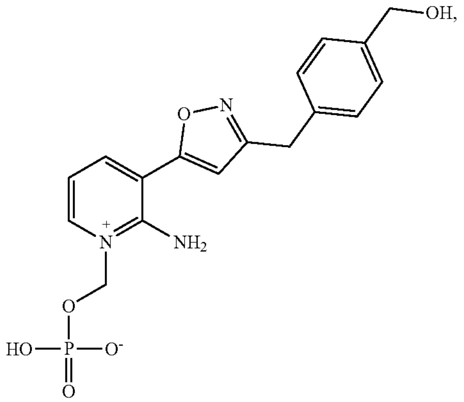

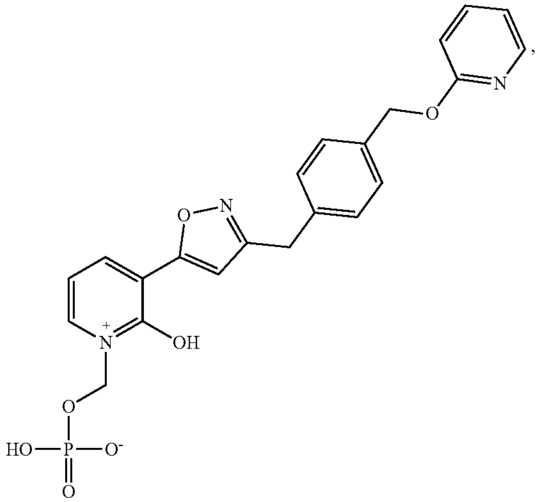

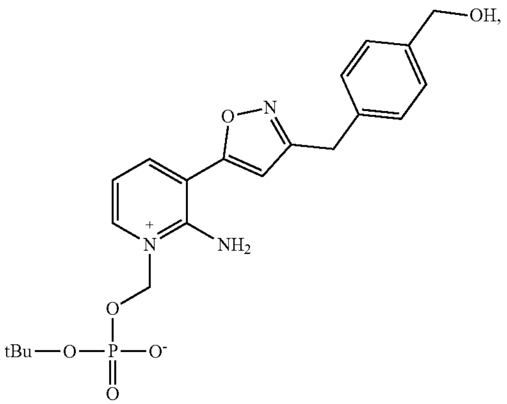

-continued

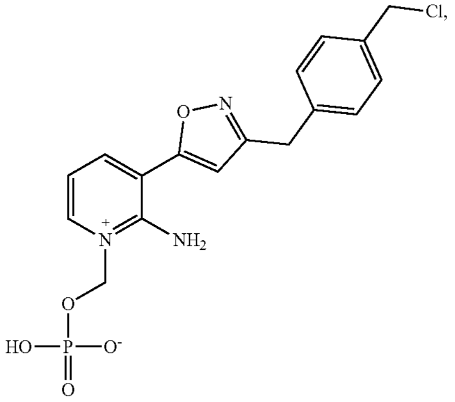

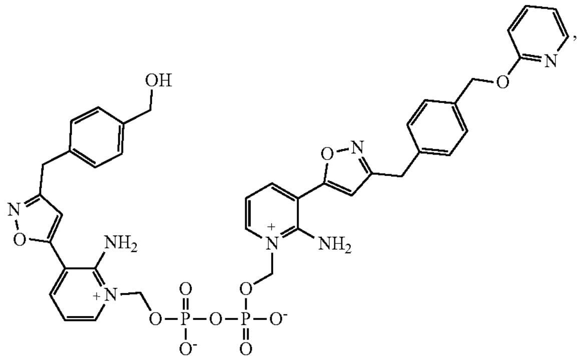

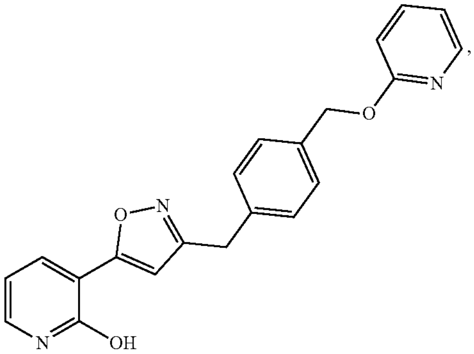

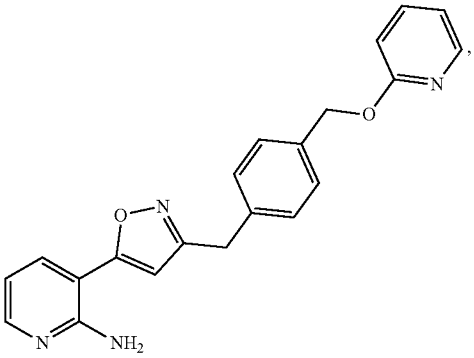

-continued

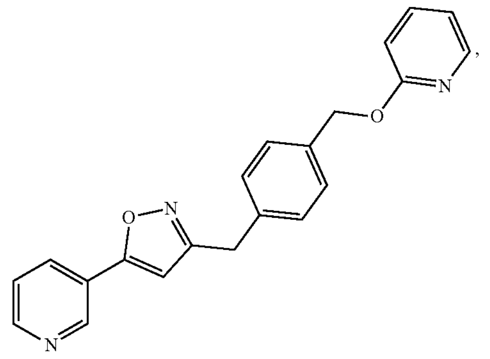

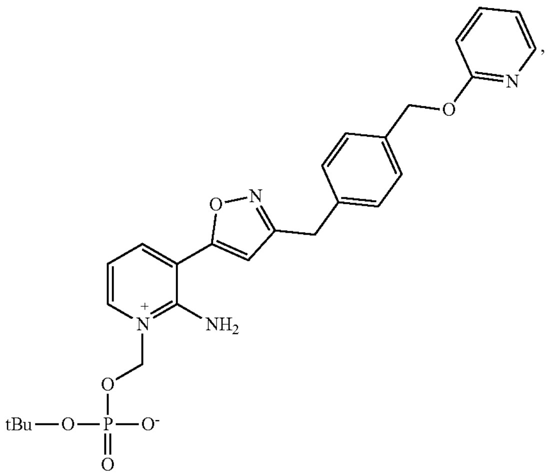

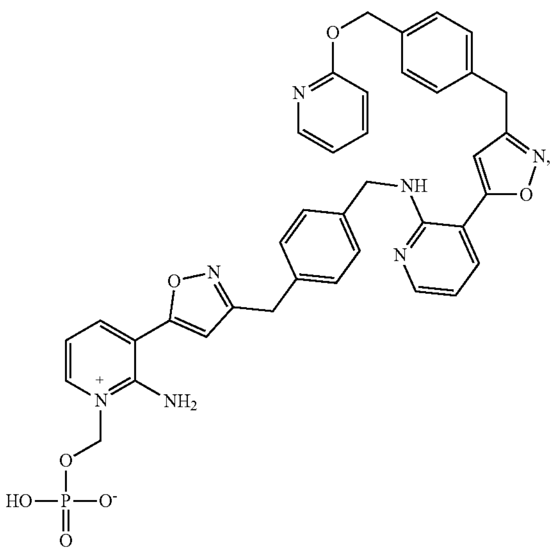

-continued

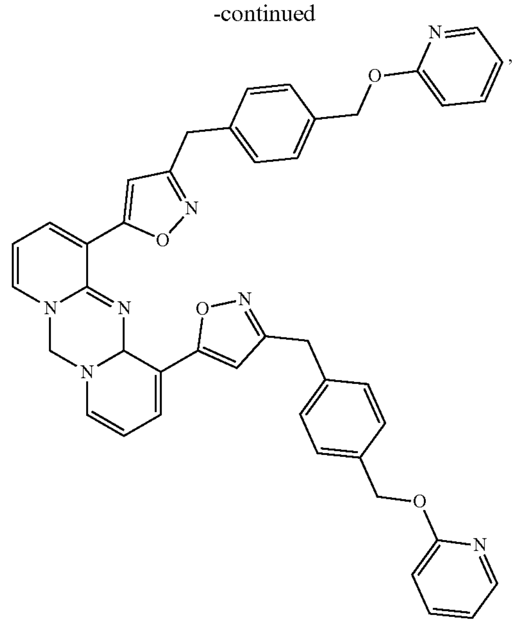

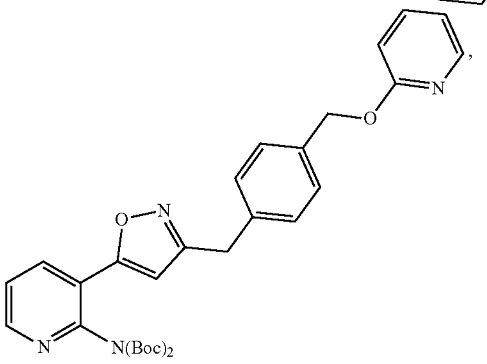

or any combination thereof.

Embodiment 76. The pharmaceutical composition of any one of Embodiments 70-72, wherein the at least one impurity is:

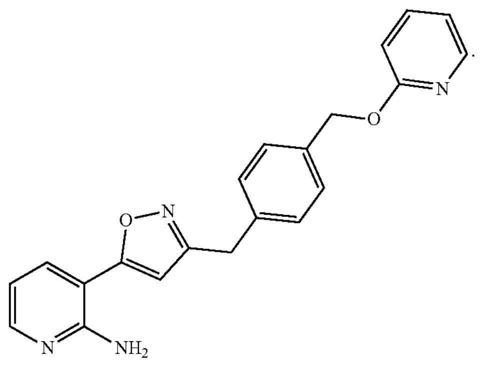

Embodiment 77. The pharmaceutical composition of any one of Embodiments 1-62, the pharmaceutical composition comprises up to about 4.0% (w/w) total impurities.

Embodiment 78. The pharmaceutical composition of any one of Embodiments 1-62 or 77, the pharmaceutical composition comprises up to about 0.5% (w/w) of any individual impurity.

Embodiment 79. The pharmaceutical composition of any one of Embodiments 1-62 or 77-78, the pharmaceutical composition comprises up to about 1.5% (w/w) of the compound:

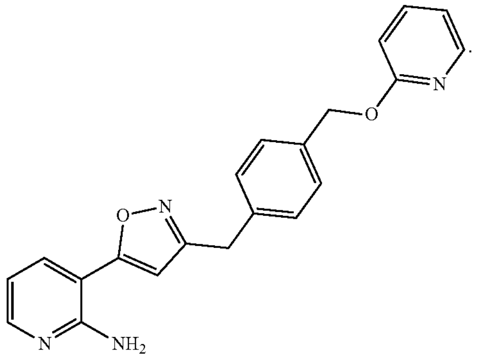 [SMILES: Nc1ncccc1-c1cc(Cc2ccc(COc3ccccn3)cc2)no1]

Embodiment 80. The pharmaceutical composition of any one of Embodiments 77-79, wherein the pharmaceutical composition comprises about 50 mg, about 100 mg, about 200 mg, about 300 mg, about 400 mg, or about 500 mg of a compound of Formula (I), or an isotopic variant, tautomer, pharmaceutically acceptable salt, solvate, or hydrate thereof.

Embodiment 81. A pharmaceutical composition, comprising:

(i) a compound of Formula (I),

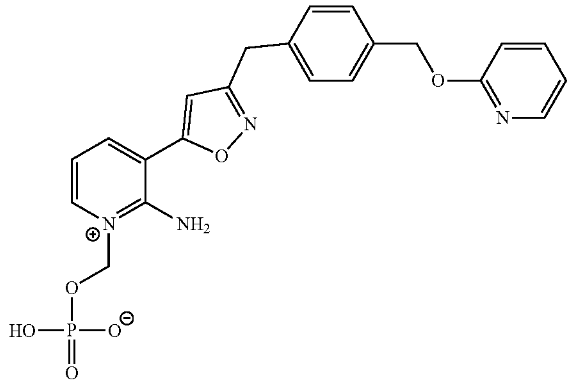 [SMILES: Nc1c(-c2cc(Cc3ccc(COc4ccccn4)cc3)no2)ccc[n+]1COP(=O)([O-])O]

or an isotopic variant, tautomer, pharmaceutically acceptable salt, solvate, or hydrate thereof; and (ii) at least one pharmaceutically acceptable excipient, wherein the pharmaceutical composition is in a dosage form for dosing or administration by injection.

Embodiment 82. The pharmaceutical composition of Embodiment 81, wherein the pharmaceutical composition is in a dosage form for intravenous (I.V.) injection or infusion, or intramuscular, subcutaneous, or intradermal injection.

Embodiment 83. The pharmaceutical composition of Embodiment 82, wherein the pharmaceutical composition is in a dosage form for I.V. injection or infusion.

Embodiment 84. The pharmaceutical composition of any one of Embodiments 81-83, wherein the pharmaceutical composition is a solution.

Embodiment 85. The pharmaceutical composition of any one of Embodiments 81-84, wheren the compound of Formula (I) or an isotopic variant, tautomer, pharmaceutically acceptable salt, solvate, or hydrate thereof; is crystalline, microcrystalline, amorphous, or lyophilized Embodiment 86. The pharmaceutical composition of Embodiment 85, wherein the compound of Formula (I) or an isotopic variant, tautomer, pharmaceutically acceptable salt, solvate, or hydrate thereof; is crystalline.

Embodiment 87. The pharmaceutical composition Embodiment 85, wherein the compound of Formula (I) or an isotopic variant, tautomer, pharmaceutically acceptable salt, solvate, or hydrate thereof; is amorphous.

Embodiment 88. The pharmaceutical composition of Embodiment 85, wherein the compound of Formula (I) or an isotopic variant, tautomer, pharmaceutically acceptable salt, solvate, or hydrate thereof; is lyophilized.

Embodiment 89. The pharmaceutical composition of any one of Embodiments 81-88, wherein the dosage form comprises a co-solvent.

Embodiment 90. The pharmaceutical composition of Embodiment 89, wherein the co-solvent comprises PEG200, PEG300, PEG400, PEG600, propylene glycol, ethanol, polysorbate 20, polysorbate 80, cremephor, glycerin, benzyl alcohol, dimethylacetamide (DMA), N-methyl-2-pyrrolidone (NMP), tert-butanol, or any combination thereof.

Embodiment 91. The pharmaceutical composition of any one of Embodiments 81-90, wherein the dosage form further comprises an oil.

Embodiment 92. The pharmaceutical composition of Embodiment 91, wherein the oil comprises sesame oil, soybean oil, vegetable oil, poppyseed oil, safflower oil, or combinations thereof.

Embodiment 93. The pharmaceutical composition of any one of Embodiments 81-92, wherein the dosage form further comprises a buffer.

Embodiment 94. The pharmaceutical composition Embodiment 93, wherein the buffer is a phosphate buffer.

Embodiment 95. The pharmaceutical composition Embodiment 94, wherein the phosphate buffer is potassium phosphate.

Embodiment 96. The pharmaceutical composition Embodiment 94 or 95, wherein the potassium phosphate is monobasic or dibasic.

Embodiment 97. The pharmaceutical composition of any one of Embodiments 81-96, wherein the pharmaceutical composition has a pH of from about 2.5 to about 11.0.

Embodiment 98. The pharmaceutical composition of any one of Embodiments 81-96, wherein the pharmaceutical composition has a pH of from about 2.5 to about 5.0 or from about 6.5 to about 10.5.

Embodiment 99. The pharmaceutical composition of any one of Embodiments 81-76, wherein the pharmaceutical composition has a pH of from about 2.5 to about 4.5 or from about 7.0 to about 9.0.

Embodiment 100. The pharmaceutical composition of any one of Embodiments 81-99, wherein the pH of the pharmaceutical composition is adjusted with hydrochloric acid and/or sodium hydroxide.

Embodiment 101. The pharmaceutical composition of any one of Embodiments 81-100, wherein the pharmaceutical composition comprises from about 5 mg/mL to about 250 mg/mL of a compound of Formula (I), or an isotopic variant, tautomer, pharmaceutically acceptable salt, solvate, or hydrate thereof.

Embodiment 102. The pharmaceutical composition of any one of Embodiments 81-101, wherein the pharmaceutical composition comprises from about 10 mg/mL to about 50 mg/mL of a compound of Formula (I), or an isotopic variant, tautomer, pharmaceutically acceptable salt, solvate, or hydrate thereof.

Embodiment 103. The pharmaceutical composition of any one of Embodiments 81-102, wherein the pharmaceutical composition comprises from about 20 mg/mL to about 40 mg/mL of a compound of Formula (I), or an isotopic variant, tautomer, pharmaceutically acceptable salt, solvate, or hydrate thereof.

Embodiment 104. The pharmaceutical composition of any one of Embodiments 81-102, wherein the pharmaceutical composition comprises about 10 mg/mL, about 15 mg/mL, about 20 mg/mL, about 25 mg/mL, or about 30 mg/mL of a compound of Formula (I), or an isotopic variant, tautomer, pharmaceutically acceptable salt, solvate, or hydrate thereof.

Embodiment 105. The pharmaceutical composition of any one of Embodiments 1-104, wherein the pharmaceutical composition comprises from about 10 mg to about 1,000 mg of a compound of Formula (I), or an isotopic variant, tautomer, pharmaceutically acceptable salt, solvate, or hydrate thereof.

Embodiment 106. The pharmaceutical composition of any one of Embodiments 1-105, wherein the pharmaceutical composition comprises from about 50 mg to about 600 mg of a compound of Formula (I), or an isotopic variant, tautomer, pharmaceutically acceptable salt, solvate, or hydrate thereof.

Embodiment 107. The pharmaceutical composition of any one of Embodiments 1-105, wherein the pharmaceutical composition comprises from about 50 mg to about 150 mg, about 150 mg to about 250 mg, about 250 mg to about 350 mg, about 350 mg to about 450 mg, about 450 mg to about 550 mg, about 550 mg to about 650 mg, about 650 mg to about 750 mg, about 850 mg to about 950 mg, or about 950 mg to about 1050 mg of a compound of Formula (I), or an isotopic variant, tautomer, pharmaceutically acceptable salt, solvate, or hydrate thereof.

Embodiment 108. The pharmaceutical composition of any one of Embodiments 81-105, wherein the pharmaceutical composition comprises about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg of a compound of Formula (I), or an isotopic variant, tautomer, pharmaceutically acceptable salt, solvate, or hydrate thereof.

Embodiment 109. The pharmaceutical composition of any one of Embodiments 81-108, wherein the pharmaceutical composition is stable for up to about 24 months at a temperature of from about −20° C. to 8° C.

Embodiment 110. The pharmaceutical composition of Embodiment 101, wherein the pharmaceutical composition is stable for a period of from about 12 to about 24 months at a temperature of about −20° C.

Embodiment 111. The pharmaceutical composition of any one of Embodiments 81-110, wherein the pharmaceutical composition is substantially free of impurities.

Embodiment 112. The pharmaceutical composition of any one of Embodiments 81-111, wherein the pharmaceutical composition is at least about 90% pure.

Embodiment 113. The pharmaceutical composition of any one of Embodiments 81-112, wherein the pharmaceutical composition is at least about 95% pure.

Embodiment 114. The pharmaceutical composition of any one of Embodiments 81-113, wherein the pharmaceutical composition is at least about 96% pure.

Embodiment 115. The pharmaceutical composition of any one of Embodiments 81-114, wherein the pharmaceutical composition is at least about 95% pure.

Embodiment 116. The pharmaceutical composition of any one of Embodiments 81-115, wherein the pharmaceutical composition is at least about 98% pure.

Embodiment 117. The pharmaceutical composition of any one of Embodiments 81-116, wherein the pharmaceutical composition is at least about 95% pure.

Embodiment 118. The pharmaceutical composition of any one of Embodiments 81-117, wherein the pharmaceutical composition is at least about 99.1%, about 99.2%, about 99.3%, about 99.4%, about 99.5%, about 99.6%, about 99.7%, about 99.8%, about 99.9%, or about 100% pure.

Embodiment 119. The pharmaceutical composition of any one of Embodiments 81-111, wherein the pharmaceutical composition comprises up to about 10% (w/w) of at least one impurity.

Embodiment 120. The pharmaceutical composition of any one of Embodiments 81-111 or 119, wherein the pharmaceutical composition comprises less than about 10% (w/w), about 9% (w/w), about 8% (w/w), about 7% (w/w), about 6% (w/w), about 5% (w/w), about 4% (w/w), about 3% (w/w), about 2% (w/w), or about 1% (w/w) of at least one impurity.

Embodiment 121. The pharmaceutical composition of any one of Embodiments 81-111 or 119-120, wherein the pharmaceutical composition comprises less than about 5% (w/w), about 4% (w/w), about 3% (w/w), about 2% (w/w), or about 1% (w/w) of at least one impurity.

Embodiment 122. The pharmaceutical composition of any one of Embodiments 81-111 or 119-121, wherein the pharmaceutical composition comprises less than about 0.9% (w/w), about 0.8% (w/w), about 0.7% (w/w), about 0.6% (w/w), about 0.5% (w/w), about 0.4% (w/w), about 0.3% (w/w), about 0.2% (w/w), or about 0.1% (w/w) of at least one impurity.

Embodiment 123. The pharmaceutical composition of any one of Embodiments 119-122, wherein the at least one impurity is a degradant.

Embodiment 124. The pharmaceutical composition of any one of Embodiments 119-123, wherein the at least one impurity is:

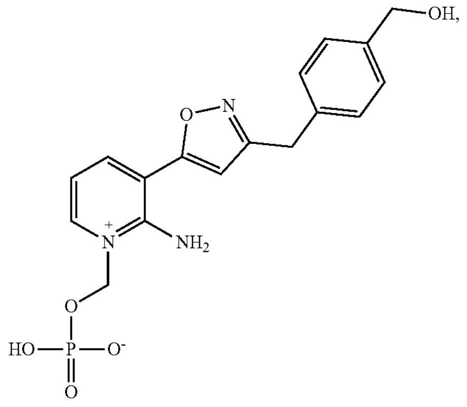

-continued
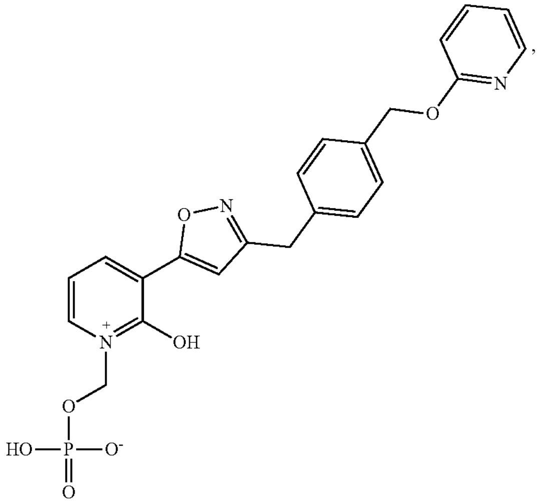
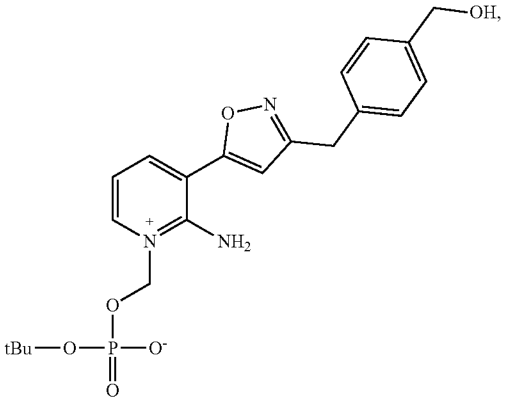
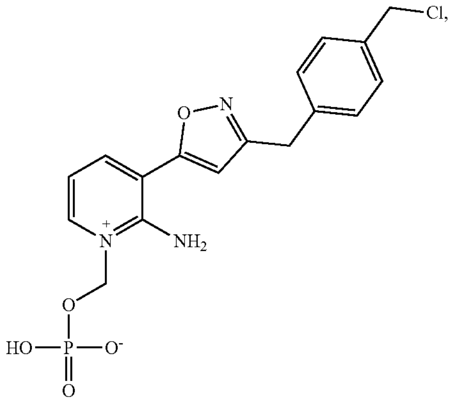
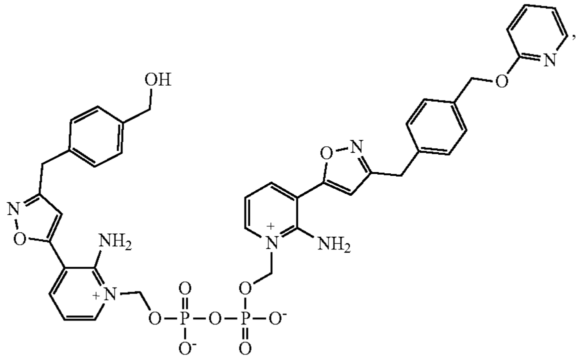
-continued
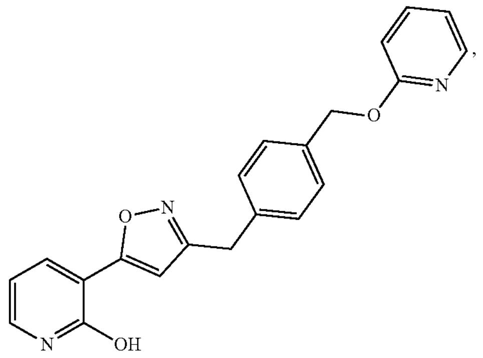
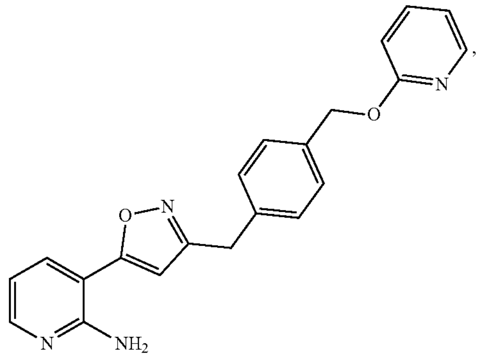
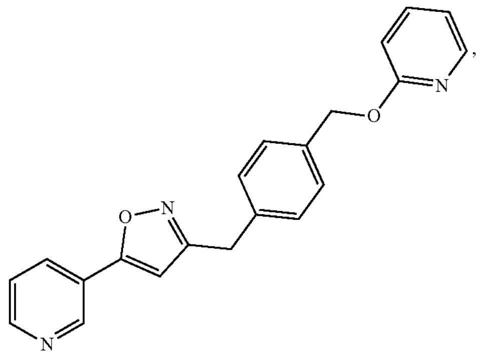
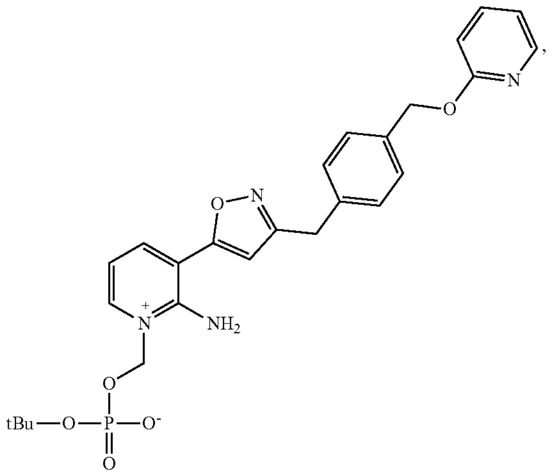

-continued

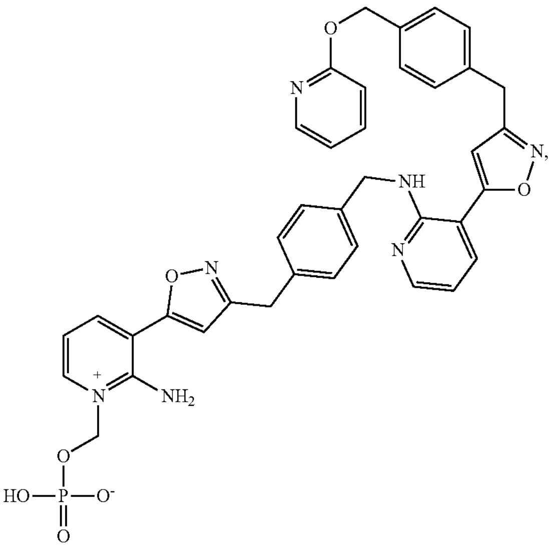

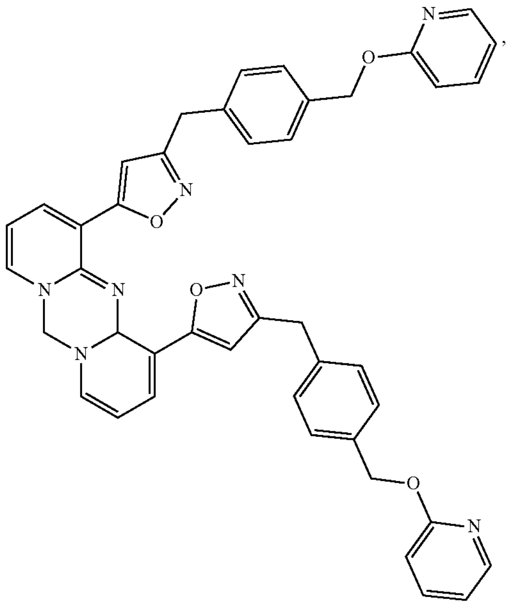

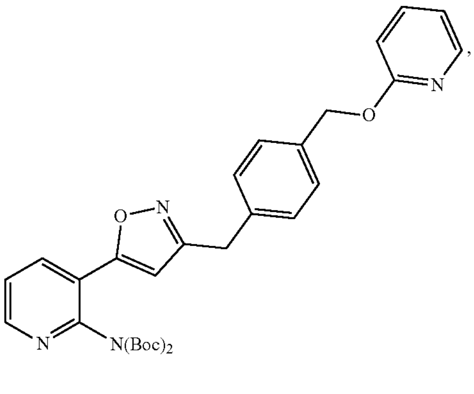

, or any combination thereof.

Embodiment 125. The pharmaceutical composition of any one of Embodiments 119-124, wherein the at least one impurity is:

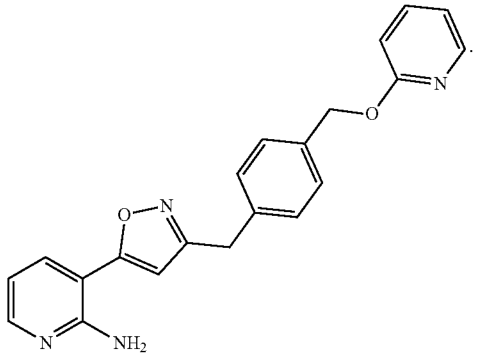 [SMILES: Nc1ncccc1-c1cc(Cc2ccc(COc3ccccn3)cc2)no1]

Embodiment 126. The pharmaceutical composition of any one of Embodiments 81-111, the pharmaceutical composition comprises up to about 4.0% (w/w) total impurities.

Embodiment 127. The pharmaceutical composition of any one of Embodiments 81-111 or 126, the pharmaceutical composition comprises up to about 0.5% (w/w) of any individual impurity.

Embodiment 128. The pharmaceutical composition of any one of Embodiments 81-111 or 126-128, the pharmaceutical composition comprises up to about 1.5% (w/w) of the compound:

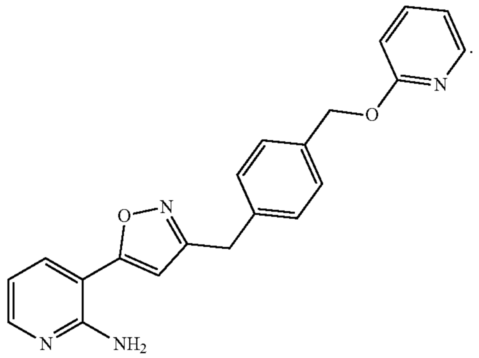 [SMILES: Nc1ncccc1-c1cc(Cc2ccc(COc3ccccn3)cc2)no1]

Embodiment 129. The pharmaceutical composition of any one of Embodiments 81-128, wherein the pharmaceutical composition comprises about 20 mg/mL of a compound of Formula (I), or an isotopic variant, tautomer, pharmaceutically acceptable salt, solvate, or hydrate thereof.

Embodiment 130. A combination composition, comprising:

(i) a compound of Formula (I):

(I)

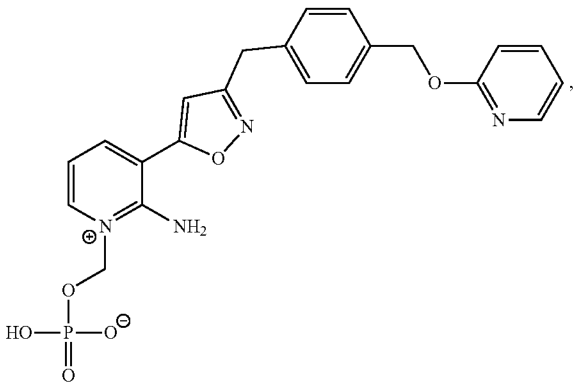

or an isotopic variant, tautomer, pharmaceutically acceptable salt, solvate, or hydrate thereof; and (ii) at least one an antifungal agent.

Embodiment 131. The composition of Embodiment 130, wherein the composition further comprises at least one pharmaceutically acceptable excipient.

Embodiment 132. The composition of Embodiment 130 or 131, wherein the at least one antifungal agent is an azole, an echinocandin, amphotericin B deoxycholate, amphotericin B cochleate, 5-fluorocytosine, terbinafine, griseofulvin, VL-2397, ibrexafungerp, orotomide F901318, or combinations thereof.

Embodiment 133. The composition of Embodiment 132, wherein the azole is ketoconazole, fluconazole, posaconazole, itraconazole, voriconazole, isavuconazole, or miconazole.

Embodiment 134. The composition of Embodiment 132, wherein the echinocandin is caspofungin, anidulafungin, micafungin, or rezafungin.

Embodiment 135. A combination composition, comprising:

(i) a compound of Formula (I):

(I)

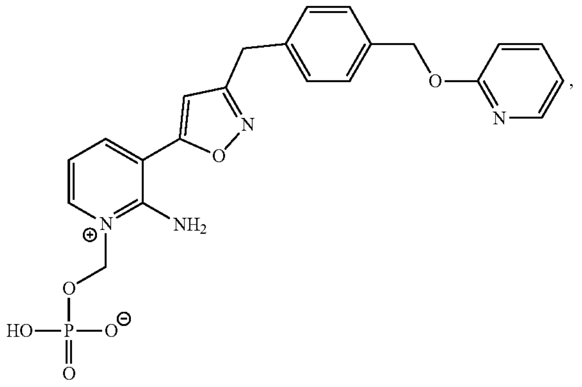

or an isotopic variant, tautomer, pharmaceutically acceptable salt, solvate, or hydrate thereof; and (ii) a compound of Formula (II)

(II)

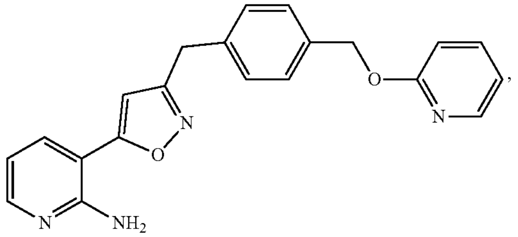

or an isotopic variant, tautomer, pharmaceutically acceptable salt, solvate, or hydrate thereof.

Embodiment 136. The composition of Embodiment 135, wherein the composition further comprises at least one pharmaceutically acceptable excipient.

Embodiment 137. The composition of Embodiment 135 or 136, wherein the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are both crystalline.

Embodiment 138. The composition of any one of Embodiments 135-137, wherein the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 10:1.

Embodiment 139. The composition of any one of Embodiments 135-138, wherein the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 9:1 to about 9.99:0.01.

Embodiment 140. The composition of any one of Embodiments 135-139, wherein the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of from about 9.5:0.5 to about 9.9:0.1.

Embodiment 141. The composition of any one of Embodiments 135-140, wherein the compound of Formula (I), or an isotopic variant, tautomer, pharmaceutically acceptable salt, solvate, or hydrate thereof and the compound of Formula (II), or an isotopic variant, tautomer, pharmaceutically acceptable salt, solvate, or hydrate thereof are present in a ratio of about 9:1, about 9.1:0.9, about 9.2:0.8, about 9.3:0.7, about 9.4:0.6, about 9.5:0.5, about 9.6:0.4, about 9.7:0.3, about 9.8:0.2, or about 9.9:0.1.

Embodiment 142. A method of treating or preventing a fungal infection or disease, comprising administering to a subject in need thereof a therapeutically effective amount of the pharmaceutical composition of any one of Embodiments 1-121 or the composition of any one of Embodiments 122-133.

Embodiment 143. The method of Embodiment 142, wherein from about 10 mg to about 8,000 mg of the compound of Formula (I), or an isotopic variant, tautomer, pharmaceutically acceptable salt, solvate, or hydrate thereof is administered to the subject.

Embodiment 144. The method of Embodiment 142 or 143, wherein from about 10 mg to about 2,400 mg of the compound of Formula (I), or an isotopic variant, tautomer, pharmaceutically acceptable salt, solvate, or hydrate thereof is administered to the subject.

Embodiment 145. The method of any one of Embodiments 142-144, wherein from about 10 mg to about 2,000 mg of the compound of Formula (I), or an isotopic variant, tautomer, pharmaceutically acceptable salt, solvate, or hydrate thereof is administered to the subject.

Embodiment 146. The method of Embodiment 142-144, wherein about 10 mg, about 30 mg, about 50 mg, about 100 mg, about 150 mg, about 200 mg, about 275 mg, about 300 mg, about 350 mg, about 400 mg, about 500 mg, about 600 mg, about 700 mg, about 800 mg, about 900 mg, about 1,000 mg, about 1,200 mg, about 1,500 mg, about 1,800 mg, about 2,000 mg, about 2,100 mg, about 2,400 mg, about 2,500 mg, about 3,000 mg, about 4,000 mg, about 5,000 mg, about 6,000 mg, about 7,000 mg, or about 8,000 mg of the compound of Formula (I), or an isotopic variant, tautomer, pharmaceutically acceptable salt, solvate, or hydrate thereof is administered to the subject.

Embodiment 147. The method of any one of Embodiments 142-146, wherein about 40 mg, about 50 mg, about 100 mg, about 200 mg, about 250 mg, about 350 mg, about 400 mg, about 500 mg, about 600 mg, about 700 mg, about 800 mg, or about 900 mg of the compound of Formula (I), or an isotopic variant, tautomer, pharmaceutically acceptable salt, solvate, or hydrate thereof is administered to the subject.

Embodiment 148. The method of any one of Embodiments 142-144, wherein about 600 mg, about 700 mg, about 800 mg, about 900 mg, 1,000 mg, about 2,000 mg, or about 3,000 mg of the compound of Formula (I), or an isotopic variant, tautomer, pharmaceutically acceptable salt, solvate, or hydrate thereof is administered to the subject.

Embodiment 149. The method of any one of Embodiments 142-148, wherein the pharmaceutical composition is administered to the subject daily.

Embodiment 150. The method of any one of Embodiments 142-149, wherein the pharmaceutical composition is administered to the subject once per day, twice per day, three times per day, or four times per day.

Embodiment 151. The method of any one of Embodiments 142-150, wherein the pharmaceutical composition is administered to the subject for a period of up to about 12 weeks.

Embodiment 152. The method of any one of Embodiments 142-151, wherein the pharmaceutical composition is administered to the subject for a period of at least one week.

Embodiment 153. The method of any one of Embodiments 1-152, wherein the pharmaceutical composition is administered to the subject for a period of at least two weeks.

Embodiment 154. The method of any one of Embodiments 1-153, wherein the pharmaceutical composition is administered to the subject for a period of one week, two weeks, 6 weeks, 12 weeks, 24 weeks, 48 weeks, or 52 weeks.

Embodiment 155. The method of any one of Embodiments 142-154, wherein the pharmaceutical composition is administered to the subject over a period of about 20 minutes, about 30 minutes, about 60 minutes, about 90 minutes, about 2 hours, about 3 hours, about 4 hours, about 5 hours, about 6 hours, about 7 hours, about 8 hours, about 9 hours, about 10 hours, about 12 hours, about 18 hours, or about 24 hours by I.V. infusion.

Embodiment 156. The method of any one of Embodiments 142-155, wherein the pharmaceutical composition is administered to the subject over a period of up to about 3 hours by I.V infusion.

Embodiment 157. The method of any one of Embodiments 142-156, wherein a loading dose is administered to the subject followed by a maintenance dose.

Embodiment 158. The method of Embodiment 157, wherein the loading dose comprises from about 1,000 mg to about 8,000 mg of a compound of Formula (I), or an isotopic variant, tautomer, pharmaceutically acceptable salt, solvate, or hydrate thereof.

Embodiment 159. The method of Embodiment 157 or 158, wherein the maintenance dose comprises from about 600 mg to about 2,400 mg of a compound of Formula (I), or an isotopic variant, tautomer, pharmaceutically acceptable salt, solvate, or hydrate thereof.

Embodiment 160. The method of any one of Embodiments 157-159, wherein the loading dose comprises from about 1,000 mg to about 2,000 mg.

Embodiment 161. The method of any one of Embodiments 157-160, wherein the loading dose is administered over a period of about 2 to about 3 hours by I.V. infusion.

Embodiment 162. The method of any one of Embodiments 157-161, wherein the loading dose is administered twice on the first day of treatment.

Embodiment 163. The method of Embodiment 162, wherein the second loading dose is administered about 9 hours after the first loading dose.

Embodiment 164. The method of any one of Embodiments 157-163, wherein the maintenance dose comprises about 600 mg, about 700 mg, about 800 mg, about 900 mg, or about 1,000 mg of a compound of Formula (I), or an isotopic variant, tautomer, pharmaceutically acceptable salt, solvate, or hydrate thereof.

Embodiment 165. The method of any one of Embodiments 157-164, wherein the maintenance dose comprises about 800 mg or about 1,000 mg of a compound of Formula (I), or an isotopic variant, tautomer, pharmaceutically acceptable salt, solvate, or hydrate thereof is administered to the subject.

Embodiment 166. The method of any one of Embodiments 157-164, wherein the maintenance dose comprises about 600 mg or about 900 mg of a compound of Formula (I), or an isotopic variant, tautomer, pharmaceutically acceptable salt, solvate, or hydrate thereof.

Embodiment 167. The method of any one of Embodiments 157-164, wherein the maintenance dose comprises about 600 mg or about 900 mg of a compound of Formula (I), or an isotopic variant, tautomer, pharmaceutically acceptable salt, solvate, or hydrate thereof and is administered orally.

Embodiment 168. The method of any one of Embodiments 157-164, wherein the maintenance dose comprises about 600 mg or about 900 mg of a compound of Formula (I), or an isotopic variant, tautomer, pharmaceutically acceptable salt, solvate, or hydrate thereof is administered over a period of about 1 hour to about 3 hours by I.V. infusion.

Embodiment 169. The method of any one of Embodiments 157-164, wherein about 600 mg of a compound of Formula (I), or an isotopic variant, tautomer, pharmaceutically acceptable salt, solvate, or hydrate thereof is administered over a period of about 3 hours by I.V. infusion.

Embodiment 170. The method of any one of Embodiments 157-169, wherein the maintenance dose is administered once daily.

Embodiment 171. The method of any one of Embodiments 157-170, wherein the maintenance dose is administered once daily starting on the second day of treatment.

Embodiment 172. The method of any one of Embodiments 157-164, wherein about 600 mg or about 800 mg of a compound of Formula (I), or an isotopic variant, tautomer, pharmaceutically acceptable salt, solvate, or hydrate thereof is administered over a period of about 3 hours by I.V. infusion starting on the second, third, or fourth day of treatment.

Embodiment 173. The method of any one of Embodiments 157-164, wherein about 800 mg or about 1,000 mg of a compound of Formula (I), or an isotopic variant, tautomer, pharmaceutically acceptable salt, solvate, or hydrate thereof is administered orally starting on the second, third, or fourth day of treatment.

Embodiment 174. The method of any one of Embodiments 142-173, wherein the fungal infection is caused by an invasive fungus.

Embodiment 175. The method of any one of Embodiments 142-174, further comprising administering to the subject at least one antifungal agent in combination with the pharmaceutical composition comprising the compound of Formula (I), or an isotopic variant, tautomer, pharmaceutically acceptable salt, solvate, or hydrate thereof.

Embodiment 176. The method of any Embodiment 175, wherein the at least one antifungal agent is an azole, an echinocandin, amphotericin B deoxycholate, amphotericin B cochleate, 5-fluorocytosine, terbinafine, griseofulvin, VL-2397, ibrexafungerp, orotomide F901318, or combinations thereof.

Embodiment 177. The method of Embodiment 176, wherein the azole is ketoconazole, fluconazole, posaconazole, itraconazole, voriconazole, isavuconazole, or miconazole.

Embodiment 178. The method of Embodiment 177, wherein the echinocandin is caspofungin, anidulafungin, micafungin, or rezafungin, or combinations thereof.

Embodiment 179. The method of any one of Embodiments 175-178, wherein the pharmaceutical composition comprising the compound of Formula (I), or an isotopic variant, tautomer, pharmaceutically acceptable salt, solvate, or hydrate thereof; and the antifungal agent are administered simultaneously, approximately simultaneously, or sequentially, in any order.

Embodiment 180. The method of Embodiment 179, wherein the pharmaceutical composition comprising the compound of Formula (I), or an isotopic variant, tautomer, pharmaceutically acceptable salt, solvate, or hydrate thereof; and the antifungal agent are administered simultaneously or approximately simultaneously.

Embodiment 181. The method of Embodiment 179, wherein the pharmaceutical composition comprising the compound of Formula (I), or an isotopic variant, tautomer, pharmaceutically acceptable salt, solvate, or hydrate thereof; and the antifungal agent are administered sequentially.

Embodiment 182. The method of Embodiment 181, wherein the pharmaceutical composition comprising the compound of Formula (I), or an isotopic variant, tautomer, pharmaceutically acceptable salt, solvate, or hydrate thereof; or a pharmaceutically acceptable salt thereof, is administered before the at least one antifungal agent.

Embodiment 183. The method of Embodiment 181, wherein the pharmaceutical composition comprising the compound of Formula (I), or an isotopic variant, tautomer, pharmaceutically acceptable salt, solvate, or hydrate thereof; or a pharmaceutically acceptable salt thereof, is administered after the at least one antifungal agent.

Embodiment 184. The method of any one of Embodiments 142-183, wherein the fungal infection or disease is caused by a *Aspergillus fumigatus, Blastomyces, Ajellomyces, Candida, Coccidioides, Cryptococcus, Histoplasm, Rhizopus muco, Cunninghamell, Apophysomyces, Absidi, Saksenaea, Entomophthora, Conidiobolus, Basidiobolus, Sporothrix, Pneumocystis, Talaromyces, Asclepias, Fusarium, Scedosporium* fungus or from a fungus from the Mucorales order, or any combination thereof.

Embodiment 185. The method of any one of Embodiments 142-183, wherein the fungal infection or disease is caused by a *Cryptococcus, Aspergillus, Candida, Fusarium, Scedosporium* fungus or from a fungus from the Mucorales order, or any combination thereof.

Embodiment 186. The method of Embodiment 185, wherein the fungal infection or disease is caused by *Aspergillus fumigatus, Aspergillus flavus, Blastomyces dermatitidis, Ajellomyces dermatitidi, Candida albican, Candida glabrata, Candida rugosa, Candida auris, Coccidioides immitis, Coccidioides posadasii, Cryptococcus neoformans, Cryptococcus gattii, Histoplasma capsulatum, Rhizopus stolonifer, Rhizopus arrhizus, Mucor indicus, Cunninghamella bertholletiae, Apophysomyces elegans, Absidia* species, *Saksenaea* species, *Rhizomucor pusillus, Entomophthora* species, *Conidiobolus* species, *Basidiobolus* species, *Sporothrix schenckii, Pneumocystis jirovecii, Talaromyces marneffei, Asclepias albicans, Fusarium solani, Scedosporium apiospermum, Rhizomucor pusillus*, or any combination thereof.

Embodiment 187. The method of Embodiment 185, wherein the fungal infection or disease is caused by a *Cryptococcus* fungus or a *Candida* fungus.

Embodiment 188. The method of Embodiment 187, wherein the fungal infection or disease is caused by *Cryptococcus neoformans, Cryptococcus gattii*, or *Candida auris*.

Embodiment 189. The method of any one of Embodiments 142-188, wherein the fungal infection or disease is azole-resistant and/or echinocandin-resistant.

Embodiment 190. The method of any one of Embodiments 142-189, wherein the subject is immunocompromised.

Embodiment 191. The method of any one of Embodiments 142-190, wherein the subject is infected with HIV/AIDS or has cancer.

Embodiment 192. The method of Embodiment 191, wherein the subject has cancer.

Embodiment 193. The method of Embodiment 192, wherein the cancer is acute myeloid leukemia (AML).

Embodiment 194. The method of any one of Embodiments 142-193, wherein the subject has neutropenia.

Embodiment 195. The method of any one of Embodiments 142-194, wherein the subject is undergoing or has undergone cancer chemotherapy treatment.

Embodiment 196. The method of any one of Embodiments 142-190, wherein the subject is undergoing or has undergone corticosteroid treatment.

Embodiment 197. The method of any one of Embodiments 142-190, wherein the subject is undergoing or has undergone TNF inhibitor treatment.

Embodiment 198. The method of any one of Embodiments 142-190, wherein the subject is a transplant recipient.

Embodiment 199. The method of any one of Embodiments 142-198, wherein the fungal infection or disease is in the bloodstream of the subject.

Embodiment 200. The method of any one of Embodiments 142-199, wherein the subject has reduced colony counts of fungi in the lungs after administration of the pharmaceutical composition.

Embodiment 201. The method of any one of Embodiments 142-200, wherein the plasma concentration versus time curve of the compound of Formula (I) in the subject has a $t_{max}$ of less than from about 30 minutes to about 180 minutes.

Embodiment 202. The method of any one of Embodiments 142-201, wherein the subject has a maximum plasma concentration ($C_{max}$) of from about 12,000 ng/ml to about 25,000 ng/ml of the compound of Formula (I).

Embodiment 203. The pharmaceutical composition of any one of Embodiments 81-129, wherein the pharmaceutical composition is stored in a pH-insensitive container.

Embodiment 204. The pharmaceutical composition of any one of Embodiments 81-129, wherein the pharmaceutical composition is stable for up to about 24 months at a temperature of from about −20° C. to 8° C. when stored as a liquid. In some embodiments, the pharmaceutical composition is stable for a period of from about 12 to about 24 months at a temperature of about −20° C. when stored as a liquid.

Embodiment 205. The pharmaceutical composition of any one of Embodiments 81-129, wherein the pharmaceutical composition is stable for a period of from about 12 to about 24 months at a temperature of about −20° C. when stored as a liquid.

Embodiment 206. The pharmaceutical composition of any one of Embodiments 81-129, wherein the pharmaceutical composition is stable for up to about 24 months at a temperature of from about −20° C. to 8° C. when stored as a liquid in a pH-insensitive container.

Embodiment 207. The pharmaceutical composition of any one of Embodiments 81-129, wherein the pharmaceutical composition is stable for a period of from about 12 to about 24 months at a temperature of about −20° C. when stored as a liquid in a pH-insensitive container.

Embodiment 208. The pharmaceutical composition of any one of Embodiments 81-129, wherein the pharmaceutical composition is stable for up to about 24 months at a temperature of from about −20° C. to 8° C. when stored as a liquid having a pH of from about 2.5 to about 11.0.

Embodiment 209. The pharmaceutical composition of any one of Embodiments 81-129, wherein the pharmaceutical composition is stable for a period of from about 12 to about 24 months at a temperature of about −20° C. when stored as a liquid having a pH of from about 2.5 to about 11.0.

Embodiment 210. The pharmaceutical composition of any one of Embodiments 81-129, wherein the pharmaceutical composition is stable for up to about 24 months at a temperature of from about −20° C. to 8° C. when stored as a liquid having a pH of from about 2.5 to about 11.0 in a pH-insensitive container.

Embodiment 211. The pharmaceutical composition of any one of Embodiments 81-129, wherein the pharmaceutical composition is stable for a period of from about 12 to about 24 months at a temperature of about −20° C. when stored as a liquid having a pH of from about 2.5 to about 11.0 in a pH-insensitive container.

Embodiment 212. The pharmaceutical composition of any one of Embodiments 203-211, wherein the pH-insensitive container is comprised of glass or plastic.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

III. EXAMPLES

Compound 1, a prodrug rapidly converted in vivo by phosphatases to the microbiologically active moiety Compound 1A, is a broad-spectrum antifungal agent in for the treatment of invasive fungal infections by both intravenous and oral routes of administration.

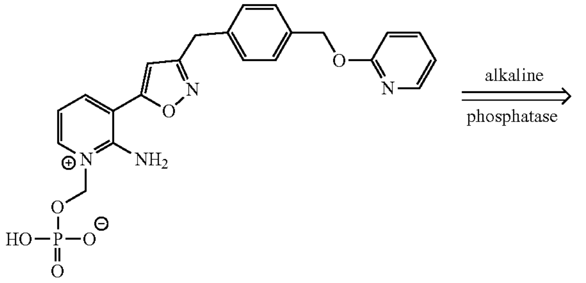

Compound 1

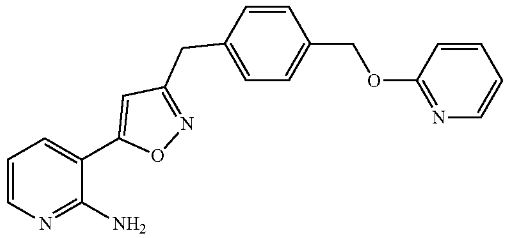

Compound 1A

Examples 1A-1B: Formulations

Compound 1 is a pro-drug with a labile phosphate moiety. The phosphate moiety improves the aqueous solubility of the drug substance at a higher pH range, but also has limited stability.

Example 1A: Compound 1 Injection

Compound 1 Injection is prepared as a sterile solution that is to be further diluted into 0.9% sodium chloride injection prior to administration.

Table 1 provides Compound 1 pH solubility at room temperature. The pH stability in buffer solutions were also evaluated for pH levels 7, 8, and 9 when stored at 40° C. The data demonstrates that Compound 1 is more stable at pH 7-8 for up to seven days with a change in potency of <3% with the parent, Compound 1A, observed as the main degradant. Compound 1 was also evaluated with up to 20 stabilizing and solubilizing excipients, which did not to decrease the rate of degradation or formation of Compound 1A.

TABLE 1

| Compound 1 pH Solubility at Room Temperature | |
|---|---|
| pH | Solubility (mg/mL) |
| Study A | |
| 1 | 3.83 |
| 3 | 0.111 |
| 4 | 0.063 |
| 5 | 0.125 |
| 6 | 0.758 |
| 7 | >17.6 |
| 7.5* | >28.5 |
| 8.5* | >80 |
| Study B | |
| 6.5 | 4.3 |
| 7.0 | 53.7 |
| 7.0 (with phosphate buffer) | 20.9 |
| 7.5 (50 mM phosphate buffer) | 141.1 |

*Saturation was not achieved in pH ≥ 7 solutions due to the amount of limited drug substance Compound 1 Injection is a solution formulated at a concentration of 20 mg/mL of Compound 1. The formulation comprises Compound 1 drug substance, sodium chloride, potassium phosphate (dibasic and monobasic), hydrochloric acid, sodium hydroxide, and Water for Injection (WFI). Compound 1 drug substance is added to the solution and the pH adjusted to 8.0±1.0 (target 7.8 to 8.2 during compounding) using hydrochloric acid/or sodium hydroxide followed by WFI to q.s. The Compound 1 solution will be aseptically filtered through a 0.2 μm membrane filter into the final primary packaging (50 mL vial) with a minimum 35 mL fill volume. Compound 1 Injection will be further diluted into 0.9% Sodium Chloride Injection prior to administration and administered as an intravenous infusion as specified in the clinical protocol. Table 2 describes the composition of a Compound 1 intravenous drug product, 20 mg/mL, for a 35 mL fill in a 50 mL vial with approximate batch sizes of 100 liters. The solution can be stored at either 2° C. to 8° C. or −20° C. for up to 12 months. The process steps for the preparation of Compound 1 Injection solution are summarized below.

TABLE 2

| Composition of Compound 1 Injection, 20 mg/mL, 35 mL Fill Volume | | |
|---|---|---|
| Component | Approximate Concentration | Content Per Unit |
| Compound 1 | 20 mg/mL | 700 mg |
| Sodium Chloride | 6.1 mg/mL | 213.5 mg |
| Potassium Phosphate, Monobasic | 0.16 mg/mL | 5.6 mg |
| Potassium Phosphate, Dibasic | 3.27 mg/mL | 114.5 mg |
| Sodium Hydroxide | As needed | As needed |
| Hydrochloric Acid | As needed | As needed |
| Water for Injection | N/A | Q.S. 35 mL |

Ph. Eur. = European Pharmacopeia;
N/A = not applicable;
NF = National Formulary;
QS = quantity sufficient for;
USP = United States Pharmacopeia 1. Add sodium chloride, potassium phosphate (monobasic and dibasic) into a vessel containing water for injection.
2. Adjust pH to 8.0 using 1M hydrochloric acid solutions and/or 1M sodium hydroxide solutions.
3. Slowly add Compound 1 drug substance to the solution and stir/mix at 15° C. to 30° C.
4. Adjust pH to 8.0 using hydrochloric acid solutions and/or sodium hydroxide solutions to dissolve.
5. Q.S. with water for injection and continue to stir at 15° C. to 30° C.
6. Aseptically filter through 2×0.2 μm membrane filters into sterile 50 mL vials with a 35 mL fill volume closed with a chlorobutyl stopper. Note: At the completion of each manufactured batch, the filter integrity is tested using a bubble point test and result is documented in the batch record.
7. The vials are inspected prior to packaging and labeling.

TABLE 3

| Compound 1 Injection Specification for Current Clinical Batches | | |
|---|---|---|
| Test | Method | Acceptance Criteria |
| Identification | HPLC | The relative retention time of the Compound 1 peak in the sample chromatogram is between 0.95 and 1.05 compared to the average retention time of the Compound 1 peak from the bracketing standard chromatograms. |
| Impurities | HPLC | |
| Compound 1A | HPLC | NMT 1.0% |
| Single Impurities, report by RRT | HPLC | NMT 0.5% |
| Total | HPLC | NMT 3.0% |
| pH | USP <791> | 7.0 to 8.5 |
| Osmolality | USP <785> | Report results (target 260 to 350 Osm/kg) |
| Assay | HPLC | 90.0-110.0% of label claim (20 mg/mL) |
| Fill Volume | USP <1> | NLT 35 mL |
| Endotoxin | USP <85> | <4.0 EU/mL |
| Particulate Matter | USP <788> | ≥10 μm: NMT 6000 particles/container<br>≥25 μm: NMT 600 particles/container |
| Sterility | USP <71> | Sterile |

EU = endotoxin units;
NLT = no less than;
NMT = no more than

During the preparation of the admixture solution containing Compound 1, Compound 1 Injection will be filtered with a 0.2 μM filter prior to infusion to remove any inherent particles.

Further formulation development for the Phase 2 clinical studies were performed for the Compound 1 injection formulation, 20 mg/mL. It was determined that having a phosphate buffer in the Phase 1 formulation added stability to the pH for longer term storage. Two formulations were prepared at pH 7.5 with a 50 mM phosphate buffer and pH 8.0 with a 20 mM phosphate buffer at a concentration of 20 mg/mL Compound 1. Table 4 shows the minor difference between the Phase 1 and Phase 2 formulations. Compound 1 Injection, 20 mg/mL, was prepared based upon the known aqueous solubility and stability. Since no other excipients were able to aid in the stability or increase solubility, the formulation was developed to be simple using GRAS excipients to the proper pH and isotonic osmolality.

TABLE 4

Composition of Compound 1 Injection, 20 mg/mL for Phase 1 and Phase 2 Formulations

| Component | Phase 1 Concentration | Phase 2 Concentration |
|---|---|---|
| Compound 1 | 20 mg/mL | 20 mg/mL |
| Sodium Chloride | 6.8 mg/mL | 6.1 mg/mL |
| Potassium Phosphate, Monobasic | Not applicable | 0.16 mg/mL |
| Potassium Phosphate, Dibasic | Not applicable | 3.27 mg/mL |
| Sodium Hydroxide | As needed | As needed |
| Hydrochloric Acid | As needed | As needed |
| Water for Injection | N/A | N/A |

Example 1B: Compound 1 Tablets

Compound 1 Tablets are formulated at strengths of 50 mg, 100 mg, and 200 mg white coated tablets. Table 3, Table 4, and Table 5 list the content of the Compound 1 Tablets, 50 mg, 100 mg and 200 mg, respectively.

TABLE 5

Composition of Compound 1 Coated Tablets, 50 mg

| Component | Amount per Tablet (% wt) | Function |
|---|---|---|
| Compound 1 | 50 mg (25.0%) | Active Ingredient |
| Microcrystalline Cellulose (Avicel PH102) | 59 mg (14.0%[1], 15.5%[2]) | Diluent |
| Lactose Monohydrate, Modified (#316 Fast Flo) | 59 mg (14.0%[1], 15.5%[2]) | Diluent |
| Colloidal silicon dioxide (Cab-o-sil M5P) | 3.5 mg (1.00%[1], 0.75%[2]) | Glidant |
| Pregelatinized Starch | 10 mg (5.0%[1]) | Disintegrant |
| Talc | 16 mg (8%[2]) | Glidant |
| Magnesium Stearate (HyQual) Vegetable Source | 2.5 mg (0.25%[1], 1.00%[2]) | Lubricant |
| Core Weight (mg) | 200 mg | |
| Opadry II AMB, coating | 10 mg (5.0%) | Film Coating |
| Purified Water | Not applicable | Solvent |
| Coated Tablet Weight (mg) | 210.0 mg | |

TABLE 6

Composition of Compound 1 Coated Tablets, 100 mg

| Component | Amount per Tablet - (% wt) | Function |
|---|---|---|
| Compound 1 | 100 mg (25.0%) | Active Ingredient |
| Avicel DG[3] | 231 mg (57.75%[1]) | Diluent |
| Pregelatinized Starch | 40 mg (5.0%[1], 5%[2]) | Disintegrant |
| Colloidal silicon dioxide (Cab-o-sil M5P) | 3 mg (0.75%[2]) | Glidant |
| Povidone | 12 mg (3.0%[1]) | Disintegrant |
| Talc | 8 mg (2.0%[1]) | Glidant |
| Magnesium Stearate (HyQual) Vegetable Source | 6 mg (0.5%[1], 1.00%[2]) | Lubricant |
| Core Weight (mg) | 400 mg | |
| Opadry II AMB, coating white | 20 mg (5.0%) | Film Coating |
| Purified Water | Not applicable | Solvent |
| Coated Tablet Weight (mg) | 420 mg | |

TABLE 7

Composition of Compound 1 Coated Tablets, 200 mg

| Component | Amount per Tablet - (% wt) | Function |
|---|---|---|
| Compound 1 | 200 mg (25.0%) | Active Ingredient |
| Avicel DG[3] | 462 mg (57.75%[1]) | Diluent |
| Pregelatinized Starch | 80 mg (5.0%[1], 5%[2]) | Disintegrant |
| Colloidal silicon dioxide (Cab-o-sil M5P) | 6 mg (0.75%[2]) | Glidant |
| Povidone | 24 mg (3.0%[1]) | Disintegrant |
| Talc | 16 mg (2.0%[1]) | Glidant |
| Magnesium Stearate (HyQual) Vegetable Source | 12 mg (0.5%[1], 1.00%[2]) | Lubricant |
| Core Weight (mg) | 800 mg | |
| Opadry II AMB, coating white | 40 mg (5.0%) | Film Coating |
| Purified Water | Not applicable | Solvent |
| Coated Tablet Weight (mg) | 840 mg | |

Manufacture of Compound 1 Tablets

Compound 1 has been evaluated extensively in preclinical studies and has demonstrated broad spectrum activity against three separate fungal infections. The drug substance is stored under frozen conditions (−20° C.) and the intermediate and the drug substance are stored at 2° C. to 8° C. The manufacturing was conducted under ambient conditions.

The drug substance was evaluated and the characteristics are noted in the table below. Compound 1 drug substance is needle shaped and has a poor flow property.

TABLE 8

Physical Properties of Compound 1

| Property | Results |
|---|---|
| Empirical Formula | $C_{22}H_{21}N_4O_6P$ |
| Molecular Weight | 468.4 g/mol |
| Bulk Density | 0.31 g/ml |
| Tapped Density | 0.42 g/ml |
| Carr's Index | 27.01 (Slightly Poor) |
| Hausner Ratio | 1.37 (Poor/Cohesive) |
| Angle of Repose | 46.5 degrees (Poor Must Agitate/Vibrate) |
| API Structure | Needle Shape Crystals |

Initial Development

Based on excipient compatibility studies and other laboratory trials, the following excipients were selected at the given percentage in the formulation.

A common blend approach was initially taken for 100 mg and 200 mg strengths with 25% drug substance in the formulation. The compositions of both strengths according to the common blend approach are exhibited in the table below.

TABLE 9

| Composition of Compound 1 Tablet (25% Drug Substance) | | |
|---|---|---|
| Component | Function | % w/w |
| INTRAGRANULAR | | |
| Compound 1 | Active | 25.00 |
| Microcrystalline Cellulose (Avicel DG), | Filler | 57.75 |
| Pregelatinized Starch, (Starch 1500) | Disintegrant/ Binder | 5.00 |
| Talc 194 | Glidant | 2.00 |
| Povidone, (Plasdone K-29/32) | Binder | 3.00 |
| Magnesium Stearate, . (Vegetable Grade, Hyqual) | Lubricant | 0.50 |
| TOTAL | | 93.25 |
| EXTRAGRANULAR | | |
| Pregelatinized Starch, (Starch 1500) | Disintegrant/ Binder | 5.00 |
| Colloidal Silicon Dioxide, (Cab-O-Sil M5P) | Glidant | 0.75 |
| Magnesium Stearate, (Vegetable Grade, Hyqual) | Lubricant | 1.00 |
| TOTAL | | 100.00 |
| FILM COATING | | |
| Opadry II AMB Moisture Barrier Coating White | Film Coat | 5.00 |
| Purified Water | Solvent | N/A |
| TOTAL | | 105.00 |

The main objective of the first batch was to evaluate the manufacturability of the proposed formulation and to achieve acceptable appearance and analytical results of the finished product. Dry granulation formulation was developed using a Roller Compactor with smooth rollers and it was observed that the formulation was prone to sticking in roller compactor and tablet tooling, and the highest achievable strength was 200 mg. Based on this information, Gerteis Mini pactor was used for roller compaction with one smooth and one knurled roller at Quotient. A 600 g batch with 25% API in the formulation was manufactured. The process by which this was attempted is as follows:

Pre-Blend

The intragranular materials: microcrystalline cellulose (Avicel DG), Compound 1 drug substance, 1500 Pregelatinized Starch, Talc 194, and Povidone (Plasdone K-29/32) were charged into a 4 qt. V Blender and blended for 250 rotations. The blend was then discharged and screened through a #30 mesh screen. The screened mixture was then loaded into the 4 qt. V-Blender and blended for 75 rotations. magnesium stearate was then screened using a #40 mesh screen and loaded into the blender and blended for 100 rotations.

Dry Granulation

The blend was discharged and divided into 3 parts which were granulated at 3 different Compaction Forces of 6 KN/cm, 8 KN/cm and 10 KN/cm on the Gerties Mini pactor.

Final Blend

Upon completion of granulation, the quantities of the extra granular materials were calculated and adjusted based on the net weight of the 3 blends. Colloidal silicon dioxide and pregelatinized starch were screened through a #30 mesh screen and magnesium stearate was screened using a #40 mesh screen. The extragranular materials were then added to the granules and bag mixed for 2 minutes to get the final blend.

Compression

The proposed formulation was a common blend for 50 mg, 100 mg, and 200 mg tablets. The highest strength tablets of 200 mg were considered as the worst case for compression. Tablets were initially compressed on Carver Press using different tooling with the target tablet weight of 800 mg. The following tooling sets were evaluated and tablets were manually compressed using carver press:

0.750"×0.3125"

0.3110"×0.6200"

0.3200"×0.6400"

The tablets were then compressed using the Korsch XL 100 press with the blend compacted at 8 KN/cm force. During the compression run in-process, tests were performed (weight, thickness, hardness, friability, and disintegration). To determine the hardness range and friability the tablets were compressed over a wide range of compression forces.

No sticking was observed in the blender, roller compactor, or on the tooling during the manufacturing run. The flow properties of the final blend improve with an increase in the roller compaction force. Hence, for the preferred flow properties of blend, compaction forces are 10 KN/cm>8 KN/cm>6 KN/cm. Particle size distribution shows that 50% to 55% of particles were retained on 40 mesh. This shows a narrow particle size distribution which is good for weight control. The percentage of fines in the 10 KN/cm blend is only about 4.5% whereas the percentage of fines in the 8 KN/cm blend is 10.5%. It is important to have certain amount of fines in the blend ($^{75}$ microns and below). Hence, based on the data, 8 KN/cm compaction force is recommended during the roller compaction run since it has a better flow than 6 KN/cm blend and more fines than the 10 KN/cm blend. Additionally, the blend may lose compressibility due to higher roller compaction forces. Based on the compression study, the recommended tooling is:

For 800 mg tablet weight: 0.3200"×0.6400" (200 mg strength)

For 1000 mg tablet weight: 0.750"×0.3125" (250 mg strength)

TABLE 10

| Physical Properties of Blends | | | |
|---|---|---|---|
| Property/ Force | 6 KN/cm | 8 KN/cm | 10 KN/cm |
| Bulk Density (g/ml) | 0.6094 | 0.6553 | 0.6882 |
| Tap Density (g/ml) | 0.8018 | 0.8295 | 0.8602 |
| Carr's Index | 24.00 | 21.00 | 20.00 |
| Hausner Ratio | 1.316 | 1.266 | 1.250 |
| Flow Characteristics | Slightly Poor | Fair | Fair |

TABLE 11

| Particle Size Distribution at 6 KN/cm for 25% Drug Substance PSD for 6 KN/cm RC force - 25% API | | | | | | |
|---|---|---|---|---|---|---|
| Microns | Screen Size | Gross Weight | Tare Weight | Net Weight | % Retention | Cumulative % |
| 850 | 20 | 44.7281 | 43.7831 | 0.945 | 20.06 | 20.06 |
| 425 | 40 | 40.5667 | 38.1996 | 2.3671 | 50.26 | 70.33 |
| 180 | 80 | 36.2893 | 35.6979 | 0.5914 | 12.56 | 82.88 |
| 125 | 120 | 34.4889 | 34.2917 | 0.1972 | 4.19 | 87.07 |
| 75 | 200 | 32.1512 | 31.8294 | 0.3218 | 6.83 | 93.90 |
| 53 | 270 | 33.2447 | 33.0627 | 0.182 | 3.86 | 97.77 |
| Fines Collector | Pan | 24.9424 | 24.8372 | 0.1052 | 2.23 | 100.00 |
| | Total | | | 4.7097 | 100.00 | |

TABLE 12

| Particle Size Distribution at 8 KN/cm for 25% Drug Substance PSD for 8 KN/cm RC force- 25% API | | | | | | |
|---|---|---|---|---|---|---|
| Microns | Screen Size | Gross Weight | Tare Weight | Net Weight | % Retention | Cumulative % |
| 850 | 20 | 44.684 | 43.7891 | 0.8949 | 18.54 | 18.54 |
| 425 | 40 | 40.8845 | 38.2227 | 2.6618 | 55.13 | 73.67 |
| 180 | 80 | 36.3232 | 35.7145 | 0.6087 | 12.61 | 86.27 |
| 125 | 120 | 34.4637 | 34.3087 | 0.155 | 3.21 | 89.48 |
| 75 | 200 | 32.0959 | 31.8489 | 0.247 | 5.12 | 94.60 |
| 53 | 270 | 33.2324 | 33.1066 | 0.1258 | 2.61 | 97.21 |
| Fines Collector | Pan | 24.643 | 24.5081 | 0.1349 | 2.79 | 100.00 |
| | Total | | | 4.8281 | 100.00 | |

TABLE 13

| Particle Size Distribution at 10 KN/cm for 25% Drug Substance PSD for 10 KN/cm RC force- 25% API | | | | | | |
|---|---|---|---|---|---|---|
| Microns | Screen Size | Gross Weight | Tare Weight | Net Weight | % Retention | Cumulative % |
| 850 | 20 | 45.347 | 43.7905 | 1.5565 | 29.42 | 29.42 |
| 425 | 40 | 41.2133 | 38.2226 | 2.9907 | 56.53 | 85.95 |
| 180 | 80 | 36.1452 | 35.7164 | 0.4288 | 8.10 | 94.05 |
| 125 | 120 | 34.3912 | 34.314 | 0.0772 | 1.46 | 95.51 |
| 75 | 200 | 31.971 | 31.8492 | 0.1218 | 2.30 | 97.81 |
| 53 | 270 | 33.174 | 33.0961 | 0.0779 | 1.47 | 99.28 |
| Fines Collector | Pan | 24.5201 | 24.4822 | 0.0379 | 0.72 | 100.00 |
| | Total | | | 5.2908 | 100.00 | |

Development Batch

Based on the manufacturing feasibility and the data generated from the first batch with 25% drug substance formulation described above, a modification in the formulation was made and a new formulation with 40% drug substance was proposed and manufactured. The new formulation was intended to be used as a common blend for 200 mg, 300 mg and 400 mg strength tablets. The aim was to increase the percentage of the drug substance in the formulation to obtain tablets with higher strength without increasing the tablet weight to over a gram. The 15% additional drug substance in the formulation was compensated by reducing the percent of the microcrystalline cellulose (Avicel DG). The proposed formulation listed in the table below. A batch of 500 grams of blend was manufactured in order to evaluate the manufacturability of higher API % in the formulation.

TABLE 14

| Composition of Compound 1 tablet (40% API) | | |
|---|---|---|
| Component | Function | % w/w |
| INTRAGRANULAR | | |
| Compound 1 | Active | 40.00 |
| Microcrystalline Cellulose (Avicel DG), | Filler | 42.75 |
| Pregelatinized Starch (Starch 1500) | Disintegrant/ Binder | 5.00 |
| Talc 194 | Glidant | 2.00 |
| Povidone, (Plasdone K-29/32) | Binder | 3.00 |
| Magnesium Stearate, (Vegetable Grade, Hyqual) | Lubricant | 0.50 |
| TOTAL | | 93.25 |
| EXTRAGRANULAR | | |
| Pregelatinized Starch, (Starch 1500) | Disintegrant/ Binder | 5.00 |
| Colloidal Silicon Dioxide, (Cab-O-Sil M5P) | Glidant | 0.75 |
| Magnesium Stearate, (Vegetable Grade, Hyqual) | Lubricant | 1.00 |
| TOTAL | | 100.00 |

Pre-Blend

The intragranular materials: microcrystalline cellulose (Avicel DG), Compound 1 API, 1500 pregelatinized starch, Talc 194 and Povidone (Plasdone K-29/32) charged into a 4 qt. V Blender and blended for 250 rotations.

The blend was then discharged and screened through a #30 mesh screen. The screened mixture was then loaded into the 4 qt. V-Blender and blended for 75 rotations. Magnesium stearate was then screened using a #40 mesh screen and loaded into the blender and blended for 100 rotations.

Dray Granulation

The blend was discharged and granulated on a Gerties Mini pactor at a compaction force of 8.0 kN/cm, granulator speed of 65 rpm, and screen size of 1.00 mm.

Final Blend

On completion of granulation, the quantities of the extra granular materials were calculated and adjusted based on the net weight of granules. Colloidal silicon dioxide and pregelatinized starch were screened through a #30 mesh screen and magnesium stearate was screened using a #40 mesh screen. The extragranular materials were then loaded into the 4 qt. V-Blender and blended for 75 rotations.

Compression

A part of the final blend was used to manufacture tablets using the manual carver press. Below are the target weights for the following strengths along with the recommended tooling.

TABLE 15

| Tablet weights and Tooling (40% Drug Substance) | | |
|---|---|---|
| Strength | Tablet Weight | Recommended Tooling |
| 200 mg | 500 mg | 13/32 Round |
| 300 mg | 750 mg | 0.3200" × 0.6400" |
| 400 mg | 1000 mg | 0.750" × 0.3125" |

The remaining final blend was divided into two (2) halves and compressed for 300 mg and 400 mg strengths. To determine the hardness range and friability the tablets were compressed over a wide range of compression forces.

Results and Discussion

Based on the data and manufacturing experience the flow of the blend is fair. No sticking was observed on the rollers post roller compaction. There was no sticking/picking issue during the compression run. The dissolution data of the 400 mg uncoated tablets looks good with almost 100% release at 10 minutes.

TABLE 16

| Physical Properties of Blend | |
|---|---|
| Property | Results |
| Bulk Density (g/ml) | 0.6534 |
| Tap Density (g/ml) | 0.8168 |

TABLE 16-continued

| Physical Properties of Blend | |
|---|---|
| Property | Results |
| Carr's Index | 20.00 |
| Hausner Ratio | 1.250 |
| Flow Characteristics | Fair |

TABLE 17

Particle Size Distribution at 8 KN/cm for 40% Drug Substance
PSD for 8 KN/cm RC force- 40% API formulation

| Microns | Screen Size | Gross Weight | Tare Weight | Net Weight | % Retention | Cumulative % |
|---|---|---|---|---|---|---|
| 850 | 20 | 44.64 | 43.9062 | 0.7338 | 15.36 | 15.36 |
| 425 | 40 | 41.081 | 38.4374 | 2.6436 | 55.35 | 70.71 |
| 180 | 80 | 36.5843 | 35.9735 | 0.6108 | 12.79 | 83.50 |
| 125 | 120 | 34.5042 | 34.3492 | 0.155 | 3.25 | 86.74 |
| 75 | 200 | 32.1574 | 31.8971 | 0.2603 | 5.45 | 92.19 |
| 53 | 270 | 33.2467 | 33.0968 | 0.1499 | 3.14 | 95.33 |
| Fines Collector | Pan | 22.112 | 21.8889 | 0.2231 | 4.67 | 100.00 |
| | Total | | | 4.7765 | 100.00 | |

TABLE 18

In Process Tests for 300 mg (40% Drug Substance)

| Set up | Specification | 1 | 2 | 3 | 4 | 5 | Avg. |
|---|---|---|---|---|---|---|---|
| Target | Weight | 757.1 | 761.1 | 761.9 | 758.2 | 759.6 | 759.6 mg |
| | Thickness | 5.75 | 5.75 | 5.83 | 5.77 | 5.76 | 5.77 mm |
| | Hardness | 21.6 | 18.1 | 21.2 | 19.2 | 19.5 | 19.9 kP |
| Low Hardness | Weight | 760.7 | 749.6 | 746.1 | 748.7 | 750.9 | 751.2 mg |
| | Thickness | 5.88 | 5.87 | 5.86 | 5.90 | 5.87 | 5.88 mm |
| | Hardness | 14.7 | 14.1 | 15.5 | 15.9 | 12.9 | 14.5 kP |
| High Hardness | Weight | 750.8 | 750.9 | 754.2 | 750.0 | 751.2 | 751.4 mg |
| | Thickness | 5.57 | 5.60 | 5.59 | 5.64 | 5.60 | 5.60 mm |
| | Hardness | 23.8 | 24.5 | 25.8 | 26.5 | 26.0 | 25.3 kP |

TABLE 19

In Process Tests for 400 mg (40% Drug Substance)

| Set up | Specification | 1 | 2 | 3 | 4 | 5 | Avg. |
|---|---|---|---|---|---|---|---|
| Target | Weight | 1030.2 | 1031.2 | 1025.7 | 1028.7 | 1010.6 | 1025.3 mg |
| | Thickness | 7.00 | 7.01 | 6.98 | 7.00 | 6.94 | 6.99 mm |
| | Hardness | 18.6 | 21.5 | 20.9 | 19.9 | 20.4 | 20.2 kP |
| Low Hardness | Weight | 993.3 | 1032.8 | 1039.1 | 996.8 | 1026.4 | 1017.7 mg |
| | Thickness | 7.31 | 7.25 | 7.20 | 7.21 | 7.24 | 7.24 mm |
| | Hardness | 18.4 | 12.1 | 14.6 | 11.8 | 10.0 | 13.4 kP |
| High Hardness | Weight | 1029.9 | 1024.0 | 1022.2 | 1025.1 | 1014.9 | 1023.2 mg |
| | Thickness | 6.77 | 6.75 | 6.70 | 6.68 | 6.72 | 6.72 mm |
| | Hardness | 30.7 | 29.4 | 28.2 | 25.6 | 28.8 | 28.5 kP |

Analytical Results

Figure 11:
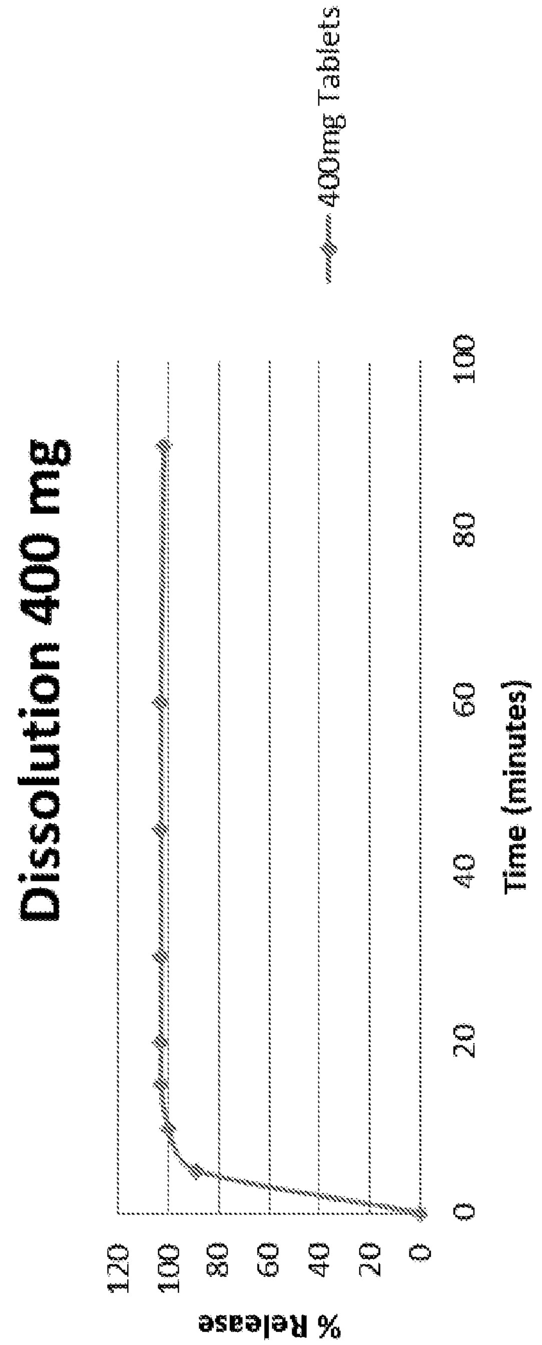
FIG. 11. Dissolution profile for 400 mg Compound 1 Tablets.

Core tablets were subjected to dissolution studies. See FIG. 11 for dissolution profile. Dissolution was started at 75 rpm and turned to 250 rpm after 60 minutes time point for the next 30 minutes.

The dissolution profile for the 40% drug substance formulation looked good as 100% release was achieved within the first 10 minutes.

TABLE 20

| Dissolution Data for 400 mg (40% Drug Substance) 400 mg Tables; Lot# 024 | | | | | | | | | |
|---|---|---|---|---|---|---|---|---|---|
| | Tablet wt (mg) | | | | | | | | |
| Time (mins) | 1026 Vessel 1 | 1037 Vessel 2 | 1019 Vessel 3 | 1027 Vessel 4 | 1027 Vessel 5 | 1025 Vessel 6 | Mean | SD | % RSD |
| 0 | 0 | 0 | 0 | 0 | 0 | 0 | 0 | 0 | 0 |
| 5 | 90 | 85 | 90 | 88 | 89 | 90 | 89 | 2 | 2.3 |
| 10 | 101 | 100 | 100 | 100 | 100 | 100 | 100 | 0 | 0.3 |
| 15 | 103 | 103 | 102 | 103 | 103 | 102 | 103 | 0 | 0.4 |
| 20 | 103 | 104 | 102 | 103 | 103 | 103 | 103 | 1 | 0.6 |
| 30 | 104 | 104 | 102 | 103 | 103 | 103 | 103 | 1 | 0.6 |
| 45 | 103 | 104 | 102 | 103 | 102 | 102 | 103 | 1 | 0.6 |
| 60 | 102 | 104 | 102 | 103 | 102 | 102 | 103 | 1 | 0.6 |
| 90 | 102 | 103 | 101 | 102 | 102 | 103 | 102.0 | 1 | 0.6 |

Results and Discussion

A 500 gram feasibility batch was manufactured and the following observations were made:

- Granules looked good and had a good flow.
- Some sticking was observed on the rolls after roller compaction which had not been previously observed. The bulk and tap density of the final blend was similar to the previous batches.
- No flow issue was observed during the compression from the hopper to the turret. There was no sticking on the tooling.
- The tablets were initially compressed at about 16 KP hardness, but some chipping/edging at the end of 200 rotations on friability was observed and hence the hardness was increased to about 19 KP for the rest of the run.
- The disintegration time was less than 2 minutes.
- The tablets were coated using Opadry AMB II High Performance Moisture Barrier Film Coating 88A180040 White. During the coating run scuff marks were observed on along with minor chipping and edging on the tablet.

Results and Discussion

In order to overcome the issues observed in the first feasibility batch (Batch #141) the following changes were recommended:

- Increase the intragranular magnesium stearate from 0.5% to 0.75% to potentially reduce sticking on the rolls during the roller compaction.
- Compress the tablets at higher hardness which would improve the friability of the tablets and reduce the potential chipping and edging during the coating. Recommended target hardness 20 kP.
- Coat the pan with Opadry prior to loading the tablets in the pan in order to prevent scuff marks.
- Try Opadry II White 85F18422 instead of Opadry AMB II High Performance Moisture Barrier Film Coating 88A180040 White.

Feasibility Batch 2

A second development batch was manufactured based on the observations and results of the first feasibility batch. The tablets were manufactured at high hardness (NLT 20 kP) and coated with Opadry II White 85F18422. No issues were observed during the manufacturing. Based on the successful manufacturing of the feasibility batch the current manufacturing process and formulation is recommended for stability and scale up batches.

TABLE 21

| Component | Function | % w/w |
|---|---|---|
| INTRAGRANULAR | | |
| Compound 1 | Active | 25.00 |
| Microcrystalline Cellulose (Avicel DG), | Filler | 57.50 |
| Pregelatinized Starch, (Starch 1500) | Disintegrant/ Binder | 5.00 |
| Talc 194 | Glidant | 2.00 |
| Povidone, (Plasdone K-29/32) | Binder | 3.00 |
| Magnesium Stearate, (Vegetable Grade, Hyqual) | Lubricant | 0.75 |
| TOTAL | | 93.25 |
| EXTRAGRANULAR | | |
| Pregelatinized Starch, (Starch 1500) | Disintegrant/ Binder | 5.00 |
| Colloidal Silicon Dioxide, /JP (Cab-O-Sil M5P) | Glidant | 0.75 |
| Magnesium Stearate, (Vegetable Grade, Hyqual) | Lubricant | 1.00 |
| TOTAL | | 100.00 |
| FILM COATING | | |
| Opadry II AMB Moisture Barrier Coating White | Film Coat | 5.00 |
| Purified Water | Solvent | N/A |
| TOTAL | | 105.00 |

Analytical Results

TABLE 22

| Time Zero- Stability Results (200 mg AMB Coating) | | |
|---|---|---|
| Test | Time Zero | |
| APPEARANCE<br>Specification: Report Results | Oval Shaped Tablets | |
| ASSAY<br>Specification: 90.0-110.0% of Label Claim | 101.9% | |
| RELATED SUBSTANCES | Relate Substance | Weight % |
| Specification: | RRT 0.37 | 0.17 |
| Compound 1A: NMT 1.0% | RRT 0.45 | 0.07 |
| Individual: NMT 0.5% | RRT 0.60 | 0.13 |
| Total: NMT 4.0% | RRT 1.43 | 0.14 |

TABLE 22-continued

| Time Zero- Stability Results (200 mg AMB Coating) | | |
|---|---|---|
| Test | Time Zero | |
| Report individual related substances by relative retention time. | (Compound 1A) | |
| | RRT 1.65 | 0.05 |
| | RRT 1.92 | 0.06 |
| | RRT 1.99 | 0.15 |
| | Total | 0.77 |
| WATER CONTENT Specification: Report Results | Prep-1: 3.1121% | |
| | Prep-2: 3.0522% | |
| | Prep-3: 3.0100% | |
| | Mean: 3.1% | |

TABLE 23

| Time Zero- Stability Results (400 mg AMB Coating) | | |
|---|---|---|
| Test | Time Zero | |
| APPEARANCE Specification: Report Results | White Oval Shaped Tablets | |
| ASSAY Specification: 90.0-110.0% of Label Claim | 103.5% | |
| RELATED SUBSTANCES | Relate Substance | Weight % |
| Specification: | RRT 0.37 | 0.17 |
| Compound 1A: NMT 1.0% | RRT 0.45 | 0.07 |
| Individual: NMT 0.5% | RRT 0.60 | 0.12 |
| Total: NMT 4.0% | RRT 1.43 (Compound 1A) | 0.13 |
| Report individual related | RRT 1.65 | 0.06 |
| substances by relative | RRT 1.92 | 0.06 |
| retention time. | RRT 1.99 | 0.15 |
| | Total | 0.76 |
| WATER CONTENT | Prep-1: 2.6745% | |
| Specification: Report Results | Prep-2: 2.6631% | |
| | Prep-3: 2.6695% | |
| | Mean: 0.2% | |

| DISSOLUTION | Time (min) | % Dissolved 1 | 2 | 3 | 4 | 5 | 6 | Mean | SD |
|---|---|---|---|---|---|---|---|---|---|
| Specification: Q = 65% at 45 minutes | 5 | 34 | 27 | 29 | 60 | 27 | 32 | 35 | 12 |
| | 10 | 87 | 65 | 64 | 97 | 77 | 74 | 77 | 13 |
| | 15 | 100 | 95 | 88 | 102 | 98 | 97 | 97 | 5 |
| | 20 | 102 | 102 | 100 | 102 | 102 | 101 | 102 | 1 |
| | 30 | 103 | 103 | 104 | 102 | 103 | 103 | 103 | 1 |
| | 45 | 103 | 103 | 104 | 102 | 103 | 103 | 103 | 1 |
| | 60 | 103 | 103 | 103 | 102 | 103 | 102 | 102 | 0 |
| | 75 | 102 | 103 | 103 | 101 | 102 | 102 | 102 | 1 |

Compound 1 drug substance exhibits a poor flow. The manufacturing process of the 25% drug load was successfully performed at Quotient Sciences. A higher drug load was developed with 40% API in the formulation. The first development batch with the new formulation was successfully manufactured to make 300 mg and 400 mg tablets.

To evaluate the manufacturing feasibility and confirm the repeatability/robustness of the formulation and the process a second lot of drug substance was used to manufacture another batch with 40% drug substance (high drug load) in the formulation. During the first feasibility batch, minor sticking was observed on the rolls during the roller compaction and scuff marks and chipping of tablets was observed during coating. Based on the first feasibility batch, a second feasibility batch was made with an increase in the intragranular magnesium stearate from 0.5% to 0.75% in the formulation and in order to overcome the defects observed during coating the tablets were compressed at a higher hardness which made them more friable and reduced the potential chipping. Also, the coating pan was coated with the coating solution prior to loading the tablets in order to reduce the scuff marks. The changes made in the formulation and the process helped to achieve an acceptable finished product with no issues in the manufacturing process.

Two stability batches one with 25% drug load (200 mg strength) and one with 40% drug load (400 mg strength) were manufactured based on the optimized process parameters from the tech transfer, development batch and feasibility batches. The coated tablets were packaged in 30 cc bottles with 14 tablets in each bottle and put on stability at 2-8° C. and 25 C/60% RH storage conditions. All process parameters and in-process test results were well within batch record provided specifications. Content uniformity results (AV Values) were 2.0 and 4.4 with a RSD=0.8% and 1.2% for 200 mg and 400 mg strengths, respectively. AV values for both strengths were well within the specification of USP guidelines of less than 15. All additional final testing met approved specifications.

Table 24 describes the composition of the Compound 1 Tablets prepared as a 14 kg common blend divided to manufacture the 100 mg and 200 mg Compound 1 Tablets.

TABLE 24

| Batch Formula for Compound 1, 100 mg and 200 mg Tablets | | | | |
|---|---|---|---|---|
| | 100 mg Compound 1 | | 200 mg Compound 1 | |
| Component | Amount per Tablet-(% wt) | Quantity for 1000 Tablets | Amount per Tablet-(% wt) | Quantity for 1000 Tablets |
| Compound 1 | 100 mg (25.0%) | 100 g | 200 mg (25.0%) | 200 g |
| Avicel DG[3] | 231 mg (57.75%[1]) | 231 g | 462 mg (57.75%[1]) | 462 g |
| Pregelatinized Starch | 40 mg (5.0%[1], 5%[2]) | 40 g | 80 mg (5.0%[1], 5%[2]) | 80 g |
| Colloidal silicon dioxide (Cab-o-sil M5P) | 3 mg (0.75 %[2]) | 3 g | 6 mg (0.75 %[2]) | 6 g |
| Povidone | 12 mg (3.0%[1]) | 12 g | 24 mg (3.0%[1]) | 24 g |
| Talc | 8 mg (2.0%[1]) | 8 g | 16 mg (2.0%[1]) | 16 g |
| Magnesium Stearate (HyQual) Vegetable Source | 6 mg (0.5%[1], 1.00%[2]) | 6 g | 12 mg (0.5%[1], 1.00%[2]) | 12 g |

TABLE 24-continued

| Batch Formula for Compound 1, 100 mg and 200 mg Tablets | | | | |
|---|---|---|---|---|
| | 100 mg Compound 1 | | 200 mg Compound 1 | |
| Component | Amount per Tablet-(% wt) | Quantity for 1000 Tablets | Amount per Tablet-(% wt) | Quantity for 1000 Tablets |
| Core Weight (mg) | 400 mg | 400 g | 800 mg | 800 g |
| Opadry II AMB, coating white[4] | 20 mg (5.0%) | 20 g | 40 mg (5.0%) | 40 g |
| Purified Water | Not applicable | N/A | Not applicable | N/A |
| Coated Tablet Weight (mg) | 420 mg | 420 g | 840 mg | 840 g |

[1]Intragranular
[2]Extragranular
[3]Avicel DG is co-processed excipient that contains Microcrystalline Cellulose and Anhydrous Dicalcium Phosphate, both of which meet USP and Ph.Eur. specifications (75% of microcrystalline cellulose and 25% anhydrous dibasic calcium phosphate)
[4]The film coating Opadry II AMB is manufactured by ColorCon and composed of polyvinyl alcohol (USP, FCC, Ph. Eur, JPE), talc (USP, FCC, Ph. Eur, JP, JECFA), titanium dioxide (USP, FCC, Ph. Eur, JP, ChP, GB), glyceryl monocaprylocaprate (NF, Ph. Eur), and sodium lauryl sulfate (NF, Ph. Eur, JP, ChP). This film coating agent is commonly used in the pharmaceutical industry.

Examples 2A-2B

Two Phase 1 studies have been completed in healthy male and female volunteers. A total of 166 subjects were enrolled in these studies; 128 received at least one dose of Compound 1 and 38 received matching placebo. Formulations of Compound 1 that were studied include Compound 1 administered intravenously, Compound 1 administered orally as a tablet, and Compound 1 administered orally as a liquid.

Study #1 of Compound 1 assessed the PK after IV administration of single and multiple doses of Compound 1, including the feasibility of a loading dose regimen. Study #2 of Compound 1 assessed the PK after single and multiple dose oral administration of Compound 1. In addition, there were three nested cohorts within study #2 of Compound 1 that assessed the iv/oral bioavailability, the effect of food on absorption, and drug-drug interaction potential.

Example 2A

Study #1 of Compound 1

This was a Phase 1, first-in-human, randomized, double-blind, placebo-controlled single ascending dose (SAD) and multiple ascending dose (MAD) escalation study of 120 healthy male and female subjects. The objectives of the study were to evaluate the safety, tolerability, and pharmacokinetics of single and multiple doses of Compound 1 administered by intravenous (IV) infusion.

In the single ascending dose (SAD) phase, Cohorts 1 to 6 and 11A to 11D received single doses. For Cohorts 11A to 11D, the infusion time varied from 0.5 to 3 hours to evaluate the relationship between $C_{max}$ and tolerability. In the multiple ascending dose (MAD) phase, Cohorts 7 to 10 received multiple doses over 14 days, and Cohort 12 examined the feasibility of a loading dose regimen. The dosing cohorts are described in Table 25.

Blood samples for the determination of Compound 1 and Compound 1A plasma concentrations were collected before and at appropriate times during all single- and multiple-dose administrations of Compound 1. For SAD Cohorts 1 to 6, urine samples for the determination of Compound 1A were collected through 48 hrs after dosing.

Eighty (80) subjects were enrolled into SAD Cohorts 1 to 6 and 11A to 11D. Within each cohort, six subjects were randomized to Compound 1 and two subjects to placebo. All 60 subjects randomized to Compound 1 completed dosing. Fifty-nine (59) subjects completed the study.

Forty (40) subjects were enrolled into MAD Cohorts 7 to 10 and Loading Dose Cohort 12.

Within each cohort, six subjects were randomized to Compound 1 and two subjects to placebo. Two (2) subjects, one in Cohort 7 (50 mg) and one in Loading Dose Cohort 12 did not complete dosing.

The PK analysis population therefore consisted of 60 subjects in the SAD phase and 28 subjects in the MAD phase.

TABLE 25

| Study # 1 of Compound 1: Treatments Administered | | | |
|---|---|---|---|
| Treatments | Infusion Duration (hours) | Frequency | Conditions |
| Cohorts 1-6, single ascending dose study | | | |
| 10 mg Compound 1 1/3 hr IV | 3 | once | fasted |
| 30 mg Compound 11/3 hr IV | 3 | once | fasted |
| 100 mg Compound 11/3 hr IV | 3 | once | fasted |
| 200 mg Compound 11/3 hr IV | 3 | once | fasted |
| 275 mg Compound 11/3 hr IV | 3 | once | fasted |
| 350 mg Compound 11/3 hr IV | 3 | once | fasted |
| Cohorts 7-10, multiple ascending dose study | | | |
| 50 mg Compound 11/3 hr IV | 3 | once per day for 14 days | fasted |
| 150 mg Compound 11/3 hr IV | 3 | once per day for 14 days | fasted |
| 300 mg Compound 11/3 hr IV | 3 | once per day for 14 days | fasted |
| 600 mg Compound 11/3 hr IV | 3 | once per day for 14 days | fasted |
| Cohorts 11a-d, single dose study - evaluation of different dosing regimens/infusion rates | | | |
| 1000 mg Compound 11/3 hr IV | 3 | once | fasted |
| 1000 mg Compound 11/2 hr IV | 2 | once | fasted |
| 1000 mg Compound 11/1 hr IV | 1 | once | fasted |
| 1000 mg Compound 11/0.5 hr IV | 0.5 | once | fasted |
| Cohort 12, multiple dose study - evaluation of different dosing regimens - loading dose | | | |
| 1000 mg loading dose + | 2 | twice a day on Day 1* | fasted |
| 600 mg multiple dose | 1 | once per day on Days 2-7 | |

*with 9 hours between the start of the infusions

Figure 2A:
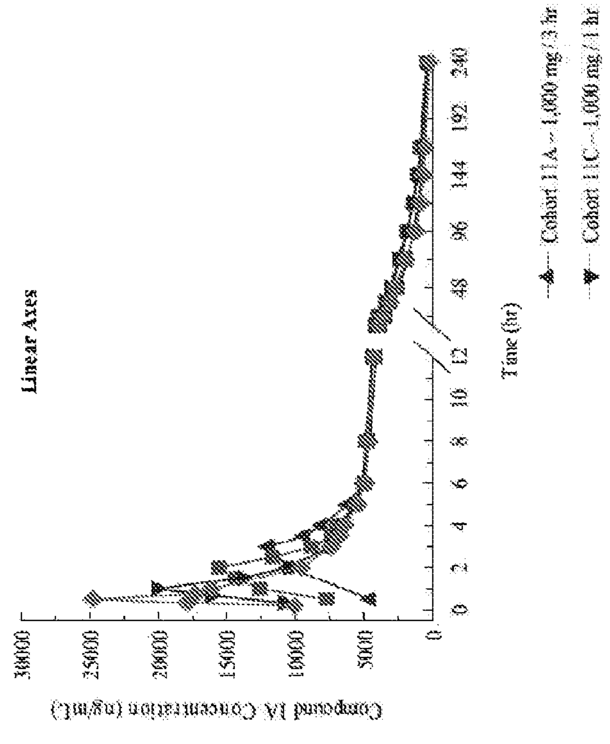
FIG. 2A-2B. Geometric mean plasma concentrations of Compound 1A after IV infusion of 1000 mg over 0.5 to 3 hrs to healthy subjects-linear (FIG. 2A) and semi logarithmic (FIG. 2B) axes.
Figure 2B:
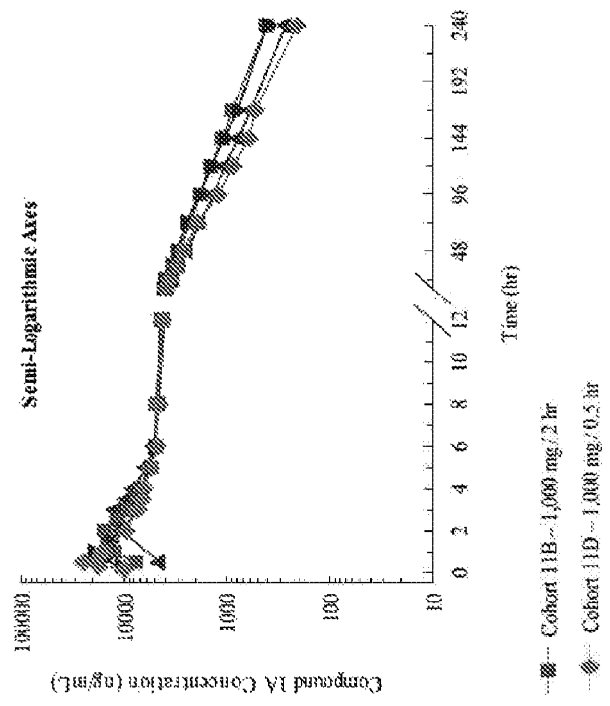

After IV administration of Compound 1 at single doses from 10 mg to 350 mg over 3 hours (FIGS. 2A-2B) and 1000 mg over 0.5 to 3 hrs, there were dose related increases in the geometric mean Compound 1A plasma concentrations (FIGS. 2A-2B). The geometric mean values for $C_{max}$, $AUC_{0-t}$, and AUC $_{(inf)}$ also increased with dose (Table 6 and Table 7) and log-log graphs of the individual subject values for $C_{max}$ (3 hr infusions) and AUC (inf) (all infusions) versus dose were linear with slopes, i.e. the power model parameter b, of 0.929±0.021 and 1.01±0.020, respectively, demonstrating dose proportional or linear PK over a 100-fold range.

The median $t_{max}$ was concordant with the infusion times for the 3 hr infusions (Groups 1 to 6 and 11A) (Table 26 and Table 27) and the 0.5 to 2 hr infusions (Groups 11B to 11D) (Table 7), indicating rapid and almost complete conversion of Compound 1 to Compound 1A.

Consistent with the decrease in infusion time, $C_{max}$ increased as the infusion time for Cohort 11, Groups 11A to 11D decreased (FIG. 2A-2B and Table 7). AUC (inf) is a function only of dose and was consistent across the 4 groups (Table 7).

The geometric mean values for CL and Vz were consistent across the ten single dose IV treatments and the geometric mean values for Ty ranged from 39.2 to 74.9 hrs (Table 6 and Table 7).

There was negligible excretion of unchanged Compound 1A in the urine, with geometric means ranging from 0.0041% to 0.0150% of the dose (Table 6).

TABLE 26

Summary of PK Parameters for Compound 1A after IV Infusion of 10, 30, 100, 200, 275, and 350 mg of Compound 1 Over 3 hrs to Healthy Subjects

| Parameter* | Cohort 1 10 mg/3 hr | Cohort 2 30 mg/3 hr | Cohort 3 100 mg/3 hr | Cohort 4 200 mg/3 hr | Cohort 5 275 mg/3 hr | Cohort 6 350 mg/3 hr |
|---|---|---|---|---|---|---|
| Cmax (ng/mL) | 161 | 477 | 1,444 | 2,412 | 3,964 | 4,326 |
| | [21.6] (6) | [13.5] (6) | [18.5] (6) | [19.3] (6) | [23.7] (6) | [14.0] (6) |
| Tmax(hr) | 3.00 (6) | 3.00 (6) | 3.00 (6) | 3.00 (6) | 3.00 (6) | 3.00 (6) |
| | [3.00-3.00] | [3.00-3.07] | [3.00-3.02] | [2.00-3.15] | [3.00-3.00] | [3.00-3.03] |
| AUC(0-24) | 1,536 | 4,325 | 14,359 | 20,748 | 37,066 | 38,168 |
| (hr × ng/mL) | [26.8] (6) | [10.5] (6) | [18.4] (6) | [20.0] (6) | [25.5] (6) | [17.4] (6) |
| AUC(0-t) | 2,379 | 14,079 | 47,400 | 76,000 | 114,256 | 153,440 |
| (hr × ng/mL) | [27.1] (6) | [22.2] (6) | [11.8] (6) | [27.7] (6) | [15.6] (6) | [11.6] (6) |
| AUC(inf) | 4,048 | 16,645 | 50,370 | 83,169 | 119,740 | 173,418 |
| (hr × ng/mL) | [26.9] (6) | [34.7] (6) | [17.85] (6) | [30.1] (6) | [15.6] (6) | [14.1] (6) |
| λz (1/hr) | 0.0177 | 0.0114 | 0.0132 | 0.0104 | 0.0143 | 0.0093 |
| | [32.9] (6) | [39.7] (6) | [41.4] (6) | [24.3] (6) | [33.2] (6) | [29.3] (6) |
| t½ (hr) | 39.2 | 61.0 | 52.5 | 67.0 | 48.6 | 74.9 |
| | [32.9] (6) | [39.7] (6) | [41.4] (6) | [24.3] (6) | [33.2] (6) | [29.3] (6) |
| CL | | | | | | |
| (mL/hr) | 1,890 | 1,379 | 1,519 | 1,840 | 1,757 | 1,544 |
| | [26.9] (6) | [34.7] (6) | [17.9] (6) | [30.1] (6) | [15.6] (6) | [14.1] (6) |
| (mL/hr/kg) | 27.0 | 19.6 | 24.8 | 25.5 | 25.0 | 20.9 |
| | [31.8] (6) | [24.8] (6) | [17.3] (6) | [25.2] (6) | [12.0] (6) | [14.6] (6) |
| Vz | | | | | | |
| (L) | 107 | 121 | 115 | 178 | 123 | 167 |
| | [34.7] (6) | [16.5] (6) | [24.3] (6) | [29.8] (6) | [33.7] (6) | [21.3] (6) |
| (L/kg) | 1.53 | 1.72 | 1.88 | 2.46 | 1.75 | 2.26 |
| | [29.4] (6) | [21.4] (6) | [28.9] (6) | [14.2] (6) | [32.2] (6) | [24.9] (6) |
| Urinary Excretion | | | | | | |
| Amount (μg) | 0.314 | 3.44 | 7.60 | 16.2 | 19.7 | 26.4 |
| | [82.7] (6) | [176] (6) | [23.4] (6) | [22.3] (6) | [27.0] (6) | [26.0] (6) |
| Percent Dose† | 0.0041 | 0.0150 | 0.0099 | 0.0106 | 0.0094 | 0.0099 |
| | [82.7] (6) | [176] (6) | [23.4] (6) | [22.3] (6) | [27.0] (6) | [26.0] (6) |

*Geometric mean [geometric % CV] (N) except tmax for which the median (N) [Range] is reported.

†Corrected for the difference in molecular weight.

TABLE 27

Summary of PK Parameters for Compound 1A after IV Infusion of 1000 mg of Compound 1 Over 0.5 to 3 Hrs to Healthy Subjects

| | Cohort 11 | | | |
|---|---|---|---|---|
| Parameter* | 1,000 mg/3 hr | 1,000 mg/2 hr | 1,000 mg/1 hr | 1,000 mg/0.5 hr |
| Cmax (ng/mL) | 11,946 [28.3] (6) | 15,648 [31.0] (6) | 20,118 [17.5] (6) | 24,892 [07.5] (6) |
| Tmax (hr) | 3.02 (6) | 2.02 (6) | 1.02 (6) | 0.52 (6) |
| | [3.00-3.05] | [1.50-2.03] | [1.00-1.18] | [0.50-1.02] |
| AUC(0-24) (hr × ng/mL) | 117,369[35.4] (6) | 129,978 [38.5] (6) | 133,888 [20.4] (6) | 131,108 [38.0] (6) |
| AUC(0-t) (hr × ng/mL) | 362, 689 [20.3] (6) | 476,305 [24.5] (6) | 480,944 [7.71] (6) | 402, 850 [18.2] (6) |
| AUC(inf) (hr × ng/mL) | 400,438 [20.9] (6) | 540,759 [26.9] (6) | 535,942 [9.24] (6) | 433,780 [17.2] (6) |

TABLE 27-continued

Summary of PK Parameters for Compound 1A after IV Infusion of 1000 mg of Compound 1 Over 0.5 to 3 Hrs to Healthy Subjects

| | Cohort 11 | | | |
|---|---|---|---|---|
| Parameter* | 1,000 mg/3 hr | 1,000 mg/2 hr | 1,000 mg/1 hr | 1,000 mg/0.5 hr |
| λz (1/hr) | 0.0125 [38.3] (6) | 0.0096 [43.7] (6) | 0.0102 [37.6] (6) | 0.0125 [ 47.1] (6) |
| t½ (hr) | 55.7 [38.3] (6) | 72.5 [43.7] (6) | 67.7 [37.6] (6) | 55.6 [47.1] (6) |
| CL | | | | |
| (mL/hr) | 1,911 [20.9] (6) | 1,415 [26.9] (6) | 1,428 [09.2] (6) | 1,764 [17.2] (6) |
| (mL/hr/kg) | 25.1 [16.7] (6) | 23.2 [28.8] (6) | 21.6 [15.6] (6) | 24.6 [15.2] (6) |
| Vz | | | | |
| (L) | 153 [49.0] (6) | 153 [49.0] (6) | 139 [31.1] (6) | 141 [50.1] (6) |
| (L/kg) | 2.02 [39.9] (6) | 2.43 [46.3] (6) | 2.11 [28.4] (6) | 19.7 [40.1] (6) |

*Geometric mean [geometric % CV] (N) except $t_{max}$ for which the median (N) [Range] is reported.

Figure 3B:
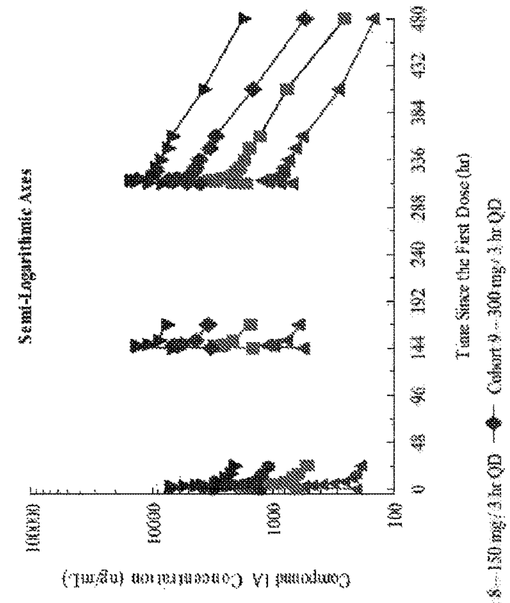
FIG. 3A-3B. Geometric mean plasma concentrations of Compound 1A after IV infusion of 50, 150, 300 and 600 mg of Compound 1 over 3 hrs qd×14 days to healthy subjects-linear (FIG. 3A) and semi logarithmic (FIG. 3B) and axes FIG. 4A-4B. Geometric mean plasma concentrations of Compound 1A after IV infusion of a loading regimen of Compound 1 of 1000 mg over 2 hrs at 0 and 9 hrs on day 1 followed by 600 mg over 1 hr qd×6 days, days 2 to 7, to healthy subjects-linear (FIG. 4A) and semi logarithmic (FIG. 4B) axes FIG. 5A-5B. Geometric mean plasma concentrations mean plasma concentrations of Compound 1 after IV infusion of 10 to 350 mg of Compound 1 over 3 hrs and 1000 mg over 0.5 to 3 hrs to healthy subjects-linear (FIG. 5A) and semi logarithmic (FIG. 5B) axes.
Figure 3A:
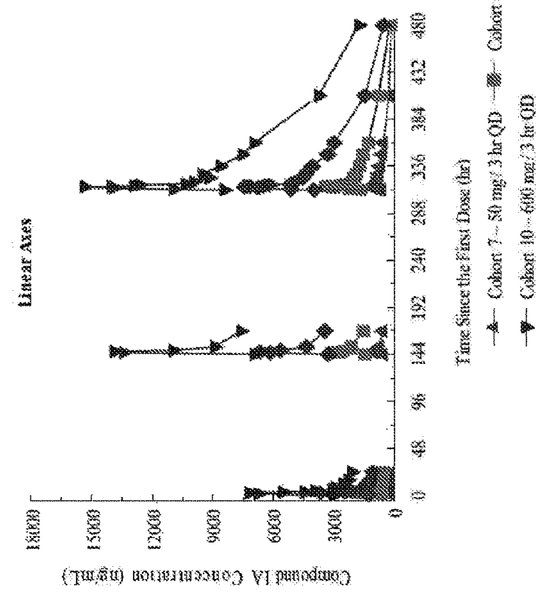

After multiple-dose IV administration of Compound 1 at 50, 150, 300, and 600 mg over 3 hrs QD×14 days, there was a dose-related increase in the geometric mean plasma concentrations of Compound 1A (FIG. 3A-3B). The geometric mean values for $C_{max}$ and $AUC_{0-24}$ also increased with dose (Table 28) and log-log graphs of the individual subject values for the steady-state $C_{max}$ (Cohorts 7 to 10, 3-hr infusions) and AUC0-24 (Cohorts 7 to 10, Day 14; Cohort 12, Day 7) vs. dose were linear with slopes, i.e. the power model parameter b, of 1.039±0.031 and 1.015±0.043, respectively, demonstrating dose proportional or linear PK.

The median $t_{max}$ was concordant with the infusion time of 3 hrs for Groups 7 to 10 (Table 28). The geometric mean values for CL and V2 were consistent among the 4 MAD IV cohorts (Table 28) and the Loading Regimen Cohort (Table 29). The geometric mean values for ty ranged from 48.0 to 69.0 hrs for these same cohorts (Table 28 and Table 29).

The median accumulation of Compound 1A, estimated as the ratio of $C_{max}$ or $AUC_{0-24}$ on Day 14 to that on Day 1, was 1.96 and 3.27, respectively, with no apparent trends among the 4 cohorts administered Compound 1 over 3 hrs.

Figure 4B:
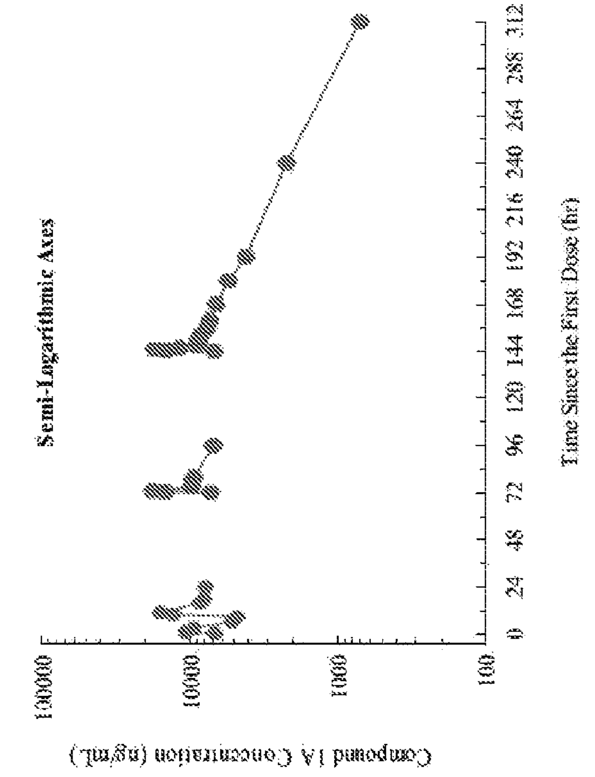
Figure 4A:
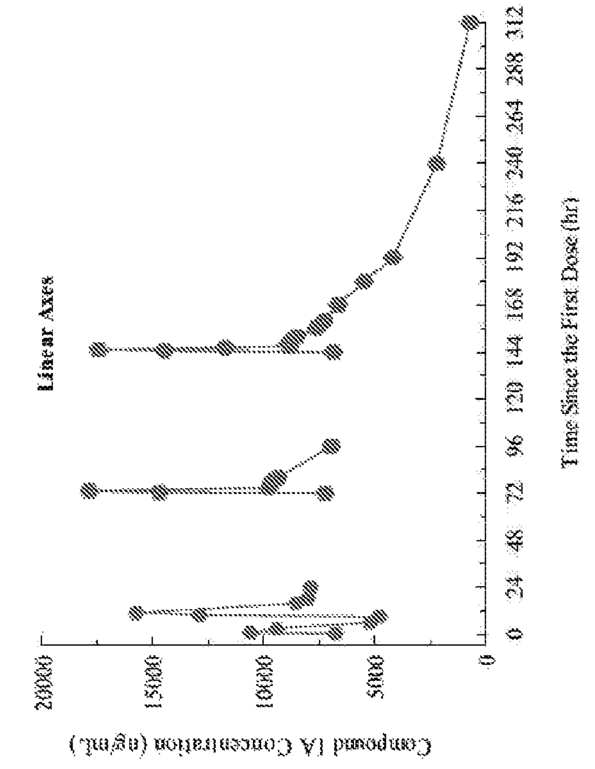

Treatment of fungal infections is best achieved by reaching therapeutic exposures as soon as possible. However, as illustrated in FIG. 3A-3B and Table 28, steady-state is reached somewhere between Day 7 and Day 14, depending on the individual subject's $t_{1/2}$. A loading regimen was therefore examined with the objective of reaching steady state exposures as soon as possible. A regimen of 1000 mg/2 hrs×2 at 0 and 9 hrs on Day 1 followed by 600 mg/l hr QD on Days 2 to 7 was chosen, based on simulations, to reach steady state as soon as possible. The geometric mean plasma Compound 1A concentrations for this regimen appear to reach steady-state by Day 4 (FIG. 4A-4B) as do the geometric mean values for $C_{max}$ and $AUC_{0-24}$ (Table 29). Comparison of the $C_{max}$ and $AUC_{0-24}$ on Day 7 for the loading regimen (Table 29) with those on Day 14 for 600 mg/3 hrs×14 days, i.e. without a loading regimen (Table 28), shows reasonable agreement when the difference in infusion times for the 600 mg dose between the 2 cohorts is taken into account. This suggests that the loading regimen meets the objective of reaching steady-state as soon as possible.

TABLE 28

Summary of PK Parameters for Compound 1A after IV Infusion of 50, 150, 300, and 600 mg of Compound 1 Over 3 Hrs QD × 14 Days to Healthy Subjects

| Parameter* | Cohort 7 50 mg/3 hr | Cohort 8 150 mg/3 hr | Cohort 9 300 mg/3 hr | Cohort 10 600 mg/3 hr |
|---|---|---|---|---|
| Day 1 | | | | |
| Cmax (ng/mL) | 669 [20.9] (5) | 1,865 [12.4] (6) | 3,687 [27.0] (6) | 7,572 [15.5] (6) |
| Tmax (hr) | 3.00 (5) [3.00-3.00] | 3.00 (6) [3.00-3.02] | 3.00 (6) [3.00-3.00] | 3.00 (6) [2.00-3.02] |
| AUC(0-24) (hr × ng/mL) | 6,388 [21.6] (5) | 19,382 [19.7] (6) | 37,059 [33.8] (6) | 72,679 [10.1] (6) |
| Day 7 | | | | |
| Cmax (ng/mL) | 1,091 [16.6] (5) | 3,090 [8.84] (6) | 6,654 [17.6] (6) | 14,491 [8.37] (6) |
| Tmax (hr) | 3.00 (5) [3.00-3.03] | 3.00 (6) [3.00-3.03] | 3.00 (6) [2.00-3.00] | 3.03 (6) [2.00-3.05] |
| AUC(0-24) (hr × ng/mL) | 17,566 [14.4] (5) | 48,682 [9.35] (6) | 104,080 [24.3] (6) | 217,089 [9.21] (6) |
| Day 14 | | | | |
| Cmax (ng/mL) | 1,182 [15.4] (5) | 3,424 [7.17] (6) | 7,523 [15.28] (6) | 15,364 [14.3] (6) |
| Tmax (hr) | 3.00 (5) | 3.02 (6) [3.00-3.52] | 3.02 (6) [3.02-3.50] | 3.00 (6) [3.00-3.00] |
| AUC(0-24) (hr × ng/mL) | 20,266 [19.5] (5) | 51,907 [14.0] (6) | 118,362 [24.6] (6) | 245,049 [12.1] (6) |

TABLE 28-continued

Summary of PK Parameters for Compound 1A after IV Infusion of 50, 150, 300, and 600 mg of Compound 1 Over 3 Hrs QD × 14 Days to Healthy Subjects

| Parameter* | Cohort 7 50 mg/3 hr | Cohort 8 150 mg/3 hr | Cohort 9 300 mg/3 hr | Cohort 10 600 mg/3 hr |
|---|---|---|---|---|
| λz (1/hr) | 0.0100 [43.9] (5) | 0.0132 [51.4] (5) | 0.0131 [30.7] (6) | 0.0107 [26.0] (6) |
| t½ (hr) | 69.0 [43.9] (5) | 52.6 [51.4] (5) | 53.1 [30.7] (6) | 64.8 [26.0] (6) |
| CL | | | | |
| (mL/hr) | 1,888 [19.5] (5) | 2,211 [14.0] (6) | 1,939 [24.6] (6) | 1,873 [12.1] (6) |
| (mL/hr/kg) | 24.5 [20.0] (5) | 27.7 [17.3] (6) | 29.0 [15.1] (6) | 29.4 [18.8] (6) |
| Vz | | | | |
| (L) | 188 [34.3] (5) | 174 [42.1] (5) | 148 [33.5] (6) | 175 [16.7] (6) |
| (L/kg) | 2.44 [35.9] (5) | 2.17 [36.9] (5) | 2.22 [28.5] (6) | 2.75 [22.9] (6) |

*Geometric mean [geometric % CV] (N) except $t_{max}$ for which the median (N) [Range] is reported.

TABLE 29

Summary of PK Parameters for Compound 1A after IV Infusion of a Loading Regimen of Compound 1 of 1000 mg Over 2 Hrs at 0 and 9 Hrs on Day 1 Followed by 600 mg Over 1-hr QD × 6 Days, Days 2 to 7, to Healthy Subjects

| | 1,000 mg/2 hr at | 600 mg/1 hr QD | |
|---|---|---|---|
| Parameter* | 0 & 9 hr Day 1 | Day 4 | Day 7 |
| Cmax (ng/mL) | 15,738 [25.2] (5) | 17,863 [11.6] (5) | 17,662 [9.14] (5) |
| Tmax (hr) | 11.0 (5) [11.0-11.1] | 1.00 (5) [1.00-1.00] | 1.00 (5) [0.50-1.00] |
| AUC(0-24) (hr × ng/mL) | 211,293 [19.9] (5) | 219,458 [5.58] (5) | 200,790 [13.3] (5) |
| λz (1/hr) | —† | —† | 0.0145 [41.4] (4) |
| t½ (hr) | —† | —† | 48.0 [41.4] (4) |
| CL | —† | —† | |
| (mL/hr) | —† | —† | 2,286 [13.3] (5) |
| (mL/hr/kg) | —† | —† | 33.4 [14.4] (5) |
| Vz | —† | —† | |
| (L) | —† | —† | 162 [30.8] (4) |
| (L/kg) | —† | —† | 2.27 [34.4] (4) |

*Geometric mean [geometric % CV] (N) except $t_{max}$ for which the median (N) [Range] is reported.
†Parameter not applicable to the study day.

Circulating phosphatases play a role in bioconversion of the phosphate prodrug, Compound 1, to the active moiety Compound 1A in human blood. This is also evident from the plasma Compound 1 concentration-time data. The prodrug is rapidly converted to the active moiety as concentrations of the prodrug are <LOQ by at most 8 hrs after the start of the infusion and $t_{max}$ for the active is reached essentially at the end of the infusion of the prodrug. Exposures to the prodrug are <5% of those to the active. PK analysis was limited to calculation of $C_{max}$, $t_{max}$, and $AUC_{0-t}$ after both single and multiple doses.

Figures 5A, 5B:
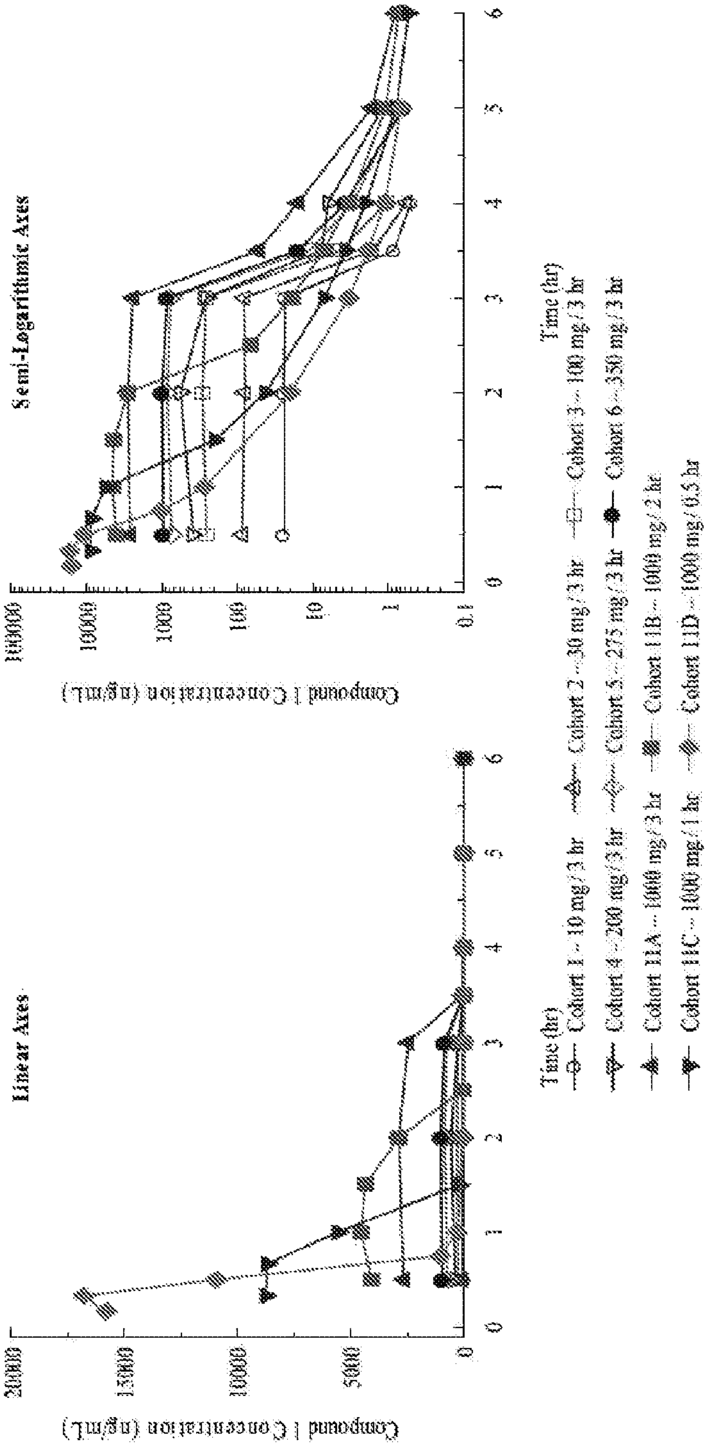

After IV administration of Compound 1 at single doses from 10 mg to 350 mg over 3 hrs and 1000 mg over 0.5 to 3 hrs, there were dose related increases in the geometric mean Compound 1 plasma concentrations (FIG. 5A-5B). The geometric mean values for $C_{max}$, $AUC_{0-t}$, and $AUC_{0-inf}$ also increased with dose (Table 10 and Table 11).

The median $t_{max}$ was generally shorter than the infusion times for the 3 hr infusions (Groups 1 to 6 and 11A) (Table 30 and Table 31) and also for the 0.5 to 2 hr infusions (Groups 11B to 11D) (Table 31), most likely due to rapid conversion of Compound 1 to Compound 1A.

TABLE 30

Summary of PK Parameters for Compound 1 after IV Infusion of 10, 30, 100, 200, 275, and 350 mg of Compound 1 Over 3 Hrs to Healthy Subjects

| Parameter* | Cohort 1 10 mg/3 hr | Cohort 2 30 mg/3 hr | Cohort 3 100 mg/3 hr | Cohort 4 200 mg/3 hr | Cohort 5 275 mg/3 hr | Cohort 6 350 mg/3 hr |
|---|---|---|---|---|---|---|
| Cmax(ng/mL) | 26.9 [8.46] (6) | 92.3 [31.3] (6) | 318 [21.9] (6) | 634 [28.1] (6) | 954 [9.58] (6) | 1,185 [39.6] (6) |
| Tmax(hr) | 2.01 (6) [0.50-3.00] | 0.50 (6) [0.50-2.00] | 2.00 (6) [0.50-3.00] | 2.00 (6) [0.50-4.00] | 2.00 (6) [0.50-3.00] | 2.00 (6) [0.50-3.03] |
| AUC(0-t) (hr × ng/mL) | 70.5 [8.24] (6) | 250 [26.9] (6) | 2,426 [10.5] (6) | 1,478 [25.2] (6) | 2,426 [10.5] (6) | 2,952 [27.6] (6) |

*Geometric mean [geometric % CV] (N) except tmax for which the median (N) [Range] is reported.

TABLE 31

Summary of PK Parameters for Compound 1 after IV Infusion of 1,000 mg of Compound 1 Over 0.5 to 3 Hrs to Healthy Subjects

| | Cohort 11 | | | |
|---|---|---|---|---|
| Parameter* | 1,000 mg/3 hr | 1,000 mg/2 hr | 1,000 mg/1 hr | 1,000 mg/0.5 hr |
| Cmax (ng/mL) | 2,913 [10.2] (6) | 4,682 [27.3] (6) | 9,244 [18.4] (6) | 17,686 [17.8] (6) |
| Tmax (hr) | 2.00 (6) [2.00-3.05] | 1.00 (6) [0.50-1.50] | 0.54 (6) [0.33-1.02] | 0.36 (6) [0.17-0.50] |
| AUC(0-t) (hr × ng/mL) | 8,185 [10.1] (6) | 8,078 [29.7] (6) | 9,019 [24.4] (6) | 8,809 [23.1] (6) |

*Geometric mean [geometric % CV] (N) except $t_{max}$ for which the median (N) [Range] is reported.

Figure 6B:
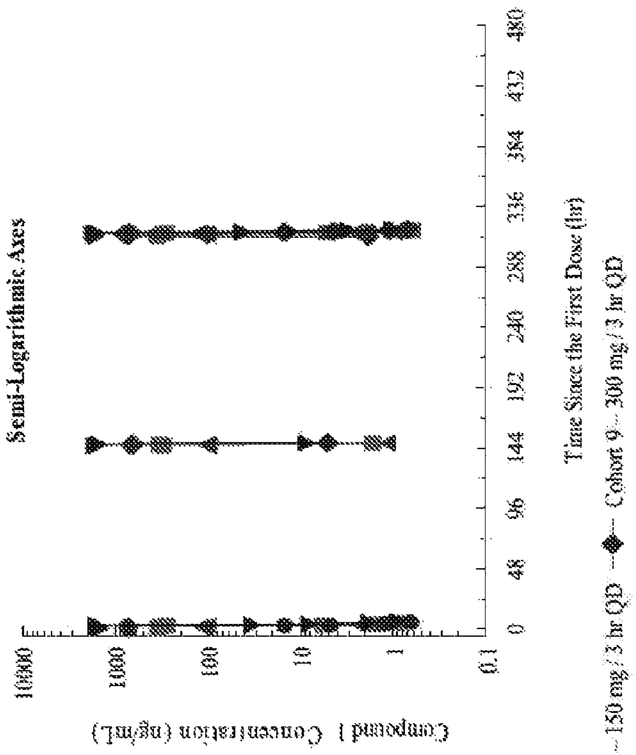
FIG. 6A-6B. Geometric mean plasma concentrations of Compound 1 after IV infusion of 50, 150, 300 and 600 mg of Compound 1 Over 3 Hrs QD×14 days to healthy subjects-linear (FIG. 6A) and semi logarithmic (FIG. 6B) axes.
Figure 6A:
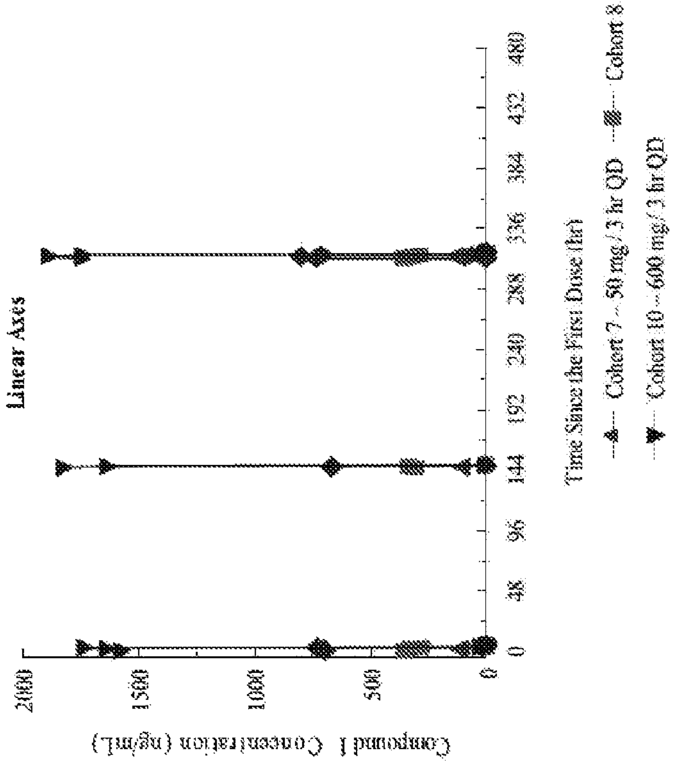

After IV administration of Compound 1 at multiple doses of 50, 150, 300, and 600 mg over 3 hrs QD×14 days, there was a dose-related increase in the geometric mean plasma concentrations of Compound 1 (FIG. 6A-6B). The geometric mean values for $C_{max}$ and $AUC_{0-t}$ also increased with dose (Table 32).

The median $t_{max}$ was generally shorter than the infusion times for the 3 hr infusions, most likely due to rapid conversion of Compound 1 to Compound 1A.

Figure 7B:
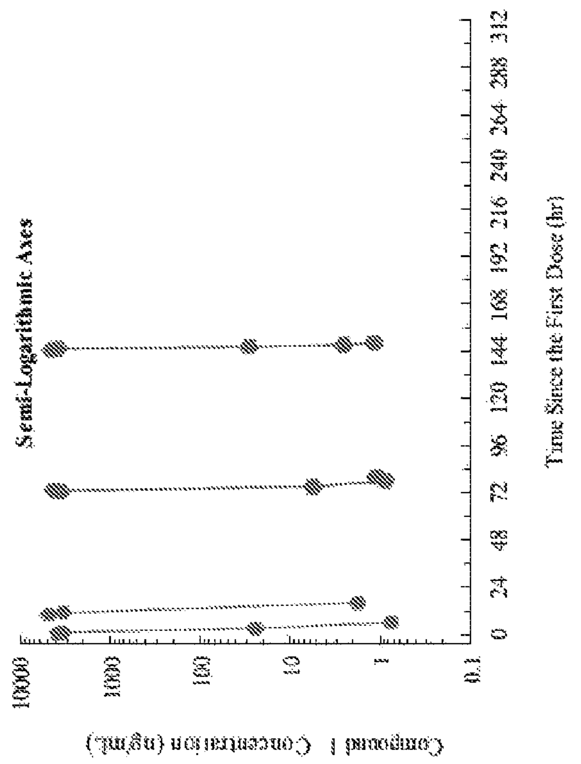
FIG. 7A-7B. Geometric mean plasma concentrations of Compound 1 after IV infusion of a loading regimen of Compound 1 of 1000 mg over 2 hrs at 0 and 9 hrs on day 1 followed by 600 mg over 1-hr qd×6 days, days 2 to 7, to healthy subjects-linear (FIG. 7A) and semi logarithmic (FIG. 7B) axes.
Figure 7A:
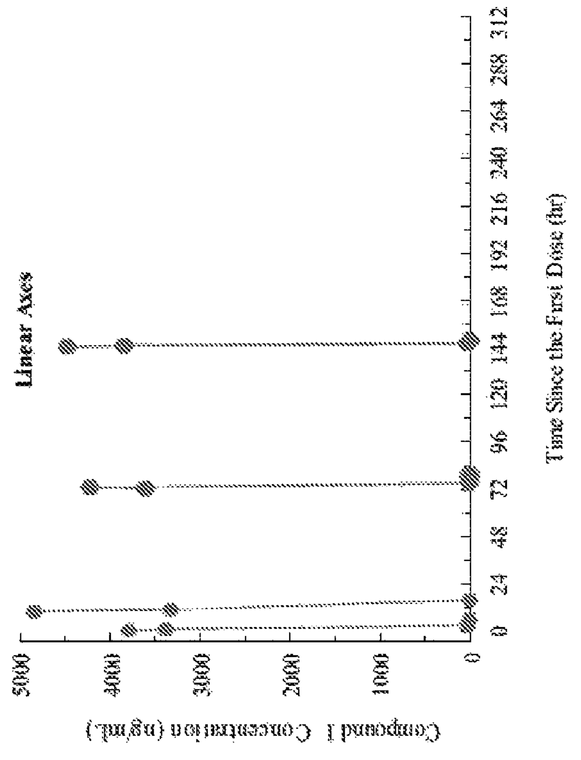

Due to the rapid conversion of Compound 1 to Compound 1A, there was essentially no accumulation with comparable values for $C_{max}$ and $AUC_{0-t}$ on Days 1, 7, and 14 (Table 32). This is also evident by comparison of Days 1, 4, and 7 for the loading dose cohort (Cohort 12) (Table 33 and FIG. 7A-7B).

TABLE 32

Summary of PK Parameters for Compound 1 after IV Infusion of 50, 150, 300, and 600 mg of Compound 1 Over 3 Hrs QD × 14 Days to Healthy Subjects

| Parameter* | Cohort 7 50 mg/3 hr | Cohort 8 150 mg/3 hr | Cohort 9 300 mg/3 hr | Cohort 10 600 mg/3 hr |
|---|---|---|---|---|
| Day 1 | | | | |
| Cmax (ng/mL) | 121 [15.2] (5) | 401 [26.4] (6) | 806 [32.2] (6) | 1,919 [13.4] (6) |
| Tmax (hr) | 2.00 (5) [0.50-3.00] | 2.01 (6) [0.50-3.00] | 2.00 (6) [0.50-3.00] | 1.25 (6) [0.50-3.00] |
| AUC(0-24) (hr × ng/mL) | 318 [6.92] (5) | 1,004 [28.4] (6) | 2,159 [28.8] (6) | 5,034 [17.1] (6) |
| Day 7 | | | | |
| Cmax (ng/mL) | 97.9 [38.1] (5) | 349 [18.0] (6) | 731 [19.0] (6) | 1,920 [6.05] (6) |
| Tmax (hr) | 3.00 (5) [2.00-3.03] | 3.00 (6) [2.00-3.03] | 2.06 (6) [2.00-3.00] | 2.51 (6) [2.00-3.05] |
| AUC(0-24) (hr × ng/mL) | 226 [48.7] (5) | 801 [18.6] (6) | 1,676 [16.9] (6) | 4,455 [7.29] (6) |
| Day 14 | | | | |
| Cmax (ng/mL) | 121 [33.8] (5) | 373 [21.2] (6) | 863 [29.3] (6) | 2,055 [20.9] (6) |
| Tmax (hr) | 0.50 (5) [0.50-3.00] | 0.50 (6) [0.50-3.00] | 2.00 (6) [0.50-3.02] | 2.00 (6) [0.50-3.00] |
| AUC(0-24) (hr × ng/mL) | 317 [39.8] (5) | 987 [20.0] (6) | 2,316 [24.0] (6) | 5,511 [17.3] (6) |

*Geometric mean [geometric % CV] (N) except $t_{max}$ for which the median (N) [Range] is reported.

TABLE 33

Summary of PK Parameters for Compound 1 After IV Infusion of a Loading Regimen of Compound 1 of 1000 mg Over 2 Hrs at 0 and 9 Hrs on Day 1 Followed by 600 mg Over 1-hr QD × 6 Days, Days 2 to 7, to Healthy Subjects

| | 1,000 mg/2 hr | 600 mg/1 hr QD | |
|---|---|---|---|
| Parameter* | at 0 & 9 hr Day 1 | Day 4 | Day 7 |
| Cmax (ng/mL) | 4,881 [20.0] (5) | 4,233 [12.5] (5) | 4,875 [17.8] (5) |
| Tmax (hr) | 10.0 (5) [0.50-10.1] | 1.00 (5) [0.50-1.00] | 1.00 (5) [0.50-1.00] |

TABLE 33-continued

Summary of PK Parameters for Compound 1 After IV Infusion of a Loading Regimen of Compound 1 of 1000 mg Over 2 Hrs at 0 and 9 Hrs on Day 1 Followed by 600 mg Over 1-hr QD × 6 Days, Days 2 to 7, to Healthy Subjects

| Parameter* | 1,000 mg/2 hr at 0 & 9 hr Day 1 | 600 mg/1 hr QD Day 4 | 600 mg/1 hr QD Day 7 |
|---|---|---|---|
| AUC(0-t) (hr × ng/mL) | 29,819 [11.2] (5) | 7,235 [17.0] (5) | 5,305 [27.1] (5) |

*Geometric mean [geometric % CV] (N) except $t_{max}$ for which the median (N) [Range] is reported.
†Parameter not applicable to the study day.

Target Compound 1A plasma exposures (AUC0-24) for clinical efficacy against *Candida* spp., *Aspergillus* spp., and the hard-to-treat rare molds (*Scedosporium* spp., *Fusarium* spp, and Mucorales fungi) were exceeded.

Compound 1

Exposures to the prodrug were short lived and <5% of those of the active Compound 1A, precluding extensive PK analysis. Exposures after single and multiple dosing increased in a dose-related manner. Due to the rapid conversion to Compound 1A, there is essentially no accumulation of Compound 1 following multiple dosing.

Single Dose-Evaluation of Different Dosing Regimens-Infusion Rates

Overall Incidence of TEAEs

A total of 27 subjects (84%) reported 87 TEAEs. Of these, 5 subjects (83%) reported 13 TEAEs in the 1000 mg/3 hr group; 6 subjects (100%) reported 22 TEAEs in the 1000 mg/2 hr group; 6 subjects (100%) reported 25 TEAEs in the 1000 mg/l hr group; and 6 subjects (100%) reported 21 TEAEs in the 1000 mg/0.5 hr group. The total number of TEAEs in the respective placebo groups (2 subjects per group) ranged between 0 and 3, reported by a total of 4 subjects (50%).

Although the percentage of subjects reporting TEAEs was similar among the different groups, the number of TEAEs was lower in the 1000 mg/3 hr group compared to the dose groups with a shorter infusion period (1000 mg/2 hr, 1000 mg/l hr and 1000 mg/0.5 hr). The number of TEAEs were similar between the 1000 mg/2 hr, 1000 mg/l hr and 1000 mg/0.5 hr groups.

Multiple Dose-Evaluation of Different Dosing Regimens-Loading Dose Overall Incidence of TEAEs All 8 subjects in Cohort 12 (100%) reported a total of 41 TEAEs. Of these, 6 subjects (100%) who were administered the Compound 1 loading dose regimen (1000 mg IV Compound 1 via a 2-hour infusion twice on Day 1 with an interval of 9 hours between start of infusions+600 mg IV Compound 1 via a 1-hr infusion QD on Days 2-7) reported 38 TEAEs and 2 subjects (100%) who were administered placebo reported 3 TEAEs.

Example 2B

Study #2 of Compound 1 was a Phase 1, double-blind, placebo-controlled, randomized study in healthy volunteers that consisted of a series of single and multiple dose treatments. In the single ascending dose (SAD) phase, subjects in Cohort 1a received a single IV dose in Period A and then rising single oral doses in Periods B to D. Subjects in Cohort 1b received a single oral dose under fed and fasted conditions in Periods E and F. Subjects in Cohorts 2 and 3 received once-daily oral doses for 14 days, as did subjects in Cohort 4 as part of an in vivo screen for drug-drug interaction (DDI) potential. All subjects in Cohort 4 received Compound 1; therefore, this cohort was open-label. The dosing cohorts are described in Table 14.

Blood samples for the determination of Compound 1 and Compound 1A plasma concentrations were collected before and at appropriate times during all single and multiple dose administrations of Compound 1. For SAD Cohorts 1a and 1b, urine samples for the determination of Compound 1A were collected through 48 hrs after dosing.

Blood samples for the determination of the CYP substrate plasma concentrations were collected before and at 0.5, 1, 2, 4, 6, 8, 12, 16, and 24 hrs after administration of single doses on Days 1 and 15.

Forty-six (46) subjects were enrolled into the study, 8 in Cohort 1a, 10 in Cohort 1b, and 8 each in Cohorts 2 and 3. Within each cohort, 2 subjects were randomized to placebo and the remainder to Compound 1. Cohort 4 consisted of 12 subjects, all of whom received Compound 1. All 38 subjects randomized to Compound 1 completed the study and comprised the PK analysis population.

TABLE 34

Study # 2 of Compound 1: Treatments Administered

| Treatments | Route of Administration | Frequency | Conditions |
|---|---|---|---|
| Cohort 1a, single ascending dose study, crossover design [same eight subjects in the four dose groups] | | | |
| 200 mg sd Compound 1 | IV | once | fasted |
| 100 mg sd Compound 1 | tablets | once | fasted |
| 300 mg sd Compound 1 | tablets | once | fasted |
| 500 mg sd Compound 1 | tablets | once | fasted |
| Cohort 1b, single dose - food effect study, crossover design | | | |
| 400 mg sd Compound 1 | tablets | once | fasted |
| 400 mg sd Compound 1 | tablets | once | fed |
| Cohorts 2 and 3, multiple ascending dose study | | | |
| 500 mg md Compound 1 | tablets | once per day for 14 days | fed |
| 1000 mg md Compound 1 | tablets | once per day for 14 days | fed |
| Cohort 4, drug-drug interaction study | | | |
| 500 mg md Compound 1* | oral solution | once per day for 14 days | fed |

Figure 8B:
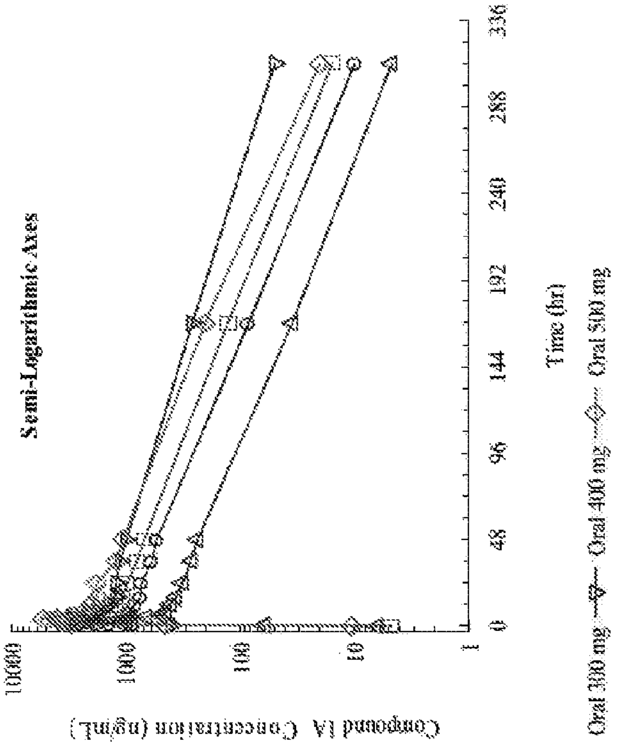
FIG. 8A-8B. Geometric mean plasma concentrations of Compound 1A after intravenous infusion of 200 mg Compound 1 over 3 hrs and oral doses of 100 to 500 mg to healthy subjects under fasted conditions-linear (FIG. 8A) and semi logarithmic (FIG. 8B) axes.
Figure 8A:
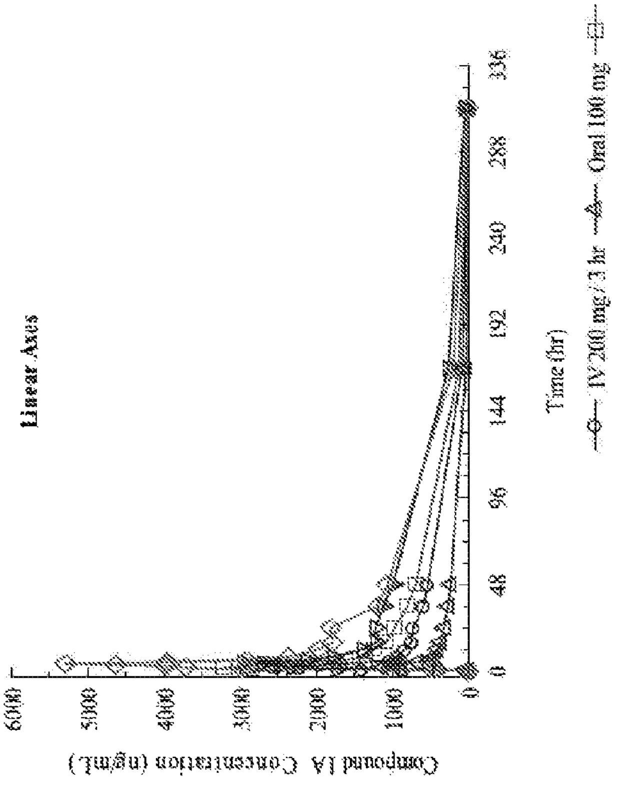

*Single oral doses of 6 CYP substrates (consisting of 1 mg midazolam, 10 mg dextromethorphan hydrobromide, 50 mg caffeine, 20 mg bupropion, 10 mg omeprazole, 10 mg flurbiprofen) were given one day before the first dose of Compound 1 and on the last day of Compound 1 dosing.
sd = single dose;
md = multiple dose Compound 1A After oral administration of Compound 1 at single doses from 100 mg to 500 mg, there were dose related increases in the geometric mean Compound 1A plasma concentrations (FIG. 8A-8B). The geometric mean values for $C_{max}$, $AUC_{0-t}$, and AUC (inf) also increased with dose (Table 35) and log-log graphs of the individual subject values for $C_{max}$ and AUC (inf) vs. dose were linear with slopes, i.e. the power model parameter b, of 0.935±0.077 and 1.04=0.046, respectively, demonstrating dose-proportional or linear pharmacokinetics. The median values for $t_{max}$ ranged from 2.0 to 3.0 hrs with consistent ranges for the 4 oral doses (Table 35).

The geometric mean values for ty, ranged from 44.9 to 64.7 hrs for the 4 oral treatments and was 49.1 hrs for the IV treatment (Table 35) indicating that absorption of Compound 1 and/or conversion to Compound 1A was not the rate limiting step in Compound 1A pharmacokinetics.

The geometric mean values for CL/F and $V_2$/F were consistent among the 4 oral treatments (Table 35) with no apparent dependence on dose. The geometric mean $t_{1/2}$, after oral administration was also consistent with that from the IV treatment in this study, 49.1 hrs (Table 35), as well as those from Study #1 of Compound 1 (Tables 26-29), indicating that absorption of Compound 1 and/or conversion to Compound 1A was not the rate limiting step in Compound 1A pharmacokinetics.

The absolute oral bioavailability of Compound 1A ranged from 90.6% to 101.2% (Table 35), indicating essentially complete absorption of Compound 1 and conversion to Compound 1A. Consequently, the geometric mean values for CL and $V_2$ after IV administration were concordant with CL/F and $V_2$/F after oral administration (Table 35).

There was negligible excretion of unchanged Compound 1A in the urine after oral administration, with geometric means ranging from 0.009% to 0.012% of the dose (Table 35).

Figure 9B:
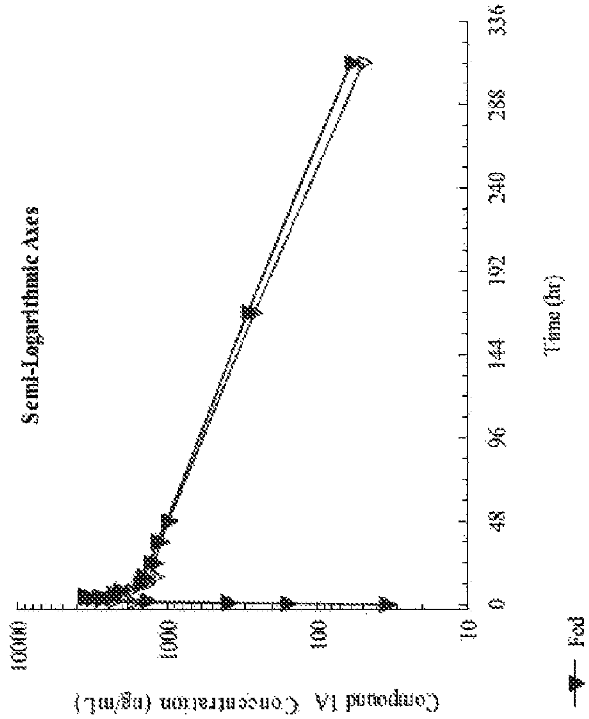
FIG. 9A-9B. Geometric mean plasma concentrations of Compound 1A after oral doses of 400 mg Compound 1 to healthy subjects under fasted and fed conditions-linear (FIG. 9A) and semi logarithmic (FIG. 9B) axes.
Figure 9A:
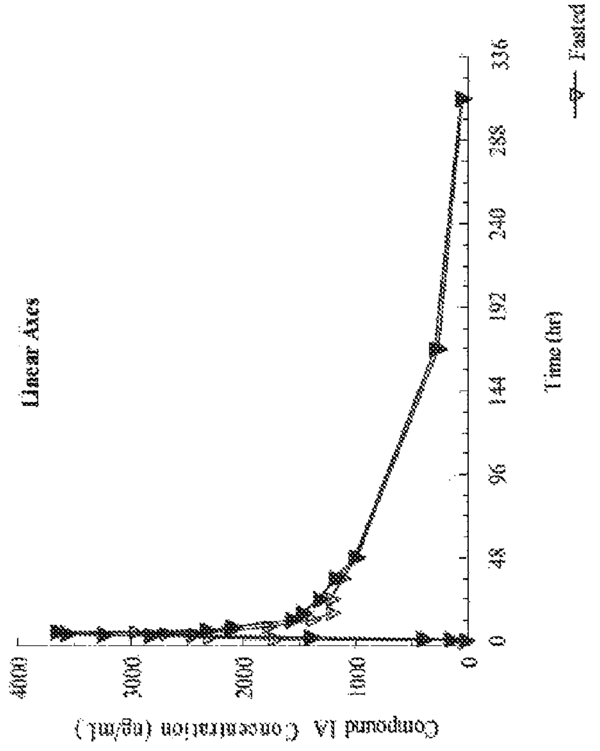

The geometric mean plasma concentrations of Compound 1A (FIG. 9A-9B) after administration of Compound 1 under fed (high fat/high calorie) and fasted conditions were comparable. The geometric mean value for $C_{max}$, $AUC_{0-t}$, and $AUC_{(inf)}$ were slightly higher after administration with food (Table 36). The least squares geometric mean ratios (LSGMR) were ~106% for all 3 parameters and the associated 90% CIs for both AUCs were within the 80.00% to 125.00% equivalence limits (Table 36). Although the median $t_{max}$ under fed conditions, 3.75 hrs, was longer than under fasted conditions, 2.50 hrs, the ranges were comparable (Table 36). Administration of Compound 1 with a high fat/high calorie meal has no significant effect on the bioavailability of Compound 1A.

TABLE 35

Summary of Pharmacokinetic Parameters for Compound 1A after Intravenous Infusion of 200 mg Compound 1 Over 3 Hrs and Oral Doses of 100 to 500 mg to Healthy Subjects Under Fasted Conditions

| | Cohort 1A | | | | |
|---|---|---|---|---|---|
| Parameter* | 200 mg/3 hr IV | 100 mg Oral | 300 mg Oral | 400 mg Oral | 500 mg Oral |
| Cmax (ng/mL) | 2,635 [12.1] (6) | 1,302 [22.7] (6) | 3,754 [23.9] (6) | 4,252 [21.9] (8) | 6,407 [21.0] (6) |
| Tmax (hr) | 3.00 (6) [2.00-3.00] | 2.00 (6) [2.00-4.00] | 2.50 (6) [1.00-4.00] | 2.50 (8) [1.00-5.00] | 3.00 (6) [2.00-4.00] |
| AUC(0-24) (hr × ng/mL) | 24,387 [22.7] (6) | 11,757 [29.6] (6) | 35,613 [27.3] (6) | 39,979 [24.3] (8) | 59,001 [25.4] (6) |
| AUC(0-t) (hr × ng/m) | 86,300 [10.9] (6) | 39,049 [14.8] (6) | 118,208 [12.1] (6) | 170,191 [16.4] (8) | 196,804 [17.6] (6) |
| AUC(inf) (hr × ng/m) | 87,530 [9.85] (6) | 39,644 [13.4] (6) | 122,230 [10.1] (6) | 177,134 [15.8] (8) | 204,624 [13.7] (4) |
| λz (1/hr) | 0.0141 [28.9] (6) | 0.0140 [27.7] (6) | 0.0132 [35.2] (6) | 0.0107 [29.0] (8) | 0.0154 [32.6] (4) |
| t½ (hr) | 49.1 [28.9] (6) | 49.5 [27.7] (6) | 52.5 [35.2] (6) | 64.7 [29.0] (8) | 44.9 [32.6] (4) |
| CL or CL/F† | | | | | |
| (mL/hr) | 1,748 [9.85] (6) | 1,930 [13.4] (6) | 1,878 [10.1] (6) | 1,728 [15.8] (8) | 1,870 [13.7] (4) |
| (mL/hr/kg) | 22.6 [8.41] (6) | 25.0 [8.93] (6) | 24.3 [4.41] (6) | 25.1 [12.2] (8) | 25.1 [13.3] (4) |
| Vz or Vz/F† | | | | | |
| (L) | 124 [37.5] (6) | 138 [41.2] (6) | 142 [45.7] (6) | 161 [35.1] (8) | 121 [44.1] (4) |
| (L/kg) | 1.60 [28.7] (6) | 1.78 [32.2] (6) | 1.84 [35.6] (6) | 2.35 [26.5] (8) | 1.62 [34.5] (4) |
| Urinary Excretion | | | | | |
| Amount (ng) | 15,783 [38.9] (6) | 8,564 [29.2] (6) | 27,075 [26.7] (6) | 36,258 [26.2] (8) | 34,200 [22.8] (6) |
| Percent Dose | 0.010 [38.9] (6) | 0.011 [29.2] (6) | 0.012 [26.7] (6) | 0.012 [26.2] (8) | 0.009 [22.8] (6) |
| F (%)‡ | — | 90.6 | 93.1 | 101.2 | 93.5 |

*Geometric mean [geometric % CV] (N) except for $t_{max}$ for which the median (N) [Range] is reported.

†CL and $V_z$ apply to the IV treatment and CL/F and $V_z$/F to the oral treatments.

‡Corrected for the difference in dose.

TABLE 36

Summary and Statistical Comparison of Pharmacokinetic Parameters for Compound 1A after Oral Doses of 400 mg Compound 1 to Healthy Subjects under Fasted and Fed Conditions

| | Cohort 1B - 400 mg | | Geometric | 90% Confidence |
|---|---|---|---|---|
| Parameter* | Fasted | Fed | Mean Ratio | Interval |
| Cmax (ng/mL) | 4,252 [21.9] (8) | 4,520 [35.3] (8) | 106.29 | 90.05-125.46 |
| Tmax (hr) | 2.50 (8) [1.00-5.00] | 3.75 (8) [2.00-5.00] | | |

TABLE 36-continued

Summary and Statistical Comparison of Pharmacokinetic Parameters for Compound 1A after Oral Doses of 400 mg Compound 1 to Healthy Subjects under Fasted and Fed Conditions

| | Cohort 1B - 400 mg | | Geometric | 90% Confidence |
|---|---|---|---|---|
| Parameter* | Fasted | Fed | Mean Ratio | Interval |
| AUC(0-24) (hr × ng/mL) | 39,979 [24.3] (8) | 43,597 [22.5] (8) | | |
| AUC(0-t) (hr × ng/mL) | 170,191 [16.4] (8) | 180,401 [14.4] (8) | 106.00 | 101.09-111.15 |
| AUC(inf) (hr × ng/mL) | 177,134 [15.8] (8) | 188,027 [14.6] (8) | 106.15 | 101.44-111.08 |
| λz (1/hr) | 0.0107 [29.0] (8) | 0.0103 [24.2] (8) | | |
| t½ (hr) | 64.7 [29.0] (8) | 67.5 [24.2] (8) | | |
| CL/F | | | | |
| (mL/hr) | 1,728 [15.8] (8) | 1,628 [14.6] (8) | | |
| (mL/hr/kg) | 25.1 [12.2] (8) | 23.7 [15.2] (8) | | |
| Vz/F | | | | |
| (L) | 161 [35.1] (8) | 159 [25.6] (8) | | |
| (L/kg) | 2.35 [26.5] (8) | 2.30 [20.9] (8) | | |
| Urinary Excretion | | | | |
| Amount (ng) | 36,258 [26.2] (8) | 39,181 [37.1] (8) | | |
| Percent Dose | 0.012 [26.2] (8) | 0.013 [37.1] (8) | | |
| F (%)† | 101.2 | 107.4 | | |

*Geometric mean [geometric % CV] (N) except $t_{max}$ for which the median (N) [Range] is reported.

†Ratio of the geometric mean $AUC_{(inf)}$ to the for the IV treatment after correction for dose.

Figure 10A:
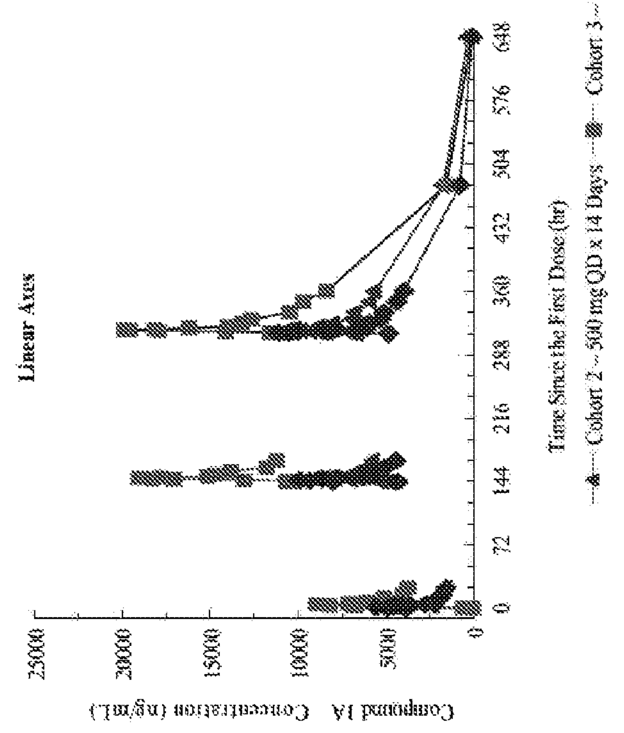
FIG. 10A-10B. Geometric mean plasma concentrations of Compound 1A after oral doses of 500 and 1000 mg of Compound 1 QD×14 days to healthy subjects under fed conditions-linear (FIG. 10A) and semi logarithmic (FIG. 10B) axes.
Figure 10B:
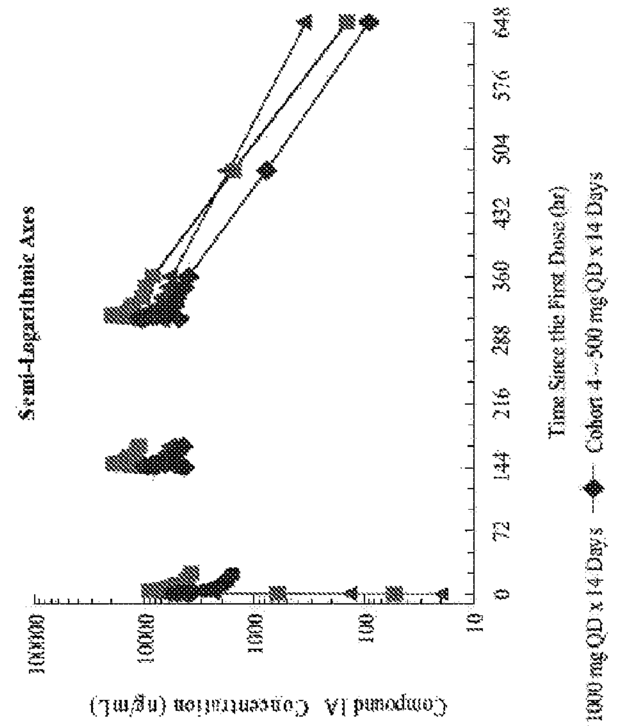

After oral administration of Compound 1 at doses of 500 mg and 1000 mg QD×14 days, there was a dose-related increase in the geometric mean plasma concentrations of Compound 1A with comparable values for the 2 cohorts administered 500 mg QD (FIG. 10A-10B). There was an approximate 2-fold increase in the geometric mean values for $C_{max}$ and $AUC_{0-24}$ on Days 1, 7, and 14, suggesting dose-proportional pharmacokinetics after multiple doses.

There was good agreement with respect to the geometric mean values for $C_{max}$ and AUC0-24 on Day 1 for the 2 cohorts administered 500 mg (Table 37) and those for Cohort 1A, Period D, in the SAD part of the study (Table 35).

The median $t_{max}$ ranged from 2.00 to 3.00 hrs across doses and study days but with overlapping ranges (Table 37), suggesting no apparent change with continued dosing. The geometric means for CL/F and $V_2$/F were consistent across the 3 cohorts as was the geometric mean ty, and all were consistent with those observed in the SAD part of the study (Table 37).

The median accumulation of Compound 1A, estimated as the ratio of $C_{max}$ and $AUC_{0-24}$ on Day 14 to that on Day 1, was 1.99 and 2.95, respectively, with no apparent trends among the 3 cohorts.

TABLE 37

Summary of Pharmacokinetic Parameters for Compound 1A after Oral Doses of 500 and 1000 mg QD x 14 Days to Healthy Subjects under Fed Conditions

| Parameter* | Cohort 2 500 mg Tablets | Cohort 3 1000 mg Tablets | Cohort 4 500 mg Oral Solution |
|---|---|---|---|
| Day 1 | | | |
| $C_{max}$ (ng/mL) | 6,176 [24.4] (6) | 10,589 [14.2] (6) | 5,854 [27.2] (12) |
| $T_{max}$ (hr) | 4.00 (6) | 4.50 (6) | 2.00 (12) |
| $AUC_{(0-24)}$ (hr × ng/mL) | 50,735 [16.8] (6) | 118,823 [15.0] (6) | 56,713 [31.2] (12) |
| Day 7 | | | |
| $C_{max}$ (ng/mL) | 10,876 [12.1] (6) | 21,332 [15.0] (6) | 10,421 [16.5] (12) |
| $T_{max}$ (hr) | 3.76 (6) | 4.00 (6) | 2.00 (12) |
| $AUC_{(0-24)}$ (hr × ng/mL) | 154,461 [8.93] (6) | 315,557 [17.3] (6) | 139,957 [17.2] (12) |
| Day 14 | | | |
| $C_{max}$ (ng/mL) | 11,959 [14.7] (6) | 21,275 [13.4] (6) | 12,297 [14.9] (12) |
| $T_{max}$ (hr) | 3.75 (6) | 3.77 (6) | 1.00 (12) |
| $AUC_{(0-24)}$ (hr × ng/mL) | 191,382 [9.03] (6) | 325,842 [16.8] (6) | 152,550 [11.7] (12) |
| $λ_z$ (1/hr) | 0.0094 [18.5] (6) | 0.0132 [25.0] (6) | 0.0125 [34.7] (10) |
| T½ (hr) | 73.4 [18.5] (6) | 52.6 [25.0] (6) | 55.4 [34.7] (10) |

TABLE 37-continued

Summary of Pharmacokinetic Parameters for Compound 1A after Oral Doses of 500 and 1000 mg QD x 14 Days to Healthy Subjects under Fed Conditions

| Parameter* | Cohort 2 500 mg Tablets | Cohort 3 1000 mg Tablets | Cohort 4 500 mg Oral Solution |
|---|---|---|---|
| | CL | | |
| (mL/hr) | 1,999 [9.03] (6) | 2,348 [16.8] (6) | 2,508 [11.7] (12) |
| (mL/hr/kg) | 27.7 [14.5] (6) | 34.9 [11.1] (6) | 33.3 [13.1] (12) |
| | $V_z$ | | |
| (L) | 212 [23.3] (6) | 178 [23.7] (6) | 193 [37.2] (10) |
| (L/kg) | 2.93 [10.2] (6) | 2.65 [17.1] (6) | 2.61 [40.5] (10) |

*Geometric mean [geometric % CV] (N) except $t_{max}$ for which the median (N) [Range] is reported.

Compound 1

Plasma concentrations of the prodrug Compound 1 were ≥LOQ only through 4 hrs after the IV infusion (Cohort 1A, Period A). For the oral treatments, only 1 sample was ≥LOQ-0.57 ng/mL, Cohort 1A, Period D, 500 mg single dose, Subject #01, 2 hrs, indicating rapid conversion of Compound 1 to Compound 1A. Consequently, no PK analyses were feasible for Compound 1.

Comparison of Results Across Studies

An IV dose of Compound 1 of 200 mg/3 hrs was administered in both Study #1 of Compound 1 (Cohort 4) and Study #2 of Compound 1 (Cohort 1A). Comparison of Table 26 (Study #1) and Table 35 (Study #2) shows comparable geometric mean values for all PK parameters for Compound 1A for both cohorts/studies, demonstrating consistency in the PK across studies and groups of subjects.

The absolute oral bioavailability of Compound 1A ranged from 90.6% to 101.2%, indicating essentially complete absorption of Compound 1 and conversion to Compound 1A. Consequently, the geometric mean values for CL and $V_2$ after IV administration (Tables 26-29 and Table 35) were concordant with CL/F and $V_2$/F after oral administration (Tables 35-37). The geometric mean tu, was also not dependent on either the dose or the route of administration.

The data demonstrate consistency in the PK of Compound 1A after IV and oral administration of Compound 1 over a wide range of single and multiple doses.

Safety

The clinical development program for Compound 1 provides an emerging safety profile of Compound 1 for healthy male and female subjects. Safety data are focused on events that were treatment emergent in these completed studies.

The safety, tolerability, and PK of single- and multiple-doses of Compound 1 administered by IV infusion and orally in healthy volunteers were assessed in the two Phase 1 studies Study #1 and Study #2.

All single and multiple IV and oral doses of Compound 1 were well tolerated. Faster infusions (single dose: 2, 1 and 0.5 hrs, and multiple dose: 1 hr) were safe and well tolerated. A loading dose of 1000 mg administered twice on Day 1 (via a 2-hr infusion, with 9 hrs between start of infusions) was safe and well tolerated. Moderate events were reported with a low frequency in both the Compound 1 and placebo groups, there were no severe or very severe TEAEs or SAEs reported, and there were no withdrawals due to treatment related TEAEs. No TEAEs or laboratory safety test results met any of the a priori rules that prevented dose escalation. There were no dose-limiting toxicities observed and the maximum tolerated dose (MTD) was not determined/not reached in these studies.

In general, the TEAE profile in both studies was similar. The most frequently reported TEAEs across all treatment groups were in the system organ classes of Nervous System Disorders, Gastrointestinal Disorders, and General Disorders and Administration Site Conditions.

In Study #1, multiple IV doses of Compound 1 up to 600 mg once daily for 14 consecutive days were well tolerated by the majority of subjects; however, the total number of TEAEs related to Gastrointestinal and Nervous System Disorders increased when the dose was increased from 300 mg to 600 mg. However, even with an increase in frequency of AEs these AEs were nearly always mild in severity and did not require any intervention. In Study #2, multiple oral doses of 500 mg and 1000 mg of Compound 1 administered once daily for 14 consecutive days were well tolerated by the majority of subjects; however, the number of moderate TEAEs, primarily those related to Gastrointestinal Disorders, increased when the oral dose of Compound 1 increased from 500 mg to 1000 mg. As with the 600 mg IV dose group, even with an increase in frequency of AEs these AEs were nearly always mild in severity and did not require any intervention. In Study #2, single-dose crossover food effect cohort, dosing under fed conditions improved tolerability by decreasing TEAEs related to Gastrointestinal (nausea, vomiting) and Nervous System Disorders (headache, fatigue). The majority of the TEAEs in the system organ class of General Disorders and Administration Site Conditions associated with the infusion site and the blood sampling catheter were reported in intravenous MAD cohorts by subjects in both placebo and Compound 1 groups. In the 4 MAD Study #1 cohorts, between 17% and 83% of the subjects reported TEAEs associated with the infusion site compared to 75% of the subjects in the placebo group. In the 4 MAD Study #1 cohorts, between 17% and 33% of subjects reported TEAEs associated with the blood sampling catheter compared to 25% of the subjects in the placebo group.

Across both studies, the most frequently reported TEAEs considered related to the study drug by preferred term were nausea, headache, vomiting and dizziness.

Study #2 was primarily designed to evaluate the safety, tolerability and the PK profile of oral doses of Compound 1 and its active moiety Compound 1A in healthy volunteers. In addition, the absolute oral bioavailability, the effect of food on tolerability and PK, and the drug-drug interaction potential of Compound 1 were evaluated.

All doses of Compound 1 were safe and well tolerated. The majority of the TEAEs were mild, transitory and resolved without intervention. No DLTs were observed and no TEAEs or laboratory safety tests results met any of the a priori rules that prevented dose escalation. The MTD was not determined/reached in this study.

Single IV doses of 200 mg Compound 1 and single oral doses in the dose range of 100 mg to 500 mg were well tolerated in a group of healthy male and female subjects.

Multiple oral doses of 500 mg and 1000 mg Compound 1 administered once daily for 14 consecutive days were well tolerated by the majority of the group of healthy male and female subjects. However, the number of moderate TEAEs (mainly related to Gastrointestinal Disorders) increased when dose increased from 500 mg to 1000 mg Compound 1.

The most frequently reported TEAEs by preferred term (PT) were nausea, headache, vomiting and fatigue, where vomiting and fatigue were mainly reported after multiple dosing with Compound 1.

Dosing under fed conditions appeared to improve tolerability by decreasing TEAEs related to Gastrointestinal and Nervous System Disorders.

There were no deaths or SAEs reported during this study, and there were no withdrawals due to AEs. There were no clinically significant findings with respect to clinical laboratory, vital signs, ECG, physical examination and body weight.

Pharmacokinetics

Single Ascending Dose under Fasted Conditions

Plasma concentrations of the prodrug, Compound 1, were ≥LOQ only through 4 hours after the IV infusion and for the oral treatments, only 1 sample was ≥LOQ, indicating rapid conversion of Compound 1 to Compound 1A. Consequently, no PK analyses were feasible for Compound 1.

Following oral administration of Compound 1 at doses from 100 mg to 500 mg, there were dose-proportional increases in the geometric mean Compound 1A plasma concentrations and values for $C_{max}$, $AUC_{0-t}$, and $AUC_{0-inf}$. The median values for $t_{max}$ ranged from 2.0 to 3.0 hrs with consistent ranges for the 4 oral doses.

The Compound 1A geometric mean values for Ty ranged from 44.9 to 64.7 hrs for the 4 oral treatments and was 49.1 hrs for the IV treatment indicating that absorption of Compound 1 and/or conversion to Compound 1A was not the rate limiting step in Compound 1A pharmacokinetics. The absolute oral bioavailability of Compound 1A ranged from 90.6% to 101.2%, indicating essentially complete absorption of Compound 1 and conversion to Compound 1A. There was negligible excretion of unchanged Compound 1A in the urine, with geometric means ranging from 0.009% to 0.012% of the dose.

Effect of Food on Bioavailability

Administration of Compound 1 with a high fat/high calorie meal has no significant effect on the exposure to Compound 1A.

Multiple Ascending Doses

There was a dose-proportional increase in the geometric mean plasma Compound 1A concentrations and geometric mean values for Compound 1A $C_{max}$ and $AUC_{0-24}$ on Days 1, 7, and 14 after administration of Compound 1 at doses of 500 mg and 1000 mg once daily over 14 days. The Compound 1A median $t_{max}$ ranged from 1 to 4.5 hrs across doses and study days but with overlapping ranges, suggesting no apparent change with continued dosing.

The Compound 1A geometric mean Ty, was consistent across the 3 cohorts and was consistent with the values observed in the SAD phase of the study. Accumulation of Compound 1A, estimated as the ratio of $C_{max}$ and $AUC_{0-24}$ on Day 14 to that on Day 1, was consistent among the 3 cohorts.

The median accumulation ratios based on $C_{max}$ and $AUC_{0-24}$ were 1.99 and 2.95, respectively Single Ascending Dose Study Overall Incidence of TEAEs A total of 6 subjects (75%) reported 15 TEAEs. Of these, 3 subjects (50%) reported 3 TEAEs in the 200 mg sd IV Compound 1 treatment period; 2 subjects (33%) reported 2 TEAEs in the 100 mg sd oral Compound 1 treatment period; 3 subjects (50%) reported 6 TEAEs in the 300 mg sd oral Compound 1 treatment period; and 1 subject (17%) reported 1 TEAE in the 500 mg sd oral Compound 1 treatment period. One subject (50%) reported 3 TEAEs in the pooled placebo sd oral treatment periods and none of the subjects reported any TEAEs in the placebo sd IV treatment period.

Multiple Ascending Dose Study

Overall incidence of TEAEs

A total of 14 subjects (88%) reported 155 TEAEs. In the 1000 mg md oral Compound 1 group, 6 subjects (100%) reported 119 TEAEs; in the 500 mg md oral Compound 1 group, 5 subjects (83%) reported 24 TEAEs; in the pooled placebo group, 3 subjects (75%) reported 12 TEAEs.

Overall, the percentage of subjects reporting TEAEs as well as the number of TEAEs increased when the dose increased from 500 mg md to 1000 mg md Compound 1.

Example 3: An Open-Label Study to Evaluate the Efficacy and Safety of Compound 1 in Non-Neutropenic Patients with Candidemia, with or without Invasive Candidiasis, Inclusive of Patients with Suspected Resistance to Standard of Care Antifungal Treatment The need for improved treatment of IFDs remains high, particularly with the growing number of immunocompromised patients, such as hematopoietic stem cell and solid organ transplant recipients, who are at particular risk for developing these infections and in whom treatment can be complex. Species of *Candida* and *Aspergillus* are recognized as two major causes of fungal diseases in these patients, although other emerging fungi, such as non-C. *Albicans* (e.g., C. *Glabrata* and *C. Auris*), *Fusarium* spp., *Scedosporium* spp., and Mucorales fungi, are contributing to the need to find new and better strategies for managing these infections. Existing antifungal agents can be difficult to use, are often poorly tolerated, or have become increasingly ineffective due to the rise of drug resistant fungal strains.

The safety, tolerability, and PK of single and multiple doses of Compound 1 administered by IV infusion and PO in healthy volunteers were studied in two Phase 1 studies, Study #1 of Compound 1 and Study #2 of Compound 1. Study #1 of Compound 1 was a first-in-human (FIH) Phase 1, randomized, placebo-controlled study to investigate the safety, tolerability, and PK of single and multiple doses of Compound 1 administered by IV infusion in healthy subjects. A final Clinical Study Report has been issued for this study. No severe or SAEs have been reported and most of the adverse events were mild, transitory, and resolved with no intervention. There were no clinically relevant changes from baseline in laboratory safety tests. The AUC from time 0 to infinity (AUCinf) and $C_{max}$ were linear and dose proportional. All doses of Compound 1 were safe and well tolerated, and the majority of TEAEs were mild, transitory, and resolved without intervention. Single IV doses of Compound 1 up to 350 mg over a 3-hour infusion and single IV doses of 1000 mg over 0.5-, 1-, 2-, and 3-hour infusions were well tolerated. Shorter infusion periods (i.e., 1000 mg over 0.5 to 2 hours) appeared to have similar toleration compared to 3-hour infusion periods. Multiple IV doses of Compound 1 up to 600 mg once daily (QD), for 14 consecutive days, were well tolerated by the majority of subjects; however, the total number of TEAEs related to gastrointestinal (GI) and nervous system disorders increased when the dose was increased from 300 mg to 600 mg. A loading dose of 1000 mg administered twice daily (BID) on Day 1 followed by a maintenance dose of 600 mg QD for 6 consecutive days was well tolerated. Study #2 of Compound 1 was a Phase 1, randomized, placebo-controlled study to investigate the safety, tolerability, and PK of single and multiple PO doses of Compound 1 and to investigate the absolute bioavailability of Compound 1, the effect of food on Compound 1, and the DDI potential of Compound 1. A final Clinical Study Report has been issued for this study. No severe or SAEs were reported and most of the adverse events were mild, transitory, and resolved with no intervention. There were no clinically relevant changes from baseline in laboratory safety tests. The AUCinf and $C_{max}$ were linear and dose proportional. There was no impact of food on the PK of Compound 1A exposures (single dose of 400 mg). In cohort 3 ($^{1000}$ mg, QD for 14 days), there was an increase in the number of subjects reporting adverse events; however, the intensity of reported events did not increase with multiple doses. All doses of Compound 1 were safe and well tolerated, and the majority of TEAEs were mild, transitory, and resolved without intervention. The single IV doses of 200 mg Compound 1 and single PO doses in the dose range of 100 mg to 500 mg were well tolerated. Multiple PO doses of 500 mg and 1000 mg of Compound 1 administered QD for 14 consecutive days were well tolerated by the majority of subjects; however, the number of moderate TEAEs, primarily those related to GI disorders, increased when the PO dose of Compound 1 increased from 500 mg to 1000 mg. Dosing under fed conditions improved tolerability by decreasing TEAEs related to GI (nausea, vomiting) and nervous system disorders (headache, fatigue). There were no deaths or SAEs reported during the study nor were there any withdrawals due to adverse events. There were no clinically significant findings with respect to laboratory safety tests, vital signs, electrocardiogram (ECG), physical examination, or weight. No DLTs were observed. No TEAEs or laboratory safety tests met any of the criteria to prevent dose escalation. The MTD was not reached in this study. Patients participating in this study will receive a drug in clinical development without regulatory approval for treatment of fungal diseases. Administration of Compound 1 in a concentration of 1000 mg IV BID will be administered on Day 1, 600 mg IV QD will be administered on Days 2 through 3, and then subsequently 600 mg IV or 700 mg PO will be administered throughout the Study Drug Treatment Period. This treatment may have advantages over standard of care (SOC) therapy against certain resistant fungal diseases, where SOC treatment might show no or limited therapeutic effectiveness.

Primary Objective

The primary objective of this study is to evaluate the efficacy and safety of Compound 1 for the treatment of adult non-neutropenic patients 18 to 80 years of age (inclusive) with candidemia that may include patients with suspected or confirmed resistance to SOC antifungal treatment.

Secondary Objectives

The secondary objectives of this study are to:

- Evaluate the time to first negative blood culture
- Evaluate the percentage of patients with Mycological Outcomes at the End of Study Drug Treatment (EOST), End of Antifungal Treatment (EOT), and 2 and 4 weeks after EOT
- Evaluate the percentage of patients with Treatment Success at EOT, and 2 and 4 weeks after EOT
- Evaluate overall survival at Study Day 30
- Evaluate safety parameters, including number of patients with TEAEs
- Evaluate PK parameters of Compound 1

Summary of Study Design

This is a multicenter, open-label, non-comparative, single-arm study to evaluate the efficacy and safety of Compound 1 for the first-line treatment for candidemia including suspected or confirmed antifungal-resistant candidemia in non-neutropenic patients 18 to 80 years of age (inclusive). Suspicion of antifungal-resistant candidemia is sufficient and subsequent documented resistance is not required for enrollment. The Study Drug Treatment Period will be up to a maximum of 14 days (inclusive of the loading dose [Study Day 1]). After completion of 14 days study drug therapy, if further antifungal treatment is indicated to complete treatment of candidemia in accordance with standard practice guidelines, fluconazole (unless susceptibility results warrant alternative antifungal therapy) may commence for up to a further 7 days. There will be a Follow-up Period of 4 weeks (+4 days) after EOT. The total duration of participation in the study is up to approximately 7.5 weeks (inclusive of the Screening Period [<96 hours prior to Baseline]).

Patients with a yeast identified in a blood culture or a positive rapid diagnostic method are eligible to be consented and screened for the study. Patients must have at least 1 positive blood test for *Candida* spp. (or yeast suspected to be *Candida*) for a diagnosis of candidemia to be considered for enrollment into the study. Patients with a positive blood culture showing yeast suspected to be *Candida* must have identification of *Candida* spp. from positive blood culture confirmed prior to dosing. Screening and Baseline procedures and the start of Compound 1 study drug will be initiated within 96 hours from the time that the SOC blood sample for the *Candida* spp. positive culture or rapid diagnostic test was drawn. Patients with 2 days (>48 hours) equivalent of prior systemic antifungal treatment at approved doses to treat the current episode of candidemia within 96 hours before first dose will be excluded. However, patients with *Candida* infections proven to be resistant to the specific antifungal administered may have received≤5 days (≤120 hours) equivalent of that prior treatment (results of susceptibility testing are required prior to enrollment).

Patients with >2 days (>48 hours) equivalent of prior systemic antifungal treatment at approved doses to treat the current episode of candidemia within 96 hours before first dose will be excluded. However, patients with *Candida* infections proven to be resistant to the specific antifungal administered may have received≤5 days (≤120 hours) equivalent of that prior treatment (results of susceptibility testing are required prior to enrollment).

On Study Day 1 (or over the first 24 hours if started in the evening), a 1000 mg Compound 1 loading dose will be administered over 3 hours by IV infusion BID. On Study Days 2 and 3 of study drug, a 600 mg Compound 1 maintenance dose will be administered over 3 hours by IV infusion QD. On Study Day 4 and onward, the Compound 1 maintenance dose will be administered as either 600 mg Compound 1 IV infusion QD over 3 hours or 700 mg PO QD. Patients who have completed a minimum of 3 days of IV Compound 1, are clinically stable as determined by the Investigator, able to swallow tablets, and have no further growth of the infecting organism 48 hours following the most recent blood culture, may switch from IV to PO dosing on Study Day 4 and onward. Study drug will be administered for a maximum of 14 days. At the Investigator's discretion, patients requiring a longer duration of antifungal therapy will be switched to fluconazole (unless susceptibility results warrant alternative antifungal therapy), to adhere to the IDSA clinical practice guidelines for the treatment of Candidiasis. *Candida* spp. bloodstream infection will be monitored by daily blood culture during Study Drug Treatment until 2 consecutive blood cultures are negative, and at EOST, EOT, and 2 and 4 weeks after EOT, or Early Termination. Simultaneously drawn blood samples will be collected for *Candida* testing by T2 magnetic resonance (T2MR) assay at Baseline, during Study Drug Treatment, and EOST, or Early Termination. Other cultures, histopathology, and imaging tests to assess the site(s) and extent of candidemia infection at other sites will be conducted as clinically indicated, and the results should be recorded in the electronic Case Report Form (eCRF). The management of intravascular catheters, intravascular devices, and, if applicable, any drains will be recorded, including any associated microbiology results. Patients will be monitored for safety throughout the duration of the study.

Plasma samples for PK (Compound 1 [prodrug] and Compound 1A [active moiety]) will be collected at Baseline (pre dose), twice weekly during Study Drug Treatment, EOST, EOT, 2 weeks after EOT, or Early Termination. Serum samples for $(^{1,3})$-β-D-glucan levels will be collected at Baseline (pre-dose) and EOST, or Early Termination (if applicable).

The evaluation of treatment outcome will be assessed at EOST, EOT, and 2 and 4 weeks after EOT, or Early Termination. The end of study will occur after the last visit of the last patient on the study. Indication: Treatment of non-neutropenic patients with candidemia, inclusive of those patients with suspected or confirmed antifungal-resistant candidemia Population:

This study will enroll male and female patients 18 to 80 years of age (inclusive) with a new diagnosis of candidemia (positive blood test for *Candida* spp.).

Inclusion Criteria:

Patients must meet all of the following criteria to be eligible for study entry:

1. Male or female 18 to 80 years of age (inclusive) 2. New diagnosis of candidemia based on a blood sample drawn within 96 hours of dosing with: a. Positive blood culture for *Candida* spp., including those *Candida* spp. with suspected (in the opinion of the Investigator) or documented resistance to at least 1 SOC systemic antifungal agent; or b. Positive result from a Sponsor-approved rapid diagnostic blood test for *Candida* spp. infection (a rapid diagnostic test may be used to begin eligibility assessments; however, a subsequent confirmatory blood culture is required prior to dosing of Compound 1) 3. Able to have pre-existing intravascular catheters removed and replaced (if necessary)

Dosing Criteria

Patients must meet the following criteria to begin dosing:

1. Confirmed diagnosis of candidemia
2. Received≤2 days (≤48 hours) equivalent of prior systemic antifungal treatment at approved doses to treat the current episode of candidemia OR≤5 days (≤120 hours) equivalent of prior treatment for candidemia caused by *Candida* spp. with documented resistance to the specific prior antifungal administered.

Treatment Groups

All patients will be administered a 1000 mg Compound 1 loading dose BID followed by a 600 mg Compound 1 maintenance dose QD on Study Day 2 and Study Day 3. From Study Day 4 onwards, the Compound 1 maintenance dose will be administered as either 600 mg Compound 1 IV infusion over 3 hours QD or may be switched to 700 mg PO QD when/if the criteria for PO dosing are met Dose In PK-PD studies, immunocompromised mice were infected with one of three spp. of *Candida* (*C. albicans, C. glabrata*, or *C. auris*) and groups of animals were dosed with Compound 1 at different dose fractionations. The AUC/MIC ratio was determined to be the PK-PD variable that best correlated with antifungal efficacy as assessed by fungal burden (colony-forming units [CFUs]) in the kidney. The probability of target attainment (PTA) was calculated separately for each *Candida* spp. tested. The PTA calculation used the Compound 1A free drug AUC level at the stasis endpoint divided by the MIC required to inhibit the growth of 90% of organisms (MIC90) of each of the *Candida* spp. tested. The AUC level was estimated from a population PK model derived primarily from the Phase 1 PK data. The stasis endpoint was defined as the quantity of *Candida* spp. in CFUs just prior to Compound 1 administration compared to CFUs at the endpoint of assessment (i.e., 24 hours for *C. albicans;* 96 hours for *C. glabrata* and *C. auris*). The MIC data for the *Candida* strains tested were obtained from recent surveillance data. Using the AUC at the stasis endpoint, along with the MIC90 from the surveillance data and the predicted exposure at the dose regimen to be used in this study, the PTA for the three *Candida* spp. tested was shown to be approximately 100%. Further, sensitivity analyses were conducted to evaluate the PTA under different scenarios including increased variability of PK parameters and higher *Candida* spp. $MIC_{90}$ values. For both scenarios the PTA remained>90%.

In 2 Phase 1 studies in healthy volunteers, Compound 1 IV and PO formulations were safe and well tolerated. The majority of the TEAEs were mild, transitory, and resolved without intervention. No DLTs were observed. Specifically, in the FIH Phase 1 clinical study, a loading dose of Compound 1 1000 mg IV 2-hour infusion BID on Day 1, followed by a maintenance dose of Compound 1 600 mg IV 1-hour infusion QD on Days 2 through 7, was safe and well tolerated. This IV dose regimen is identical to the IV dose regimen that will be used in this study. In the second Phase 1 clinical study, a dose of Compound 1 at 1000 mg administered PO QD on Days 1 through 14 was safe and well tolerated. This PO-dose regimen is higher than the 700 mg PO dose that will be used in this study.

Schedule

To ensure the safety and tolerability of Compound 1 dosing for 14 days, this study will use a Compound 1 dose and infusion duration already studied in Phase 1 for 14 days of therapy inclusive of IV and PO investigational drug therapy. The loading dose 1000 mg IV BID over a 3-hour infusion followed by 600 mg IV QD over a 3-hour infusion will optimize patient safety and tolerability on study. At Study Day 4, provided a patient meets the protocol-defined criteria for a PO switch, then the switch will occur to PO Compound 1 dose at 700 mg QD for no more than 14 days of combined IV and PO Compound 1 therapy.

Randomization and Blinding

This is a non-randomized, open-label study.

Drug Supplies

Formulation and Packaging Compound 1 Injection is formulated at a concentration of 20 mg/mL. The formulation consists of Compound 1 drug substance, sodium chloride, potassium phosphate (dibasic and monobasic), hydrochloric acid, sodium hydroxide, and sterile water for injection. A 50 mL sterile vial is filled with 35 mL of Compound 1 Injection. Compound 1 Injection will be reconstituted and administered as an IV infusion. Preparation and dilution instructions will be provided in the Pharmacy Manual.

Compound 1 Tablets are formulated at strengths of 100 mg and 200 mg white-coated tablets. The formulation consists of Compound 1 drug substance, microcrystalline cellulose, anhydrous dibasic calcium phosphate, colloidal silicon dioxide, pregelatinized starch, povidone, talc, magnesium Study Drug Administration On Study Day 1 (or over the first 24 hours if started in the evening), a 1000 mg Compound 1 loading dose will be administered over 3 hours by IV infusion BID. On Study Days 2 and 3 of study drug, a 600 mg Compound 1 maintenance dose will be administered over 3 hours by IV infusion QD. On Study Day 4 and onward, the Compound 1 maintenance dose will be administered as either 600 mg Compound 1 IV infusion QD over 3 hours or 700 mg PO QD. Patients who have completed a minimum of 3 days of IV Compound 1, are clinically stable as determined by the Investigator, able to swallow tablets, and have no further growth of the infecting organism 48 hours following the most recent blood culture, may switch from IV to PO dosing on Study Day 4 and onward. Study drug will be administered for a maximum of 14 days (inclusive of the loading dose [Study Day 1]). Tablets are to be administered at the same time each day, whole, and taken by mouth with water within 30 minutes of being removed from the refrigerator. No splitting or crushing of tablets is allowed. If antifungal treatment is indicated for longer than 14 days, fluconazole may commence at the Investigator's discretion (unless susceptibility results warrant alternative antifungal therapy) for up to a further 7 days of therapy, to adhere to IDSA clinical practice guidelines for the treatment of Candidiasis.

At End of Antifungal Treatment (EOT):

After completion of 14 days study drug therapy, if further antifungal treatment is indicated to complete treatment of candidemia in accordance with standard practice guidelines, fluconazole (unless susceptibility results warrant alternative antifungal therapy) may commence for up to a further 7 days. If applicable, an assessment of efficacy will also be made at the end of this antifungal treatment at EOT. Treatment Success is defined as meeting all of the following criteria:

- Two consecutive blood cultures negative for *Candida* spp.
- Alive at EOT
- No additional systemic antifungal therapies (except for protocol-allowed step-down treatment [e.g., fluconazole]) through EOT
- Treatment Failure is defined as any case that does not meet the criteria for Treatment Success.

Mycological Outcome:

Eradication is defined as a negative blood culture(s) for *Candida* spp. in the absence of additional antifungal therapy (except for protocol-allowed step-down treatment [e.g., fluconazole]) through EOT At Follow-up (2 Weeks and 4 Weeks after End of Antifungal Treatment):

Recurrence (mycological) is defined as a mycologically confirmed infection based on blood culture with the same Baseline *Candida* spp. during the 4 weeks after EOT. Relapse (DRC Assessment) is defined as re-occurrence of *Candida* in blood culture during the Follow-up Period, or diagnostic parameters indicative of recurrence or late spread of the *Candida* infection Although the invention has been described with reference to the above example, it will be understood that modifications and variations are encompassed within the spirit and scope of the invention. Accordingly, the invention is limited only by the following claims.

Example 4: A Phase 2 Open-Label Study to Evaluate the Efficacy and Safety of Compound 1 in Patients with Candidemia and/or Invasive Candidiasis Caused by *Candida auris*

This study will enroll male and female patients aged 18 years and above with an established diagnosis of candidemia and/or invasive candidiasis caused by *Candida auris* from a sample taken<120 hours (for patients with candidemia) or <168 hours (for patients with invasive candidiasis without candidemia) of inclusion in the study. Patients will have limited or no treatment options due to resistance, contraindication, intolerance or lack of clinical response to standard of care antifungal therapy, as advocated by the relevant regional/country treatment guidelines (e.g. South Africa: The Federation of Infectious Diseases Societies of Southern Africa (FIDSSA), 2019 in press; CDC:

Recommendations for treatment of *Candida auris* infections). *Candida auris* must be confirmed in culture from blood or other tissue, aspirate or fluid sampled from a normally sterile site, and all eligibility criteria must be met prior to qualification for the study and subsequent dosing.

Indication: Treatment of patients with candidemia and/or invasive candidiasis caused by *Candida auris*

Objectives:

The primary objective of this study is to evaluate the efficacy and safety of Compound 1 for the treatment of adult patients aged 18 years and above, with candidemia and/or invasive candidiasis caused by *Candida auris*, who have limited antifungal treatment options.

The secondary objectives of this study are to:

- Evaluate the time to first negative blood culture.
- Evaluate the percentage of patients with successful Mycological Outcomes at End of Study Drug Treatment (EOST), and 2 and 4 weeks after EOST
- Evaluate the percentage of patients with Treatment Success 2 and 4 weeks after EOST
- Evaluate all-cause mortality at Study Day 30
- Evaluate safety parameters, including number of patients with treatment-emergent adverse events (TEAEs)
- Evaluate pharmacokinetic (PK) parameters of Compound 1

This study will enroll male and female patients aged 18 years and above with an established diagnosis of candidemia and/or invasive candidiasis caused by *Candida auris* from a sample taken<120 hours (for patients with candidemia) or <168 hours (for patients with invasive candidiasis without candidemia) of inclusion in the study. Patients will have limited or no treatment options due to resistance, contraindication, intolerance, or lack of clinical response to standard of care antifungal therapy, as advocated by the relevant regional/country treatment guidelines (e.g., South Africa: The Federation of Infectious Diseases Societies of Southern Africa (FIDSSA), 2019 in press; CDC: Recommendations for treatment of *Candida auris* infections). *Candida auris* must be confirmed in culture from blood or other tissue, aspirate or fluid sampled from a normally sterile site, and all eligibility criteria must be met prior to qualification for the study and subsequent dosing.

Inclusion Criteria

Patients must meet all of the following criteria to be eligible for study entry:

1. Male or female aged 18 years and above
2. Limited or no treatment options due to resistance, contraindication, intolerance or lack of clinical response to standard of care antifungal therapy, as advocated by the relevant regional/country treatment guidelines
3. Established mycological and clinical diagnosis of candidemia and/or invasive candidiasis from a sample taken<120 hours (for candidemia) or <168 hours (for invasive candidiasis without candidemia) before study qualification:
   a. Candidemia criteria
      i. ≥1 blood culture positive for *Candida* spp. identified as *C. auris* plus:
      ii. Clinical signs attributable to candidemia within the 120 hours prior to qualification for the study, to include at least one of the following: (a) fever (>38° C.), or (b) hypothermia (<36° C.), or (c) hypotension (SBP<90 mmHg or decrease of >30 mmHg);
   b. Invasive candidiasis criteria
      i. ≥1 specimen (e.g., tissue, aspirate/fluid) sampled aseptically from a normally sterile site culture positive for yeast/*Candida* spp. identified as *C. auris*; plus:
      ii. Clinical signs attributable to invasive candidiasis within the 168 hours prior to qualification for the study, to include at least one of the following: (a) fever (>38° C.), or (b) hypothermia (<36° C.), or (c) hypotension (SBP<90 mmHg or decrease of >30 mmHg), or (d) signs associated with organ/site infected with *Candida* (e.g. eye, intra-abdominal).
4. Patients with single *C. auris* infection, or mixed *Candida auris* plus other *Candida* spp. (other than *C. krusei*) infection, are eligible for the study.
5. Able to have pre-existing intravascular catheters removed and replaced (if necessary).
6. Females of childbearing potential with male partners, and males with female partner(s) of childbearing potential, must agree to use 2 forms of highly effective contraception, 1 of which must be a barrier method, throughout the duration of the study and for 90 days following the last study drug administration. Acceptable barrier forms of contraception are condom and diaphragm. Acceptable non-barrier forms of contraception for this study are oral contraceptives (e.g. oral birth control pill, depot, patch, or injectable), abstinence, intrauterine device, and/or spermicide. Post-menopausal is defined as amenorrhea for >12 months without an alternative medical cause or documented surgical sterilization (e.g., bilateral salpingectomy, bilateral oophorectomy, or hysterectomy).

True abstinence, when in line with the preferred and usual lifestyle of the patient, is considered a highly effective method only if defined as refraining from heterosexual intercourse during the entire period of risk associated with the study drug treatment.

(Periodic abstinence [e.g. calendar, ovulation, symptothermal, post-ovulation methods] and withdrawal are not acceptable methods of contraception)

7. Females of childbearing potential must have a negative urine pregnancy test within 96 hours prior to Baseline (i.e. pre-dose on Study Day 1)
8. Willing to participate in the study, willing to give written informed consent, and willing to comply with the study restrictions; where permitted by local regulations, written informed consent from a legal authorized representative (LAR) will be obtained for patients who are unable to give consent.

Exclusion Criteria

Patients who meet any of the following criteria will not be eligible for the study:

1. Blood culture, or any other culture, positive for *C. krusei*
2. Life expectancy of <7 days in the opinion of the Investigator
3. Severe or moderate hepatic impairment (Child-Pugh Score>6 points) at any time during 2 weeks prior to dosing
4. Severe or moderate renal impairment (i.e. estimated glomerular filtration rate (GFR)<60 mL/min calculated by Modification to Diet in Renal Disease [MDRD] study equation) at any time during 2 weeks prior to dosing
5. Baseline neurological conditions such as abnormal movements or convulsive disorders
6. Human immunodeficiency virus-infected patients who are receiving antiretroviral therapy that are moderate to strong inducers of CYP3A4, or who have detectable viremia, or who have had an active opportunistic infection within 6 months prior to Screening
7. Alanine aminotransferase or aspartate aminotransferase≥5× upper limit of normal (ULN)
8. Total bilirubin>3× ULN, unless isolated hyperbilirubinemia or due to documented Gilbert's disease.
9. Female patient is pregnant or lactating
10. Inappropriate fungal infection source control (e.g. persistent indwelling catheters or intravascular devices)
11. Investigational drug administered within 30 days prior to dosing or five half-lives whichever is longer
12. Concomitant use of medication that is a strong inducer of CYP enzymes (e.g. rifampin, carbamazepine, phenytoin, rifabutin, efavirenz, nevirapine, phenobarbital, modafinil, nafcillin, St. John's Wort, and enzalutamide)
13. Any other condition or laboratory abnormality that, in the opinion of the Investigator, would put the patient at unacceptable risk for participation in the study or may interfere with the assessments included in the study
14. Diagnosis of deep-seated *Candida*-related infections causing hardware associated septic arthritis, osteomyelitis, endocarditis, myocarditis, hepatosplenic candidiasis, or a central nervous system infection or site of infection that would require antifungal therapy to exceed the maximal duration of study drug treatment (i.e. 6 weeks [42 days]).

Dosing Criteria

Patients must meet the following criteria to begin dosing: Confirmed diagnosis of candidemia and/or invasive candidiasis caused by *C. auris* (in a single or mixed *Candida* spp. infection) within <120 hours (for candidemia) or <168 hours (for invasive candidiasis without candidemia) of the indicative positive blood culture or indicative positive culture from a specimen sampled from a normally sterile site, plus confirmation that all other eligibility criteria are met, qualify the patient for dosing with Compound 1. The initiation of the first dose of Compound 1 must occur within 12 hours of qualification for the study.

Sample Size Determination:

A sample size of approximately 15 patients with documented *C. auris* infection will be recruited in this open-label study. No formal statistical assessment for sample size determination has been performed. This sample size is considered adequate to provide the necessary data to evaluate the efficacy and safety of Compound 1 in patients with documented candidemia and/or invasive candidiasis caused by *C. auris.*

Study Design and Duration:

This is a multicenter, open-label, non-comparative, single-arm study to evaluate the efficacy and safety of Compound 1 for the treatment of candidemia and/or invasive candidiasis caused by *C. auris* in patients aged 18 years and over with limited antifungal treatment options. The Study Drug Treatment Period will be up to a maximum of 42 days (inclusive of the loading dose [Study Day 1]). There will be a Follow-up Period of 4 weeks (+4 days) after EOST. The total duration of participation in the study is up to approximately 10.5 weeks (inclusive of the Screening Period [≤168 hours prior to Baseline]). Patients must have had *C. auris* confirmed in culture<120 hours (for candidemia) or <168 hours (for invasive candidiasis without candidemia) prior to qualification and dosing in the study.

Screening and Baseline procedures will be performed within no more than 120 hours (for candidemia) or 168 hours (for invasive candidiasis without candidemia) from the time that the SOC blood and/or tissue sample or aspirate/fluid positive for *C. auris* was collected, and any outstanding baseline procedures completed before the first dose of study medication.

All patients (or the patient's LAR) will sign an ICF before any protocol specified procedures that are not indicated by SOC may be conducted. Inclusion/exclusion criteria assessments, medical history, demographics, and Acute Physiology and Chronic Health Evaluation II score will be collected before dosing. When an LAR is used for the initial consent, the patient will be consented during the study as soon as he/she is able to do so.

On Study Day 1 (or over the first 24 hours if dosing starts in the evening), a 1000 mg Compound 1 loading dose will be administered over 3 hours by IV infusion twice daily (BID). On Study Days 2 and 3, a 600 mg Compound 1 maintenance dose will be administered over 3 hours by IV infusion once daily (QD). On Study Day 4 and onward, the Compound 1 maintenance dose will be administered as either 600 mg Compound 1 IV infusion QD over 3 hours or 800 mg PO QD. Patients who have completed a minimum of 3 days of IV Compound 1, are clinically stable as determined by the Investigator, and are able to swallow tablets, may switch from IV to PO dosing on Study Day 4 and onward. Study drug will be administered for 14 days after clearance of *Candida* organisms from the bloodstream (two consecutive negative blood cultures), and in accordance with clinical judgment as applicable for other infected sites, up a maximum of 42 days.

Patients will be monitored by daily blood culture from signing informed consent, through dosing during Study Drug Treatment until 2 consecutive blood cultures are negative for *Candida* spp., at EOST, and at 2 and 4 weeks after EOST, or Early Termination. For patients diagnosed with invasive candidiasis, relevant cultures, histopathology, and imaging tests to assess the site(s), extent, progress, and outcome of the *Candida* infection will be conducted as clinically indicated. All results should be recorded in the electronic Case Report Form. The management of intravascular catheters, intravascular devices, and, if applicable, any drains will be recorded, including any associated microbiology results.

Patients will be monitored for safety throughout the duration of the study. Safety assessments will include vital signs, clinical laboratory assessments (serum chemistry, hematology, coagulation, and urinalysis), physical examinations, neurological assessments (twice weekly on treatment), prior and concomitant medication reporting, and adverse event reporting. A 12-lead electrocardiogram (ECG) will be performed at Baseline (pre-dose), EOST, and 4 weeks after EOST, or Early Termination. A dilated fundoscopic examination will be performed at least once during the baseline period, which exclusively for this assessment may be up to Day 3 of the study. Follow-up fundoscopic examinations are required at EOST, and 4 weeks after EOST, or Early Termination for those patients who had positive findings up to Day 3 (or more if clinically indicated). A urine pregnancy test (for females of childbearing potential only) will be performed at Screening and Baseline (pre-dose), every 30 days during treatment if required by local regulations, at EOST, and 2 and 4 weeks after EOST, or Early Termination.

In the event of an inadequate response/failure on Compound 1 study treatment, the study drug may be discontinued and alternative antifungal treatment instituted.

Plasma samples for PK (Compound 1 [prodrug] and Compound 1A [active moiety]) will be collected at Baseline (pre-dose), twice weekly during Study Drug Treatment, and at EOST, 2 weeks after EOST, or Early Termination. Plasma samples for PK will be collected at the same time as samples are collected for the study's clinical laboratory assessments. Serum samples for $(^{1,3})$-β-D-glucan levels will be collected at Baseline (pre-dose) and EOST, or Early Termination (if applicable).

Optionally, if body fluids are sampled as part of routine patient management (e.g., bronchoalveolar lavage, lumbar puncture, paracentesis, vitreous fluid collection, abscess drainage) within approximately 2 hours of blood sampling for PK, these samples may be stored for future analysis of Compound 1 and Compound 1A levels.

The evaluation of treatment outcome will be assessed at EOST, and 2 and 4 weeks after EOST, or Early Termination.

The end of study will occur after the last visit of the last patient on the study.

Dosage Forms and Route of Administration:

On Study Day 1 (or over the first 24 hours if dosing starts in the evening), a 1000 mg Compound 1 loading dose will be administered over 3 hours by IV infusion BID.

On Study Days 2 and 3, a 600 mg Compound 1 maintenance dose will be administered over 3 hours by IV infusion QD.

The infusion volume for both the 1000 mg and the 600 mg Compound 1 doses will be 250 mL.

On Study Day 4 and onward, a Compound 1 maintenance dose will be administered as either:

600 mg Compound 1 IV infusion QD over 3 hours, or 800 mg PO QD

Criteria for Switching From Intravenous to Oral Dose:

Patients who have completed a minimum of 3 days of Compound 1 IV administration may be eligible for PO switch on Study Day 4 and onward. Patients must meet all of the following criteria to switch from IV to PO dosing of Compound 1:

Is clinically stable, as determined by the Investigator

Is able to swallow tablets

Rationale for Dose And Schedule Selection:

Dose

In pharmacokinetic/pharmacodynamic (PK-PD) studies, immunocompromised mice were infected with one of three spp. of *Candida* (*C. albicans, C. glabrata*, or *C. auris*) and groups of animals were dosed with Compound 1 at different dose fractionations. The AUC/MIC ratio was determined to be the PK-PD variable that best correlated with antifungal efficacy as assessed by fungal burden (CFUs) in the kidney. The probability of target attainment (PTA) was calculated separately for each *Candida* spp. tested. The PTA calculation used the Compound 1A free drug AUC level at the stasis endpoint divided by the MIC required to inhibit the growth of 90% of organisms ($MIC_{90}$) of each of the *Candida* spp. tested.

The AUC level was estimated from a population PK model derived primarily from the Phase 1 PK data. The stasis endpoint was defined as the quantity of *Candida* spp. in CFUs just prior to Compound 1 administration compared to CFUs at the endpoint of assessment (i.e. 24 hours for *C. albicans;* 96 hours for *C. glabrata* and *C. auris*). The MIC data for the *Candida* strains tested were obtained from recent surveillance data.

Using the AUC at the stasis endpoint, along with the $MIC_{90}$ from the surveillance data and the predicted exposure at the dose regimen to be used in this study, the PTA for the 3 *Candida* spp. tested was shown to be approximately 100%. Further, sensitivity analyses were conducted to evaluate the PTA under different scenarios including increased variability of PK parameters and higher *Candida* spp. $MIC_{90}$ values. For both scenarios the PTA remained>90%.

In two Phase 1 studies in healthy volunteers, Compound 1 IV and PO formulations were safe and well tolerated. The majority of TEAEs were mild, transitory, and resolved without intervention. No DLTs were observed. Specifically, in the first-in-human Phase 1 clinical study, a loading dose regimen of Compound 1 1000 mg IV 2-hour infusion BID on Day 1, followed by a maintenance dose of Compound 1 600 mg IV 1-hour infusion QD on Days 2 through 7, was safe and well tolerated. In an additional Phase 1 study of Compound 1, a dose regimen consisting of a loading dose of Compound 1 1000 mg IV 3-hour infusion BID on Day 1, followed by a maintenance dose of Compound 1 600 mg IV 3-hour infusion QD on Days 2 through 7, and then Compound 1 800 mg orally QD on Days 8 through 42 was also safe and well tolerated.

Schedule

To ensure the safety and tolerability of Compound 1 dosing for 42 days, this study will use an Compound 1 dose and infusion duration already studied in Phase 1 for 42 days of therapy inclusive of IV and PO investigational drug therapy. The loading dose regimen of Compound 1 1000 mg IV BID over a 3-hour infusion followed by Compound 1 600 mg IV QD over a 3-hour infusion has been designed to optimize patient safety and tolerability during the study. At Study Day 4 and onward, provided the protocol-defined criteria for a PO switch are met, the patient may be switched to oral Compound 1 800 mg QD. Study drug will be administered for 14 days after clearance of *Candida* organisms from the bloodstream, and in accordance with clinical judgment as applicable for other infected sites, up to a maximum of 42 total days combined IV and PO Compound 1 therapy.

Efficacy Endpoints:

The primary efficacy parameter is percentage of patients with Treatment Success at EOST as determined by the Data Review Committee (DRC).

The secondary efficacy parameters include the following:

- Time to first negative blood culture
- Percentage of patients with successful Mycological Outcomes at EOST, and at 2 and 4 weeks after EOST
- Percentage of patients with Treatment Success at EOST as determined by the investigator.
- Percentage of patients with Treatment Success 2 and 4 weeks after EOST, as determined by the investigator and the DRC
- All-cause mortality at Study Day 30
- Number of patients with TEAEs The exploratory efficacy parameters include the following: Change in serum (1,3)-β-D-glucan levels from Baseline (pre-dose) to EOST Efficacy Assessments:

At End of Study Drug Treatment (EOST):

Treatment Success is defined as meeting all of the following criteria:

- Two consecutive blood cultures negative for *Candida* spp., and/or for patients with a deep-seated site of infection, at least one negative tissue culture or aspirate/fluid culture
  - For patients with a deep-seated site of infection involving visceral organs from which a tissue culture is not obtainable, resolution of the attributable clinical signs of infection recorded at Baseline, and, as applicable, radiological improvement associated with the site of infection is required
- Alive at EOST.
- No concomitant use of any other systemic antifungal therapies through EOST Note: administration of another systemic antifungal immediately following EOST for suspected or documented *Candida* infection at any site does not constitute a treatment success at EOST Treatment Failure is defined as any case that does not meet the criteria for Treatment Success.

Successful Mycological Outcomes:

- Eradication is defined as a negative blood (and/or other infection site) culture(s) for *Candida* spp. in the absence of concomitant antifungal therapy through EOST
- Presumed Eradication (applicable to invasive candidiasis) is defined as clinical resolution of invasive *Candida* spp. infection where tissue samples are unavailable (supported by evidence of resolution/improvement in the diagnostic parameters used at Baseline)

Both of the above definitions are in the absence of concomitant or additional systemic antifungal therapy.

At Follow-up (2 Weeks and 4 Weeks After End of Study Drug Treatment [EOST]):

- Treatment Success (sustained) is defined as having met the criteria for Treatment Success at EOST with no change during the follow-up period
- Relapse is defined as re-occurrence of *Candida* in blood culture, or from other infection sites during the Follow-up Period, or diagnostic parameters indicative of recurrence or late spread of the *Candida* infection
- Other:
  - Death
  - Unavailable for follow-up, or unevaluable at follow up for other reasons Additional DRC assessment categories are provided in the DRC Charter Mycological Recurrence is defined as mycologically confirmed infection based on blood culture (or other specimen(s) cultured from a normally sterile site), with the same Baseline *Candida* spp. during the 4 weeks after EOST.

Safety Variables:

Safety parameters include the following:

- Evaluation of adverse events at Screening, Baseline, during Study Drug Treatment, at EOST, and 2 and 4 weeks after EOST, or Early Termination Infusion site reactions should be graded according to the current version of the Common Terminology Criteria for Adverse Events
- Vital signs (temperature, blood pressure, heart rate, respiratory rate, oxygen saturation, and weight) collected at Screening, Baseline (pre-dose), daily on Study Days 1 through 4 and twice weekly thereafter during Study Drug Treatment for outpatients (daily while inpatient), at EOST, and 2 and 4 weeks after EOST, or Early Termination. Height will be collected (from the patient's medical record) at Baseline
- Clinical laboratory assessments (serum chemistry, hematology, coagulation, and urinalysis) will occur at Screening, Baseline (pre-dose), twice weekly during Study Drug Treatment, at EOST, and 2 and 4 weeks after EOST, or Early Termination. If clinically indicated and at the discretion of the Investigator, or if a suspected adverse event is identified, clinical laboratory assessments may be conducted at any time during the study and compared to Baseline.
- Physical examination, including a neurological assessment at Baseline (pre-dose), during Study Drug Treatment (neurological assessments twice weekly), at EOST, and 2 and 4 weeks after EOST, or Early Termination
- ECGs at Baseline (pre-dose), EOST, and 4 weeks after EOST, or Early Termination Risk/Benefit Subjects participating in this study will receive a drug in clinical development without regulatory approval for treatment of fungal diseases. Administration of Compound 1 in a concentration of 1000 mg IV BID will be administered on Day 1, 600 mg IV QD will be administered on Days 2 through 3, and then subsequently 600 mg IV or 800 mg PO QD will be administered throughout the Study Drug Treatment Period. This treatment may have advantages over standard of care (SOC) therapy against certain resistant fungal diseases, where SOC treatment might show no or limited therapeutic effectiveness, furthermore Compound 1 has a differentiated safety profile, is available as IV and oral formulation and may have fewer drug-drug interactions than SOC. Since the efficacy of Compound 1 has not yet been proven in patients, no additional protection of Compound 1 in this concentration can be assured. Potential adverse events associated with Compound 1 were headache, dizziness, fatigue, nausea and vomiting. For more information on Compound 1 safety profile please refer to the Investigator's Brochure. Subjects participating in this clinical study will receive more intense health monitoring as detailed in the schedule of procedures Formulation and Packaging Compound 1 Injection is formulated at a concentration of 20 mg/mL. The formulation consists of Compound 1 drug substance, sodium chloride, hydrochloric acid, sodium hydroxide, and sterile water for injection. A 50 mL sterile vial is filled with 35 mL of Compound 1 Injection. Compound 1 Injection will be reconstituted and administered as an IV infusion. Preparation and dilution instructions will be provided in the Pharmacy Manual.

Compound 1 Tablets are formulated at a strength of 200 mg white-coated tablets. The formulation consists of Compound 1 drug substance, microcrystalline cellulose, modified lactose monohydrate, colloidal silicon dioxide, pregelatinized starch, talc, magnesium stearate, and white coating (Opadry II AMB), and purified water. The tablets are stored in high-density polyethylene bottles with a child-resistant container.

Although the size of the vial used for Compound 1 Injection and/or the Compound 1 Tablet strength may be potentially modified (as re-supplies are manufactured), the Compound 1 doses to be administered will not change. Any changes will be detailed in the Pharmacy Manual.

All Compound 1 supplies will be labeled according to the requirements of local law and legislation, as well as current Good Manufacturing Practice and Good Clinical Practice (GCP) guidelines Study Drug Administration On Study Day 1 (or over the first 24 hours if started in the evening), a 1000 mg Compound 1 loading dose will be administered over 3 hours by IV infusion BID.

The infusion volume for both the 1000 mg and the 600 mg Compound 1 doses will be 250 mL.

On Study Day 4 and onward, an Compound 1 maintenance dose will be administered as either:

600 mg Compound 1 IV infusion QD over 3 hours, or.

800 mg Compound 1 PO QD

Subjects who have completed a minimum of 3 days of IV Compound 1, are clinically stable as determined by the Investigator, and able to swallow tablets may switch from IV to PO dosing on Study Day 4 and onward. Study drug will be administered for a minimum of 14 days after clearance of *Candida* spp. Duration of Compound 1 treatment for other deep-seated sites of infection will be according to investigator judgment and treatment guidelines, but may not exceed up to a maximum of 6 weeks total ($^{42}$ days, inclusive of the loading dose [Study Day 1]).

Tablets are to be administered at the same time each day, whole, and taken by mouth with water within 30 minutes of being removed from the refrigerator. No splitting or crushing of tablets is allowed. Compound 1 Injection will be stored at −20° C. and tablets will be stored at 2 to 8° C.

Examples 5A-5C: Stability Testing

Examples 5A: Binary Excipient Compatibility

A binary excipient compatibility study was performed with Compound 1 and potential excipients to be used in the clinical formulation (see Tables B1-B15). For each excipient screened, there were 3 conditions ($^{5}$° C., room temperature, 40° C./75% RH, 50° C.) that could be pulled at 3 weeks or 4 weeks as shown in Table 85. For contingency, one vial was stored at each condition per excipient. At each time point, an appropriate active sample control vial from each condition was reconstituted and analyzed in addition to the compatibility samples.

TABLE B1

| List of Materials used for Excipient Compatibility Study Materials | |
|---|---|
| Compound 1 | Colloidal Silicon Dioxide (Cab-o-Sil M-5P) |
| Microcrystalline Cellulose | Magnesium Stearate (HyQual ®) |
| Lactose Monohydrate Fast Flo (Product Code 316) | Sodium Starch Glycolate |
| Pregelatinized Starch (Starch 1500 ®) | Anhydrous Dibasic Calcium Phosphate (Emcompress ®) |
| Povidone K29/32 | Opadry ® AMB II Moisture Barrier Coating* |
| Hyproxypropyl Methylcellulose (Methocel E5) | Croscarmellose sodium (Ac-di-Sol) |

TABLE B2

Compound 1 Excipient Compatibility Results for Lot 381-1A to 381-1C

| Sample | Test | | Initial 0 | Open Packaging 3 Weeks | Open Packaging 3 Weeks |
|---|---|---|---|---|---|
| A | API Strength/Excipient: | | Control | | |
| | Conditions: | | RT | 40° C./75% RH | 50° C. |
| | Assay (% LC) | | 100.1 | 100.0 | 100.0 |
| | Impurities (%) | Compound 1A | 0.10 | 0.26 | 0.41 |
| | | Total Unknown | 0.31 | 0.31 | 0.35 |
| | | Total | 0.41 | 0.57 | 0.76 |
| B | API Strength/Excipient: | | 50% (w/w)/Microcrystalline Cellulose | | |
| | Conditions: | | RT | 40° C./75% RH | 50° C. |
| | Assay(% LC) | | 100.5 | 102.1 | 105.0 |
| | Impurities (%) | Compound 1A | 0.11 | 0.27 | 0.43 |
| | | Total Unknown | 0.31 | 0.30 | 0.36 |
| | | Total | 0.42 | 0.57 | 0.79 |
| C | API Strength/Excipient: | | 50% (w/w)/Lactose Monohydrate | | |
| | Conditions: | | RT | 40° C./75% RH | 50° C. |
| | Assay (% LC) | | 100.7 | 104.2 | 102.7 |
| | Impurities (%) | Compound 1A | 0.10 | 0.27 | 0.42 |
| | | Total Unknown | 0.31 | 0.32 | 0.35 |
| | | Total | 0.41 | 0.59 | 0.78 |

TABLE B3

Compound 1 Excipient Compatibility Results for Lot 381-1D to 381-1F

| Sample | Test | | Initial 0 | Open Packaging 3 Weeks | Open Packaging 3 Weeks |
|---|---|---|---|---|---|
| D | API Strength/Excipient: | | 50% (w/w)/ regelatinized Starch | | |
| | Conditions: | | RT | 40° C./75% RH | 50° C. |
| | Assay (% LC) | | 99.4 | 99.8 | 105.0 |
| | Impurities | Compound 1A | 0.11 | 0.26 | 0.43 |
| | (%) | Total Unknown | 0.30 | 0.30 | 0.36 |
| | | Total | 0.41 | 0.56 | 0.79 |
| E | API Strength/Excipient: | | 50% (w/w)/Povidone K29/32 | | |
| | Conditions: | | RT | 40° C./75% RH | 50° C. |
| | Assay (% LC) | | 99.1 | 132.1 | 101.2 |
| | Impurities | Compound 1A | 0.11 | 0.36 | 0.41 |
| | (%) | Total Unknown | 0.30 | 0.46 | 0.35 |
| | | Total | 0.41 | 0.82 | 0.76 |
| F | API Strength/Excipient: | | 50% (w/w)/Hyproxypropyl Methylcellulose (Methocel E5) | | |
| | Conditions: | | RT | 40° C./75% RH | 50° C. |
| | Assay(% LC) | | 97.4 | 95.6 | 106.7 |
| | Impurities | Compound 1A | | 0.36 | 0.43 |
| | (%) | Total Unknown | 0.35 | 0.31 | 0.37 |

TABLE B4

Compound 1 Excipient Compatibility Results for Lot 381-1G to 381-1I

| Sample | Test | | Initial 0 | Open Packaging 3 Weeks | Open Packaging 3 Weeks |
|---|---|---|---|---|---|
| G | API Strength/Excipient: | | 67%(w/w)/Colloidal Silicon Dioxide (Cab-o-Sil M-5P) | | |
| | Conditions: | | RT | 40° C./75% RH | 50° C. |
| | Assay (% LC) | | 92.5 | 101.1 | 104.4 |
| | Impurities | Compound 1A | 0.10 | 0.27 | 0.43 |
| | (%) | Total Unknown | 0.28 | 0.30 | 0.36 |
| | | Total | 0.38 | 0.57 | 0.79 |

TABLE B4-continued

Compound 1 Excipient Compatibility Results for Lot 381-1G to 381-1I

| Sample | Test | | Initial 0 | Open Packaging 3 Weeks | Open Packaging 3 Weeks |
|---|---|---|---|---|---|
| H | API Strength/Excipient: | | 67%(w/w)/Magnesium Stearate (HyQual ®) | | |
| | Conditions: | | RT | 40° C./75% RH | 50° C. |
| | Assay (% LC) | | 96.3 | 98.4 | 100.9 |
| | Impurities | Compound 1A | 0.10 | 0.30 | 0.41 |
| | (%) | Total Unknown | 0.28 | 0.30 | 0.35 |
| | | Total | 0.38 | 0.60 | 0.76 |
| I | API Strength/Excipient: | | 67%(w/w)/Sodium Starch Glycolate | | |
| | Conditions: | | RT | 40° C./75% RH | 50° C. |
| | Assay(% LC) | | 102.5 | 109.1 | 103.4 |
| | Impurities | Compound 1A | 0.11 | 0.32 | 0.42 |
| | (%) | Total Unknown | 0.37 | 0.38 | 0.36 |
| | | Total | 0.48 | 0.57 | 0.78 |

TABLE B5

Compound 1 Excipient Compatibility Results for Lot 381-1J to 381-1L

| Sample | Test | | Initial 0 | Open packaging 3 weeks | Open packaging 3 weeks |
|---|---|---|---|---|---|
| J | API strength/excipient: | | 50%(w/w)/anhydrous dibasic calcium phosphate | | |
| | Conditions: | | Rt | 40° C./75% rh | 50° C. |
| | Assay (% lc) | | 100.6 | 101.6 | 97.6 |
| | Impurities | Compound 1A | 0.11 | 0.27 | 0.40 |
| | (%) | Total unknown | 0.36 | 0.30 | 0.34 |
| | | Total | 0.47 | 0.57 | 0.74 |
| K | API strength/excipient: | | 50% (w/w)/opadry ® amb ii moisture barrier coating | | |
| | Conditions: | | Rt | 40° C./75% rh | 50° C. |
| | Assay (% lc) | | 103.5 | 100.9 | 101.0 |

TABLE B5-continued

| Compound 1 Excipient Compatibility Results for Lot 381-1J to 381-1L | | | | | |
|---|---|---|---|---|---|
| | | | Initial | Open packaging | |
| Sample | Test | | 0 | 3 weeks | 3 weeks |
| | Impurities (%) | Compound 1A | 0.13 | 0.89 | 0.42 |
| | | Total unknown | 0.37 | 0.30 | 0.34 |
| | | Total | 0.50 | 1.19 | 0.76 |
| L | Api strength/excipient: | | 67%(w/w)/croscarmellose sodium (ac-di-sol) | | |
| | Conditions: | | Rt | 40° C./75% rh | 50° C. |
| | Assay (% lc) | | 98.7 | 101.2 | 101.7 |
| | Impurities (%) | Compound 1A | 0.11 | 0.27 | 0.41 |
| | | Total unknown | 0.36 | 0.30 | 0.35 |
| | | Total | 0.47 | 0.57 | 0.76 |

The results of the binary excipient compatibility study indicate that Compound 1 is compatible with the tested excipients after 3 weeks at either storage condition based on the total purity profile and show good stability results comparable to neat API (control) and are at low risk for interaction with the API. This supports a dry blend granulation process.

Compound 1 Tablets for both the Phase 1 and Phase 2 tablet formulations were prepared based upon the excipient compatibility and known stability. Since no other excipients were required to aid in the stability or increased solubility, the formulation was developed to be simple using GRAS excipients.

TABLE B6

Stability Data for Compound 1 Tablets 100 mg, Lot 381-100C, 25° C./60% RH, 30 Count HDPE Bottle

| Test | | 0 Mo | 2 Weeks | 1 Mo | 3 Mo | 6 Mo | 9 Mo |
|---|---|---|---|---|---|---|---|
| Appearance | | Conforms | Conforms | Conforms | Conforms | Conforms | NS |
| Assay (%) | | 96.1 | 97.4 | 97.9 | 98.9 | 96.2 | NS |
| Related Substances (%) | | | | | | | |
| Compound 1A (%) | | 0.19 | 0.23 | 0.25 | 0.39 | 0.43 | NS |
| Individual Unknown Impurity (%) | ~RRT 0.38 | 0.24 | 0.23 | 0.24 | 0.25 | 0.24 | NS |
| | ~RRT 0.50 | 0.15 | 0.14 | 0.14 | 0.12 | 0.19 | NS |
| | ~RRT 0.62 | 0.42 | 0.42 | 0.42 | 0.47 | 0.51 | NS |
| | ~RRT 1.18 | 0.34 | 0.32 | 0.32 | 0.31 | 0.31 | NS |
| | ~RRT 1.45 | 0.19 | 0.18 | 0.18 | 0.15 | 0.18 | NS |
| | ~RRT 2.00 | 0.68 | 0.69 | 0.69 | 0.69 | 0.67 | NS |
| Total Related Substances (%) | | 2.21 | 2.21 | 2.24 | 2.38 | 2.50 | NS |
| Dissolution | Mean | 99 | 96 | 98 | 94 | 96 | NS |
| (% dissolved at 45 minutes) | Min | 96 | 94 | 97 | 87 | 95 | NS |
| | Max | 101 | 99 | 100 | 100 | 99 | NS |
| | % RSD | 1.8 | 1.8 | 1.3 | 4.7 | 1.6 | NS |
| Water Content | | 3.3 | 3.0 | 3.0 | 2.9 | 3.8 | NS |
| Total Aerobic Microbial Count (cfu/g) | | NS | NS | NS | NS | NS | NS |
| Total Combined Yeasts and Molds Count (cfu/g) | | NS | NS | NS | NS | NS | NS |
| *E. Coli* | | NS | NS | NS | NS | NS | NS |

RRT = relative retention time, NS = not scheduled, ND = not detected or <0.05%

TABLE B7

Stability Data for Compound 1 Tablets 100 mg, Lot 381-100C, 5° C., 30 Count HDPE Bottle

| Test | | 0 Mo | 2 Weeks | 1 Mo | 3 Mo | 6 Mo | 9 Mo | 12 Mo | 18 Mo |
|---|---|---|---|---|---|---|---|---|---|
| Appearance | | Conforms | Conforms | Conforms | Conforms | Conforms | Conforms | Conforms | Conforms |
| Assay (%) | | 96.1 | 98.0 | 97.6 | 97.9 | 95.9 | 96.7 | 97.0 | 97.1 |
| Related Substances (%) | | | | | | | | | |
| Compound 1A (%) | | 0.19 | 0.20 | 0.18 | 0.24 | 0.22 | 0.22 | 0.20 | 0.28 |
| Individual Unknown Impurity (%) | ~RRT 0.38 | 0.24 | 0.23 | 0.23 | 0.25 | 0.23 | 0.25 | 0.23 | 0.24 |
| | ~RRT 0.50 | 0.15 | 0.14 | 0.14 | 0.13 | 0.19 | 0.18 | 0.20 | 0.15 |
| | ~RRT 0.62 | 0.42 | 0.41 | 0.40 | 0.42 | 0.43 | 0.45 | 0.37 | 0.43 |
| | ~RRT 1.18 | 0.34 | 0.33 | 0.32 | 0.31 | 0.31 | 0.30 | 0.32 | 0.31 |
| | ~RRT 1.45 | 0.19 | 0.18 | 0.18 | 0.15 | 0.17 | 0.12 | 0.18 | 0.11 |
| | ~RRT 2.00 | 0.68 | 0.70 | 0.69 | 0.69 | 0.68 | 0.67 | 0.67 | 0.68 |
| Total Related Substances (%) | | 2.21 | 2.19 | 2.14 | 2.19 | 2.2 | 2.2 | 2.2 | 2.2 |
| Dissolution | Mean | 99 | 97 | 97 | 96 | 94 | 96 | 98 | 94 |
| (% dissolved at 45 minutes) | Min | 96 | 93 | 93 | 93 | 94 | 95 | 97 | 93 |
| | Max | 101 | 99 | 100 | 100 | 89 | 98 | 100 | 97 |
| | % RSD | 1.8 | 2.2 | 1.3 | 2.8 | 4.0 | 1.2 | 1.4 | 1.7 |
| Water Content | | 3.3 | 3.3 | 3.1 | 3.2 | 3.0 | 3.9 | 3.3 | 3.0 |
| Total Aerobic Microbial Count (cfu/g) | | NS | NS | NS | NS | NS | NS | NS | NS |

TABLE B7-continued

| Stability Data for Compound 1 Tablets 100 mg, Lot 381-100C, 5° C., 30 Count HDPE Bottle | | | | | | | | |
|---|---|---|---|---|---|---|---|---|
| Test | 0 Mo | 2 Weeks | 1 Mo | 3 Mo | 6 Mo | 9 Mo | 12 Mo | 18 Mo |
| Total Combined Yeasts and Molds Count (cfu/g) | NS | NS | NS | NS | NS | NS | NS | NS |
| *E. Coli* | NS | NS | NS | NS | NS | NS | NS | NS |

RRT = relative retention time, NS = not scheduled, ND = not detected or <0.05%

TABLE B8

| Stability Data for Compound 1 Tablets 200 mg, Lot 381-200C, 25° C./60% RH, 30 Count HDPE Bottle | | | | | | | |
|---|---|---|---|---|---|---|---|
| Test | | 0 Mo | 2 Weeks | 1 Mo | 3 Mo | 6 Mo | 9 Mo |
| Appearance | | Conforms | Conforms | Conforms | Conforms | Conforms | Conforms |
| Assay (%) | | 98.3 | 99.1 | 98.1 | 99.1 | 96.9 | 98.4 |
| Related Substances (%) | | | | | | | |
| Compound 1A (%) | | 0.18 | 0.21 | 0.22 | 0.35 | 0.38 | 0.44 |
| Individual Unknown Impurity (%) | ~RRT 0.38 | 0.24 | 0.24 | 0.24 | 0.26 | 0.24 | 0.26 |
| | ~RRT 0.50 | 0.14 | 0.14 | 0.14 | 0.12 | 0.19 | 0.18 |
| | ~RRT 0.62 | 0.41 | 0.41 | 0.41 | 0.46 | 0.50 | 0.55 |
| | ~RRT 1.18 | 0.32 | 0.33 | 0.32 | 0.32 | 0.31 | 0.30 |
| | ~RRT 1.45 | 0.17 | 0.18 | 0.18 | 0.15 | 0.18 | 0.12 |
| | ~RRT 2.00 | 0.69 | 0.71 | 0.70 | 0.70 | 0.68 | 0.68 |
| Total Related Substances (%) | | 2.15 | 2.22 | 2.21 | 2.36 | 2.50 | 2.50 |
| Dissolution | Mean | 98 | 96 | 96 | 95 | 95 | 96 |
| (% dissolved at 45 minutes) | Min | 93 | 94 | 94 | 93 | 93 | 93 |
| | Max | 103 | 98 | 99 | 98 | 98 | 98 |
| | % RSD | 3.6 | 1.8 | 1.9 | 2.5 | 2.5 | 2.3 |
| Water Content | | 3.2 | 3.0 | 3.0 | 2.7 | 3.8 | 3.2 |
| Total Aerobic Microbial Count (cfu/g) | | NS | NS | NS | NS | NS | NS |
| Total Combined Yeasts and Molds Count (cfu/g) | | NS | NS | NS | NS | NS | NS |
| *E. Coli* | | NS | NS | NS | NS | NS | NS |

RRT = relative retention time, NS = not scheduled, ND = not detected or <0.05%

TABLE B9

| Stability Data for Compound 1 Tablets 200 mg, Lot 381-200C, 5° C., 30 Count HDPE Bottle | | | | | | | | | |
|---|---|---|---|---|---|---|---|---|---|
| Test | | 0 Mo | 2 Weeks | 1 Mo | 3 Mo | 6 Mo | 9 Mo | 12 Mo | 18 Mo |
| Appearance | | Conforms | Conforms | Conforms | Conforms | Conforms | Conforms | Conforms | Conforms |
| Assay (%) | | 98.3 | 98.6 | 99.4 | 99.2 | 97.5 | 98.7 | 97.76 | 98.5 |
| Related Substances (%) | | | | | | | | | |
| Compound 1A (%) | | 0.18 | 0.19 | 0.17 | 0.23 | 0.21 | 0.20 | 0.1418 | 0.26 |
| Individual Unknown Impurity (%) | ~RRT 0.38 | 0.24 | 0.23 | 0.24 | 0.25 | 0.24 | 0.25 | 0.2423 | 0.24 |
| | ~RRT 0.50 | 0.14 | 0.14 | 0.14 | 0.13 | 0.19 | 0.19 | 0.2220 | 0.15 |
| | ~RRT 0.62 | 0.41 | 0.40 | 0.40 | 0.42 | 0.43 | 0.45 | 0.4437 | 0.43 |
| | ~RRT 1.18 | 0.32 | 0.33 | 0.33 | 0.32 | 0.31 | 0.31 | 0.32 | 0.32 |
| | ~RRT 1.45 | 0.17 | 0.18 | 0.18 | 0.15 | 0.18 | 0.12 | 0.2418 | 0.11 |
| | ~RRT 2.00 | 0.69 | 0.70 | 0.71 | 0.70 | 0.69 | 0.70 | 0.6968 | 0.70 |
| Total Related Substances (%) | | 2.15 | 2.17 | 2.17 | 2.20 | 2.30 | 2.20 | 2.3020 | 2.20 |
| Dissolution | Mean | 98 | 98 | 98 | 95 | 94 | 94 | 97 | 94 |
| (% dissolved at 45 minutes) | Min | 93 | 94 | 94 | 93 | 90 | 92 | 95 | 93 |
| | Max | 103 | 102 | 101 | 98 | 96 | 97 | 99 | 97 |
| | % RSD | 3.6 | 2.8 | 3.1 | 1.9 | 2.5 | 2.2 | 1.2 | 2.2 |
| Water Content | | 3.2 | 2.9 | 3.1 | 2.9 | 4.0 | 3.2 | 3.0 | 3.4 |
| Total Aerobic Microbial Count (cfu/g) | | NS | NS | NS | NS | NS | NS | NS | NS |
| Total Combined Yeasts and Molds Count (cfu/g) | | NS | NS | NS | NS | NS | NS | NS | NS |
| *E. Coli* | | NS | NS | NS | NS | NS | NS | NS | NS |

RRT = relative retention time, NS = not scheduled, ND = not detected or <0.05%

TABLE B10

Stability Data for Compound 1 Tablets 100 mg, Lot 645, 25° C./60% RH, 10 Count HDPE Bottle

| Test | | 0 Mo | 1 Mo | 3 Mo | 6 Mo | 9 Mo | 12 Mo |
|---|---|---|---|---|---|---|---|
| Appearance | | Conforms | Conforms | Conforms | Conforms | Conforms | Conforms |
| Assay (%) | | 101.8 | 100.1 | 100.9 | 100.0 | 99.8 | 99.4 |
| Related Substances (%) | | | | | | | |
| Compound 1A (%) | | 0.31 | 0.43 | 0.51 | 0.57 | 0.67 | 0.70 |
| Individual Unknown Impurity (%) | ~RRT 0.38 | 0.15 | 0.15 | 0.15 | 0.15 | 0.15 | 0.15 |
| | ~RRT 0.62 | 0.16 | 0.17 | 0.18 | 0.18 | 0.23 | 0.23 |
| | ~RRT 0.78 | ND | ND | 0.12 | ND | 0.11 | 0.10 |
| | ~RRT 2.05 | 0.33 | 0.32 | 0.32 | 0.31 | 0.31 | 0.31 |
| Total Related Substances (%) | | 0.98 | 1.1 | 1.3 | 1.2 | 1.5 | 1.5 |
| Dissolution (% dissolved at 45 minutes) | Mean | 95 | 93 | 93 | 93 | 96 | 92 |
| | Min | 91 | 88 | 90 | 90 | 92 | 87 |
| | Max | 98 | 99 | 98 | 96 | 98 | 95 |
| | % RSD | 2.9 | 3.9 | 3.3 | 2.6 | 2.1 | 3.2 |
| Water Content | | 2.81 | 2.9 | 2.3 | 2.4 | 2.1 | 1.5 |
| Total Aerobic Microbial Count (cfu/g) | | <10 | NS | NS | NS | NS | <10 |
| Total Combined Yeasts and Molds Count (cfu/g) | | <10 | NS | NS | NS | NS | <10 |
| *E. Coli* | | Absent/1g | NS | NS | NS | NS | Absent/1g |

RRT = relative retention time, NS = not scheduled, ND = not detected or < 0.05%

TABLE B11

Stability Data for Compound 1 Tablets 100 mg, Lot 645, 5° C., 10 Count HDPE Bottle

| Test | | 0 Mo | 1 Mo | 3 Mo | 6 Mo | 9 Mo | 12 Mo |
|---|---|---|---|---|---|---|---|
| Appearance | | Conforms | Conforms | Conforms | Conforms | Conforms | Conforms |
| Assay (%) | | 101.8 | 100.3 | 100.8 | 100.3 | 100.5 | 100.6 |
| Related Substances (%) | | | | | | | |
| Compound 1A (%) | | 0.31 | 0.37 | 0.36 | 0.33 | 0.36 | 0.36 |
| Individual Unknown Impurity (%) | ~RRT 0.38 | 0.15 | 0.15 | 0.15 | 0.15 | 0.15 | 0.15 |
| | ~RRT 0.62 | 0.16 | 0.17 | 0.15 | 0.13 | 0.18 | 0.17 |
| | ~RRT 0.78 | ND | ND | 0.10 | ND | 0.10 | 0.10 |
| | ~RRT 2.05 | 0.33 | 0.32 | 0.32 | 0.32 | 0.32 | 0.32 |
| Total Related Substances (%) | | 0.98 | 1.0 | 1.1 | 0.93 | 1.1 | 1.1 |
| Dissolution (% dissolved at 45 minutes) | Mean | 95 | 92 | 95 | 90 | 97 | 94 |
| | Min | 91 | 87 | 89 | 84 | 93 | 85 |
| | Max | 98 | 99 | 98 | 98 | 99 | 103 |
| | % RSD | 2.9 | 4.3 | 3.5 | 6.1 | 2.1 | 6.2 |
| Water Content | | 2.81 | 2.9 | 3.0 | 2.5 | 2.1 | 1.6 |
| Total Aerobic Microbial Count (cfu/g) | | <10 | NS | NS | NS | NS | <10 |
| Total Combined Yeasts and Molds Count (cfu/g) | | <10 | NS | NS | NS | NS | <10 |
| *E. Coli* | | Absent/1g | NS | NS | NS | NS | Absent/1g |

RRT = relative retention time, NS = not scheduled, ND = not detected or <0.05%

TABLE B12

Stability Data for Compound 1 Tablets 200 mg, Lot 646, 25° C./60% RH, 30 Count HDPE Bottle

| Test | | 0 Mo | 1 Mo | 3 Mo | 6 Mo | 9 Mo | 12 Mo |
|---|---|---|---|---|---|---|---|
| Appearance | | Conforms | Conforms | Conforms | Conforms | Conforms | Conforms |
| Assay (%) | | 101.7 | 100.8 | 101.1 | 99.6 | 100.6 | 99.3 |
| Related Substances (%) | | | | | | | |
| Compound 1A (%) | | 0.23 | 0.39 | 0.48 | 0.56 | 0.67 | 0.71 |
| Individual Unknown Impurity (%) | ~RRT 0.38 | 0.15 | 0.15 | 0.15 | 0.15 | 0.15 | 0.16 |
| | ~RRT 0.62 | 0.15 | 0.17 | 0.17 | 0.16 | 0.23 | 0.22 |
| | ~RRT 2.05 | 0.33 | 0.32 | 0.32 | 0.31 | 0.32 | 0.31 |
| Total Related Substances (%) | | 0.86 | 1.0 | 1.1 | 1.2 | 1.4 | 1.4 |
| Dissolution (% dissolved at 45 minutes) | Mean | 90 | 93 | 95 | 90 | 95 | 89 |
| | Min | 84 | 87 | 91 | 85 | 93 | 86 |
| | Max | 100 | 98 | 98 | 95 | 100 | 92 |
| | % RSD | 6.1 | 3.8 | 3.2 | 4.2 | 3.0 | 2.5 |
| Water Content | | 3.19 | 3.3 | 3.1 | 3.2 | 2.8 | 1.9 |

TABLE B12-continued

| Stability Data for Compound 1 Tablets 200 mg, Lot 646, 25° C./60% RH, 30 Count HDPE Bottle | | | | | | |
|---|---|---|---|---|---|---|
| Test | 0 Mo | 1 Mo | 3 Mo | 6 Mo | 9 Mo | 12 Mo |
| Total Aerobic Microbial Count (cfu/g) | <10 | NS | NS | NS | NS | <10 |
| Total Combined Yeasts and Molds Count (cfu/g) | <10 | NS | NS | NS | NS | <10 |
| *E. Coli* | Absent/1 g | NS | NS | NS | NS | Absent/1 g |

RRT = relative retention time,
NS = not scheduled,
ND = not detected or <0.05%

TABLE B13

| Stability Data for Compound 1 Tablets 200 mg, Lot 646, 5° C., 30 Count HDPE Bottle | | | | | | | |
|---|---|---|---|---|---|---|---|
| Test | | 0 Mo | 1 Mo | 3 Mo | 6 Mo | 9 Mo | 12 Mo |
| Appearance | | Conforms | Conforms | Conforms | Conforms | Conforms | Conforms |
| Assay (%) | | 101.7 | 100.0 | 100.6 | 100.8 | 99.8 | 100.3 |
| Related Substances (%) | | | | | | | |
| Compound 1A (%) | | 0.23 | 0.32 | 0.30 | 0.28 | 0.30 | 0.31 |
| Individual Unknown Impurity (%) | ~RRT 0.38 | 0.15 | 0.15 | 0.15 | 0.15 | 0.14 | 0.15 |
| | ~RRT 0.62 | 0.15 | 0.16 | 0.15 | 0.13 | 0.17 | 0.15 |
| | ~RRT 2.05 | 0.33 | 0.32 | 0.32 | 0.32 | 0.33 | 0.32 |
| Total Related Substances (%) | | 0.86 | 1.0 | 0.92 | 0.88 | 0.94 | 0.93 |
| Dissolution | Mean | 90 | 92 | 95 | 92 | 96 | 90 |
| (% dissolved at 45 minutes) | Min | 84 | 89 | 91 | 87 | 93 | 86 |
| | Max | 100 | 99 | 98 | 97 | 100 | 93 |
| | % RSD | 6.1 | 3.9 | 2.8 | 3.9 | 3.5 | 2.7 |
| Water Content | | 3.19 | 3.4 | 2.9 | 3.3 | 2.8 | 1.7 |
| Total Aerobic Microbial Count (cfu/g) | | <10 | NS | NS | NS | NS | <10 |
| Total Combined Yeasts and Molds Count (cfu/g) | | <10 | NS | NS | NS | NS | <10 |
| *E. Coli* | | Absent/1 g | NS | NS | NS | NS | Absent/1 g |

TABLE B14

| Stability Data for Compound 1 Tablets 200 mg, Lot 192, 25° C./60% RH, 30 count HDPE Bottle | | | | |
|---|---|---|---|---|
| Test | | 0 Mo | 3 Mo | 6 Mo |
| Appearance | | Conforms | Conforms | Conforms |
| Assay (%) | | 98.3 | 96.8 | 98.7 |
| Related Substances (%) | | | | |
| Compound 1A (%) | | 0.20 | 0.48 | 0.55 |
| Individual Unknown | ~RRT 0.39 | 0.10 | 0.10 | 0.11 |
| Impurity (%) | ~RRT 0.63 | 0.21 | 0.22 | 0.26 |
| | ~RRT 0.78 | ND | ND | 0.10 |
| | ~RRT 1.46 | 0.18 | 0.17 | 0.19 |
| | ~RRT 2.01 | 0.24 | 0.23 | 0.23 |
| Total Related Substances (%) | | 0.93 | 1.2 | 1.4 |
| Dissolution | Mean | 96 | 94 | 98 |
| (% dissolved at 45 | Min | 91 | 91 | 95 |
| minutes) | Max | 102 | 96 | 102 |
| | % RSD | 4.8 | 2.1 | 2.9 |
| Water Content | | 3.4 | 3.4 | 3.8 |
| Total Aerobic Microbial Count (cfu/g) | | <10 | NS | NS |
| Total Combined Yeasts and Molds Count (cfu/g) | | <10 | NS | NS |
| *E. Coli* | | Absent/1 g | NS | NS |

RRT = relative retention time, NS = not scheduled, ND = not detected or <0.05%

TABLE B15

| Stability Data for Compound 1 Tablets 200 mg, Lot 192, 5° C., 30 count HDPE Bottle | | | | |
|---|---|---|---|---|
| Test | | 0 Mo | 3 Mo | 6 Mo |
| Appearance | | Conforms | Conforms | Conforms |
| Assay (%) | | 98.3 | 99.6 | 99.9 |
| Related Substances (%) | | | | |
| Compound 1A (%) | | 0.20 | 0.23 | 0.25 |
| Individual Unknown | ~RRT 0.39 | 0.10 | 0.10 | 0.10 |
| Impurity (%) | ~RRT 0.63 | 0.21 | 0.20 | 0.22 |
| | ~RRT 0.78 | 0.18 | 0.18 | 0.19 |
| | ~RRT 1.46 | 0.24 | 0.24 | 0.24 |
| | ~RRT 2.01 | 0.10 | 0.10 | 0.10 |
| Total Related Substances (%) | | 0.93 | 0.95 | 1.0 |
| Dissolution | Mean | 96 | 98 | 96 |
| (% dissolved at 45 | Min | 91 | 94 | 90 |
| minutes) | Max | 102 | 101 | 99 |
| | % RSD | 4.8 | 2.9 | 3.3 |
| Water Content | | 3.4 | 3.5 | 3.8 |
| Total Aerobic Microbial Count (cfu/g) | | <10 | NS | NS |
| Total Combined Yeasts and Molds Count (cfu/g) | | <10 | NS | NS |
| *E. Coli* | | Absent/1 g | NS | NS |

RRT = relative retention time, NS = not scheduled, ND = not detected or < 0.05%

Example 5B: Compound 1 Injection Stability Studies

The HPLC method used in the stability studies for Compound 1 Injections, 20 mg/mL is a specific and stability-indicating method used for the determination of assay, related substances, content uniformity, identification, and absence of Compound 1 in Compound 1 Injection at 20 mg/mL. The method is a gradient reverse phase HPLC system to measure assay, purity, and related substances. The assay (% w/w) is determined by comparing the peak response of the sample to that of a standard. The same HPLC method used for purity and related substances is used to measure related substances. Related substances to Compound 1 drug substance are reported as area percent. The area of an impurity is divided by the total area of all sample-related peaks. Related substances are reported by retention time relative to the parent peak (RRT).

Identification by Retention Time $$\text{Relative Retention Time} = \frac{RTsam}{RTsd}$$

Assay:

$$\%\ LC\ \text{Compound 1} = \frac{Rsam}{Rstd} \times \frac{Wstd \times P}{Vstd} \times \frac{1}{Dsam} \times \frac{Vsam}{Vpip} \times \frac{100}{LC}$$

Related Substances:

$$\%\ \text{Impurity} = \frac{Rimp}{Rstd} \times \frac{Wstd \times P}{Vstd} \times \frac{1}{Dsam} \times \frac{Vsam}{Vpip} \times \frac{100}{LC} \times RRF$$

Legend:

Rsam=Area response of Compound 1 from sample injection

Rstd=Average area response of Compound 1 from bracketing standard injections

Wstd=Weight of Compound 1 reference standard (mg)

P=Purity of Compound 1 from reference standard (decimal form)

Vstd=Volume of standard solution (mL)

Dsam=Dilution of sample solution

Vsam=Volume of sample solution (mL)

Vpip=Volume of standard solution pipetted (mL)

LC=Label Claim of Compound 1 ([20] mg/ml in liquid samples)

100=Conversion to percent

Rimp=Peak area response of impurity peaks in the sample injection

RTsam=Average retention time of the sample (duplicate injections)

RTstd=Average retention time of the bracketing standards

RRF=Relative response factor. Assume 1.00 for all unknown impurites and for Compound 1A. RF for Compound 1A will be determined during method validation.

Compound 1 Injection, Phase 1 Formulation

Compound 1 Injection, 20 mg/mL, was prepared as a non-buffered solution suitable for Phase 1 clinical studies containing Compound 1, sodium chloride, and pH adjustment using hydrochloric acid and/or sodium hydroxide to pH 7.5. Compound 1 Injection, 20 mg/mL, has been prepared and placed on a short-term stability that includes a freeze thaw ([3] cycles) and ambient storage condition that will cover the time for preparation and dosing, i.e., <72 hours. Additionally, Compound 1 Injection has been placed on an ICH stability program at −20° C. and 5° C. for longer term storage. Samples have been analyzed for appearance, assay, related substance, and pH. Compound Injection, engineering batch #707 manufactured under GMP was placed on an ICH stability program at 5° C. and 25° C./60% RH. Samples have been analyzed for appearance, assay, related substance, particulate matter, and pH. These samples have been tested up to 12-months (e.g., at initial, one-month, two-month, three-month, six-month, nine-month, and 12-month time points). There were no significant physical or assay related changes reported from the short-term stability study (<72 hoursIn the 12-month stability, data have been analyzed and no significant physical or chemical changes reported.

Each clinical batch of Compound 1, 20 mg/mL injection vials were tested against the approved specifications. Table 38 presents the testing data from the supportive stability studies. Table 39 provides the analytical results of Compound 1 Injection CTM batches for use in clinical studies that ranged up to 4 liters.

TABLE 38

Analytical Results of Compound 1 Injection Batches

| Analytical Procedure | Results Batch 817-1 | Results Batch 707 |
|---|---|---|
| Appearance | Clear solution | Clear solution |
| Identification | Conforms | Conforms |
| Assay | 100.2% | 98.8% |
| Related Substances, Total | 0.37% | 2.37%[1] |
| pH | 7.3 | 7.1 |
| Osmolality | 279 mOsm | 296 mOsm |
| Sterility | Not tested | Sterile |
| Particulate Matter | Not tested | |
| ≥10 μM | | 602 particles |
| ≥25 μM | | 17 particles |

[1]The amount of total impurities is higher in the drug substance for the drug substance lot used. The amount of Compound 1A was 0.17%.

TABLE 39

Analytical Results of Compound 1 Injection CTM Batches

| Analytical Procedure | Results: Lot # 792 08 Jun. 2016 | Lot # 792 18 Aug. 2016 | Lot # 792 21 Nov. 2016 | Lot # 792 28 Sep. 2016 | Lot # 792 10 Feb. 2017 | Lot # 792 13 Jul. 2016 | Lot # 792 21 Dec. 2016 | Lot # 792 05 Apr. 2016 | Lot # 792 18 Jul. 2017 | Lot # 792 24 Aug. 2017 |
|---|---|---|---|---|---|---|---|---|---|---|
| Appearance | Clear solution | Clear solution | Clear solution | Clear solution | Clear solution | Clear solution | Clear solution | Clear solution | Clear solution | Clear solution |
| Identification | 1.00 | 1.00 | 1.00 | 1.00 | 1.00 | 1.00 | 1.00 | 1.00 | 1.00 | 0.96 |
| Assay | 99.4% | 98.4% | 99.1% | 99.4% | 98.7% | 98.5% | 103.4% | 102.0% | 99.3% | 98.9% |
| Related Substances | 0.09% | 0.10% | 0.11% | 0.11% | 0.09% | 0.12% | 0.09% | 0.10% | 0.14% | 0.14% |

TABLE 39-continued

| Analytical Results of Compound 1 Injection CTM Batches | | | | | | | | | | |
|---|---|---|---|---|---|---|---|---|---|---|
| | Results | | | | | | | | | |
| Analytical Procedure | Lot # 792 08 Jun. 2016 | Lot # 792 18 Aug. 2016 | Lot # 792 21 Nov. 2016 | Lot # 792 28 Sep. 2016 | Lot # 792 10 Feb. 2017 | Lot # 792 13 Jul. 2016 | Lot # 792 21 Dec. 2016 | Lot # 792 05 Apr. 2016 | Lot # 792 18 Jul. 2017 | Lot # 792 24 Aug. 2017 |
| Compound 1A | | | | | | | | | | |
| RRT - 0.39 | Not detected | Not detected | Not detected | Not detected | Not detected | Not detected | Not detected | Not detected | 0.16% | 0.16% |
| RRT - 0.50 | Not detected | Not detected | Not detected | Not detected | Not detected | Not detected | Not detected | Not detected | 0.08% | 0.08% |
| RRT - 0.63 | Not detected | Not detected | Not detected | Not detected | Not detected | Not detected | Not detected | Not detected | 0.10% | 0.12% |
| RRT - 1.33 | Not detected | Not detected | Not detected | Not detected | Not detected | Not detected | Not detected | Not detected | 0.05% | Not detected |
| RRT - 1.48 | 0.07% | 0.07% | 0.07% | 0.08% | 0.07% | 0.07% | 0.06% | 0.06% | Not detected | Not detected |
| RRT - 1.67 | Not detected | Not detected | Not detected | Not detected | Not detected | Not detected | Not detected | Not detected | 0.06% | 0.06% |
| RRT - 1.89 | Not detected | Not detected | 0.05% | Not detected | Not detected | Not detected | Not detected | Not detected | Not detected | Not detected |
| RRT - 1.94 | Not detected | Not detected | Not detected | Not detected | Not detected | Not detected | Not detected | Not detected | 0.06% | 0.05% |
| RRT - 2.03 | 0.22% | 0.22% | 0.23% | 0.23% | 0.23% | 0.23% | 0.24% | 0.24% | 0.16% | 0.15% |
| RRT - 2.49 | Not detected | Not detected | Not detected | Not detected | Not detected | Not detected | Not detected | Not detected | 0.08% | Not detected |
| Total | 0.39% | 0.39% | 0.47% | 0.41% | 0.39% | 0.41% | 0.38% | 0.39% | 0.89% | 0.76% |
| pH | 7.3 | 7.2 | 7.3 | 7.2 | 7.4 | 7.3 | 7.3 | 7.2 | 7.7 | 7.8 |
| Osmolality | 261 mOsm/kg | 264 mOsm/kg | 260 mOsm/kg | 262 mOsm/kg | 265 mOsm/kg | 264 mOsm/kg | 263 mOsm/kg | 264 mOsm/kg | 262 mOsm/kg | 266 mOsm/kg |
| Endotoxin | <3.50 EU/mL | <3.50 EU/mL | <3.50 EU/mL | <3.50 EU/mL | <3.50 EU/mL | <3.50 EU/mL | 4.38 EU/mL | <3.50 EU/mL | <3.50 EU/mL | <7.00 EU/mL |
| Particulate Matter ≥10 µM | 894 particles | 690 particles | 644 particles | 894 particles | 2889 particles | 3558 particles | 3639 particles | 1200 particles | 4960 particles | 2508 particles |
| ≥25 µM | 42 particles | 66 particles | 0 particles | 132 particles | 189 particles | 346 particles | 111 particles | 60 particles | 12 particles | 12 particles |

Table 40 shows the admixture compatibility study for up to 48 hours when stored at 20° C. and 5° C. at concentrations of 0.04 mg/mL and 4.0 mg/mL. Table 40 shows that the admixed solutions are stable for up to 48 hours at 0.04 mg/mL and 4 mg/mL. Impurities were not reported for this study as the 0.04 mg/mL is 10-fold below the nominal concentration of the analytical method and the 72-hour stability data at 20 mg/mL shows that Compound 1 shows degradation of <0.10%.

Table 40 shows the 12-month stability results of Compound 1 Injection Development Batch 717-1 when stored at −20° C., 5° C. and 1-month stability results when stored at 25° C./60% RH. As expected, the main change noted in the stability data is some increase in Compound 1A, the main known degradant of Compound 1, which is also the active component of the Compound 1 prodrug. The drug substance batch used to manufacture Compound 1 Injection Batch 717-1 contained very few impurities, and there was virtually no chemical change either in known impurities or new related substance degradants, measured under any of the three storage conditions.

Table 42 shows the 12-month stability results of Compound 1 Injection Engineering Batch when stored at 5° C. and at 25° C./60% RH. The GMP engineering batch 707 was manufactured using drug substance Lot 171A, which contained more impurities as indicated by the initial timepoint related substance data. In this study the expected increase in Compound 1 A is observed but increases in some related substance impurities indicate potential temperature dependent degradants at RRT ~0.40, RRT ~0.50 and RRT ~0.65. Some changes were noted in other impurities at RRT ~1.30 and RRT ~1.45, however these did not show a consistent trend over timepoints and may reflect variability between timepoints.

TABLE 40

| Compound 1 Injection Admixture Stability Data | | | | | | | |
|---|---|---|---|---|---|---|---|
| | | Assay | | Osmolality | Particulate Matter | | |
| Condition/Timepoints | Appearance | (% LC) | Endotoxin | (mOsm/kg) | ≥10 µm | ≥25 µm | pH |
| 20° C. | | | | | | | |
| Initial at 0.04 mg/mL | Clear colorless solution | 101.1% | <0.500 EU/mL | 289 | 18 | 1 | 7.4 |
| Initial at 4 mg/mL | Clear slightly solution | 98.0% | <0.500 EU/mL | 291 | 16 | 1 | 7.2 |
| 0.04 mg/mL at 6 Hours | Clear colorless solution | 97.7% | Not tested | 288 | 1 | 0 | 8.0 |

TABLE 40-continued

| Compound 1 Injection Admixture Stability Data | | | | | | | |
|---|---|---|---|---|---|---|---|
| Condition/Timepoints | Appearance | Assay (% LC) | Endotoxin | Osmolality (mOsm/kg) | Particulate Matter ≥10 µm | Particulate Matter ≥25 µm | pH |
| 0.04 mg/mL at 24 Hours | Clear colorless solution | 99.6% | Not tested | 291 | 7 | 0 | 7.7 |
| 0.04 mg/mL at 48 Hours | Clear colorless solution | 98.8% | Not tested | 287 | 1 | 0 | 7.6 |
| 4 mg/mL at 6 Hours | Clear slightly solution | 99.3% | Not tested | 289 | 7 | 1 | 7.2 |
| 4 mg/mL at 24 Hours | Clear slightly solution | 97.9% | Not tested | 288 | 15 | 1 | 7.1 |
| 4 mg/mL at 48 Hours | Clear slightly solution | 99.2% | Not tested | 288 | 9 | 0 | 7.2 |
| 5° C. | | | | | | | |
| 0.04 mg/mL at 24 Hours | Clear solution | 97.8% | Not tested | 290 | 2 | 1 | 7.3 |
| 0.04 mg/mL at 48 Hours | Clear solution | 99.3% | Not tested | 289 | 1 | 0 | 7.4 |
| 4 mg/mL at 24 Hours | Clear solution | 98.8% | Not tested | 288 | 15 | 0 | 7.3 |
| 4 mg/mL at 48 Hours | Clear solution | 101.5% | Not tested | 290 | 12 | 1 | 7.2 |

TABLE 41

Stability Data for Compound 1 Vials 20 mg/mL, Lot 381, 2° C./60% RH Upright, 10 mL pH 7.5

| Test | | 0 Mo | 1 Mo |
|---|---|---|---|
| Appearance | | Conforms | Conforms |
| pH | | 7.3 | 6.8 |
| Assay (%) | | 100.2 | 97.1 |
| Related Substances (%) | | | |
| Compound 1A (%) | | 0.13 | 2.15 |
| Individual Unknown Impurity (%) | ~RRT 1.46 | ND | 0.14 |
| | ~RRT 2.00 | 0.24 | 0.22 |
| Total Related Substances (%) | | 0.37 | 2.51 |
| Sterility | | NS | NS |
| Particulate Matter | ≥10 µm | NS | NS |
| | ≥25 µm | NS | NS |

RRT = relative retention time, NS = not scheduled, ND = not detected or <0.05%

TABLE 42

Stability Data for Compound 1Vials 20 mg/mL, Lot 381, 5° C. RH Upright, 10 mL pH 7.5

| Test | | 0 Mo | 1 Mo | 2 Mo | 3 Mo | 6 Mo | 9 Mo | 12 Mo |
|---|---|---|---|---|---|---|---|---|
| Appearance | | Conforms | Conforms | Conforms | Conforms | Conforms | Conforms | Conforms |
| pH | | 7.3 | 7.4 | 7.4 | 7.3 | 7.2 | 7.2 | 7.1 |
| Assay (%) | | 100.2 | 99.9 | 100.9 | 100.4 | 99.5 | 99.9 | 100.2 |
| Related Substances (%) | | | | | | | | |
| Compound 1A (%) | | 0.13 | 0.13 | 0.18 | 0.22 | 0.34 | 0.48 | 0.61 |
| Individual Unknown Impurity (%) | ~RRT 1.46 | ND | ND | ND | ND | ND | ND | 0.11 |
| | ~RRT 2.00 | 0.24 | 0.23 | 0.24 | 0.24 | 0.24 | 0.24 | 0.25 |
| Total Related Substances (%) | | 0.37 | 0.36 | 0.42 | 0.46 | 0.58 | 0.72 | 0.97 |
| Sterility | | NS | NS | NS | NS | NS | NS | NS |
| Particulate Matter | ≥10 µm | NS | NS | NS | NS | NS | NS | NS |
| | ≥25 µm | NS | NS | NS | NS | NS | NS | NS |

RRT = relative retention time,
NS = not scheduled,
ND = not detected or <0.05%

TABLE 43

Stability Data for Compound 1Vials 20 mg/mL, Lot 381, −20° C. RH Upright, 10 mL pH 7.5

| Test | 0 Mo | 1 Mo | 2 Mo | 3 Mo | 6 Mo | 9 Mo | 12 Mo |
|---|---|---|---|---|---|---|---|
| Appearance | Conforms | Conforms | Conforms | Conforms | Conforms | Conforms | Conforms |
| pH | 7.3 | 7.5 | 7.5 | 7.4 | 7.5 | 7.4 | 7.4 |
| Assay (%) | 100.2 | 99.3 | 101.7 | 100.1 | 99.7 | 99.9 | 100.8 |

TABLE 43-continued

Stability Data for Compound 1Vials 20 mg/mL, Lot 381, −20° C. RH Upright, 10 mL pH 7.5

| Test | | 0 Mo | 1 Mo | 2 Mo | 3 Mo | 6 Mo | 9 Mo | 12 Mo |
|---|---|---|---|---|---|---|---|---|
| Related Substances (%) | | | | | | | | |
| Compound 1A (%) | | 0.13 | 0.10 | 0.10 | 0.11 | 0.11 | 0.12 | 0.14 |
| Individual Unknown Impurity (%) | ~RRT 2.00 | 0.24 | 0.23 | 0.24 | 0.24 | 0.24 | 0.24 | 0.26 |
| Total Related Substances (%) | | 0.37 | 0.33 | 0.34 | 0.35 | 0.35 | 0.36 | 0.40 |
| Sterility | | NS | NS | NS | NS | NS | NS | NS |
| Particulate Matter | ≥10 μm | NS | NS | NS | NS | NS | NS | NS |
| | ≥25 μm | NS | NS | NS | NS | NS | NS | NS |

RRT = relative retention time, NS = not scheduled, ND = not detected or <0.05%

TABLE 44

Stability Data for Compound 1Vials 20 mg/mL, Lot 707, 25° C./60% RH Upright, 10 mL pH

| Test | | 0 Mo | 1 Mo | 3 Mo | 6 Mo |
|---|---|---|---|---|---|
| Appearance | | Conforms | DNC | DNC | DNC |
| pH | | 7.1 | 6.7 | 6.5 | 6.3 |
| Assay (%) | | 98.8 | 95.1 | 91.4 | 86.0 |
| Related Substances (%) | | | | | |
| Compound 1A (%) | | 0.17 | 1.85 | 4.28 | 5.69 |
| Individual Unknown | ~RRT 0.38 | 0.43 | 0.63 | 0.68 | 0.78 |
| Impurity (%) | ~RRT 0.45 | 0.41 | ND | ND | ND |
| | ~RRT 0.61 | 0.56 | 1.00 | 0.99 | 0.99 |
| | ~RRT 1.30 | 0.11 | 0.18 | 0.19 | 0.19 |
| | ~RRT 1.45 | ND | 0.18 | 0.34 | 0.57 |
| | ~RRT 1.75 | ND | ND | 0.39 | 1.36 |
| | ~RRT 2.00 | 0.69 | 0.69 | 0.64 | 0.58 |
| Total Related Substances (%) | | 2.37 | 4.53 | 7.51 | 10.16 |
| Sterility | | NS | NS | NS | NS |
| Particulate Matter | ≥10 μm | 602 | 2500 | 1286 | NS |
| | ≥25 μm | 17 | 149 | 74 | NS |

RRT = relative retention time, NS = not scheduled, ND = not detected or <0.05%, DNC = does not conform

TABLE 45

Stability Data for Compound 1Vials 20 mg/mL, Lot 707, 5° C. RH Upright, 10 mL pH 7.5

| Test | | 0 Mo | 3 Mo | 6 Mo | 9 Mo | 12 Mo |
|---|---|---|---|---|---|---|
| Appearance | | Conforms | Conforms | Conforms | Conforms | Conforms |
| pH | | 7.1 | 6.9 | 6.9 | 6.9 | 6.9 |
| Assay (%) | | 98.8 | 97.4 | 97.7 | 97.1 | 97.4 |
| Related Substances (%) | | | | | | |
| Compound 1A (%) | | 0.17 | 0.34 | 0.40 | 0.48 | 0.66 |
| Individual Unknown Impurity (%) | ~RRT 0.38 | 0.43 | 0.51 | 0.56 | 0.58 | 0.59 |
| | ~RRT 0.47 | 0.41 | 0.26 | ND | 0.06 | ND |
| | ~RRT 0.61 | 0.56 | 0.92 | 1.14 | 1.23 | 1.30 |
| | ~RRT 1.30 | 0.11 | 0.15 | 0.17 | 0.18 | 0.20 |
| | ~RRT 1.45 | ND | 0.13 | 0.17 | 0.12 | 0.23 |
| | ~RRT 2.00 | ND | 0.71 | 0.72 | 0.71 | 0.71 |
| | ~RRT 2.48 | ND | ND | ND | ND | 0.07 |
| Total Related Substances (%) | | 2.37 | 3.02 | 3.16 | 3.36 | 3.70 |
| Sterility | | NS | NS | NS | NS | NS |
| Particulate Matter | ≥10 μm | 602 | 895 | 1515 | 1445 | 1239 |
| | ≥25 μm | 17 | 40 | 67 | 45 | 66 |

RRT = relative retention time, NS = not scheduled, ND = not detected or <0.05%

Compound 1 Injection, Phase 2 Formulation

Compound 1 Injection, 20 mg/mL, was prepared as a phosphate-buffered solution suitable for Phase 2 clinical studies containing Compound 1, sodium chloride, potassium phosphate (monobasic and dibasic), and pH adjustment using hydrochloric acid and/or sodium hydroxide to pH 7.5 and 8.0. The Phase 2 formulation has been placed at a long-term storage, −20° C., for up to 24 months and accelerated storage, 5° C., for up to 12 months per ICH guidelines (Table 48 and 49). The tests being performed are appearance, HPLC assay and related substances, pH, and particulate matter at all time points and sterility at 12 and 24-month timepoints for the clinical trial material. The test and specifications for the shelf-life are shown in Table 47. All Compound 1 Injection, 20 mg/mL, batches to be used in the Phase 2 clinical studies will be placed on an ICH stability study.

Each clinical batch of Compound 1, 20 mg/mL injection vials will be tested against the approved specifications prior to use in clinical studies and placed on an ICH stability program. Table 46 presents the testing data from the supportive stability studies.

TABLE 46

| Analytical Results of Compound 1 Injection Batches | | | | |
|---|---|---|---|---|
| | Results | | | |
| Analytical Procedure | Lot# 107 (pH 7.5 buffered with 50 mM Phosphate) | Lot# 108[1] (pH 8.0 buffered with 20 mM Phosphate) | Lot# 592 | Lot# 217 |
| Quality | Development | Development | GMP | GMP |
| Appearance | Clear solution | Clear solution | Conforms, solution | Conforms, solution |
| Identification | 1.00 | 1.00 | Conforms | Conforms |
| Assay | 99.2% | 99.5% | 101.4% | 101.0% |
| Related Substances | | | | |
| Compound 1A | 0.13% | 0.12% | 0.15% | 0.17% |
| Largest Unknown | 0.71% | 0.72% | RRT 0.42-0.10% | RRT 0.38-0.12% |
| | | | RRT 0.50-0.06% | RRT 0.46-0.06% |
| | | | RRT 0.63-0.22% | RRT 0.61-0.18% |
| | | | RRT 1.46-0.23% | RRT 1.45-0.23% |
| | | | RRT 2.01-0.23% | RRT 1.98-0.27% |
| Total | 2.19% | 2.20% | 0.99% | 0.95% |
| pH | 7.4 | 7.8 | 8.2 | 8.2 |
| Osmolality | 283 mOsm/kg | 288 mOsm/kg | 290 mOsm/kg | 284 mOsm/kg |
| Fill Volume | Not tested | Not tested | 36.8 mL | 36.9 mL |
| Sterility | Not tested | Not tested | Conforms | Conforms |
| Bacterial Endotoxins | Not tested | Not tested | <1.0 EU/mL | <1.0 EU/mL |
| Particulate Matter | | | | |
| ≥10 μm | 165 particles | 188 particles | 68 particles | 525 particles |
| ≥25 μm | 7 particles | 2 particles | 0 particles | 7 particles |

[1]This formulation will be used in the Phase 2 clinical studies.

No additional degradants are expected to be present in the Compound 1 Injection other than Compound 1A (degradation from Compound 1 to Compound 1A, loss of phosphate moiety).

TABLE 47

| Current Compound 1 Injection Stability Specification for Clinical Trial Material | | |
|---|---|---|
| Test | Method | Acceptance Criteria |
| Appearance | Visual | Clear solution |
| pH | USP <791> | 7.0 to 8.5 |
| Assay | HPLC | 90.0 to 110.0% of label claim (20 mg/mL) |
| Related Substances Impurities | | |
| Compound 1A | HPLC | NMT 1.5% |
| Each Individual Impurity by RRT | HPLC | NMT 0.5% |
| Total | HPLC | NMT 4.0% |
| Sterility | USP <71> | Sterile |
| Particulate Matter | USP <788> | ≥10 μm: NMT 6000 particles/container<br>≥25 μm: NMT 600 particles/container |

NMT = no more than

The current stability specification for Compound 1 Injection has limits on related substances and impurities which are slightly broader than the specification for batch release. For future clinical batches the release specification and stability specification will be aligned in terms of related substances and impurities. The Specification for future batches of Compound 1 Injection will include related substance categories including (1) specified known impurities/degradants, (2) specified, unknown impurities/degradants and (3) unspecified unknown impurity/degradants. The limits for the specified known and unknown categories will be set based on stage of development, manufacturing experience, and impurity qualification. The limit for unspecified, unknown impurities/degradants will be set at the identification threshold of 0.2%. Appropriate efforts to identify, qualify, and control impurities and degradants in the Compound 1 Injection, according to ICHQ3A, will continue throughout development.

The stability studies to date show that Compound 1 Injection is very stable when stored at −20° C., the long-term storage condition. The main related substance changes are the expected increase in Compound 1A the active component of the Compound 1 prodrug. In some batches, impurities RRT ~0.40, RRT ~0.50, and most notably RRT ~0.65, slightly increase, primarily under accelerated conditions. It was noted in the studies for one batch in the Phase 1 Formulation and several batches in Phase 2 Formulation, that increases to the related substances at RRT ~0.40, RRT ~0.50 and RRT ~0.65, seemed to be greater when these impurities were present at higher levels in initial timepoint data (reflecting their presence in the original drug substance). The impurities are not increasing significantly in the GMP batches and stored at −20° C. for 12 months and 9 months, respectively. These degradants have been qualified in non-clinical studies and they will continue to be monitored and identified during development as appropriate.

Table 50 summarizes admixture compatibility studies for up to 48 hours when stored at 15° C. to 25° C. and 2° C. to 8° C. at concentrations of 1 mg/mL, 4 mg/mL, 10 mg/mL, 16 mg/mL and 20 mg/mL. Table 50 shows that the admixed solutions are stable for up to 48 hours at all concentrations tested. Individual impurities were not reported in the dossier for the admixture studies for all evaluated concentrations, since the change in total impurity was less than 0.16%, and individual impurities did not change by more than 0.07%, over the time period stored and tested.

The stability data for development batches 107 and 108 stored at −20° C. and 5° C. for 12 months and 25° C. for 1 month are shown in Tables 51-58. These batches were prepared using a development drug substance batch with higher levels of impurities as indicated by the initial timepoint related substance data. Although prepared under GMP, drug substance Lot 171A had higher levels of impurities and was not released for use in clinical studies but was used for Compound 1 Injection development studies. In these studies, the expected increase in Compound 1A is observed, but increases in some related substance impurities suggest potential temperature dependent degradants at approximate RRT ~0.40, RRT ~0.50 and RRT ~0.65. Some changes were also noted in other impurities at RRT ~1.30 and RRT ~1.45; however, these did not show a consistent trend over timepoints and may reflect variability between timepoints rather than degradation.

Results for the 12-month ongoing stability study of GMP Lot 592 are provided in Table 57 and Table 58, and the 9-month ongoing stability results of GMP Lot 217 in Table 59 and Table 60, when stored at −20° C. and 5° C. Both batches remain within specification at 12 and 9 months respectively, for both storage conditions. The main change is the expected increase in Compound 1A under the 5° C. storage conditions, with 0.43% increase at 12 months (592) and 0.32% increase at 9 months (217), and virtually no change in either study at −20° C. There is an increase of 0.09% and 0.09% noted in the RRT ~0.65 impurity (a main degradant seen previously) at 12 and 9 months respectively at only the 5° C. condition. There were no obvious trends in other related substance impurities at either condition. No significant changes in other stability parameters were noted at −20° C. and 5° C. for the timepoints tested. Based upon ICH Q1E, the ongoing stability data for the GMP Phase 2 clinical batches, and the supporting stability from development batches and Phase 1 Formulation studies, Compound 1 Injection has a re-test date of 24 months when stored at −20° C. The re-test date/shelf life for current GMP Phase 2 Compound 1 Injection will be updated based on additional stability data from ongoing, concurrent ICH stability studies of clinical batches as described in Table 49, and according to the Specification in Table 47.

TABLE 48

Stability Plan for Long-term Storage for Development Batches

| Temperature | Initial | 1 Month | 2 Month | 3 Month | 6 Month | 9 Month | 12 Month | 18 Month | 24 Month |
|---|---|---|---|---|---|---|---|---|---|
| −20° C. | X | X | X | X | X | X | X | X | X |
| 5° C. | X | X | X | X | X | X | X | | |
| 25° C. | X | X | | | | | | | |

Samples are subjected to appearance, assay/related substances, particulate matter and pH analysis.

TABLE 49

Stability Plan for Long-term Storage for the Clinical Trial Material Batches

| Temperature | Initial | 1 Month | 2 Month | 3 Month | 6 Month | 9 Month | 12 Month | 18 Month | 24 Month | 36 Month |
|---|---|---|---|---|---|---|---|---|---|---|
| −20° C. | X | X | X | X | X | X | X | X | X | X |
| 5° C. | X | X | X | X | X | X | X | | | |

Samples are subjected to appearance, assay/related substances, particulate matter and pH analysis. Sterility is tested for the stability samples at 12, 24 and 36 months.

TABLE 50

Compound 1 Injection Admixture Stability Data - High Concentration

| Condition/Timepoints | Appearance | Assay (% LC) | Endotoxin | Osmolality (mOsm/kg) | Particulate Matter ≥10 μm | Particulate Matter ≥25 μm | pH |
|---|---|---|---|---|---|---|---|
| 15 to 25° C. | | | | | | | |
| Initial at 1 mg/mL | Clear solution | 97.8 | <1.00 EU/mL | 300 | 6 | 0 | 7.5 |
| Initial at 4 mg/mL | Clear solution | 100.0 | <1.00 EU/mL | 298 | 15 | 1 | 7.7 |
| Initial at 10 mg/mL | Clear solution | 99.8 | <1.00 EU/mL | 311 | 22 | 3 | 7.8 |
| Initial at 16 mg/mL | Clear solution | 97.1 | <0.250 EU/mL | 307 | 10 | 1.7 | 8.0 |
| Initial at 20 mg/mL | Clear solution | 96.7 | <0.250 EU/mL | 310 | 3.7 | 1.7 | 8.0 |
| 1 mg/mL at 5 Hours | Clear solution | 98.4 | Not tested | Not tested | Not tested | Not tested | 7.7 |
| 1 mg/mL at 24 Hours | Clear solution | 98.6 | Not tested | Not tested | Not tested | Not tested | 7.7 |
| 1 mg/mL at 48 Hours | Clear solution | 100.6 | Not tested | Not tested | Not tested | Not tested | 7.7 |
| 4 mg/mL at 5 Hours | Clear solution | 100.0 | Not tested | Not tested | Not tested | Not tested | 7.9 |
| 4 mg/mL at 24 Hours | Clear solution | 98.8 | Not tested | Not tested | Not tested | Not tested | 7.8 |
| 4 mg/mL at 48 Hours | Clear solution | 101.3 | Not tested | Not tested | Not tested | Not tested | 7.8 |

TABLE 50-continued

| Compound 1 Injection Admixture Stability Data - High Concentration | | | | | | | |
|---|---|---|---|---|---|---|---|
| | | Assay | | Osmolality | Particulate Matter | | |
| Condition/Timepoints | Appearance | (% LC) | Endotoxin | (mOsm/kg) | ≥10 μm | ≥25 μm | pH |
| 10 mg/mL at 5 Hours | Clear solution | 100.2 | Not tested | Not tested | Not tested | Not tested | 7.9 |
| 10 mg/mL at 24 Hours | Clear solution | 96.7 | Not tested | Not tested | Not tested | Not tested | 7.9 |
| 10 mg/mL at 48 Hours | Clear solution | 98.2 | Not tested | Not tested | Not tested | Not tested | 7.9 |
| 16 mg/mL at 6 Hours | Clear solution | 98.6 | Not tested | Not tested | Not tested | Not tested | 8.0 |
| 16 mg/mL at 24 Hours | Clear solution | 97.5 | Not tested | Not tested | Not tested | Not tested | 8.0 |
| 16 mg/mL at 48 Hours | Clear solution | 97.7 | Not tested | Not tested | Not tested | Not tested | 8.0 |
| 20 mg/mL at 6 Hours | Clear solution | 98.5 | Not tested | Not tested | Not tested | Not tested | 8.0 |
| 20 mg/mL at 24 Hours | Clear solution | 96.9 | Not tested | Not tested | Not tested | Not tested | 8.0 |
| 20 mg/mL at 48 Hours | Clear solution | 96.6 | Not tested | Not tested | Not tested | Not tested | 8.0 |
| 2 to 8° C. | | | | | | | |
| 1 mg/mL at 24 Hours | Clear solution | 99.7 | Not tested | Not tested | Not tested | Not tested | 7.7 |
| 1 mg/mL at 48 Hours | Clear solution | 98.8 | Not tested | Not tested | Not tested | Not tested | 7.7 |
| 4 mg/mL at 24 Hours | Clear solution | 103.0 | Not tested | Not tested | Not tested | Not tested | 7.9 |
| 4 mg/mL at 48 Hours | Clear solution | 103.2 | Not tested | Not tested | Not tested | Not tested | 7.9 |
| 10 mg/mL at 24 Hours | Clear solution | 100.4 | Not tested | Not tested | Not tested | Not tested | 7.9 |
| 10 mg/mL at 48 Hours | Clear solution | 100.7 | Not tested | Not tested | Not tested | Not tested | 7.9 |
| 16 mg/mL at 24 Hours | Clear solution | 97.6 | Not tested | Not tested | Not tested | Not tested | 8.0 |
| 16 mg/mL at 48 Hours | Clear solution | 96.3 | Not tested | Not tested | Not tested | Not tested | 8.0 |
| 20 mg/mL at 24 Hours | Clear solution | 96.6 | Not tested | Not tested | Not tested | Not tested | 8.0 |
| 20 mg/mL at 48 Hours | Clear solution | 96.1 | Not tested | Not tested | Not tested | Not tested | 8.0 |

NOTE: Study 1 for the admixture study included only the 16 mg/mL and 20 mg/mL concentrations. An additional admixture study, Study 2, was conducted to analyze a wider range of pontetial concentrations at 1 mg/mL, 4 mg/mL and 10 mg/mL.

TABLE 51

| Stability Data for Compound 1 Vials 20 mg/mL, Lot 107, 25° C./60% RH Upright, 10 mL pH 7.5 | | | |
|---|---|---|---|
| Test | | 0 Mo | 1 Mo |
| Appearance | | Conforms | Conforms |
| pH | | 7.4 | 7.4 |
| Assay (%) | | 99.2 | 97.0 |
| Related Substances (%) | | | |
| Compound 1A (%) | | 0.13 | 2.22 |
| Individual Unknown Impurity (%) | ~RRT 0.38 | 0.38 | 0.61 |
| | ~RRT 0.50 | 0.22 | ND |
| | ~RRT 0.62 | 0.36 | 0.98 |
| | ~RRT 1.30 | 0.26 | 0.19 |
| | ~RRT 1.45 | 0.12 | 0.25 |
| | ~RRT 2.05 | 0.71 | 0.69 |
| | ~RRT 2.35 | 0.12 | 0.15 |
| Total Related Substances (%) | | 2.19 | 5.09 |
| Sterility | | NS | NS |
| Particulate Matter | ≥10 μm | 165 | 3091 |
| | ≥25 μm | 7 | 156 |

RRT = relative retention time, NS = not scheduled, ND = not detected or <0.05%

TABLE 52

| Stability Data for Compound 1 Vials 20 mg/mL, Lot 107, 5° C. RH Upright, 10 mL pH 7.5 | | | | | | | |
|---|---|---|---|---|---|---|---|
| Test | | 0 Mo | 1 Mo | 3 Mo | 6 Mo | 9 Mo | 12 Mo |
| Appearance | | Conforms | Conforms | Conforms | Conforms | Conforms | Conforms |
| pH | | 7.4 | 7.4 | 7.5 | 7.4 | 7.4 | 7.7 |
| Assay (%) | | 99.2 | 98.7 | 99.4 | 99.5 | 98.9 | 97.2 |
| Related Substances (%) | | | | | | | |
| Compound 1A (%) | | 0.13 | 0.27 | 0.27 | 0.36 | 0.52 | 0.61 |
| Individual Unknown Impurity (%) | ~RRT 0.38 | 0.27 | 0.42 | 0.49 | 0.54 | 0.57 | 0.57 |
| | ~RRT 0.50 | 0.22 | 0.42 | 0.20 | 0.12 | 0.07 | ND |
| | ~RRT 0.62 | 0.36 | 0.64 | 0.92 | 1.17 | 1.30 | 1.40 |
| | ~RRT 1.30 | 0.26 | 0.12 | 0.15 | 0.17 | 0.21 | 0.19 |
| | ~RRT 1.45 | 0.12 | 0.15 | 0.16 | 0.05 | 0.21 | 0.12 |
| | ~RRT 1.52 | ND | ND | ND | ND | ND | 0.06 |

TABLE 52-continued

| Stability Data for Compound 1 Vials 20 mg/mL, Lot 107, 5° C. RH Upright, 10 mL pH 7.5 | | | | | | | |
|---|---|---|---|---|---|---|---|
| Test | | 0 Mo | 1 Mo | 3 Mo | 6 Mo | 9 Mo | 12 Mo |
| | ~RRT 2.05 | 0.71 | 0.71 | 0.72 | 0.71 | 0.70 | 0.69 |
| | ~RRT 2.35 | 0.12 | 0.15 | ND | ND | 0.06 | ND |
| Total Related Substances (%) | | 2.19 | 2.88 | 2.91 | 3.24 | 3.60 | 3.7 |
| Sterility | | NS | NS | NS | NS | NS | NS |
| Particulate Matter | ≥10 μm | 165 | 1201 | 1863 | 2184 | 1748 | 1994 |
| | ≥25 μm | 7 | 45 | 87 | 128 | 78 | 60 |

RRT = relative retention time,
NS = not scheduled,
ND = not detected or <0.05%

TABLE 53

| Stability Data for Compound 1A Vials 20 mg/mL, Lot 107, −20° C. RH Upright, 10 mL pH 7.5 | | | | |
|---|---|---|---|---|
| Test | | 0 Mo | 3 Mo | 12 Mo |
| Appearance | | Conforms | Conforms | Conforms |
| pH | | 7.4 | 7.5 | 7.4 |
| Assay (%) | | 99.2 | 100.5 | 99.2 |
| Related Substances (%) | | | | |
| Compound 1A (%) | | 0.13 | 0.16 | 0.17 |
| Individual Unknown Impurity (%) | ~RRT 0.38 | 0.27 | 0.38 | 0.36 |
| | ~RRT 0.50 | 0.22 | 0.35 | 0.47 |
| | ~RRT 0.62 | 0.36 | 0.46 | 0.48 |
| | ~RRT 1.32 | ND | ND | 0.05 |
| | ~RRT 1.40 | ND | ND | 0.09 |
| | ~RRT 1.45 | 0.12 | 0.16 | 0.12 |
| | ~RRT 1.55 | ND | ND | 0.06 |
| | ~RRT 2.00 | ND | ND | 0.05 |
| | ~RRT 2.05 | 0.71 | 0.72 | 0.70 |
| | ~RRT 2.35 | 0.12 | ND | ND |
| Total Related Substances (%) | | 2.19 | 2.23 | 2.6 |
| Sterility | | NS | NS | NS |
| Particulate Matter | ≥10 μm | 165 | 1311 | 959 |
| | ≥25 μm | 7 | 86 | 36 |

RRT = relative retention time, NS = not scheduled, ND = not detected or <0.05%

TABLE 54

| Stability Data for Compound 1 Vials 20 mg/mL, Lot 108, 25° C./60% RH, 10 mL pH 8.0 | | | |
|---|---|---|---|
| Test | | 0 Mo | 1 Mo |
| Appearance | | Conforms | Conforms |
| pH | | 7.8 | 7.6 |
| Assay (%) | | 99.5 | 96.0 |
| Related Substances (%) | | | |
| Compound 1A (%) | | 0.12 | 2.09 |
| Individual Unknown Impurity (%) | ~RRT 0.38 | 0.27 | 0.61 |
| | ~RRT 0.50 | 0.22 | ND |
| | ~RRT 0.62 | 0.36 | 0.98 |
| | ~RRT 1.32 | ND | 0.18 |
| | ~RRT 1.45 | 0.13 | 0.28 |
| | ~RRT 2.05 | 0.72 | 0.69 |
| | ~RRT 2.37 | 0.12 | 0.15 |
| Total Related Substances (%) | | 2.20 | 4.98 |
| Sterility | | NS | NS |
| Particulate Matter | ≥10 μm | 188 | 3250 |
| | ≥25 μm | 2 | 171 |

RRT = relative retention time, NS = not scheduled, ND = not detected or <0.05%

TABLE 55

| Stability Data for Compound 1 Vials 20 mg/mL, Lot 108, 5° C., 10 mL pH 8.0 | | | | | | | | |
|---|---|---|---|---|---|---|---|---|
| Test | | 0 Mo | 1 Mo | 2 Mo | 3 Mo | 6 Mo | 9 Mo | 12 Mo |
| Appearance | | Conforms | Conforms | Conforms | Conforms | Conforms | Conforms | Conforms |
| pH | | 7.8 | 7.8 | 7.8 | 7.8 | 7.8 | 7.8 | 7.4 |
| Assay (%) | | 99.2 | 98.2 | 98.7 | 98.9 | 99.3 | 98.1 | 97.2 |
| Related Substances (%) | | | | | | | | |
| Compound 1A (%) | | 0.12 | 0.27 | 0.30 | 0.27 | 0.35 | 0.5 | 0.59 |
| Individual Unknown Impurity (%) | ~RRT 0.38 | 0.27 | 0.43 | 0.48 | 0.50 | 0.56 | 0.58 | 0.58 |
| | ~RRT 0.50 | 0.22 | 0.37 | 0.24 | 0.19 | 0.11 | 0.06 | ND |
| | ~RRT 0.62 | 0.36 | 0.67 | 0.84 | 0.94 | 1.17 | 1.30 | 1.30 |
| | ~RRT 1.32 | ND | 0.12 | 0.14 | 0.15 | 0.17 | 0.20 | 0.18 |
| | ~RRT 1.40 | ND | ND | ND | ND | 0.05 | ND | ND |
| | ~RRT 1.45 | 0.13 | 0.15 | 0.13 | 0.17 | 0.12 | 0.22 | 0.14 |
| | ~RRT 1.52 | ND | ND | ND | ND | ND | ND | 0.06 |
| | ~RRT 2.05 | 0.72 | 0.7 | 0.70 | 0.71 | 0.71 | 0.70 | 0.69 |
| | ~RRT 2.37 | 0.12 | 0.15 | ND | ND | ND | 0.07 | ND |
| Total Related Substances (%) | | 2.20 | 2.87 | 2.83 | 2.93 | 3.24 | 3.60 | 3.60 |
| Sterility | | NS | NS | NS | NS | NS | NS | NS |
| Particulate Matter | ≥10 μm | 188 | 1264 | 1279 | 1839 | 2580 | 1711 | 2658 |
| | ≥25 μm | 2 | 76 | 63 | 101 | 214 | 93 | 110 |

RRT = relative retention time,
NS = not scheduled,
ND = not detected or <0.05%

TABLE 56

Stability Data for Compound 1 Vials 20 mg/mL, Lot 108, −20° C., 10 mL pH 8.0

| Test | | 0 Mo | 3 Mo | 12 Mo |
|---|---|---|---|---|
| Appearance | | Conforms | Conforms | Conforms |
| pH | | 7.8 | 7.8 | 7.7 |
| Assay (%) | | 99.5 | 98.6 | 98.7 |
| Related Substances (%) | | | | |
| Compound 1A (%) | | 0.12 | 0.16 | 0.16 |
| Individual Unknown | ~RRT 0.38 | 0.27 | 0.39 | 0.39 |
| Impurity (%) | ~RRT 0.50 | 0.22 | 0.34 | 0.42 |
| | ~RRT 0.62 | 0.36 | 0.50 | 0.63 |
| | ~RRT 1.32 | ND | 0.10 | 0.05 |
| | ~RRT 1.40 | ND | ND | 0.10 |
| | ~RRT 1.45 | 0.13 | 0.15 | 0.12 |
| | ~RRT 1.55 | ND | ND | 0.06 |
| | ~RRT 2.00 | ND | ND | 0.05 |
| | ~RRT 2.05 | 0.72 | 0.71 | 0.70 |
| | ~RRT 2.37 | 0.12 | ND | ND |
| Total Related Substances (%) | | 2.20 | 2.35 | 2.70 |
| Sterility | | NS | NS | NS |
| Particulate Matter | ≥10 µm | 188 | 1225 | 1513 |
| | ≥25 µm | 2 | 45 | 66 |

RRT = relative retention time, NS = not scheduled, ND = not detected or <0.05%

TABLE 57

Stability Data for Compound 1 Injection 20 mg/mL, GMP Lot 592, 5° C., 35 mL pH 8.0

| Test | | 0 Mo | 1 Mo | 3 Mo | 6 Mo | 9 Mo | 12 Mo | 18 Mo | 24 Mo |
|---|---|---|---|---|---|---|---|---|---|
| Appearance | | Conform | Conform | Conform | Conform | Conform | Conform | | |
| pH | | 8.2 | 8.2 | 8.1 | 8.1 | 8.0 | 8.1 | | |
| Assay (%) | | 100.4 | 101.7 | 100.5 | 100.1 | 99.6 | 99.8 | | |
| Related Substances (%) | | | | | | | | | |
| Compound 1A (%) | | 0.18 | 0.28 | 0.23 | 0.40 | 0.53 | 0.61 | | |
| Individual Unknown | ~RRT 0.40 | 0.11 | 0.13 | 0.12 | 0.14 | 0.14 | 0.15 | | |
| Impurity (%) | ~RRT 0.65 | 0.23 | 0.27 | 0.27 | 0.30 | 0.32 | 0.32 | | |
| | ~RRT 1.29 | 0.05 | 0.05 | ND | 0.06 | 0.05 | 0.05 | | |
| | ~RRT 1.46 | 0.24 | 0.24 | 0.29 | 0.28 | 0.30 | 0.30 | | |
| | ~RRT 2.10 | 0.24 | 0.23 | 0.22 | 0.22 | 0.22 | 0.22 | | |
| Total Related Substances (%) | | 1.05 | 1.2 | 1.1 | 1.4 | 1.6 | 1.7 | | |
| Sterility | | Conform | NS | NS | NS | NS | Conform | | |
| Particulate Matter | ≥10 µm | 68 | 23 | 51 | 229 | 826 | 280 | | |
| | ≥25 µm | 0 | 0 | 0 | 12 | 37 | 7 | | |

RRT = relative retention time,
NS = not scheduled,
ND = not detected or <0.05%

TABLE 58

Stability Data for Compound 1 Injection 20 mg/mL, GMP Lot 592, −20° C., 35 mL pH 8.0

| Test | | 0 Mo | 1 Mo | 3 Mo | 6 Mo | 9 Mo | 12 Mo | 18 Mo | 24 Mo |
|---|---|---|---|---|---|---|---|---|---|
| Appearance | | Conforms | Conforms | Conforms | Conforms | Conforms | Conforms | | |
| pH | | 8.2 | 8.2 | 8.2 | 8.2 | 8.1 | 8.2 | | |
| Assay (%) | | 100.4 | 100.9 | 100.4 | 100.4 | 100.2 | 100.3 | | |
| Related Substances (%) | | | | | | | | | |
| Compound 1A (%) | | 0.18 | 0.24 | 0.22 | 0.19 | 0.22 | 0.18 | | |
| Individual Unknown | ~RRT 0.40 | 0.11 | 0.12 | 0.11 | 0.11 | 0.11 | 0.11 | | |
| Impurity (%) | ~RRT 0.65 | 0.23 | 0.25 | 0.23 | 0.24 | 0.25 | 0.24 | | |
| | ~RRT 1.29 | 0.05 | 0.05 | ND | 0.05 | 0.05 | ND | | |
| | ~RRT 1.46 | 0.24 | 0.23 | 0.19 | 0.24 | 0.25 | 0.22 | | |
| | ~RRT 2.10 | 0.24 | 0.22 | 0.21 | 0.22 | 0.23 | 0.23 | | |

TABLE 58-continued

| Stability Data for Compound 1 Injection 20 mg/mL, GMP Lot 592, −20° C., 35 mL pH 8.0 | | | | | | | | | |
|---|---|---|---|---|---|---|---|---|---|
| Test | | 0 Mo | 1 Mo | 3 Mo | 6 Mo | 9 Mo | 12 Mo | 18 Mo | 24 Mo |
| Total Related Substances (%) | | 1.05 | 1.1 | 0.96 | 1.1 | 1.1 | 1.0 | | |
| Sterility | | Conforms | NS | NS | NS | NS | Conforms | | |
| Particulate Matter | ≥10 μm | 68 | 56 | 19 | 12 | 14 | 7 | | |
| | ≥25 μm | 0 | 0 | 0 | 0 | 0 | 0 | | |

RRT = relative retention time,
NS = not scheduled,
ND = not detected or <0.05%

TABLE 59

| Stability Data for Compound 1 Injection 20 mg/mL, GMP Lot 217, 5° C., 35 mL pH 8.0 | | | | | | | | | |
|---|---|---|---|---|---|---|---|---|---|
| Test | | 0 Mo | 1 Mo | 3 Mo | 6 Mo | 9 Mo | 12 Mo | 18 Mo | 24 Mo |
| Appearance | | Conform | Conform | Conform | Conform | Conform | | | |
| pH | | 8.2 | 8.1 | 8.1 | 8.1 | 8.1 | | | |
| Assay (%) | | 98.9 | 100.3 | 100.4 | 99.2 | 99.4 | | | |
| Related Substances (%) | | | | | | | | | |
| Compound 1A (%) | | 0.18 | 0.21 | 0.30 | 0.39 | 0.50 | | | |
| Individual Unknown | ~RRT 0.38 | 0.13 | 0.14 | 0.15 | 0.16 | 0.18 | | | |
| Impurity (%) | ~RRT 0.51 | 0.06 | 0.06 | ND | ND | ND | | | |
| | ~RRT 0.65 | 0.21 | 0.21 | 0.26 | 0.30 | 0.32 | | | |
| | ~RRT 1.36 | 0.05 | 0.06 | 0.07 | 0.05 | 0.07 | | | |
| | ~RRT 1.46 | 0.16 | 0.17 | 0.19 | 0.19 | 0.21 | | | |
| | ~RRT 1.97 | 0.08 | ND | ND | 0.05 | 0.05 | | | |
| | ~RRT 2.10 | 0.27 | 0.26 | 0.26 | 0.26 | 0.27 | | | |
| Total Related Substances (%) | | 1.1 | 1.1 | 1.2 | 1.4 | 1.6 | | | |
| Sterility | | Conform | NS | NS | NS | NS | | | |
| Particulate Matter | ≥10 μm | 525 | 68 | 196 | 292 | 159 | | | |
| | ≥25 μm | 7 | 0 | 0 | 0 | 0 | | | |

RRT = relative retention time,
NS = not scheduled,
ND = not detected or <0.05%

TABLE 60

| Stability Data for Compound 1 Injection 20 mg/mL, GMP Lot 217, −20° C., 35 mL pH 8.0 | | | | | | | | | |
|---|---|---|---|---|---|---|---|---|---|
| Test | | 0 Mo | 1 Mo | 3 Mo | 6 Mo | 9 Mo | 12 Mo | 18 Mo | 24 Mo |
| Appearance | | Conforms | Conforms | Conforms | Conforms | Conforms | | | |
| pH | | 8.2 | 8.2 | 8.1 | 8.0 | 8.1 | | | |
| Assay (%) | | 98.9 | 100.5 | 100.1 | 100.3 | 99.6 | | | |
| Related Substances (%) | | | | | | | | | |
| Compound 1A (%) | | 0.18 | 0.18 | 0.18 | 0.18 | 0.18 | | | |
| Individual Unknown | ~RRT 0.38 | 0.13 | 0.13 | 0.13 | 0.12 | 0.13 | | | |
| Impurity (%) | ~RRT 0.51 | 0.06 | 0.07 | 0.07 | ND | 0.07 | | | |
| | ~RRT 0.65 | 0.21 | 0.20 | 0.20 | 0.22 | 0.22 | | | |
| | ~RRT 1.36 | 0.05 | 0.06 | 0.06 | ND | 0.05 | | | |
| | ~RRT 1.46 | 0.16 | 0.16 | 0.17 | 0.15 | 0.16 | | | |
| | ~RRT 1.97 | 0.08 | ND | ND | 0.07 | ND | | | |
| | ~RRT 2.10 | 0.27 | 0.26 | 0.26 | 0.26 | 0.27 | | | |
| Total Related Substances (%) | | 1.1 | 1.1 | 1.1 | 1.0 | 1.1 | | | |
| Sterility | | Conforms | NS | NS | NS | NS | | | |
| Particulate Matter | ≥10 μm | 525 | 140 | 58 | 105 | 61 | | | |
| | ≥25 μm | 7 | 2 | 0 | 0 | 0 | | | |

RRT = relative retention time, NS = not scheduled, ND = not detected or <0.05%

Example 5C: Compound 1 Tablet Stability Studies

Assay and Related Substances

The HPLC method is a specific and stability-indicating method used for the determination of assay, related substances, content uniformity, identification, and absence of Compound 1 in Compound 1 Tablets with strengths of 100 mg and 200 mg. The method is a gradient reverse phase HPLC system to measure assay, purity, and related substances. A sample of Compound 1 drug substance and Compound 1 reference standard are prepared at a concentration of 0.4 mg/mL in the diluent (70:30 10 mM Phosphate Buffer: ACN). The sample and standard are injected onto a reverse phase HPLC system utilizing an Mightysil RP-18 GP, 4.6×150 mm, 3 μm column with a 10 μL injection volume, a flow rate of 1.0 mL/min, a detection wavelength of 271 nm, and a gradient mobile phase consisting of Mobile Phase A (900:100:1:0.1 Water: MeOH: TFA: $H_3PO_4$) and Mobile Phase B (100:900:1:0.1 Water:MeOH:TFA:$H_3PO_4$). Compounds are eluted from the column using a gradient over a 40 minute run time. The assay (% w/w) is determined by comparing the peak response of the sample to that of a standard.

The same HPLC method used for purity and related substances is used to measure related substances. Related substances to Compound 1 drug substance are reported as area percent. The area of an impurity is divided by the total area of all sample-related peaks from injection of a 0.4 mg/ml sample preparation. Related substances are reported by retention time relative to the parent peak (RRT).

Assay, Content Uniformity, and Absence of Active:

$$\% \, LC \text{ Compound } 1 = \frac{Rsam}{Rstd} \times \frac{Wstd \times P}{Vstd} \times \frac{1}{Dsam} \times \frac{Vsam}{\#\text{ Tabs}} \times \frac{100}{LC}$$

Blend Uniformity:

$$\% \, LC \text{ Compound } 1 = \frac{Rsam}{Rstd} \times \frac{Wstd \times P}{Vstd} \times \frac{Vsam}{Wsam} \times \frac{VsamWrun}{\# \, LCTabs} \times 100$$

Related Substances:

$$\% \text{ Impurity} = \frac{Rimp}{Rstd} \times \frac{Wstd \times P}{Vstd} \times \frac{1}{Dsam} \times \frac{Vsam}{\#\text{ Tabs}} \times \frac{100}{LC} \times \frac{1}{RRF}$$

Legend:

Rsam=Area response of Compound 1 from sample injection

Rstd=Average area response of Compound 1 from bracketing standard injections

Wstd=Weight of Compound 1 reference standard (mg)

P=Purity of Compound 1 from reference standard (decimal form)

Vstd=Volume of standard solution (mL)

Dsam=Dilution of sample solution

Vsam=Volume of sample solution (mL) #Tabs Total number of tablets assayed

Wsam=Weight of Compound 1 blend uniformity sample

Wrun=Theoretical (target) tablet run weight (mg)

LC=Label Claim of Compound 1 ([10] mg/tablet, 50 mg/tablet, 100m/tablet, or 200 mg/tablet)

100=Conversion to percent

Rimp=Peak area response of impurity peaks in the sample injection

RRF=Relative response factor; Compound 1A RRF=1.28; Assume 1.00 for all unknown impurites.

The dissolution method is based on USP dissolution method <711>using Apparatus II (paddles), with 900 mL of 50 mM phosphate buffer pH 6.8 for the 100 mg strength and 200 mg strength with a paddle speed of 75 rpm. Samples are collected at 5, 10, 15, 30, 45, and 60 minutes (infinity with a paddle speed of 250 rpm). The concentrations of Compound 1 are determined by HPLC.

The analytical method is an isocratic reverse phase HPLC system utilizing an ACE Excel C18, 3×50 mm, 2 μm) with a 5 μL injection volume, a flow rate of 1.0 mL/min, a detection wavelength of 271 nm and a gradient mobile phase. Compounds are eluted from the column using a gradient over a 5-minute run time. The assay (w/w %) is determined by comparing the peak response of the sample to that of a standard.

Compound 1 Tablets, Phase 1 Formulation

Tables 139-142 show the 12-month development stability results of Compound 1 Tablets when stored at 5° C. and 25° C./60% RH. Tables 143-146 show up to 24-month stability results of Compound 1 Tablets for clinical use when stored at 5° C. and accelerated stability at 25° C./60% RH. The data show no significant chemical or physical changes for samples stored at 5° C. and 25° C./60% RH for the lots placed on stability. The available stability data supports an expiry date of 36 months for Compound 1 Tablets.

Table 61 shows the analytical results for the development batches produced and Tables 62-63 show the analytical results for the clinical batches produced.

TABLE 61

Analytical Results of Compound 1 Tablet Development Batches

| Analytical Procedure | Batch 381-2 50 mg | Batch 381-3 200 mg |
|---|---|---|
| Appearance | White intact, round, convex tablets | White intact, oval, convex tablets |
| Identification | Conforms | Conforms |
| Assay (%) | 93.4 | 96.4 |
| Related Substances | | |
| Compound 1A | 0.37% | 0.38% |
| RRT-0.38 | 0.21% | 0.21% |
| RRT-0.46 | 0..12% | 0.12% |
| RRT-0.61 | 0.42% | 0.43% |
| RRT-0.94 | 0.13% | 0.13% |
| RRT-1.45 | 0.38% | 0.39% |
| RRT-1.97 | 0.99% | 1.09% |
| Total | 2.6% | 2.7% |
| Dissolution | | |
| 5 minutes | 48% | 86% |
| 10 minutes | 84% | 94% |
| 15 minutes | 93% | 95% |
| 20 minutes | 93% | 95% |
| 30 minutes | 94% | 95% |
| 45 minutes | 95% | 95% |
| 60 minutes | 95% | 96% |
| Moisture Content | 3.4% | 3.4% |

TABLE 62

Analytical Results of Compound 1 Tablet Clinical Batches

| Test Items | Release Criteria | Batch Number<br>683<br>50 mg | <br>684<br>200 mg |
|---|---|---|---|
| Appearance | White to off-white coated round shape tablets (50 mg) White to off-white coated oval shape tablets (200 mg) | White, coated round tablets | White, coated oval shaped tablets |
| Identification | Conforms to Reference | Conforms | Conforms |
| Assay (% label claim) | 90.0% to 110.0% | 101.1% | 100.7% |
| Related Substances (Area %) | Total: NMT 4.0% | 0.45% | 0.45% |
| | Compound 1A: NMT 1.0% | 0.21% | 0.21% |
| | Each individual: NMT 0.5% | 0.24% (RRT 2.01) | 0.24% (RRT 2.01) |
| Uniformity of Content | Complies with USP <905> Content Uniformity | Conforms 101.0% | Conforms 100.3% |
| Dissolution Test | Each unit: ≥70% dissolved (Q + 5%) at 45 min | 104% | 105% |
| Moisture Content | Report results | 3.09% | 3.19% |
| Microbial Limit Test | Total Aerobic Microbial Count: NMT 1000 CFU/g Total Yeast and Mold Count: NMT 100 CFU/g *Escherichia coli*: Absent in 1 g | Total Aerobic Microbial Count: 10 CFU/g Total Yeast and Mold Count: <10 CFU/g *Escherichia coli*: Absent in 1 g | Total Aerobic Microbial Count: <10 CFU/g Total Yeast and Mold Count: <10 CFU/g *Escherichia coli*: Absent in 1 g |

TABLE 63

Analytical Results of Compound 1 Tablet Clinical Batches

| Test Items | Release Criteria | Batch Number<br>B617<br>50 mg | <br>618<br>200 mg |
|---|---|---|---|
| Appearance | Coated round shape tablets (50 mg) Coated oval shape tablets (200 mg) | Coated round tablets | Coated oval shaped tablets |
| Identification | Conforms to Reference | Conforms | Conforms |
| Assay (% label claim) | 90.0% to 110.0% | 102.1% | 101.6% |
| Related Substances (Area %) | Total: NMT 4.0% | 0.92% | 0.85% |
| | Compound 1A: NMT 1.0% | 0.29% | 0.22% |
| | Each individual: NMT 0.5% | 0.34% (RRT 2.00) | 0.34% (RRT 2.00) |
| Uniformity of Content | Complies with USP <905> Content Uniformity | Conforms 99.0% | Conforms 98.0% |
| Dissolution Test | Each unit: ≥70% dissolved (Q + 5%) at 45 min | 102% | 99% |
| Moisture Content | Report results | 2.84% | 3.52% |
| Microbial Limit Test | Total Aerobic Microbial Count: NMT 1000 CFU/g Total Yeast and Mold Count: NMT 100 CFU/g *Escherichia coli*: Absent in 1 g | Total Aerobic Microbial Count: 10 CFU/g Total Yeast and Mold Count: <10 CFU/g *Escherichia coli*: Absent in 1 g | Total Aerobic Microbial Count: <10 CFU/g Total Yeast and Mold Count: <10 CFU/g *Escherichia coli*: Absent in 1 g |

No additional degradants are expected to be present in the Compound 1 Tablets other than Compound 1A.

Compound 1 Tablets, 50 mg and 200 mg development batches, have been prepared and placed on a stability study with timepoints described in Table 64. Additionally, Compound 1 Tablets, 50 mg and 200 mg, GMP batches have been placed on an ICH stability program as shown in Table 65. Samples have been analyzed for appearance, assay, related substance, dissolution, moisture content, and microbial limits. These samples from development batches and GMP batches have been tested after 12-months.

The excipient compatibility and stability to date have been analyzed and there were no significant physical or chemical changes reported. The test and specifications for the shelf-life are shown in Table 66.

TABLE 64

Stability Schedule for Compound 1 Tablets, 50 mg and 200 mg Development Batches

| Temperature | Initial | 1 month | 2 month | 3 month | 6 month | 9 month | 12 month | 18 month | 24 month |
|---|---|---|---|---|---|---|---|---|---|
| 5° C. | B | A | A | A | A | A | B | A | B |
| 25° C./60% RH | | A | | A | A | | | | |

Test Matrix A - appearance, assay, related substances, dissolution, and Karl Fischer moisture.

Test Matrix B - appearance, assay, related substances, dissolution, Karl Fischer moisture, and microbial limits.

TABLE 65

| Stability Schedule for Compound 1 Tablets, 50 mg and 200 mg, Clinical Trial Batches | | | | | | | | | |
|---|---|---|---|---|---|---|---|---|---|
| Temperature | Initial | 1 month | 2 month | 3 month | 6 month | 9 month | 12 month | 18 month | 24 month |
| 50 mg | | | | | | | | | |
| 5° C. | B | | | A | A | A | A | | B |
| 25° C./60% RH | | | | A | A | A | A | A | A |
| 200 mg | | | | | | | | | |
| 5° C. | B | A | | | | A | | | |
| 25° C./60% RH | | A | | A | A | A | | | |

Test Matrix A - appearance, assay, related substances, dissolution, and Karl Fischer moisture.
Test Matrix B - appearance, assay, related substances, dissolution, Karl Fischer moisture, and microbial limits.

TABLE 66

| Compound 1 Tablets Stability Specification | | |
|---|---|---|
| Test Items | Methods | Release Criteria |
| Appearance | Visual Method | Coated round shape tablets (50 mg)<br>Coated oval shape tablets (200 mg) |
| Identification | HPLC Method | Conforms to Reference |
| Assay (% label claim) | HPLC Method | 90.0% to 110.0% |
| Related Substances (Area %) | HPLC Method | Total: NMT 4.0%<br>Compound 1A: NMT 1.5%<br>Each individual impurity: NMT 0.5% |
| Dissolution Test | USP <711>, HPLC Method | Each unit: ≥70% dissolved (Q + 5%) at 45 min |
| Moisture Content | USP <921> Method 1a | Report results |
| Microbial Limit Test | USP <61>, <62> | Conforms |

Abbreviations: HPLC = high performance liquid chromatography; NMT = not more than; USP = United States Pharmacopeia.

TABLE 67

| Stability Data for Compound 1 Tablets 50 mg, Lot 381-2, 25° C./60% RH, 30 Count HDPE Bottle | | | | | | | |
|---|---|---|---|---|---|---|---|
| Test | | 0 Mo | 1 Mo | 3 Mo | 6 Mo | 9 Mo | 12 Mo |
| Appearance | | Conforms | Conforms | Conforms | Conforms | Conforms | Conforms |
| Assay (%) | | 93.4 | 90.5 | 93.6 | 87.8 | 91.6 | 92.5 |
| Related Substances (%) | | | | | | | |
| Compound 1A (%) | | 0.37 | 0.39 | 0.33 | 0.44 | 0.44 | 0.47 |
| Individual Unknown | ~RRT 0.38 | 0.21 | 0.20 | 0.22 | 0.21 | 0.22 | 0.22 |
| Impurity (%) | ~RRT 0.45 | 0.12 | 0.16 | 0.15 | 0.15 | 0.16 | ND |
| | ~RRT 0.62 | 0.42 | 0.42 | 0.46 | 0.46 | 0.51 | ND |
| | ~RRT 0.95 | 0.13 | 0.12 | 0.13 | 0.12 | 0.12 | 0.13 |
| | ~RRT 1.47 | 0.38 | 0.38 | 0.38 | 0.43 | 0.41 | 0.39 |
| | ~RRT 2.00 | 0.99 | 0.94 | 0.97 | 0.92 | 0.98 | 0.95 |
| Total Related Substances (%) | | 2.6 | 2.61 | 2.64 | 2.73 | 2.8 | 2.67 |
| Dissolution | Mean | 95 | 92 | 94 | 91 | 95 | 97 |
| (% dissolved at 45 minutes) | Min | 93 | 89 | 91 | 89 | 93 | 93 |
| | Max | 96 | 97 | 96 | 92 | 98 | 99 |
| | % RSD | 1.6 | 3.8 | 2.1 | 1.1 | 2.0 | 2.1 |
| Water Content | | 3.3 | 2.88 | 2.35 | 2.87 | 3.0 | 3.23 |
| Total Aerobic Microbial Count (cfu/g) | | NS | NS | NS | NS | NS | NS |
| Total Combined Yeasts and Molds Count (cfu/g) | | NS | NS | NS | NS | NS | NS |
| *E. Coli* | | NS | NS | NS | NS | NS | NS |

RRT = relative retention time, NS = not scheduled, ND = not detected or <0.05%

TABLE 68

| Stability Data for Compound 1 Tablets 50 mg, Lot 381-2, 5° C., 30 Count HDPE Bottle | | | | | | | |
|---|---|---|---|---|---|---|---|
| Test | | 0 Mo | 1 Mo | 3 Mo | 6 Mo | 9 Mo | 12 Mo |
| Appearance | | Conforms | Conforms | Conforms | Conforms | Conforms | Conforms |
| Assay (%) | | 93.4 | 90.4 | 91.7 | 94.1 | 94.0 | 95.2 |
| Related Substances (%) | | | | | | | |
| Compound 1A (%) | | 0.37 | 0.32 | 0.21 | 0.29 | 0.23 | 0.24 |
| Individual Unknown | ~RRT 0.38 | 0.21 | 0.19 | 0.21 | 0.22 | 0.21 | 0.21 |
| Impurity (%) | ~RRT 0.45 | 0.12 | 0.17 | 0.16 | 0.16 | 0.17 | 0.10 |
| | ~RRT 0.62 | 0.42 | 0.40 | 0.42 | 0.43 | 0.45 | 0.44 |
| | ~RRT 0.95 | 0.13 | 0.12 | 0.12 | 0.13 | 0.13 | 0.13 |
| | ~RRT 1.47 | 0.38 | 0.38 | 0.37 | 0.46 | 0.42 | 0.40 |
| | ~RRT 2.00 | 0.99 | 0.94 | 0.96 | 1.02 | 1.03 | 0.99 |
| Total Related Substances (%) | | 2.6 | 2.52 | 2.45 | 2.71 | 2.6 | 2.51 |
| Dissolution | Mean | 95 | 94 | 95 | 91 | 95 | 99 |
| (% dissolved at 45 minutes) | Min | 93 | 91 | 91 | 88 | 90 | 97 |
| | Max | 96 | 96 | 97 | 95 | 98 | 101 |
| | % RSD | 1.6 | 2.3 | 2.4 | 2.9 | 3.5 | 1.1 |
| Water Content | | 3.3 | 2.7 | 2.38 | 2.81 | 3.1 | 3.22 |
| Total Aerobic Microbial Count (cfu/g) | | NS | NS | NS | NS | NS | NS |
| Total Combined Yeasts and Molds Count (cfu/g) | | NS | NS | NS | NS | NS | NS |
| *E. Coli* | | NS | NS | NS | NS | NS | NS |

RRT = relative retention time, NS = not scheduled, ND = not detected or <0.05%

TABLE 69

| Stability Data for Compound 1 Tablets 200 mg, Lot 381-3, 25° C./60% RH, 30 Count HDPE Bottle | | | | | | | |
|---|---|---|---|---|---|---|---|
| Test | | 0 Mo | 1 Mo | 3 Mo | 6 Mo | 9 Mo | 12 Mo |
| Appearance | | Conforms | Conforms | Conforms | Conforms | Conforms | Conforms |
| Assay (%) | | 96.4 | 94.5 | 94.8 | 94.2 | 95.6 | 96.6 |
| Related Substances (%) | | | | | | | |
| Compound 1A (%) | | 0.38 | 0.39 | 0.32 | 0.45 | 0.45 | 0.49 |
| Individual Unknown | ~RRT 0.38 | 0.21 | 0.21 | 0.22 | 0.22 | 0.23 | 0.22 |
| Impurity (%) | ~RRT 0.45 | 0.12 | 0.46 | 0.16 | 0.16 | 0.17 | 0.10 |
| | ~RRT 0.62 | 0.43 | 0.61 | 0.46 | 0.48 | 0.52 | 0.52 |
| | ~RRT 0.95 | 0.13 | 0.95 | 0.13 | 0.13 | 0.13 | 0.13 |
| | ~RRT 1.47 | 0.39 | 0.40 | 0.39 | 0.46 | 0.42 | 0.41 |
| | ~RRT 2.00 | 1.03 | 0.98 | 0.99 | 1.00 | 1.02 | 0.99 |
| Total Related Substances (%) | | 2.7 | 2.71 | 2.67 | 2.90 | 2.9 | 2.9 |
| Dissolution | Mean | 95 | 93 | 94 | 91 | 96 | 98 |
| (% dissolved at 45 minutes) | Min | 95 | 92 | 93 | 87 | 95 | 95 |
| | Max | 98 | 96 | 96 | 94 | 98 | 99 |
| | % RSD | 1.2 | 1.6 | 1.2 | 2.6 | 1.2 | 1.8 |
| Water Content | | 3.4 | 2.28 | 2.49 | 2.47 | 2.5 | 3.03 |
| Total Aerobic Microbial Count (cfu/g) | | NS | NS | NS | NS | NS | NS |
| Total Combined Yeasts and Molds Count (cfu/g) | | NS | NS | NS | NS | NS | NS |
| *E. Coli* | | NS | NS | NS | NS | NS | NS |

RRT = relative retention time, NS = not scheduled, ND = not detected or <0.05%

TABLE 70

| Stability Data for Compound 1 Tablets 200 mg, Lot 381-3, 5° C., 30 Count HDPE Bottle | | | | | | | |
|---|---|---|---|---|---|---|---|
| Test | | 0 Mo | 1 Mo | 3 Mo | 6 Mo | 9 Mo | 12 Mo |
| Appearance | | Conforms | Conforms | Conforms | Conforms | Conforms | Conforms |
| Assay (%) | | 96.4 | 94.9 | 93.8 | 96.0 | 96.1 | 96.6 |
| Related Substances (%) | | | | | | | |
| Compound 1A (%) | | 0.38 | 0.33 | 0.21 | 0.28 | 0.23 | 0.24 |
| Individual Unknown | ~RRT 0.38 | 0.21 | 0.20 | 0.21 | 0.22 | 0.22 | 0.22 |
| Impurity (%) | ~RRT 0.45 | 0.12 | 0.19 | 0.16 | 0.17 | 0.17 | 0.11 |

TABLE 70-continued

| Stability Data for Compound 1 Tablets 200 mg, Lot 381-3, 5° C., 30 Count HDPE Bottle | | | | | | | |
|---|---|---|---|---|---|---|---|
| Test | | 0 Mo | 1 Mo | 3 Mo | 6 Mo | 9 Mo | 12 Mo |
| | ~RRT 0.62 | 0.43 | 0.42 | 0.42 | 0.43 | 0.45 | 0.44 |
| | ~RRT 0.95 | 0.13 | 0.12 | 0.13 | 0.13 | 0.13 | 0.13 |
| | ~RRT 1.47 | 0.39 | 0.39 | 0.38 | 0.47 | 0.43 | 0.41 |
| | ~RRT 2.00 | 1.03 | 0.99 | 0.99 | 1.03 | 1.05 | 1.02 |
| Total Related Substances (%) | | 2.7 | 2.64 | 2.50 | 2.73 | 2.7 | 2.57 |
| Dissolution | Mean | 95 | 94 | 95 | 94 | 95 | 99 |
| (% dissolved at 45 minutes) | Min | 93 | 93 | 92 | 93 | 93 | 98 |
| | Max | 97 | 96 | 99 | 95 | 97 | 101 |
| | % RSD | 1.7 | 1.5 | 2.6 | 1.0 | 1.7 | 1.1 |
| Water Content | | 3.4 | 2.59 | 2.82 | 2.84 | 2.4 | 3.34 |
| Total Aerobic Microbial Count (cfu/g) | | NS | NS | NS | NS | NS | NS |
| Total Combined Yeasts and Molds Count (cfu/g) | | NS | NS | NS | NS | NS | NS |
| *E. Coli* | | NS | NS | NS | NS | NS | NS |

RRT = relative retention time, NS = not scheduled, ND = not detected or <0.05%

TABLE 71

| Stability Data for Compound 1 Tablets 50 mg, Lot 660, 25° C./60% RH, 30 Count HDPE Bottle | | | | | | | | |
|---|---|---|---|---|---|---|---|---|
| Test | | 0 Mo | 3 Mo | 6 Mo | 9 Mo | 12 Mo | 18 Mo | 24 Mo |
| Appearance | | Conforms | Conforms | Conforms | Conforms | Conforms | Conforms | Conforms |
| Assay (%) | | 101.1 | 105.5 | 104.3 | 102.1 | 104.6 | 102.8 | 103.5 |
| Related Substances (%) | | | | | | | | |
| Compound 1A (%) | | 0.21 | 0.45 | 0.44 | 0.53 | 0.59 | 0.63 | 0.73 |
| Individual Unknown | ~RRT 0.77 | ND | ND | 0.13 | 0.13 | 0.14 | ND | ND |
| Impurity (%) | ~RRT 2.00 | 0.24 | 0.23 | 0.22 | 0.24 | 0.24 | 0.22 | 0.23 |
| Total Related Substances (%) | | 0.45 | 0.68 | 0.79 | 0.90 | 0.97 | 0.85 | 1.00 |
| Dissolution | Mean | 104 | 100 | 104 | 105 | 106 | 106 | 107 |
| (% dissolved at 45 minutes) | Min | 101 | 93 | 99 | 97 | 102 | 103 | 102 |
| | Max | 108 | 105 | 108 | 114 | 111 | 110 | 112 |
| | % RSD | 2.6 | 4.4 | 3.8 | 5.6 | 3.0 | 3.4 | 3.0 |
| Water Content | | 3.09 | 2.24 | 2.97 | 3.31 | 2.59 | 3.20 | 3.20 |
| Total Aerobic Microbial Count (cfu/g) | | 10 | NS | NS | NS | NS | NS | NS |
| Total Combined Yeasts and Molds Count (cfu/g) | | <10 | NS | NS | NS | NS | NS | NS |
| *E. Coli* | | Absent/1g | NS | NS | NS | NS | NS | NS |

RRT = relative retention time, NS = not scheduled, ND = not detected or <0.05%

TABLE 72

| Stability Data for Compound 1 Tablets 50 mg, Lot 660, 5° C., 30 Count HDPE Bottle | | | | | | | | |
|---|---|---|---|---|---|---|---|---|
| Test | | 0 Mo | 3 Mo | 6 Mo | 9 Mo | 12 Mo | 18 Mo | 24 Mo |
| Appearance | | Conforms | Conforms | Conforms | Conforms | Conforms | NS | Conforms |
| Assay (%) | | 101.1 | 101.9 | 103.9 | 103.1 | 103.9 | NS | 101.9 |
| Related Substances (%) | | | | | | | | |
| Compound 1A (%) | | 0.21 | 0.23 | 0.19 | 0.23 | 0.24 | NS | 0.25 |
| Individual Unknown Impurity (%) | ~RRT 2.00 | 0.24 | 0.24 | 0.23 | 0.24 | 0.24 | NS | 0.23 |
| Total Related Substances (%) | | 0.45 | 0.47 | 0.42 | 0.47 | 0.48 | NS | 0.48 |
| Dissolution | Mean | 104 | 99 | 107 | 106 | 104 | NS | 108 |
| (% dissolved at 45 minutes) | Min | 101 | 96 | 105 | 102 | 103 | NS | 104 |
| | Max | 108 | 106 | 110 | 110 | 106 | NS | 112 |
| | % RSD | 2.6 | 3.8 | 2.0 | 2.7 | 1.3 | NS | 2.5 |
| Water Content | | 3.09 | 2.41 | 3.11 | 3.18 | 2.61 | NS | 3.00 |
| Total Aerobic Microbial Count (cfu/g) | | 10 | NS | NS | NS | NS | NS | <10 |
| Total Combined Yeasts and Molds Count (cfu/g) | | <10 | NS | NS | NS | NS | NS | <10 |
| *E. Coli* | | Absent/1g | NS | NS | NS | NS | NS | Absent/1g |

RRT = relative retention time, NS = not scheduled, ND = not detected or <0.05%

TABLE 73

| Stability Data for Compound 1 Tablets 200 mg, Lot 661, 25° C./60% RH, 30 Count HDPE Bottle | | | | | | |
|---|---|---|---|---|---|---|
| Test | | 0 Mo | 1 Mo | 3 Mo | 6 Mo | 9 Mo |
| Appearance | | Conforms | DNC | Conforms | Conforms | Conforms |
| Assay (%) | | 100.7 | 104.0 | 102.3 | 102.7 | 102.7 |
| Related substances (%) | | | | | | |
| Compound 1A (%) | | 0.21 | 0.26 | 0.45 | 0.50 | 0.50 |
| Individual Unknown Impurity (%) | ~RRT 2.00 | 0.24 | 0.25 | 0.25 | 0.24 | 0.24 |
| Total Related Substances (%) | | 0.45 | 0.51 | 0.70 | 0.74 | 0.74 |
| Dissolution | Mean | 105 | 106 | 102 | 104 | 105 |
| (% dissolved at 45 minutes) | Min | 104 | 100 | 98 | 102 | 102 |
| | Max | 109 | 108 | 106 | 107 | 108 |
| | % RSD | 0.9 | 3.0 | 3.2 | 2.1 | 2.1 |
| Water Content | | 3.19 | 2.70 | 2.80 | 3.18 | 3.12 |
| Total Aerobic Microbial Count (cfu/g) | | <10 | NS | NS | NS | NS |
| Total Combined Yeasts and Molds Count (cfu/g) | | <10 | NS | NS | NS | NS |
| *E. Coli* | | Absent/1g | NS | NS | NS | NS |

RRT = relative retention time, NS = not scheduled, ND = not detected or <0.05%, DNC = does not conform

TABLE 74

| Stability Data for Compound 1 Tablets 200 mg, Lot 661, 5° C., 30 Count HDPE Bottle | | | | |
|---|---|---|---|---|
| Test | | 0 Mo | 1 Mo | 9 Mo |
| Appearance | | Conforms | DNC | Conforms |
| Assay (%) | | 100.7 | 102.2 | 104.9 |
| Related Substances (%) | | | | |
| Compound 1A (%) | | 0.21 | 0.21 | 0.23 |
| Individual Unknown Impurity (%) | ~RRT 2.00 | 0.24 | 0.24 | 0.25 |
| Total Related Substances (%) | | 0.45 | 0.45 | 0.48 |
| Dissolution | Mean | 105 | 109 | 102 |
| (% dissolved at 45 minutes) | Min | 104 | 104 | 100 |
| | Max | 109 | 114 | 105 |
| | % RSD | 0.9 | 3.5 | 2.1 |
| Water Content | | 3.19 | 2.91 | 3.28 |
| Total Aerobic Microbial Count (cfu/g) | | <10 | NS | NS |
| Total Combined Yeasts and Molds Count (cfu/g) | | <10 | NS | NS |
| *E. Coli* | | Absent/1 g | NS | NS |

RRT = relative retention time, NS = not scheduled, ND = not detected or <0.05%, DNC = does not conform

TABLE 75

| Stability Data for Compound 1 Tablets 50 mg, Lot 617, 25° C./60% RH, 30 Count HDPE Bottle | | | | | | | | | |
|---|---|---|---|---|---|---|---|---|---|
| Test | | 0 Mo | 1 Mo | 3 Mo | 6 Mo | 9 Mo | 12 Mo | 18 Mo | 24 Mo |
| Appearance | | Conforms | Conform | Conform | Conform | Conform | Conforms | | |
| Assay (%) | | 98.6 | 99.8 | 100.2 | 101.4 | 100.5 | 98.7 | | |
| Related Substances (%) | | | | | | | | | |
| Compound 1A (%) | | 0.33 | 0.45 | 0.63 | 0.72 | 0.86 | 0.86 | | |
| Individual Unknown | ~RRT 0.37 | 0.15 | 0.15 | 0.14 | 0.16 | 0.16 | 0.16 | | |
| Impurity (%) | ~RRT 0.60 | 0.14 | 0.16 | 0.17 | 0.20 | 0.23 | 0.25 | | |
| | ~RRT 2.05 | 0.33 | 0.33 | 0.29 | 0.33 | 0.31 | 0.29 | | |
| Total Related Substances (%) | | 0.95 | 1.1 | 1.2 | 1.4 | 1.6 | 1.6 | | |
| Dissolution | Mean | 99 | 102 | 99 | 100 | 100 | 104 | | |
| (% dissolved at 45 minutes) | Min | 95 | 99 | 92 | 96 | 97 | 101 | | |
| | Max | 103 | 104 | 104 | 104 | 101 | 106 | | |
| | % RSD | 3.6 | 1.7 | 4.4 | 2.6 | 2.4 | 2.0 | | |
| Water Content | | 2.8 | 3.2 | 3.8 | 3.8 | 3.7 | 3.8 | | |
| Total Aerobic Microbial Count (cfu/g) | | <10 | NS | NS | NS | NS | 10 | | |
| Total Combined Yeasts and Molds Count (cfu/g) | | <10 | NS | NS | NS | NS | <10 | | |
| *E. Coli* | | Absent/1 | NS | NS | NS | NS | Absent/1 | | |

RRT = relative retention time, NS = not scheduled, ND = not detected or <0.05%

TABLE 76

| Stability Data for Compound 1 Tablets 50 mg, Lot 617, 5° C., 30 Count HDPE Bottle | | | | | | | | | |
|---|---|---|---|---|---|---|---|---|---|
| Test | | 0 Mo | 1 Mo | 3 Mo | 6 Mo | 9 Mo | 12 Mo | 18 Mo | 24 Mo |
| Appearance | | Conforms | Conform | Conform | Conform | Conform | Conforms | | |
| Assay (%) | | 98.6 | 100.2 | 98.3 | 99.9 | 99.0 | 101.3 | | |
| Related Substances (%) | | | | | | | | | |
| Compound 1A (%) | | 0.33 | 0.37 | 0.35 | 0.30 | 0.34 | 0.30 | | |
| Individual Unknown | ~RRT 0.37 | 0.15 | 0.15 | 0.13 | 0.15 | 0.15 | 0.14 | | |
| Impurity (%) | ~RRT 0.60 | 0.14 | 0.15 | 0.13 | 0.15 | 0.16 | 0.16 | | |
| | ~RRT 2.05 | 0.33 | 0.33 | 0.30 | 0.32 | 0.31 | 0.32 | | |
| Total Related Substances (%) | | 0.95 | 1.0 | 0.91 | 0.92 | 1.0 | 0.92 | | |
| Dissolution | Mean | 99 | 104 | 100 | 104 | 100 | 109 | | |
| (% dissolved at 45 minutes) | Min | 95 | 95 | 91 | 102 | 87 | 111 | | |
| | Max | 103 | 104 | 105 | 109 | 108 | 107 | | |
| | % RSD | 3.6 | 2.9 | 5.2 | 3.0 | 6.8 | 1.7 | | |
| Water Content | | 2.8 | 3.2 | 3.7 | 4.0 | 3.6 | 4.0 | | |
| Total Aerobic Microbial Count (cfu/g) | | <10 | NS | NS | NS | NS | <10 | | |
| Total Combined Yeasts and Molds Count (cfu/g) | | <10 | NS | NS | NS | NS | <10 | | |
| *E. Coli* | | Absent/1 | NS | NS | NS | NS | Absent/1 | | |

RRT = relative retention time, NS = not scheduled, ND = not detected or <0.05%

TABLE 77

| Stability Data for Compound 1 Tablets 200 mg, Lot 618, 25° C./60% RH, 30 Count HDPE Bottle | | | | | | | | | |
|---|---|---|---|---|---|---|---|---|---|
| Test | | 0 Mo | 1 Mo | 3 Mo | 6 Mo | 9 Mo | 12 Mo | 18 Mo | 24 Mo |
| Appearance | | Conforms | Conforms | Conforms | Conforms | Conforms | Conforms | | |
| Assay (%) | | 98.8 | 99.0 | 100.4 | 98.2 | 98.7 | 100.3 | | |
| Related Substances (%) | | | | | | | | | |
| Compound 1A (%) | | 0.23 | 0.29 | 0.40 | 0.50 | 0.58 | 0.62 | | |
| Individual Unknown | ~RRT 0.37 | 0.15 | 0.15 | 0.14 | 0.15 | 0.15 | 0.16 | | |
| Impurity (%) | ~RRT 0.60 | 0.14 | 0.15 | 0.16 | 0.18 | 0.22 | 0.24 | | |
| | ~RRT 2.05 | 0.33 | 0.32 | 0.31 | 0.31 | 0.30 | 0.30 | | |
| Total Related Substances (%) | | 0.85 | 0.91 | 1.0 | 1.1 | 1.3 | 1.3 | | |
| Dissolution | Mean | 97 | 99 | 98 | 96 | 97 | 98 | | |
| (% dissolved at 45 minutes) | Min | 89 | 97 | 96 | 93 | 95 | 91 | | |
| | Max | 102 | 103 | 101 | 98 | 100 | 101 | | |
| | % RSD | 5.0 | 2.1 | 1.6 | 2.0 | 1.9 | 3.7 | | |
| Water Content | | 3.2 | 3.4 | 3.7 | 3.9 | 3.7 | 4.0 | | |
| Total Aerobic Microbial Count (cfu/g) | | <10 | NS | NS | NS | NS | <10 | | |
| Total Combined Yeasts and Molds Count (cfu/g) | | <10 | NS | NS | NS | NS | <10 | | |
| *E. Coli* | | Absent/1g | NS | NS | NS | NS | Absent/1g | | |

RRT = relative retention time, NS = not scheduled, ND = not detected or <0.05%

TABLE 78

| Stability Data for Compound 1 Tablets 200 mg, Lot 618, 5° C., 30 Count HDPE Bottle | | | | | | | | | |
|---|---|---|---|---|---|---|---|---|---|
| Test | | 0 Mo | 1 Mo | 3 Mo | 6 Mo | 9 Mo | 12 Mo | 18 Mo | 24 Mo |
| Appearance | | Conforms | Conform | Conform | Conform | Confrom | Conforms | | |
| Assay (%) | | 98.8 | 98.9 | 99.9 | 100.1 | 99.0 | 101.0 | | |
| Related Substances (%) | | | | | | | | | |
| Compound 1A (%) | | 0.23 | 0.23 | 0.23 | 0.23 | 0.22 | 0.21 | | |
| Individual Unknown | ~RRT 0.37 | 0.15 | 0.15 | 0.14 | 0.15 | 0.14 | 0.14 | | |
| Impurity (%) | ~RRT 0.60 | 0.14 | 0.14 | 0.13 | 0.14 | 0.16 | 0.15 | | |
| | ~RRT 2.05 | 0.33 | 0.33 | 0.31 | 0.33 | 0.31 | 0.32 | | |
| Total Related Substances (%) | | 0.85 | 0.85 | 0.81 | 0.85 | 0.83 | 0.82 | | |
| Dissolution | Mean | 97 | 99 | 100 | 98 | 97 | 100 | | |
| (% dissolved at 45 | Min | 89 | 97 | 94 | 95 | 95 | 97 | | |

TABLE 78-continued

| Stability Data for Compound 1 Tablets 200 mg, Lot 618, 5° C., 30 Count HDPE Bottle | | | | | | | | | |
|---|---|---|---|---|---|---|---|---|---|
| Test | | 0 Mo | 1 Mo | 3 Mo | 6 Mo | 9 Mo | 12 Mo | 18 Mo | 24 Mo |
| minutes) | Max | 102 | 103 | 103 | 101 | 100 | 104 | | |
| | % RSD | 5.0 | 2.1 | 3.2 | 2.3 | 2.0 | 2.2 | | |
| Water Content | | 3.2 | 3.4 | 3.7 | 3.9 | 3.6 | 4.0 | | |
| Total Aerobic Microbial Count (cfu/g) | | <10 | NS | NS | NS | NS | <10 | | |
| Total Combined Yeasts and Molds Count (cfu/g) | | <10 | NS | NS | NS | NS | <10 | | |
| *E. Coli* | | Absent/1 | NS | NS | NS | NS | Absent/1 | | |

RRT = relative retention time, NS = not scheduled, ND = not detected or <0.05%

Compound 1 Tablets, Phase 2 Formulation

Tables 89-92 show up to 18 months development stability results of Compound 1 Tablets when stored at 5° C. and up to 9 months accelerated stability at 25° C./60% RH. Tables 93-96 show the 12-month stability results of GMP Compound 1 100 mg and 200 mg tablets Lot #645 and 646, respectively, when stored at 5° C. and 25° C./60% RH. The data show no significant chemical or physical changes for samples stored at 5° C. and 25° C./60% RH for the time-points tested and is consistent with the Phase 1 tablet stability data. Similarly, data in Table 97 and Table 98 indicate Lot 192 200 mg tablets are stable at the 6 month timepoint for both the 5° C. and 25° C./60% RH condition.

Based upon ICH Q1E, the available stability data supports a shelf-life of 30 months when Compound 1 Tablets are stored at 5° C. based upon the low temperature storage data, excipient compatibility data, Phase 1 formulation stability data, and current Phase 2 stability data. The re-test date/shelf-life for GMP Compound 1 Tablets will be updated based on additional stability data from ongoing and future ICH stability studies run concurrently with clinical studies, as described in Table 81 and according to the specification shown in Table 83.

Batch Analysis Each clinical batch of Compound 1 100 mg and 200 mg tablets will be tested against the approved specifications prior to use in clinical studies and placed on an ICH stability program. Tables 79-80 present the testing data from the supportive stability studies.

TABLE 79

| Analytical Results of Compound 1 Tablet Development Batches | | |
|---|---|---|
| Analytical Procedure | Batch 381-100C 100 mg | Batch 381-200C 200 mg |
| Appearance | White round convex coated tablets | White oval convex coated tablets |
| Identification | Conforms | Conforms |
| Assay (%) | 95.1% | 98.1% |
| Related Substances | | |
| RRT-0.39 | 0.24% | 0.25% |
| RRT-0.51 | 0.15% | 0.16% |
| RRT-0.63 | 0.39% | 0.41% |
| RRT-1.19 | 0.33% | 0.34% |
| Compound 1A | 0.19% | 0.19% |
| RRT-1.47 | 0.18% | 0.18% |
| RRT-2.00 | 0.66% | 0.69% |
| Total | 2.1% | 2.2% |
| Dissolution | | |
| 5 minutes | 23% | 61% |
| 10 minutes | 48% | 91% |
| 15 minutes | 87% | 94% |
| 20 minutes | 95% | 95% |
| 30 minutes | 97% | 96% |
| 45 minutes | 99% | 97% |
| 60 minutes | 100% | 98% |
| Moisture Content | 3.4% | 3.2% |

TABLE 80

| Analytical Results of Compound 1 Tablet Clinical Batches | | | | |
|---|---|---|---|---|
| | | Batch Number | | |
| Test Items | Release Criteria | 645 100 mg | 646 200 mg | 192 200 mg |
| Appearance | Coated round shape tablets (50 mg) Coated oval shape tablets (200 mg) | Conforms, off-white, coated round tablets | Conforms, off-white, coated oval shaped tablets | Conforms, off-white coated oval shaped tablets |
| Identification | Conforms to Reference | Conforms | Conforms | Conforms |
| Assay (% label claim) | 90.0% to 110.0% | 101.8% | 101.7% | 98.3% |
| Related Substances (Area %) | Total: NMT 4.0% | 0.98% | 0.86% | 0.93% |
| | Compound 1A: NMT 1.0% | 0.31% | 0.23% | 0.20% |
| | Each individual: NMT 0.5% | RRT 0.38-0.15%<br>RRT 0.61-0.16%<br>RRT 2.02-0.33% | RRT 0.38-0.15%<br>RRT 0.61-0.15%<br>RRT 2.02-0.33% | RRT 0.39-0.10%<br>RRT 0.63-0.21%<br>RRT 1.46-0.18%<br>RRT 2.01 -0.24% |
| Uniformity of Content | Complies with USP <905> Content Uniformity | Conforms AV = 2.7 | Conforms AV = 4.2 | Conforms AV = 7.2 |
| Dissolution Test | Each unit: ≥70% dissolved (Q + 5%) at 45 min | 95% | 90% | 96% |

TABLE 80-continued

| Analytical Results of Compound 1 Tablet Clinical Batches | | | | |
|---|---|---|---|---|
| | | Batch Number | | |
| Test Items | Release Criteria | 645<br>100 mg | 646<br>200 mg | 192<br>200 mg |
| Moisture Content | Report results | 2.81% | 3.19% | 3.4% |
| Microbial Limit Test | Total Aerobic Microbial Count: NMT 1000 CFU/g<br>Total Yeast and Mold Count: NMT 100 CFU/g<br>*Escherichia coli*: Absent in 1 g | Total Aerobic Microbial Count: <10 CFU/g<br>Total Yeast and Mold Count: <10 CFU/g<br>*Escherichia coli*: Absent in 1 g | Total Aerobic Microbial Count: <10 CFU/g<br>Total Yeast and Mold Count: <10 CFU/g<br>*Escherichia coli*: Absent in 1 g | Total Aerobic Microbial Count: <10 CFU/g<br>Total Yeast and Mold Count: <10 CFU/g<br>*Escherichia coli*: Absent in 1 g |

Compound 1 Tablets, 100 mg and 200 mg development batches, have been prepared and placed on a stability with timepoints described in Tables 81-82. Additionally, Compound 1 Tablets, 100 mg and 200 mg, GMP batches will be placed on an ICH stability program as shown in Tables 81-82. Samples will be analyzed for appearance, assay, related substance, dissolution, moisture content, and microbial limits.

The Phase 2 clinical batches have been placed on ICH stability studies prior to commencing the Phase 2 clinical trial. As additional batches are manufactured to support the Compound 1 clinical program, each lot will also be placed on stability. The excipient compatibility and stability to date have been analyzed and there were no significant physical or chemical changes reported. The test and specifications for the shelf-life are shown in Table 66.

TABLE 81

| Stability Schedule for Compound 1 Tablets, 100 mg and 200 mg Development Batches | | | | | | | |
|---|---|---|---|---|---|---|---|
| Temperature | Initial | 2 weeks | 1 month | 3 month | 6 month | 9 month | 12 month |
| 5° C. | B | A | A | A | A | A | B |
| 25° C./60% RH | | A | | A | A | | |

Test Matrix A - appearance, assay, related substances, dissolution, and Karl Fischer moisture.
Test Matrix B - appearance, assay, related substances, dissolution, Karl Fischer moisture, and microbial limits.

TABLE 82

| Stability Schedule for Compound 1 Tablets, 100 mg and 200 mg Clinical Trial Batches | | | | | | | | | |
|---|---|---|---|---|---|---|---|---|---|
| Temperature | Initial | 1[1] month | 2 month | 3 month | 6 month | 9[1] month | 12 month | 18 month | 24 month | 36 month |
| 5° C. | B | A | A | A | A | A | B | A | B | B |
| 25° C./60% RH | | A | | A | A | | | | | |

Test Matrix A - appearance, assay, related substances, dissolution, and Karl Fischer moisture.

Test Matrix B - appearance, assay, related substances, dissolution, Karl Fischer moisture, and microbial limits.

[1]1 month and 9 month time points optional for subsequent GMP batches

TABLE 83

| Proposed Compound 1 Tablets Stability Specification | | |
|---|---|---|
| Test Items | Methods | Release Criteria |
| Appearance | Visual Method | Coated round shape tablets (100 mg) Coated oval shape tablets (200 mg) |
| Identification | HPLC Method | Conforms to Reference |
| Assay (% label claim) | HPLC Method | 90.0% to 110.0% |
| Related Substances (Area %) | HPLC Method | Total: NMT 4.0% Compound 1A: NMT 1.5% Each individual impurity NMT 0.5% |
| Dissolution Test | USP <711> | Each unit: ≥70% dissolved (Q + 5%) at 45 min |
| Moisture Content | USP <921> Method 1a | Report results |
| Microbial Limit Test | USP <61>, <62> | Conforms |

Abbreviations: HPLC = high performance liquid chromatography; NMT = not more than; USP = United States Pharmacopeia.

The proposed clinical dosage form for Compound 1 is formulated as a direct blend dry granulation with roller compaction. The blend is compressed into 400 mg round white coated tablets and 800 mg coated white oval shape tablets. The 100 mg and 200 mg active pharmaceutical ingredient (API) dosage strengths are achieved by utilizing the same excipients and formulation. The tablets are compressed into two different shapes, sizes, and weights to obtain 100 mg and 200 mg strength Compound 1 Tablets. The dosage form will be administered orally. The tablets are packaged in HDPE bottles with child-resistant closure (CRC).

Further formulation development for the Phase 2 clinical studies were performed for Compound 1 Tablets. During the Phase 1 tablet manufacture and on scale-up, it was determined that the formulation and process needed some optimization. The overall strategy of the formulation remained the same, blending, roller compaction, milling, and compaction using the similar GRAS excipients all evaluated during the excipient compatibility study. After the formulation and process of the Phase 2 tablets were established, multikilogram blends were prepared with compression and coating of 50 mg, 100 mg, and 200 mg tablets. The 100 mg and 200 mg batches were tested and placed on an ICH stability program and shown to be consistent with the Phase 1 formulation with improved processing.

Formulation Development Plan

Compound 1 is to be administered orally as 100 mg and 200 mg solid dosage units for the proposed Phase 2 clinical study as the Phase 1 study used 50 mg and 200 mg tablets. Solid dose formulations were evaluated using a dry granulation that utilizes roller compaction followed by a direct blend so that the blend is compressed to produce tablets for both the Phase 1 and Phase 2 tablet formulations. Roller compaction is required due to the flow characteristics of the blend to improve the granulation. Excipient stability/compatibility, manufacturability, and in vitro dissolution were used during formulation development to select the clinical formulation for both the Phase 1 and Phase 2 tablet formulations.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A pharmaceutical composition, in the form of an aqueous solution, comprising:

(i) water;

(ii) a compound of Formula (I):

(I)

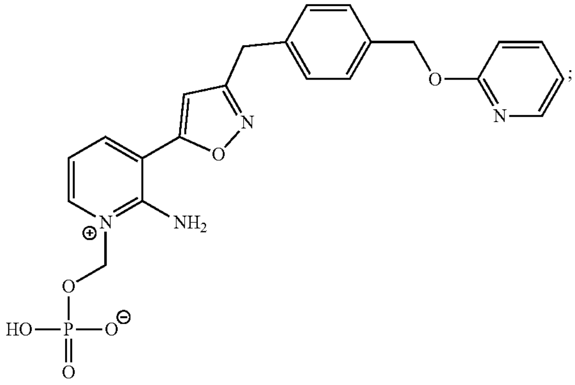

;

or an isotopic variant, tautomer, or pharmaceutically acceptable salt thereof; and (iii) 20 mM to 50 mM potassium phosphate buffer, wherein the potassium phosphate buffer comprises monobasic potassium phosphate and dibasic potassium phosphate;

wherein the pharmaceutical composition has a pH of 7.5 to 8.5;

wherein the pharmaceutical composition is in a dosage form for dosing or administration by injection or I.V. infusion;

wherein the pharmaceutical composition comprises from 10 mg/mL to 50 mg/mL of the compound of Formula (I); and wherein the pharmaceutical composition is stable for a period of up to 12 months at a temperature of −20° C.

2. The pharmaceutical composition of claim 1, comprising from 10 mg/mL to 30 mg/mL of the compound of Formula (I).

3. The pharmaceutical composition of claim 1, comprising less than about 5% (w/w) of a compound that has the following structure:

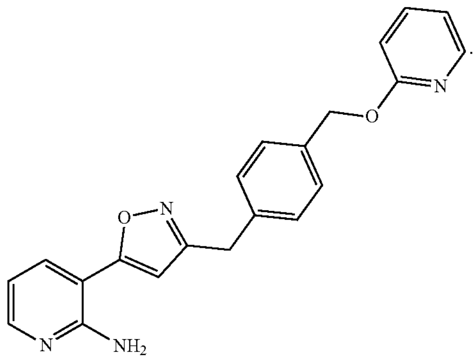 [SMILES: Nc1ncccc1-c1cc(Cc2ccc(COc3ccccn3)cc2)no1]

.

4. The pharmaceutical composition of claim 1, comprising about 20 mg/mL of the compound of Formula (I).

5. The pharmaceutical composition of claim 1, comprising from 10 to 1000 mg of the compound of Formula (I).

6. The pharmaceutical composition of claim 1, wherein the pharmaceutical composition has a pH of 8.0.

7. The pharmaceutical composition of claim 1, wherein the pharmaceutical composition comprises 50 mg to 600 mg of the compound of Formula (I).

8. The pharmaceutical composition of claim 1, wherein the pharmaceutical composition comprises 250 mg to 450 mg of the compound of Formula (I).

9. The pharmaceutical composition of claim 1, wherein the pharmaceutical composition comprises 350 mg of the compound of Formula (I).

10. The pharmaceutical composition of claim 1, comprising from 10 mg/mL to 40 mg/mL of the compound of Formula (I).

11. The pharmaceutical composition of claim 1, comprising 20 mg/mL of the compound of Formula (I).

12. The pharmaceutical composition of claim 1, wherein the concentration of the potassium phosphate buffer is 20 mM.

13. The pharmaceutical composition of claim 1, wherein the pharmaceutical composition is in a dosage form for I.V. injection or infusion.

14. The pharmaceutical composition of claim 1,
wherein the pharmaceutical composition comprises from 10 mg/mL to 40 mg/mL of the compound of Formula (I); and
wherein the pharmaceutical composition is in a dosage form for I.V. injection or infusion.

15. The pharmaceutical composition of claim 1, wherein the pharmaceutical composition comprises:
(i) water;
(ii) from 250 mg to 450 mg of a compound of Formula (I); and
(iii) 20 mM to 50 mM potassium phosphate buffer, wherein the potassium phosphate buffer comprises monobasic potassium phosphate and dibasic potassium phosphate;
wherein the pharmaceutical composition has a pH of 7.5 to 8.5;
wherein the pharmaceutical composition comprises from 10 mg/mL to 30 mg/mL of the compound of Formula (I); and
wherein the pharmaceutical composition is in a dosage form for I.V. injection or infusion.

16. The pharmaceutical composition of claim 1, wherein the pharmaceutical composition comprises:
(i) water;
(ii) 350 mg of a compound of Formula (I); and
(iii) 20 mM of a potassium phosphate buffer, wherein the potassium phosphate buffer comprises monobasic potassium phosphate and dibasic potassium phosphate;
wherein the pharmaceutical composition has a pH of 8.0;
wherein the pharmaceutical composition comprises 20 mg/mL of the compound of Formula (I); and
wherein the pharmaceutical composition is in a dosage form for I.V. infusion.

17. A method of preparing a pharmaceutical composition comprising:
([1]) providing a pharmaceutical composition in the form of an aqueous solution comprising:
(i) water;
(ii) a compound of Formula (I):

(I)

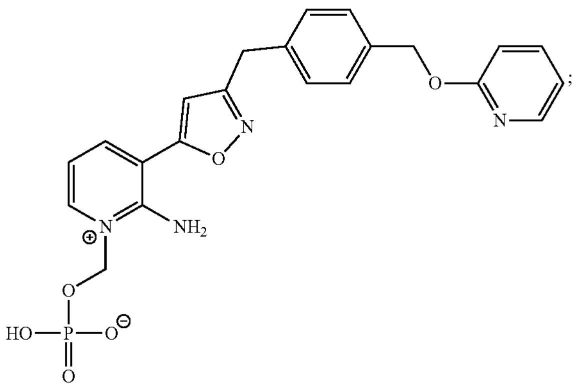

and
(iii) 20 mM to 50 mM potassium phosphate buffer, wherein the potassium phosphate buffer comprises monobasic potassium phosphate and dibasic potassium phosphate;
wherein the pharmaceutical composition has a pH of 7.5 to 8.5;
wherein the pharmaceutical composition comprises from 10 mg/mL to 50 mg/mL of the compound of Formula (I); and
wherein the pharmaceutical composition is in a dosage form for dosing or administration by injection or I.V. infusion; and
([2]) storing the pharmaceutical composition at a temperature of −20° C.

18. The method of claim 17, wherein the pharmaceutical composition comprises:
(i) water;
(ii) from 250 mg to 450 mg of a compound of Formula (I); and
(iii) 20 mM to 50 mM potassium phosphate buffer, wherein the potassium phosphate buffer comprises monobasic potassium phosphate and dibasic potassium phosphate;
wherein the pharmaceutical composition has a pH of 7.5 to 8.5;
wherein the pharmaceutical composition comprises from 10 mg/mL to 30 mg/ml of the compound of Formula (I); and
wherein the pharmaceutical composition is in a dosage form for I.V. injection or infusion.

19. The method of claim 17, wherein the pharmaceutical composition comprises:
(i) water;
(ii) 350 mg of a compound of Formula (I); and
(iii) 20 mM of a potassium phosphate buffer, wherein the potassium phosphate buffer comprises monobasic potassium phosphate and dibasic potassium phosphate;
wherein the pharmaceutical composition has a pH of 8.0;
wherein the pharmaceutical composition comprises 20 mg/mL of the compound of Formula (I); and
wherein the pharmaceutical composition is in a dosage form for I.V. infusion.

20. A method of preparing a pharmaceutical composition for I.V. administration, comprising:
obtaining a pharmaceutical composition in the form of an aqueous solution from storage at −20° C., wherein the pharmaceutical composition comprises:

(i) water;

(ii) a compound of Formula (I):

(I)

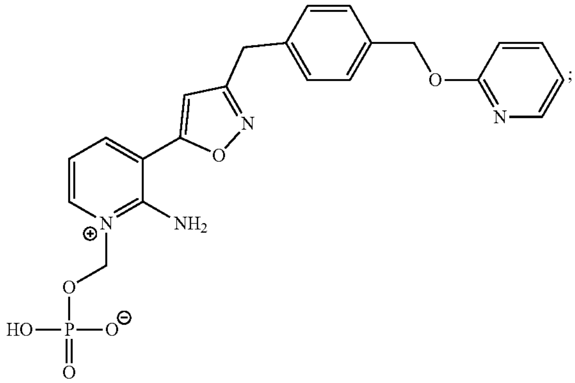

;

and (iii) 20 mM to 50 mM potassium phosphate buffer, wherein the potassium phosphate buffer comprises monobasic potassium phosphate and dibasic potassium phosphate;

wherein the pharmaceutical composition has a pH of 7.5 to 8.5;

wherein the pharmaceutical composition comprises from 10 mg/mL to 50 mg/mL of the compound of Formula (I); and wherein the pharmaceutical composition is in a dosage form for dosing or administration by I.V. injection or infusion.

21. The method of claim 20, wherein the method includes diluting the pharmaceutical composition with a non-toxic parenterally-acceptable diluent or solvent prior to administration.

22. The method of claim 21, wherein the non-toxic parenterally-acceptable diluent or solvent is a sodium chloride solution.

23. The method of claim 20, wherein the pharmaceutical composition comprises:

(i) water;

(ii) from 250 mg to 450 mg of a compound of Formula (I); and (iii) 20 mM to 50 mM potassium phosphate buffer, wherein the potassium phosphate buffer comprises monobasic potassium phosphate and dibasic potassium phosphate;

wherein the pharmaceutical composition has a pH of 7.5 to 8.5;

wherein the pharmaceutical composition comprises from 10 mg/mL to 40 mg/mL of the compound of Formula (I); and wherein the pharmaceutical composition is in a dosage form for I.V. injection or infusion.

24. The method of claim 20, wherein the pharmaceutical composition comprises:

(i) water;

(ii) 350 mg of a compound of Formula (I); and (iii) 20 mM to 50 mM of a potassium phosphate buffer, wherein the potassium phosphate buffer comprises monobasic potassium phosphate and dibasic potassium phosphate;

wherein the pharmaceutical composition has a pH of 8.0;

wherein the pharmaceutical composition comprises 20 mg/mL of the compound of Formula (I); and wherein the pharmaceutical composition is in a dosage form for I.V. injection or infusion.

25. A pharmaceutical composition, in the form of an aqueous solution, comprising:

(i) water;

(ii) a compound of Formula (I):

(I)

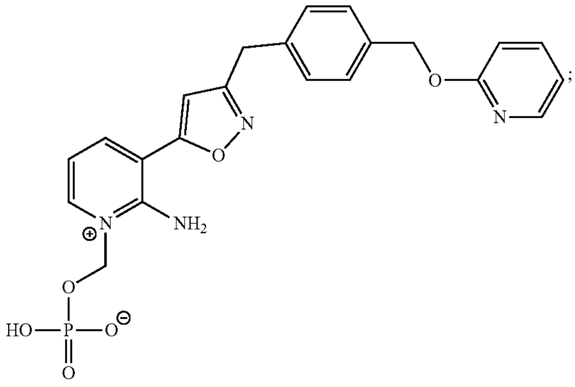

;

or an isotopic variant, tautomer, or pharmaceutically acceptable salt thereof; and (iii) 20 mM to 50 mM potassium phosphate buffer, wherein the potassium phosphate buffer comprises monobasic potassium phosphate and dibasic potassium phosphate;

wherein the pharmaceutical composition has a pH of 7.5 to 8.5;

wherein the pharmaceutical composition is in a dosage form for dosing or administration by injection or I.V. infusion;

wherein the pharmaceutical composition comprises from 10 mg/mL to 50 mg/mL of the compound of Formula (I).

26. The pharmaceutical composition of claim 25, wherein the pharmaceutical composition comprises from 10 mg/mL to 40 mg/ml of the compound of Formula (I); and wherein the pharmaceutical composition is in a dosage form for I.V. injection or infusion.

27. The pharmaceutical composition of claim 25, wherein the pharmaceutical composition comprises:

(i) water;

(ii) from 250 mg to 450 mg of a compound of Formula (I); and (iii) 20 mM to 50 mM potassium phosphate buffer, wherein the potassium phosphate buffer comprises monobasic potassium phosphate and dibasic potassium phosphate;

wherein the pharmaceutical composition has a pH of 7.5 to 8.5;

wherein the pharmaceutical composition comprises from 10 mg/mL to 30 mg/mL of the compound of Formula (I); and wherein the pharmaceutical composition is in a dosage form for I.V. injection or infusion.

28. The pharmaceutical composition of claim 25, wherein the pharmaceutical composition comprises:

(i) water;

(ii) 350 mg of a compound of Formula (I); and (iii) 20 mM of a potassium phosphate buffer, wherein the potassium phosphate buffer comprises monobasic potassium phosphate and dibasic potassium phosphate;

wherein the pharmaceutical composition has a pH of 8.0;

wherein the pharmaceutical composition comprises 20 mg/mL of the compound of Formula (I); and wherein the pharmaceutical composition is in a dosage form for I.V. injection or infusion.

* * * * *